US008937078B2

(12) United States Patent
Bembenek et al.

(10) Patent No.: US 8,937,078 B2
(45) Date of Patent: Jan. 20, 2015

(54) QUINAZOLINONES AS PROLYL HYDROXYLASE INHIBITORS

(75) Inventors: Scott D. Bembenek, San Diego, CA (US); Frances M. Hocutt, San Diego, CA (US); Barry Eastman Leonard, Jr., San Diego, CA (US); Michael H. Rabinowitz, San Diego, CA (US); Mark D. Rosen, San Diego, CA (US); Kyle T. Tarantino, San Diego, CA (US); Hariharan Venkatesan, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 185 days.

(21) Appl. No.: 12/703,705

(22) Filed: Feb. 10, 2010

(65) Prior Publication Data
US 2010/0204226 A1 Aug. 12, 2010

Related U.S. Application Data

(60) Provisional application No. 61/151,429, filed on Feb. 10, 2009.

(51) Int. Cl.
*A61K 31/517* (2006.01)
*C07D 403/04* (2006.01)

(52) U.S. Cl.
CPC .................................. *C07D 403/04* (2013.01)
USPC ................... 514/266.3; 514/266.23; 544/284; 544/287

(58) Field of Classification Search
CPC ............................ C07D 403/04; C07D 403/14
USPC .................................................. 544/284, 287
See application file for complete search history.

(56) References Cited

U.S. PATENT DOCUMENTS

| 8,524,699 B2 | 9/2013 | Thede et al. |
| 2006/0276477 A1 | 12/2006 | Klaus et al. |
| 2007/0299086 A1 | 12/2007 | Kawamoto |
| 2009/0239876 A1 | 9/2009 | Clements et al. |

FOREIGN PATENT DOCUMENTS

| JP | 39023409 | * 10/1964 |
| RU | 2 145 959 | 2/2000 |
| RU | 2 302 200 | 7/2007 |
| WO | WO 2004 052284 A2 | 6/2004 |
| WO | WO 2004 052285 A2 | 6/2004 |
| WO | WO 2007 070359 A2 | 6/2007 |
| WO | WO 2007 103905 A2 | 9/2007 |
| WO | WO 2007 150011 A2 | 12/2007 |
| WO | WO 2009 117269 A1 | 9/2009 |
| WO | 2009/134750 A | 11/2009 |

OTHER PUBLICATIONS

International Search Report for Corresponding International Application No. PCT/US2010/023794 Mailed on May 7, 2010, 3 pgs.
Abbott et al "Stromal Cell-Derived Factor-1α Plays a Critical Role in Stem Cell Recruitment to the Heart After Myocardialinfarction but is not Sufficient to Induce Homing in the Absence of Injury" Circulation 2004 vol. 110(21) pp. 3300-3305.
Al-Sheikh et al "Disturbance in the HIF-1α Pathway Associated With Erythrocytosis: Further Evidences Brought by Frameshift and Nonsense Mutations in the Prolylhydroxylase Domain Protein 2 (PHD2) Gene" Blood Cells Mol Dis 2008 vol. 40 pp. 160-165.
Aragones et al "Deficiency or Inhibition of Oxygen Sensor PHD1 Induces Hypoxia Tolerance by Reprogramming Basal Metabolism"Nat Genet 2008 vol. 40(2) pp. 170-180.
Arcasoy et al "The Non-Haematopoietic Biological Effects of Erythropoietin" Br J Haematol 2008 vol. 141 pp. 14-31.
Armellini et al "The Effects of High Altitude Trekking on Body Composition and Resting Metabolic Rate" Horm Metab Res 1997 vol. 29(9) pp. 458-461.
Bagshawe et al "Antibody-Directed Enzyme Prodrug Therapy: A Review " Drug Dev Res 1995 vol. 34 pp. 220-230.
Berge et al "Pharmaceutical Salts" J Pharm Sci 1977 vol. 66 pp. 1-19.
Bernaudin et al "Normobaric Hypoxia Induces Tolerance to Focal Permanent Cerebral Ischemia in Association With an Increased Expression of Hypoxia-Inducible Factor-1 and its Target Genes, Erythropoietin and VEGF, in the Adult Mouse Brain " J Cereb Blood Flow Metab 2002 vol. 22(4) pp. 393-403.
Bernhardt et al "Organ Protection by Hypoxia and Hypoxia-inducible Factors" Methods Enzymol 2007 vol. 435 pp. 221-245.
Berra et al "HIF Prolyl-Hydroxylase 2 is the Key Oxygen Sensor Setting Low Steady-State Levels of HIF-1A in Normoxia" EMBO J 2003 vol. 22 pp. 4082-4090.
Bertolini et al "A New Rational Hypothesis for the Pharmacophore of the Active Metabolite of Leflunomide, A Potent Immunosuppressive Drug" J Med Chem 1997 vol. 40 pp. 2011-2016.
Bodor et al "Novel Approaches to the Design of Safer Drugs: Soft Drugsand Site-Specific Chemical Delivery Systems" Adv Drug Res 1984 vol. 13 pp. 224-331.
Braliou et al "2-Oxoglutarate-Dependent Oxygenases Control Hepcidin Gene Expression" J Hepatol 2008 vol. 48 pp. 801-810.
Breen et al "VEGF in Biological Control" J Cell Biochem 2007 vol. 102(6) pp. 1358-1367.

(Continued)

*Primary Examiner* — Brian McDowell

(57) ABSTRACT

Quinazolinone compounds of formula (I) are described,

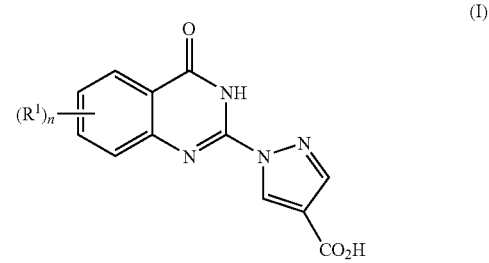

which are useful as prolyl hydroxylase inhibitors. Such compounds may be used in pharmaceutical compositions and methods for the treatment of disease states, disorders, and conditions mediated by prolyl hydroxylase activity. Thus, the compounds may be administered to treat, e.g., anemia, vascular disorders, metabolic disorders, and wound healing.

13 Claims, No Drawings

(56) References Cited

OTHER PUBLICATIONS

Bundgaard Design of Prodrugs 1985 Ed. H. Bundgaard Elsevier.
Cai et al "Complete Loss of Ischaemic Preconditioning-Induced Cardioprotection in Mice With Partial Deficiency of HIF-1α" Cardiovasc Res 2008 vol. 77(3) pp. 463-470.
Carmeliet et al "Manipulating Angiogenesis in Medicine" J Intern Med 2004 vol. 255(5) pp. 538-561.
Carriere et al "Mitochondrial Reactive Oxygen Species Control the Transcription Factor Chop-10/GADD153 and Adipocyte Differentiation a Mechanism for Hypoxia-Dependent Effect" J Biol Chem 2004 vol. 279(39) pp. 40462-40469.
Ceradini et al "Progenitor Cell Trafficking is Regulated by Hypoxic Gradients Through HIF-1 Induction of SDF-1" Nat Med 2004 vol. 10(8) pp. 858-864.
Ceradini et al "Homing to Hypoxia: HIF-1 as a Mediator of Progenitor Cell Recruitment to Injured Tissue" Trends Cardiovasc Med 2005 vol. 15(2) pp. 57-63.
Chang et al "Age Decreases Endothelial Progenitor Cell Recruitment Through Decreases in Hypoxia-Inducible Factor 1α Stabilization During Ischemia" Circulation 2007 vol. 116(24) pp. 2818-2829.
Chin et al "Hypoxia-Inducible Factor 1α Stabilization by Carbon Monoxide Results in Cytoprotective Preconditioning" Proc Natl Acad Sci USA 2007 vol. 104(12) pp. 5109-5114.
Darling et al "Postconditioning' the Human Heart: Multiple Balloon Inflations During Primary Angioplasty May Confer Cardioprotection" Basic Res Cardiol 2007 vol. 102(3) pp. 274-278.
Das et al "Molecular Mechanism of Preconditioning"IUBMB Life 2008 vol. 60(4) pp. 199-203.
Ebert et al "Hypdxia and Mitochondrial Inhibitors Regulate Expression of Glucose Transporter-1 Via Distinct CIS-Acting Sequences" J Biol Chem 1995 vol. 270(49) pp. 29083-29089.
Elson et al "Induction of Hypervascularity Without Leakage or Inflammation in Transgenic Mice Overexpressing Hypoxia-Inducible Factor-1α" Genes Dev 2001 vol. 15(19) pp. 2520-2532.
Epstein et al "C. Elegans EGL-9 and Mammalian Homologs Define a Family of Dioxygenases That Regulate HIF by Prolyl Hydroxylation" Cell 2001 vol. 107 pp. 43-54.
Feldser et al "Reciprocal Positive Regulation of Hypoxia-Inducible Factor 1α and Insulin-Like Growth Factor 21" Cancer Res 1999 vol. 59 pp. 3915-3918.
Firth et al "Oxygen-Regulated Control Elements in the Phosphoglycerate Kinase 1 and Lactate Dehydrogenase a Genes: Similarities With the Erythropoietin 3+ Enhancer" Proc Natl Acad Sci USA 1994 vol. 91 pp. 6496-6500.
Fleisher et al "Improved Oral Drug Delivery: Solubility Limitations Overcome by the Use of Prodrugs" Adv Drug Delivery Rev 1996 vol. 19 pp. 115-130.
Floyd et al "Effects of Prolyl Hydroxylase Inhibitors on Adipogenesis and Hypoxia Inducible Factor 1 Alpha Levels Under Normoxic Conditions" J Cell Biochem 2007 vol. 101 pp. 1545-1557.
Fukuda et al "HIF-1 Regulates Cytochrome Oxidase Subunits to Optimize Efficiency of Respiration in Hypoxic Cells" Cell 2007 vol. 129(1) pp. 111-122.
Grosfeld et al "Hypoxia-Inducible Factor 1 Transactivates the Human Leptin Gene Promoter" J Biol Chem 2003 vol. 277(45) pp. 42953-42957.
Gustaffson et al "Exercise-Induced Angiogenesis-Related Growth and Transcription Factors in Skeletal Muscle, and Their Modification in Muscle Pathology" Front Biosci 2001 vol. 6 pp. D75-D89.
Hu et al "Transplantation of Hypoxia-Preconditioned Mesenchymal Stem Cells Improves Infarcted Heart Function Via Enhanced Survival of Implanted Cells and Angiogenesis" J Thorac Cardiovasc Surg 2008 vol. 135(4) pp. 799-808.
Ivan et al "Biochemical Purification and Pharmacological Inhibition of a Mammalian Prolyl Hydroxylase Acting on Hypoxia-Inducible Factor" Proc Natl Acad Sci USA 2002 vol. 99(21) pp. 13459-13464.
Ivan et al "HIF-Alpha Targeted for VHL-Mediated Destruction by Proline Hydroxylation: Implications for O2 Sensing" Science 2001 vol. 292(5516): pp. 464-468.

Jaakkola et al "Targeting of HIF-α to the Von Hippel-Lindau Ubiquitylation Complex by O2-Regulated Prolyl Hydroxylation" Science 2001 vol. 292 pp. 468-472.
Robinson et al "Discovery of the Hemifumarate and (α-L-Alanyloxy)Methyl Ether as Prodrugs of an Antirheumatic Oxindole: Prodrugs for the Enolic OH Group" J Med Chem 1996 vol. 39 pp. 10-18.
Feng et al "Discovery of Alogliptin: A Potent, Selective, Bioavailable, and Efficacious Inhibitor of Dipeptidyl Peptidase IV" Journal of Medicinal Chemistry 2007 vol. 50 pp. 2297-2300.
Zeghida et al "Concise Synthesis of 2-Amino-4(3H)-Quinazolinones From Simple (Hetero)Aromatic Amines" Journal of Organic Chemistry 2008 vol. 73(6) pp. 2473-2475.
Zhichkin et al "The Use of Formamidine Protection for the Derivatization of Aminobenzoic Acids" J Org Chem 2008 vol. 73 pp. 8954-8959.
Kaelin et al "Proline Hydroxylation and Gene Expression" Annu Rev Biochem 2005 vol. 74 pp. 115-128.
Ke et al "Hypoxia-Inducible Factor-1 (HIF-1)" Mol Pharmacol 2006 vol. 70(5) pp. 1469-1480.
Kelly et al "Cell Type-Specific Regulation of Angiogenic Growth Factor Gene Expression and Induction of Angiogenesis in Nonischemic Tissue by a Constitutively Active Form of Hypoxia-Inducible Factor 1" Circ Res 2003 vol. 93(11) pp. 1074-1081.
Kim et al "HIF-1-Mediated Expression of Pyruvate Dehydrogenase Kinase: A Metabolic Switch Required for Cellular Adaptation to Hypoxia" Cell Metab 2006 vol. 3 pp. 177-185.
Kojima et al "Protective Role of Hypoxia-Inducible Factor-2α Against Ischemic Damage and Oxidative Stress in the Kidney" J Am Soc Nephrol 2007 vol. 18 pp. 1218-1226.
Larsen et al Design and Application of Prodrugs Drugs Design and Development 1991 Krogsgaard-Larsen et al Eds, Harwood Academic Publishers.
Lee et al J "Hypoxia-Inducible Factor-1 Mediates Transcriptional Activation of the Heme Oxygenase-1 Gene in Response to Hypoxia" Biol Chem 1997 vol. 272(9) pp. 5375-5381.
Lin et al "Differentiation Arrest by Hypoxia" J Biol Chem 2006 vol. 281(41) pp. 30678-30683.
Liu et al "Hypoxia Regulates Vascular Endothelial Growth Factor Gene Expression in Endothelial Cells" Circ Res 1995 vol. 77(3) pp. 638-643.
Lok et al J "Identification of a Hypoxia Response Element in the Transferrin Receptor Gene" Biol Chem 1999 vol. 274(34) pp. 24147-24152.
Luttun et al "Placental Growth Factor (PIGF) and its Receptor FLT-1 (VEGFR-1)" Ann NY Acad Sci 2002 vol. 979 pp. 80-93.
Mace et al "Sustained Expression of HIF-1A in the Diabetic Environment Promotes Angiogenesis and Cutaneous Wound Repair" Wound Repair Regen 2007 vol. 15(5) pp. 636-645.
Mallick et al "Ischemia-Reperfusion Injury of the Intestine and Protective Strategies Against Injury" Dig Dis Sci 2004 vol. 49(9) pp. 1359-1377.
Metzen et al "Intracellular Localisation of Human HIF-1α Hydroxylases: Implications for Oxygen Sensing" J Cell Sci 2003 vol. 116(7) pp. 1319-1326.
Mukhoipadhyay et al "Role of Hypoxia-Inducible Factor-1 in Transcriptional Activation of Ceruloplasmin by Iron Deficiency" J Biol Chem 2000 vol. 275(28) pp. 21048-21054.
Murry et al "Preconditioning With Ischemia: A Delay of Lethal Cell Injury in Ischemic Myocardium" Circulation 1986 vol. 74(5) pp. 1124-1136.
Nagai et al "Becaplermin: Recombinant Platelet Derived Growth Factor, a New Treatment for Healing Diabetic Foot Ulcers" Expert Opin Biol Ther 2002 vol. 2(2) pp. 211-218.
Natarajan et al "Hypoxia Inducible Factor-1 Activation by Prolyl 4-Hydroxylase-2 Gene Silencing Attenuates Myocardial Ischemia Referfusion Injury" Circ Res 2006 vol. 98(1) pp. 133-140.
Natarajan et al "Hypoxia Inducible Factor-1 Upregulates Adiponectin in Diabetic Mouse Hearts and Attenuates Post-Ischemic Injury" J Cardiovasc Pharmacol 2008 vol. 51(2) pp. 178-187.
Goto et al "The Process Development of a Novel Aldose Reductase Inhibitor, FK366, Part 1. Improvement of Discovery Process and

(56) References Cited

OTHER PUBLICATIONS

New Syntheses of 1-Substituted Quinazolinediones" Organic Process Research & Development 2003 vol. 7 pp. 700-706.
Pajusola et al "Stabilized HIF-1α is Superior VEGF for Angiogenesis in Skeletal Muscle Via Adeno-Associated Virus Gene Transfer" Faseb J 2005 vol. 19(10) pp. 1365-1367.
Papandreou et al "HIF-1 Mediates Adaption to Hypoxia by Actively Downregulating Mitochondrial Oxygen Consumption" Cell Metab 2006 vol. 3 pp. 187-197.
Pasupathy et al "Ischaemic Preconditioning Protects Against Ischaemia/Reperfusioninjury: Emerginc Concepts" Eur J Vasc Endovasc Surg 2005 vol. 29 pp. 106-115.
Paulekuhn et al Trends in Active Pharmaceutical Ingredients Salt Selection Based on Analysis of the Orange Book Database J Med Chem 2007 vol. 50 pp. 6665-6672.
Percy et al "A Family With Erythrocytosis Establishes a Role for Prolyl Hydroxylase Domain Protein 2 in Oxygen Homeostatis" PNAS 2007 vol. 103(3) pp. 654-659.
Peyssonnaux et al "HIF1α Expression Regulates the Bactericidal Capacity of Phagocytes" J Clin Investigation 2005 vol. 115(7) pp. 1806-1815.
Peyssonnaux et al "Regulation of Iron Homeostatis by the Hypoxia-Inducible Transcription Factors (HIFs)" J Clin Invest 2007 vol. 117(7) pp. 1926-1932.
Peyssonnaux et al "Critical Role of HIF-1α in Keratinocyte Defense Against Bacterial Infection" J Invest Dermatol 2008 vol. Aug 128(8) pp. 1964-1968.
Pfander et al "HIF-1α Controls Extracellular Matrix Synthesis by Epiphyseal Chondrochytes" J Cell Sci 2003 vol. 116(PT9) pp. 1819-1826.
Ram et al "Synthesis and Antihyperglycemic Activity of Suitably Functionalized 3H-Quinazolin-4-Ones" Bioorganic & Medicinal Chemistry 2003 vol. 11 pp. 2439-2444.
Hirota et al "Targeting Hypoxia-Inducible Factor-1 (HIF-1) Signaling in Therapeutics: Implications for the Treatment of Inflammatory Bowel Disease" Recent Patents on Inflammation and Allergy Drug Discovery 2009 vol. 3 pp. 1-16.
Robinson et al "Mucosal Protection by Hypoxia-Inducible Factor Prolyl Hydroxylase Inhibition" Gastroenterology 2008 vol. 134(1) pp. 145-155.
Rolfs et al "Oxygen-Regulated Transferrin Expression is Mediated by Hypoxia-Inducible Factor-1" J Biol Chem 1997 vol. 272(32) pp. 20055-20062.
Scheuermann et al "Hypoxia-Inducible Factors Per /ARNT/ Sim Domains: Structure and Function" Methods Enzymol 2007 vol. 435 pp. 3-24.
Schmid et al "HIF-1 and P53: Communication of Transcription Factors Under Hypoxia" J Cell Mol Med 2004 vol. 8 pp. 423-431.
Schultz et al "Hypoxia and Hypoxia-Inducible Factor-1α Promote Growth Factor-Induced Proliferation of Human Vascular Smooth Muscle Cells" Am J Physiol Heart Circ Physiol 2006 vol. 290(6) pp. H2528-H2534.
Semenza et al "Oxygen-Dependent Regulation of Mitochondrial Respiration by Hypoxia-Inducible Factor 1" Biochem J 2007 vol. 405 pp. 1-9.
Semenza et al "Regulation of Tissue Perfusion in Mammals by Hypoxia-Inducible Factor 1" Exp Physiol 2007 vol. 92(6) pp. 988-991.
Semenza et al "A Nuclear Factor Induced by Hypoxia Via De Novo Protein Syntheis Binds to the Human Erythropoietin Gene Enhancer at a Site Required for Transcriptional Activation" Mol Cell Biol 1992 vol. 12(12) pp. 5447-5454.
Semenza et al "Hypoxia-Inducible Factor 1 (HIF-1) Pathway" Sci STKE 2007 vol. 407(CM8) pp. 1-3.
Semenza et al "Hypoxia-Inducible Factor 1: Oxygen Homeostatis and Disease Pathophysiology" Trends Mol Med 2001 vol. 7(8) pp. 345-350.
Semenza et al "Vasculogenesis, Angiogenesis, and Arteriogenesis: Mechanisms of Blood Vessel Formation and Remodeling" J Cell Biochem 2007 vol. 102 pp. 840-847.

Shan et al "Prodrug Strategies Bases on Intramolecular Cyclization Reactions " J Pharm Sci 1997 vol. 86(7) pp. 765-767.
Shaw et al "Glucose Metabolism and Cancer" Curr Opin Cell Biol 2006 vol. 18(6) pp. 598-608.
Shyu et al "Intramyocardial Injection of Naked DNA Encoding HIF-1α/VIP16 Hybrid to Enhance Angiogenesis in an Acute Myocardial Infarction Model in the Rat" Cardiovasc Res 2002 vol. 54 pp. 576-583.
Siddiq et al "Hypoxia-Inducible Factor Prolyl 4-Hydroxylase Inhibition" J Biol Chem 2005 vol. 280(50) pp. 41732-41743.
Simon et al "The Role of Oxygen Availability in Embryonic Development and Stem Cell Function" Nat Rev Mol Cell Biol 2008 vol. 9 pp. 285-296.
Stahl and Wermuth Handbook of Pharmaceutical Salts Properties Selection and Use Stahl and Wermuth Eds Wiley-VCH and VHCA Zurich 2002.
Steed et al "Clinical Evaluation of Recombinant Human Platelet-Derived Growth Factor for the Treatment of Lower Extremity Ulcers" Plast Reconstr Surg 2006 vol. 117 (7 Suppl) pp. 143S-149S.
Tacchini et al "Transferin Receptor Induction by Hypoxia" J Biol Chem 1999 vol. 274(34) pp. 24142-24146.
Thurson et al "Leakage-Resistant Blood Vessels in Mice Transgenically Overexpressing Angiopoietin-1" Science 1999 vol. 286 pp. 2511-2514.
Thurston et al "Angiopoietin-1 Protects the Adult Vasculature Against Plasma Leakage" Nat Med 2000 vol. 6(4) pp. 460-463.
Vincent ET "Angiogenesis is Induced in a Rabbit Model of a Hindlimb Ischemia by Naked DNA Encoding an HIF-1α/VP16 Hybrid Transcription Factor" AL Circulation 2000 vol. 102 pp. 2255-2261.
Wang et al "Characterization of Hypoxia-Inducible Factor 1 and Regulation of DNA Binding Actiity by Hypoxia" J Biol Chem 1993 vol. 268(29) pp. 21513-21518.
Wang et al "General Involvement of Hypoxia-Inducible Factor 1 in Transcriptional Response to Hypoxia" Proc Natl Acad Sci 1993 vol. 90 pp. 4304-4308.
Wang et al "Purification and Characterization of Hypoxia-Inducible Factor 1" J Biol Chem 1995 vol. 270(3) vol. 1230-1237.
Wang et al "The Hypoxia-Inducible Factor α Pathway Couples Angiogenesis to Osteogenesis During Skeletal Development" J Clin Invest 2007 vol. 117(6) pp. 1616-1626.
Warshakoon et al"A Novel Series of Imidazol[1,2-a[Pyridine Derivatives as HIF-1α Prolyl Hydroxylase Inhibitors" Bioorg Med Chem Lett 2006 vol. 16(21) pp. 5598-5601.
Warshakoon et al "Design and Synthesis of Substituted Pyridine Derivatives as HIF-1α Prolyl Hydroxylase Inhibitors" Bioorg Med Chem Lett 2006 vol. 16(21) pp. 5616-5620.
Warshakoon et al "Design and Synthesis of a Series of Novel Pyrazolopyridines as HIF 1-αProlyl Hydroxylase Inhibitors" Bioorg Med Chem Lett 2006 vol. 16(21) pp. 5687-5690.
Yoshida et al "Hypoxia Inducible Factor 1-α Regulates of Platelet Derived Growth Factor-B in Human Glioblastoma Cells" J Neurooncol 2006 vol. 76(1) pp. 13-21.
Yun et al "Inhibition of PPAR Gamma 2 Gene Expression by the HIF1-Regulated Gene DEC1/STRA13: A Mechanism for Regulation of Adipogenesis by Hypoxia " Dev Cell 2002 vol. 2 pp. 331-341 Dev Cell 2002 vol. 2 pp. 331-341.
Zhang et al "Mitochondrial Autophagy is an HIF-1-Dependent Adaptive Metabolic Resonse to Hypoxia" J Biol Chem 2008 vol. 283 pp. 10892-10903.
Zinkernagel et al Pharmacologie Augmentation of Hypoxia-Inducible Factor-1A With Mimosine Boosts the Bactericidal Capacity of Phagocytes The Journal of Infectious Diseases 2008 vol. 197 pp. 214-217.
Becaplermin (Regranex) Label Issued Jan. 1998.
Smith et al "Infection With a Helminth Parasite Prevents Experimental Colitis Via a Macrophae-Mediated Mechanism" J Immunol 2007 vol. 178 pp. 4557-4566.

\* cited by examiner

QUINAZOLINONES AS PROLYL HYDROXYLASE INHIBITORS

CROSS REFERENCE TO RELATED APPLICATIONS

This application claims the benefit of U.S. provisional patent application Ser. No. 61/151,429, filed Feb. 10, 2009, which is hereby incorporated by reference.

FIELD OF THE INVENTION

The present invention relates to certain quinazolinone compounds, pharmaceutical compositions containing them, and methods of using them for the treatment of disease states, disorders, and conditions mediated by prolyl hydroxylase activity.

BACKGROUND OF THE INVENTION

Cells respond to hypoxia by activating the transcription of genes involved in cell survival, oxygen delivery and utilization, angiogenesis, cellular metabolism, regulation of blood pressure, hematopoiesis, and tissue preservation. Hypoxia-inducible factors (HIFs) are key transcriptional regulators of these genes (Semenza et al., 1992, *Mol Cell Biol.*, 12(12): 5447-54; Wang et al., 1993, *J Biol Chem.*, 268(29):21513-18; Wang et al., 1993, *Proc Natl Acad Sci.*, 90:4304-08; Wang et al., 1995, *J Biol Chem.*, 270(3):1230-37). Three forms of HIF-α have been described: HIF-1α, HIF-2α and HIF-3α (Scheuermann et al., 2007, *Methods Enzymol.*, 435:3-24). Pairing of a HIFα sub-unit with HIF-1β forms a functional heterodimeric protein that subsequently recruits other transcriptional factors such as p300 and CBP (Semenza, 2001, *Trends Mol Med.*, 7(8):345-50).

A family of highly conserved oxygen, iron, and 2-oxoglutarate-dependent prolyl hydroxylase (PHD) enzymes mediate the cells response to hypoxia via post-translational modification of HIF (Ivan et al., 2001, *Science*, 292:464-68; Jaakkola et al., 2001, *Science*, 292:468-72). Under normoxic conditions, PHD catalyzes the hydroxylation of two conserved proline residues within HIF. Von Hippel Lindau (VHL) protein binds selectively to hydroxylated HIF. The binding of VHL renders HIF a target for polyubiquitination by the E3 ubiquitin ligase complex and its subsequent degradation by the 26S proteasome (Ke et al., 2006, *Mol Pharmacol.* 70(5):1469-80; Semenza, *Sci STKE.*, 2007, 407(cm8):1-3). As the affinity of PHD for oxygen is within the physiological range of oxygen and oxygen is a necessary co-factor for the reaction, PHD is inactivated when oxygen tension is reduced. In this way, HIF is rapidly degraded under normoxic conditions but accumulates in cells under hypoxic conditions or when PHD is inhibited.

Four isotypes of PHD have been described: PHD1, PHD2, PHD3, and PHD4 (Epstein et al., 2001, *Cell*, 107:43-54; Kaelin, 2005, *Annu Rev Biochem.*, 74:115-28; Schmid et al., 2004, *J Cell Mol Med.*, 8:423-31). The different isotypes are ubiquitously expressed but are differentially regulated and have distinct physiological roles in the cellular response to hypoxia. There is evidence that the various isotypes have different selectivity for the three different HIFα sub-types (Epstein et al., supra). In terms of cellular localization, PHD1 is primarily nuclear, PHD2 is primarily cytoplasmic, and PHD3 appears to be both cytoplasmic and nuclear (Metzen E, et al. 2003, *J Cell Sci.*, 116(7):1319-26). PHD2 appears to be the predominant HIFα prolyl hydroxylase under normoxic conditions (Ivan et al., 2002. *Proc Natl Acad Sci. USA*, 99(21):13459-64; Berra et al., 2003, *EMBO J.*, 22:4082-90). The three isotypes have a high degree of amino-acid homology and the active site of the enzyme is highly conserved.

The HIF target gene products are involved in a number of physiological and pathophysiological processes including but not limited to: erythropoiesis, angiogenesis, regulation of energy metabolism, vasomotor function, and cell apoptosis/proliferation. The first gene described as a HIF target was that encoding erythropoietin (EPO) (Wang et al., 1993, supra). It was recognized that a reduction in the oxygen carrying capacity of the blood is sensed in the kidney and that the kidney and liver respond by releasing more EPO, the hormone that stimulates red blood cell proliferation and maturation. EPO has a number of other important effects on non-hematopoietic cell types and has emerged as a key tissue-protective cytokine (Arcasoy, 2008, *Br J Haematol.*, 141:14-31). Thus EPO is now implicated in wound healing and angiogenesis as well as the response of tissues to ischemic insult. Most of the enzymes involved in anaerobic glycolysis are encoded by HIF target genes and as a result glycolysis is increased in hypoxic tissues (Shaw, 2006, *Curr Opin Cell Biol.*, 18(6): 598-608). The known HIF target gene products in this pathway include but are not limited to: glucose transporters such as GLUT-1 (Ebert et al., 1995, *J Biol Chem.*, 270(49):29083-89), enzymes involved in the break down of glucose to pyruvate such as hexokinase and phosphoglycerate kinase 1 (Firth et al., 1994, *Proc Natl Acad Sci. USA*, 91:6496-6500) as well as lactate dehydrogenase (Firth et al., supra). HIF target gene products are also involved in the regulation of cellular metabolism. For example, pyruvate dehydrogenase kinase-1 is a target HIF gene product and regulates the entry of pyruvate into the Kreb's cycle by reducing the activity of pyruvate dehydrogenase by phosphorylation (Kim et al., 2006, *Cell Metab.*, 3:177-85; Papandreou et al., 2006, *Cell Metab.*, 3:187-197). HIF target gene products are also involved in angiogenesis. For example, vascular endothelial growth factor (VEGF) (Liu et al., 1995, *Circ Res.*, 77(3):638-43) is a known regulator of angiogenesis and vasculogenesis. HIF target gene products also function in the regulation of vascular tone and include heme oxygenase-1 (Lee et al., 1997, *J Biol Chem.*, 272(9):5375-81). A number of HIF regulated gene products such as platelet-derived growth factor (PDGF) (Yoshida et al., 2006, *J Neurooncol.*, 76(1):13-21), vascular endothelial growth factor (Breen, 2007, *J Cell Biochem.*, 102(6):1358-67) and EPO (Arcasoy, supra) also function in the coordinated response to wound healing.

Targeted disruption of the prolyl hydroxylase (PHD) enzyme activity by small molecules has potential utility in the treatment of disorders of oxygen sensing and distribution. Examples include but are not limited to: anemia; sickle cell anemia; peripheral vascular disease; coronary artery disease; heart failure; protection of tissue from ischemia in conditions such as myocardial ischemia, myocardial infarction and stroke; preservation of organs for transplant; treatment of tissue ischemia by regulating and/or restoring blood flow, oxygen delivery and/or energy utilization; acceleration of wound healing particularly in diabetic and aged patients; treatment of burns; treatment of infection; bone healing, and bone growth. In addition, targeted disruption of PHD is expected to have utility in treating metabolic disorders such as diabetes, obesity, ulcerative colitis, inflammatory bowel disease and related disorders such as Crohn's disease. (*Recent Patents on Inflammation & Allergy Drug Discovery*, 2009, 3, 1-16).

HIF has been shown to be the primary transcriptional factor that leads to increased erythropoietin production under conditions of hypoxia (Wang et al., 1993, supra). While treatment with recombinant human erythropoietin has been demonstrated to be an effective method of treating anemia, small molecule mediated PHD inhibition can be expected to offer advantages over treatment with erythropoietin. Specifically, the function of other HIF gene products are necessary for hematopoesis and regulation of these factors increases the efficiency of hematopoesis. Examples of HIF target gene products that are critical for hematopoesis include: transferrin (Rolfs et al., 1997, *J Biol Chem.*, 272(32):20055-62), transferrin receptor (Lok et al., 1999, *J Biol Chem.*, 274(34): 24147-52; Tacchini et al., 1999, *J Biol Chem.*, 274(34):24142-46) and ceruloplasmin (Mukhopadhyay et al., 2000, *J Biol Chem.*, 275(28):21048-54). Hepcidin expression is also suppressed by HIF (Peyssonnaux et al., 2007, *J Clin Invest.*, 117(7):1926-32) and small molecule inhibitors of PHD have been shown to reduce hepcidin production (Braliou et al., 2008, *J Hepatol,* 48:801-10). Hepcidin is a negative regulator of the availability of the iron that is necessary for hematopoesis, so a reduction in hepcidin production is expected to be beneficial to the treatment of anemia. PHD inhibition may also be useful when used in conjunction with other treatments for anemia including iron supplementation and/or exogenous erythropoietin. Studies of mutations in the PHD2 gene occurring naturally in the human population provide further evidence for the use of PHD inhibitors to treat anemia. Two recent reports have shown that patients with dysfunctional mutations in the PHD2 gene display increased erythrocytosis and elevated blood hemoglobin (Percy et al., 2007, *PNAS,* 103(3):654-59; Al-Sheikh et al., 2008, *Blood Cells Mol Dis.,* 40:160-65). In addition, a small molecule PHD inhibitor has been evaluated in healthy volunteers and patients with chronic kidney disease (U.S. pat. appl. US2006/0276477, Dec. 7, 2006). Plasma erythropoietin was increased in a dose-dependent fashion and blood hemoglobin concentrations were increased in the chronic kidney disease patients.

Metabolic adaptation and preservation of tissues are jeopardized by ischemia. PHD inhibitors increase the expression of genes that lead to changes in metabolism that are beneficial under ischemic conditions (Semenza, 2007, *Biochem J.,* 405: 1-9). Many of the genes encoding enzymes involved in anaerobic glycolysis are regulated by HIF and glycolysis is increased by inhibiting PHD (Shaw, supra). Known HIF target genes in this pathway include but are not limited to: GLUT-1 (Ebert et al., supra), hexokinase, phosphoglycerate kinase 1, lactate dehydrogenase (Firth et al., supra), pyruvate dehydrogenase kinase-1 (Kim et al., supra; Papandreou et al., supra). Pyruvate dehydrogenase kinase-1 suppresses the entry of pyruvate into the Kreb's cycle. HIF mediates a switch in the expression of the cytochromes involved in electron transport in the mitochondria (Fukuda et al., 2007, *Cell,* 129 (1):111-22). This change in the cytochrome composition optimizes the efficiency in ATP production under hypoxic conditions and reduces the production of injurious oxidative phosphorylation by-products such as hydrogen peroxide and superoxide. With prolonged exposure to hypoxia, HIF drives autophagy of the mitochondria resulting a reduction in their number (Zhang H et al., 2008, *J Biol Chem.* 283: 10892-10903). This adaptation to chronic hypoxia reduces the production of hydrogen peroxide and superoxide while the cell relies on glycolysis to produce energy. A further adaptive response produced by HIF elevation is up-regulation of cell survival factors. These factors include: Insulin-like growth factor (IGF) 2, IGF-binding protein 2 and 3 (Feldser et al., 1999, *Cancer Res.* 59:3915-18). Overall accumulation of HIF under hypoxic conditions governs an adaptive up-regulation of glycolysis, a reduction in oxidative phosphorylation resulting in a reduction in the production of hydrogen peroxide and superoxide, optimization of oxidative phosphorylation protecting cells against ischemic damage. Thus, PHD inhibitors are expected to be useful in organ and tissue transplant preservation (Bernhardt et al., 2007, *Methods Enzymol.,* 435:221-45). While benefit may be achieved by administering PHD inhibitors before harvesting organs for transplant, administration of an inhibitor to the organ/tissue after harvest, either in storage (e.g., cardioplegia solution) or post-transplant, may also be of therapeutic benefit.

PHD inhibitors are expected to be effective in preserving tissue from regional ischemia and/or hypoxia. This includes ischemia/hypoxia associated with inter alia: angina, myocardial ischemia, stroke, ischemia of skeletal muscle. There are a number of lines of experimental evidence that support the concept that PHD inhibition and subsequent elevation of HIF as a useful method for preserving ischemic tissue. Recently, ischemic pre-conditioning has been demonstrated to be a HIF-dependent phenomenon (Cai et al., 2008, *Cardiovasc Res.,* 77(3):463-70). Ischemic pre-conditioning is a well known phenomenon whereby short periods of hypoxia and/or ischemia protect tissue from subsequent longer periods of ischemia (Murry et al., 1986, *Circulation,* 1986 74(5):1124-36; Das et al., 2008, *IUBMB Life,* 60(4):199-203). Ischemic pre-conditioning is known to occur in humans as well as experimental animals (Darling et al., 2007, *Basic Res Cardiol.,* 102(3):274-8; Kojima I et al., 2007, *J Am Soc Nephrol.,* 18:1218-26). While the concept of pre-conditioning is best known for its protective effects in the heart, it also applies to other tissues including but not limited to: liver, skeletal muscle, liver, lung, kidney, intestine and brain (Pasupathy et al., 2005, *Eur J Vasc Endovasc Surg.,* 29:106-15; Mallick et al., 2004, *Dig Dis Sci.,* 49(9):1359-77). Experimental evidence for the tissue protective effects of PHD inhibition and elevation of HIF have been obtained in a number of animal models including: germ-line knock out of PHD1 which conferred protection of the skeletal muscle from ischemic insult (Aragonés et al., 2008, *Nat Genet.,* 40(2):170-80), silencing of PHD2 through the use of siRNA which protected the heart from ischemic insult (Natarajan et al., 2006, *Circ Res.,* 98(1): 133-40), inhibition of PHD by administering carbon monoxide which protected the myocardium from ischemic injury (Chin et al., 2007, *Proc Natl Acad Sci. U.S.A.,* 104(12):5109-14), hypoxia in the brain which increased the tolerance to ischemia (Bernaudin et al., 2002, *J Cereb Blood Flow Metab.,* 22(4):393-403). In addition, small molecule inhibitors of PHD protect the brain in experimental stroke models (Siddiq et al., 2005, *J Biol Chem.,* 280(50):41732-43). Moreover, HIF up-regulation has also been shown to protect the heart of diabetic mice, where outcomes are generally worse (Natarajan et al., 2008, *J Cardiovasc Pharmacol.,* 51(2):178-187). The tissue protective effects may also be observed in Buerger's disease, Raynaud's disease, and acrocyanosis.

The reduced reliance on aerobic metabolism via the Kreb's cycle in the mitochondria and an increased reliance on anaerobic glycolysis produced by PHD inhibition may have beneficial effects in normoxic tissues. It is important to note that PHD inhibition has also been shown to elevate HIF under normoxic conditions. Thus, PHD inhibition produces a pseudohypoxia associated with the hypoxic response being initiated through HIF but with tissue oxygenation remaining normal. The alteration of metabolism produced by PHD inhibition can also be expected to provide a treatment paradigm for diabetes, obesity and related disorders, including co-morbidities.

Globally, the collection of gene expression changes produced by PHD inhibition reduce the amount of energy generated per unit of glucose and will stimulate the body to burn more fat to maintain energy balance. The mechanisms for the increase in glycolysis are discussed above. Other observations link the hypoxic response to effects that are expected to be beneficial for the treatment of diabetes and obesity. Thus, high altitude training is well known to reduce body fat (Armellini et al., 1997, *Horm Metab Res.*, 29(9):458-61). Hypoxia and hypoxia mimetics such as desferrioxamine have been shown to prevent adipocyte differentiation (Lin et al., 2006, *J Biol Chem.*, 281(41):30678-83; Carrière et al., 2004, *J Biol Chem.*, 279(39):40462-69). The effect is reversible upon returning to normoxic conditions. Inhibition of PHD activity during the initial stages of adipogenesis inhibits the formation of new adipocytes (Floyd et al., 2007, *J Cell Biochem.*, 101:1545-57). Hypoxia, cobalt chloride and desferrioxamine elevated HIF and inhibited PPAR gamma 2 nuclear hormone receptor transcription (Yun et al., 2002, *Dev Cell.*, 2:331-41). As PPAR gamma 2 is an important signal for adipocyte differentiation, PHD inhibition can be expected to inhibit adipocyte differentiation. These effects were shown to be mediated by the HIF-regulated gene DEC1/Stra13 (Yun et al., supra).

Small molecular inhibitors of PHD have been demonstrated to have beneficial effects in animal models of diabetes and obesity (Intl. Pat. Appl. Publ. WO2004/052284, Jun. 24, 2004; WO2004/052285, Jun. 24, 2004). Among the effects demonstrated for PHD inhibitors in mouse diet-induced obesity, db/db mouse and Zucker fa/fa rat models were lowering of: blood glucose concentration, fat mass in both abdominal and visceral fat pads, hemoglobin A1c, plasma triglycerides, body weight as well as changes in established disease biomarkers such as increases in the levels of adrenomedullin and leptin. Leptin is a known HIF target gene product (Grosfeld et al., 2002, *J Biol Chem.*, 277(45):42953-57). Gene products involved in the metabolism in fat cells were demonstrated to be regulated by PHD inhibition in a HIF-dependent fashion (Intl. Pat. Appl. Publ. WO2004/052285, supra). These include apolipoprotein A-IV, acyl CoA thioesterase, carnitine acetyl transferase, and insulin-like growth factor binding protein (IGFBP)-1.

PHD inhibitors are expected to be therapeutically useful as stimulants of vasculogenesis, angiogenesis, and arteriogenesis. These processes establish or restore blood flow and oxygenation to the tissues under ischemia and/or hypoxia conditions (Semenza et al., 2007, *J Cell Biochem.*, 102:840-47; Semenza, 2007, *Exp Physiol.*, 92(6):988-91). It has been shown that physical exercise increases HIF-1 and vascular endothelial growth factor in experimental animal models and in humans (Gustafsson et al. 2001, *Front Biosci.*, 6:D75-89) and consequently the number of blood vessels in skeletal muscle. VEGF is a well-known HIF target gene product that is a key driver of angiogenesis (Liu et al., supra). While administration of various forms of VEGF receptor activators are potent stimuli for angiogenesis, the blood vessel resulting from this potential form of therapy are leaky. This is considered to limit the potentially utility of VEGF for the treatment of disorders of oxygen delivery. The increased expression of a single angiogenic factor may not be sufficient for functional vascularization (Semenza, 2007, supra). PHD inhibition offers a potential advantage over other such angiogenic therapies in that it stimulates a controlled expression of multiple angiogenic growth factors in a HIF-dependent fashion including but not limited to: placental growth factor (PLGF), angiopoietin-1 (ANGPT1), angiopoietin-2 (ANGPT2), platelet-derived growth factor beta (PDGFB) (Carmeliet, 2004, *J Intern Med.*, 255:538-61; Kelly et al., 2003, *Circ Res.*, 93:1074-81) and stromal cell derived factor 1 (SDF-1) (Ceradini et al., 2004, *Nat Med.*, 10(8):858-64). Expression of angiopoietin-1 during angiogenesis produces leakage-resistant blood vessels, in contrast to the vessels produced by administration of VEGF alone (Thurston et al., 1999, *Science*, 286:2511-14; Thurston et al., 2000, *Nat Med.*, 6(4):460-3; Elson et al., 2001, *Genes Dev.*, 15(19):2520-32). Stromal cell derived factor 1 (SDF-1) has been shown to be critical to the process of recruiting endothelial progenitor cells to the sites of tissue injury. SDF-1 expression increased the adhesion, migration and homing of circulating CXCR4-positive progenitor cells to ischemic tissue. Furthermore inhibition of SDF-1 in ischemic tissue or blockade of CXCR4 on circulating cells prevents progenitor cell recruitment to sites of injury (Ceradini et al., 2004, supra; Ceradini et al., 2005, *Trends Cardiovasc Med.*, 15(2):57-63). Importantly, the recruitment of endothelial progenitor cells to sites of injury is reduced in aged mice and this is corrected by interventions that increase HIF at the wound site (Chang et al., 2007, *Circulation*, 116(24):2818-29). PHD inhibition offers the advantage not only of increasing the expression of a number of angiogenic factions but also a co-ordination in their expression throughout the angiogenesis process and recruitment of endothelial progenitor cells to ischemic tissue.

Evidence for the utility of PHD inhibitors as pro-angiogenic therapies is provided by the following observations. Adenovirus-mediated over-expression of HIF has been demonstrated to induce angiogenesis in non-ischemic tissue of an adult animal (Kelly et al., 2003, *Circ Res.*, 93(11):1074-81) providing evidence that therapies that elevate HIF, such as PHD inhibition, will induce angiogenesis. Placental growth factor (PLGF), also a HIF target gene, has been show to play a critical role in angiogenesis in ischemic tissue (Carmeliet, 2004, *J Intern Med.*, 255(5):538-61; Luttun et al., 2002, *Ann N Y Acad Sci.*, 979:80-93). The potent pro-angiogenic effects of therapies that elevate HIF have been demonstrated, via HIF over-expression, in skeletal muscle (Pajusola et al., 2005, *FASEB J.*, 19(10):1365-7; Vincent et al., 2000, *Circulation*, 102:2255-61) and in the myocardium (Shyu et al., 2002, *Cardiovasc Res.*, 54:576-83). The recruitment of endothelial progenitor cells to the ischemic myocardium by the HIF target gene SDF-1 has also been demonstrated (Abbott et al., 2004, *Circulation*, 110(21):3300-05). These findings support the general concept that PHD inhibitors will be effective in stimulating angiogenesis in the setting of tissue ischemia, particularly muscle ischemia. It is expected that therapeutic angiogenesis produced by PHD inhibitors will be useful in restoring blood flow to tissues and therefore the treatment of disease including but not restricted to angina pectoris, myocardial ischemia and infarction, peripheral ischemic disease, claudication, gastric and duodenal ulcers, ulcerative colitis, and inflammatory bowel disease.

PHD and HIF play a central role in tissue repair and regeneration including healing of wounds and ulcers. Recent studies have demonstrated that an increased expression of all three PHDs at wound sites in aged mice with a resulting reduction in HIF accumulation (Chang et al., supra). Thus, elevation of HIF in aged mice by administering desferrioxamine increased the degree of wound healing back to levels observed in young mice. Similarly, in a diabetic mouse model, HIF elevation was suppressed compared to non-diabetic litter mates (Mace et al., 2007, *Wound Repair Regen.*, 15(5):636-45). Topical administration of cobalt chloride, a hypoxia mimetic, or over-expression of a murine HIF that lacks the oxygen-dependent degradation domain and thus provides for a constitutively active form of HIF, resulted in increased HIF at the wound site, increased expression of HIF target genes such as VEGF, Nos2, and Hmox1 and accelerated wound healing. The beneficial effect of PHD inhibition is not restricted to the skin and small molecule inhibitors of PHD have recently been demonstrated to provide benefit in a mouse model of colitis (Robinson et al., 2008, *Gastroenterology*, 134(1):145-55).

PHD inhibition resulting in accumulation of HIF is expected to act by at least four mechanisms to contribute to accelerated and more complete healing of wounds: 1) protection of tissue jeopardized by hypoxia and/or ischemia, 2) stimulation of angiogenesis to establish or restore appropriate blood flow to the site, 3) recruitment of endothelial progenitor cells to wound sites, 4) stimulation of the release of growth factors that specifically stimulate healing and regeneration.

Recombinant human platelet-derived growth factor (PDGF) is marketed as becaplermin (Regranex™) and has been approved by the Food and Drug Administration of the United States of America for "Treatment of lower extremity diabetic neuropathic ulcers that extend into the subcutaneous tissue or beyond, and have adequate blood supply". Becaplermin has been shown to be effective in accelerating wound healing in diabetic patients (Steed, 2006, *Plast Reconstr Surg.*, 117(7 Suppl):143S-149S; Nagai et al., 2002, *Expert Opin Biol Ther.*, 2(2):211-8). As PDGF is a HIF gene target (Schultz et al., 2006, *Am J Physiol Heart Circ Physiol.*, 290 (6):H2528-34; Yoshida et al., 2006, *J Neurooncol.*, 76(1):13-21), PHD inhibition is expected to increase the expression of endogenous PDGF and produce a similar or more beneficial effect to those produced with becaplermin alone. Studies in animals have shown that topical application of PDGF results in increased wound DNA, protein, and hydroxyproline amounts; formation of thicker granulation and epidermal tissue; and increased cellular repopulation of wound sites. PDGF exerts a local effect on enhancing the formation of new connective tissue. The effectiveness of PHD inhibition is expected to be greater than that produced by becaplermin due to the additional tissue protective and pro-angiogenic effects mediated by HIF.

The beneficial effects of inhibition of PHD are expected to extend not only to accelerated wound healing in the skin and colon but also to the healing of other tissue damage including but not limited to gastrointestinal ulcers, skin graft replacements, burns, chronic wounds and frost bite.

Stem cells and progenitor cells are found in hypoxic niches within the body and hypoxia regulates their differentiation and cell fate (Simon et al., 2008, *Nat Rev Mol Cell Biol.*, 9:285-96). Thus PHD inhibitors may be useful to maintain stem cells and progenitor cells in a pluripotent state and to drive differentiation to desired cell types. Stem cells may be useful in culturing and expanding stem cell populations and may hold cells in a pluripotent state while hormones and other factors are administered to the cells to influence the differentiation and cell fate.

A further use of PHD inhibitors in the area of stem cell and progenitor cell therapeutics relates to the use of PHD inhibitors to condition these cells to withstand the process of implantation into the body and to generate an appropriate response to the body to make the stem cell and progenitor cell implantation viable (Hu et al., 2008, *J Thorac Cardiovasc Surg.*, 135(4):799-808). More specifically PHD inhibitors may facilitate the integration of stem cells and draw in an appropriate blood supply to sustain the stem cells once they are integrated. This blood vessel formation will also function to carry hormones and other factors released from these cells to the rest of the body.

PHD inhibitors may also be useful in the treatment of infection (Peyssonnaux et al., 2005, *J Invest Dermatol.*, 115 (7):1806-15; Peyssonnaux et al., 2008 *J Clin Investigation*, 2008 August; 128(8):1964-8). HIF elevation has been demonstrated to increase the innate immune response to infection in phagocytes and in keratinocytes. Phagocytes in which HIF is elevated show increased bactericidal activity, increased nitric oxide production and increased expressed of the antibacterial peptide cathelicidin. These effects may also be useful in treating infection from burns.

HIF has also been shown to be involved in bone growth and healing (Pfander D et al., 2003 *J Cell Sci.*, 116(Pt 9):1819-26., Wang et al., 2007 *J Clin Invest.*, 117 (6):1616-26.) and may therefore be used to heal or prevent fractures. HIF stimulates of glycolysis to provide energy to allow the synthesis of extracellular matrix of the epiphyseal chondrocytes under a hypoxic environment. HIF also plays a role in driving the release of VEGF and angiogenesis in bone healing process. The growth of blood vessels into growing or healing bone can be the rate limiting step in the process.

Certain small molecules with Prolyl Hydroxylase antagonistic activities have been described in the literature. These include, but are not limited to, certain imidazo[1,2-a]pyridine derivatives (Warshakoon et al., 2006, *Bioorg Med Chem Lett.*, 16(21):5598-601), substituted pyridine derivatives (Warshakoon et al., 2006, *Bioorg Med Chem Lett.*, 16(21):5616-20), certain pyrazolopyridines (Warshakoon et al., 2006, *Bioorg Med Chem Lett.*, 16(21):5687-90), certain bicyclic heteroaromatic N-substituted glycine derivatives (Intl. Pat. Appl. Publ. WO2007/103905, Sep. 13, 2007), quinoline based compounds (Intl. Pat. Appl. Publ. WO2007/070359, Jun. 21, 2007), certain pyrimidinetrione N-substituted glycine derivatives (Intl. Pat. Appl. Publ. WO2007/150011, Dec. 27, 2007), substituted aryl or heteroaryl amide compounds (U.S. Pat. Appl. Publ. No.: US 2007/0299086, Dec. 27, 2007) and substituted 4-hydroxypyrimidine-5-carboxamides (Intl. Pat. Appl. Publ. WO2009/117269, Sep. 24, 2009).

However, there remains a need for potent prolyl hydroxylase modulators with desirable pharmaceutical properties. Certain quinazolinone derivatives have been found in the context of this invention to have prolyl hydroxylase modulating activity.

SUMMARY OF THE INVENTION

The present invention is directed to compounds which are useful inhibitors of PHD. The compounds of the present invention are of general Formula (I),

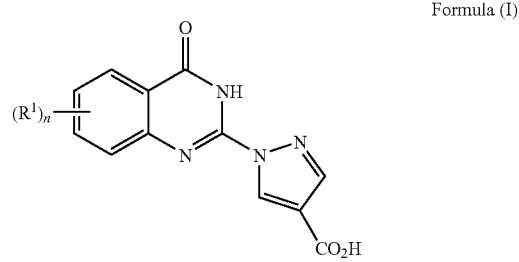

Formula (I)

wherein:
n is 0-3
R$^1$ is a member independently selected from the group consisting of halo, —C$_{1-4}$alkyl, —C$_{1-4}$alkynyl, —C$_{1-4}$alkenyl optionally substituted with halo, —CF$_3$, —OCF$_3$, —SCF$_3$, S(O)CF$_3$, —C(O)—R$^c$, —C(O)N—R$^c$, —OH, —NO$_2$, —CN, —OC$_{1-4}$alkyl, —SC$_{1-4}$alkyl, —SO$_2$—C$_{1-4}$alkyl, —S—R$^c$, —S(O)—R$^c$, —SO$_2$—R$^c$, —SO$_2$N—R$^c$, —O—R$^a$R$^b$, 2,3-dihydro-benzo[1,4]

dioxine, benzo[1,3]dioxole, 1H-indole, benzyl, biphenyl optionally substituted with one or more $R^d$ members, benzyloxy optionally substituted with one or more $R^d$ members, phenyl or monocyclic heteroaryl optionally substituted with one or more $R^d$ members, —$C_{3-8}$cycloalkyl optionally substituted with one or more $R^d$ members, —$C_{3-8}$heterocycloalkyl optionally substituted with one or more $R^c$ members, and two adjacent $R^1$ groups may be joined to form an optionally substituted 3-8 member ring optionally containing one or more O, S or N;

$R^a$ and $R^b$ are independently selected from the group consisting of H, $C_{1-4}$alkyl, —$C(O)C_{1-4}$alkyl, —$C(O)$—$R^c$, —$C(O)NH$—$R^c$, —$SO_2$—$R^c$, —$SO_2$—$C_{1-4}$alkyl, phenyl optionally substituted with $R^d$, benzyl optionally substituted with $R^d$ or monocyclic heteroaryl ring optionally substituted with $R^d$; or $R^a$ and $R^b$ can be taken together with the nitrogen to which they are attached to form an optionally substituted monocyclic heterocycloalkyl ring containing one or more O, S or N;

$R^c$ is a member independently selected from the group consisting of —$C_{3-8}$cycloalkyl, —$C_{3-8}$heterocycloalkyl, biphenyl, phenyl optionally substituted with one or more $R^d$ members, benzyl optionally substituted with $R^d$, naphthyl, indanyl, 5,6,7,8-tetrahydro-naphthyl, and pyridyl optionally substituted with one or more $R^d$ members;

$R^d$ is a member independently selected from the group consisting of —H, halo, —OH, —$C_{1-4}$alkyl, —$SO_2$—$C_{1-4}$alkyl, —CN, or —$CF_3$, —$OCF_3$, —$OC_{1-4}$alkyl, —$C(O)NH_2$, —O-phenyl, and —O-benzyl;
and pharmaceutically acceptable salts thereof.

Isomeric forms of the compounds of formula (I), and of their pharmaceutically acceptable salts, are encompassed within the present invention, and reference herein to one of such isomeric forms is meant to refer to at least one of such isomeric forms. One of ordinary skill in the art will recognize that compounds according to this invention may exist, for example, in a single isomeric form whereas other compounds may exist in the form of a regioisomeric mixture.

The invention also relates to pharmaceutically acceptable salts, pharmaceutically acceptable prodrugs, and pharmaceutically active metabolites of compounds of Formula (I). In certain preferred embodiments, the compound of Formula (I) is a compound selected from those species described or exemplified in the detailed description below.

In a further general aspect, the invention relates to pharmaceutical compositions each comprising: (a) an effective amount of a compound of Formula (I), or a pharmaceutically acceptable salt, pharmaceutically acceptable prodrug, or pharmaceutically active metabolite thereof; and (b) a pharmaceutically acceptable excipient.

In another general aspect, the invention is directed to a method of treating a subject suffering from or diagnosed with a disease, disorder, or medical condition mediated by a prolyl hydroxylase enzyme activity, comprising administering to the subject in need of such treatment an effective amount of a compound of Formula (I), or a pharmaceutically acceptable salt, pharmaceutically acceptable prodrug, or pharmaceutically active metabolite thereof.

In certain preferred embodiments of the inventive method, the disease, disorder, or medical condition is selected from: anemia, vascular disorders, metabolic disorders, and wound healing.

Additional embodiments, features, and advantages of the invention will be apparent from the following detailed description and through practice of the invention.

DETAILED DESCRIPTION

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by the symbol, "/"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "alkenyl" refers to a straight- or branched-chain alkenyl group having from 2 to 12 carbon atoms in the chain. (The double bond of the alkenyl group is formed by two $sp^2$ hybridized carbon atoms.) Illustrative alkenyl groups include prop-2-enyl, but-2-enyl, but-3-enyl, 2-methylprop-2-enyl, hex-2-enyl, and the like.

The term "alkynyl" refers to a straight- or branched-chain alkynyl group having from 2 to 12 carbon atoms in the chain. (The triple bond of the alkynyl group is formed by two sp hybridized carbon atoms.) Illustrative alkynyl groups include prop-2-ynyl, but-2-ynyl, but-3-ynyl, 2-methylbut-2-ynyl, hex-2-ynyl, and the like.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

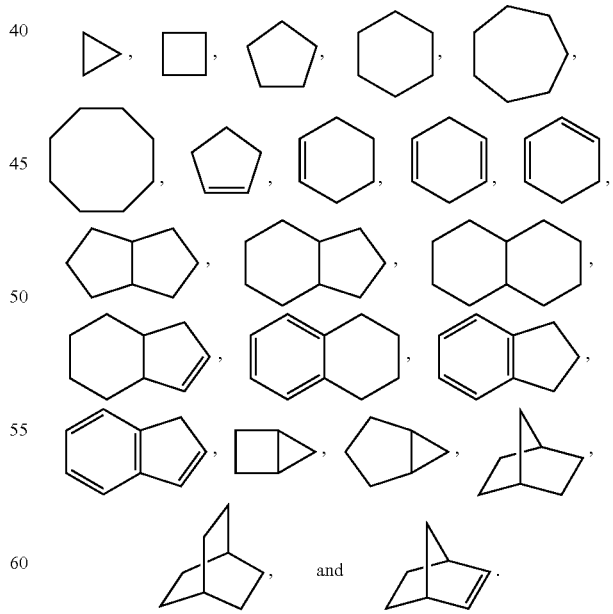

A "heterocycloalkyl" refers to a monocyclic ring structure that is saturated or partially saturated, monocyclic, fused polycyclic, and has from 3 to 8 ring atoms per ring structure selected from carbon atoms and up to two heteroatoms selected from nitrogen, oxygen, and sulfur. The ring structure may optionally contain up to two oxo groups on sulfur ring members. Illustrative entities, in the form of properly bonded moieties, include:

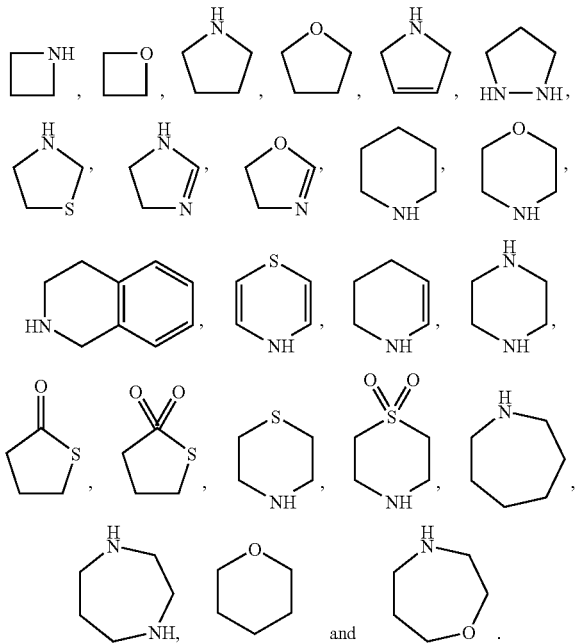

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

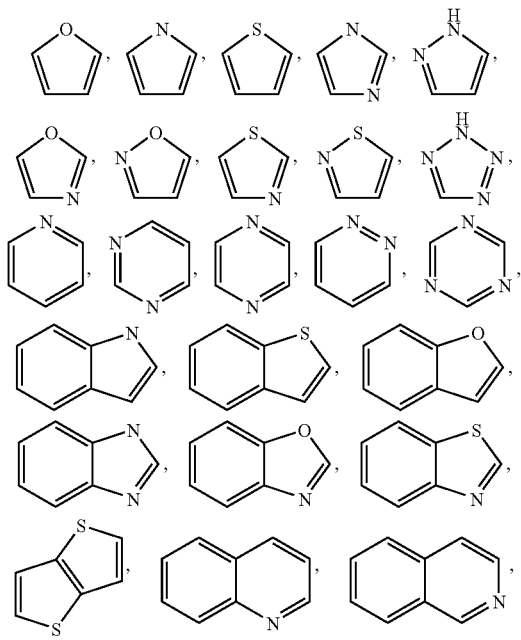

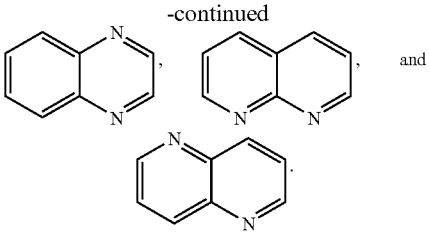

Those skilled in the art will recognize that the species of cycloalkyl, heterocycloalkyl, and heteroaryl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any formula given herein is intended to embrace hydrates, solvates, and polymorphs of such compounds, and mixtures thereof.

Additionally, any formula given herein is intended to refer also to hydrates, solvates, and polymorphs of such compounds, and mixtures thereof, even if such forms are not listed explicitly. Certain compounds of Formula (I) or pharmaceutically acceptable salts of compounds of Formula (I) may be obtained as solvates. Solvates include those formed from the interaction or complexation of compounds of the invention with one or more solvents, either in solution or as a solid or crystalline form. In some embodiments, the solvent is water and then the solvates are hydrates. In addition, certain crystalline forms of compounds of Formula (I) or pharmaceutically acceptable salts of compounds of Formula (I) may be obtained as co-crystals. In certain embodiments of the invention, compounds of Formula (I) were obtained in a crystalline form. In other embodiments, crystalline forms of compounds of Formula (I) were cubic in nature. In other embodiments, pharmaceutically acceptable salts of compounds of Formula (I) were obtained in a crystalline form. In still other embodiments, compounds of Formula (I) were obtained in one of several polymorphic forms, as a mixture of crystalline forms, as a polymorphic form, or as an amorphous form. In other embodiments, compounds of Formula (I) convert in solution between one or more crystalline forms and/or polymorphic forms.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Reference to a chemical entity herein stands for a reference to any one of: (a) the actually recited form of such chemical entity, and (b) any of the forms of such chemical entity in the medium in which the compound is being considered when named. For example, reference herein to a compound such as R—COOH, encompasses reference to any one of, for example, R—COOH$_{(s)}$, R—COOH$_{(sol)}$, and R—COO$^-_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological Inerest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula H$_2$NCH$_2$COOH, and it exists in some media (in this case in neutral media) in the form of the zwitterion $^+$H$_3$NCH$_2$COO$^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$O, $^{17}$O, $^{32}$P, $^{35}$S, $^{18}$F, $^{36}$Cl, $^{125}$, respectively. Such isotopically labeled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^1$, $R^2$, A, $X^4$, $X^5$, $X^6$, $X^7$, $R^a$, $R^b$, $R^c$, $R^d$, $R^e$, $R^f$ and $R^g$ and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^1$, $R^2$, A, $X^4$, $X^5$, $X^6$, $X^7$, $R^a$, $R^b$, $R^c$, $R^d$, $R^e$, $R^f$ and $R^g$ and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies n≤N≤m, with m>n.

Any disubstituent referred to herein is meant to encompass the various attachment possibilities when more than one of such possibilities are allowed. For example, reference to disubstituent -A-B—, where A≠B, refers herein to such disubstituent with A attached to a first substituted member and B attached to a second substituted member, and it also refers to such disubstituent with A attached to the second substituted member and B attached to the first substituted member.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

Chemical depictions are intended to portray the compound portions containing the orientations as written.

The present invention includes the use of compounds of Formula (I),

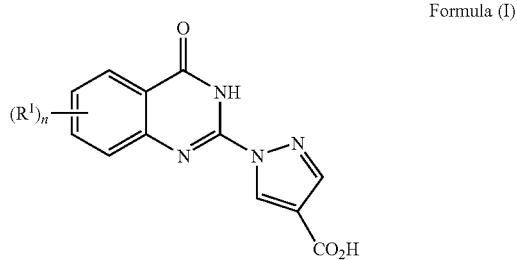

Formula (I)

the use of compounds of Formula (I) and pharmaceutical compositions containing such compounds thereof to treat patients (humans or other mammals) with disorders related to the modulation of the prolyl hydroxylase enzyme. The instant invention also includes methods of making such a compound, pharmaceutical composition, pharmaceutically acceptable salt, pharmaceutically acceptable prodrug, and pharmaceutically active metabolites thereof.

In the present invention described by of Formula (I), where n is 0-3, and $R^1$ is independently halo, hydroxyl, alkyl, alkenyl, alkynyl, alkoxy, thioalkyl, alkyl sulfoxide, alkyl sulfone, optionally substituted 3-8 membered aliphatic or aromatic or heterocyclic ring, amino, alkylamino, alkyl sulfonamide, aryl sulfonamide, nitro, cyano, —$SCF_3$, substituted phenoxy, benzyloxy, substituted biaryl, substituted aryl sulfone, substituted aryl sulfoxide, or substituted aryl sulfonyl.

In further preferred embodiments, n is 1-2, $R^1$ can independently be halo, straight- or branched-chain $C_{1-4}$alkyl, straight- or branched-chain $C_{1-4}$triflouroalkoxy, straight- or branched-chain $C_{1-4}$triflouroalkyl, or monocyclic $C_{3-8}$carbocycle saturated or partially saturated.

In some other preferred embodiments, two adjacent $R^1$ groups may be joined to form an optionally substituted 3-8 member saturated or unsaturated carbocyclic or heterocyclic ring.

In some other preferred embodiments, n is 2, and $R^1$ is independently halo, $C_{1-4}$alkyl, —$CF_3$, —$OCF_3$, substituted phenoxy, and optionally substituted 3-8 membered aromatic carbocycle.

In further preferred embodiments, n is 1, and $R^1$ is phenoxy optionally substituted with one to three halo, —$C_{1-4}$alkyl or —$C_{1-4}$alkoxy groups, phenylsulfanyl optionally substituted with one to three halo, —$C_{1-4}$alkyl or —$C_{1-4}$alkoxy groups, cyclohexyl, chloro, fluoro, iodo, —$OCF_3$ and —$CF_3$.

In some other preferred embodiments, one to three $R^1$ members are independently selected from the group consisting of chloro, fluoro, bromo, iodo, —$NO_2$, —OH, —$CF_3$, —$CH_3$, —$CH_2CH_3$, —$CH_2CH_2CH_3$, —$OCF_3$, —$OCH_3$, —$OCH_2CH_3$, —$SCH_3$, —$SCF_3$, —S(O)$CF_3$, —$SO_2CH_3$, —$NH_2$, —N($CH_3$)$_2$, —NH($CH_2CH_3$), cyano, isopropoxy, isopropyl, sec-butyl, tert-butyl, ethynyl, 1-chloro-vinyl, 4-methyl-piperazinyl, morpholin-4-yl, pyrrolidinyl, pyrrolidine-1-carbonyl, piperidinyl, phenyl, benzyl, biphenyl, tolyl, phenoxy, cyclopropyl, cyclohexyl, phenylsulfanyl, 3,4-dimethoxy-phenylsulfanyl, 4-tert-butyl-phenylsulfanyl, 7-piperidinyl, 2,6-dimethyl-phenoxy, 3,4,5-trimethoxy-phenoxy, naphthalen-1-yloxy, naphthalen-2-yloxy, 5,6,7,8-tetrahydro-naphthalen-1-yloxy, indan-5-yloxy, 3-chlorophenoxy, 4-chlorophenoxy, 2,3-dichloro-phenoxy, 3-methoxyphenoxy, 4-fluorophenoxy, 2-fluorophenoxy, 3-fluorophenoxy, 3,5-di-tert-butyl-phenoxy, 3-methylphenoxy, 2,6-dichloro-phenoxy, 2,5-dichlorophenoxy, 4-methoxyphenoxy, pyridin-3-yloxy, tetrahydro-pyran-4-yl, 3,4-dihydro-1H-isoquinolin-2-yl, 7-bromo-3,4-dihydro-1H-isoquinolin-2-yl, 3-methoxyphenyl-piperidinyl, and benzenesulfonyl.

In further preferred embodiments, n is 1.
In further preferred embodiments, n is 2.
In further preferred embodiments, n is 3.
In further preferred embodiments, —$R^aR^b$ is a member independently selected from the group consisting of —H, —$CH_3$, —$CH_2CH_3$, benzoyl, 2,6-dimethylbenzoyl, acetyl, —C(O)NH-phenyl, benzenesulfonyl, methanesulfonyl, benzyl, 2-methylbenzyl, 2-chlorobenzyl, 2,6-dimethylbenzyl, 2,6-difluorobenzyl, 2-cyanobenzyl, 3-cyanobenzyl, 3-carbamoyl-benzyl, 2,6-dichlorobenzyl, 3-chlorobenzyl, and 4-methylbenzyl.

In further preferred embodiments, $R^a$ and $R^b$ can be taken together with the nitrogen to which they are attached to form an optionally substituted N-methylpiperazin-1-yl, 3,4-dihydro-1H-isoquinolin-2-yl, piperidinyl, morpholin-4-yl, and pyrrolidinyl.

In further preferred embodiments, $R^c$ is a member independently selected from the group consisting of phenyl, cyclohexyl, 4-tert-butyl-phenyl, 3,4-dimethoxy-phenyl, 2,6-dimethyl-phenyl, 3,4,5-trimethoxy-phenyl, naphthalen-1-yl, 3-chloro-phenyl, 4-chloro-phenyl, 3-methoxy-phenyl, 4-fluoro-phenyl, 2-fluoro-phenyl, 3-fluoro-phenyl, 3,5-di-tert-butyl-phenyl, 4-oxo-6-m-tolyl, 4-oxo-6-o-tolyl, 2,6-dichloro-phenyl, 2,4-dichloro-phenyl, 2,5-dichloro-phenyl, 4-methoxy-phenyl, 2,6-dimethyl-phenyl, naphthalen-2-yl, 5,6,7,8-tetrahydro-naphthalen-1-yl, 4-chloro-phenyl, p-tolyl, indan-5-yl, 2,3-dichloro-phenyl, and pyridin-3-yl.

In further preferred embodiments, $R^d$ is a member independently selected from the group consisting of —H, chloro, fluoro, bromo, iodo, —$C_{1-4}$alkyl, —$CF_3$, —$OCF_3$, —$OC_{1-4}$ alkyl, phenyl, —O-phenyl, or —O-benzyl.

In certain preferred embodiments, the compound of Formula (I) is selected from the group consisting of:

| Ex. | Chemical Name |
|---|---|
| 1 | 1-(7-Chloro-4-oxo-3,4-dihydro-quinazolin-2-yl)-1H-pyrazole-4-carboxylic acid; |
| 2 | 1-(7-Trifluoromethyl-4-oxo-3,4-dihydro-quinazolin-2-yl)-1H-pyrazole-4-carboxylic acid; |
| 3 | 1-(6,7-Dichloro-4-oxo-3,4-dihydro-quinazolin-2-yl)-1H-pyrazole-4-carboxylic acid; |
| 4 | 1-(6-Fluoro-4-oxo-3,4-dihydro-quinazolin-2-yl)-1H-pyrazole-4-carboxylic acid; |
| 5 | 1-(6,7-Difluoro-4-oxo-3,4-dihydro-quinazolin-2-yl)-1H-pyrazole-4-carboxylic acid; |
| 6 | 1-(5-Chloro-4-oxo-3,4-dihydro-quinazolin-2-yl)-1H-pyrazole-4-carboxylic acid; |
| 7 | 1-(8-Methoxy-4-oxo-3,4-dihydro-quinazolin-2-yl)-1H-pyrazole-4-carboxylic acid; |
| 8 | 1-(6-Methyl-4-oxo-3,4-dihydro-quinazolin-2-yl)-1H-pyrazole-4-carboxylic acid; |
| 9 | 1-(8-Methyl-4-oxo-3,4-dihydro-quinazolin-2-yl)-1H-pyrazole-4-carboxylic acid; |
| 10 | 1-(7-Methyl-4-oxo-3,4-dihydro-quinazolin-2-yl)-1H-pyrazole-4-carboxylic acid; |
| 11 | 1-(8-Bromo-4-oxo-3,4-dihydro-quinazolin-2-yl)-1H-pyrazole-4-carboxylic acid; |
| 12 | 1-(6-Iodo-4-oxo-3,4-dihydro-quinazolin-2-yl)-1H-pyrazole-4-carboxylic acid; |
| 13 | 1-(6-Bromo-4-oxo-3,4-dihydro-quinazolin-2-yl)-1H-pyrazole-4-carboxylic acid; |
| 14 | 1-(8-Chloro-4-oxo-3,4-dihydro-quinazolin-2-yl)-1H-pyrazole-4-carboxylic acid; |
| 15 | 1-(4-Oxo-6-trifluoromethoxy-3,4-dihydro-quinazolin-2-yl)-1H-pyrazole-4-carboxylic acid; |
| 16 | 1-(4-Oxo-8-trifluoromethyl-3,4-dihydro-quinazolin-2-yl)-1H-pyrazole-4-carboxylic acid; |
| 17 | 1-(6,7-Dimethoxy-4-oxo-3,4-dihydro-quinazolin-2-yl)-1H-pyrazole-4-carboxylic acid; |
| 18 | 1-(5,6,7-Trimethoxy-4-oxo-3,4-dihydro-quinazolin-2-yl)-1H-pyrazole-4-carboxylic acid |
| 19 | 1-(6-tert-Butyl-4-oxo-3,4-dihydro-quinazolin-2-yl)-1H-pyrazole-4-carboxylic acid; |
| 20 | 1-(4-Oxo-6-phenoxy-3,4-dihydro-quinazolin-2-yl)-1H-pyrazole-4-carboxylic acid; |
| 21 | 1-(6-Cyclohexyl-4-oxo-3,4-dihydro-quinazolin-2-yl)-1H-pyrazole-4-carboxylic acid; |
| 22 | 1-(7-Chloro-4-oxo-6-trifluoromethoxy-3,4-dihydro-quinazolin-2-yl)-1H-pyrazole-4-carboxylic acid; |
| 23 | 1-(1-Oxo-2,7-dihydro-1H-pyrrolo[3,2-f]quinazolin-3-yl)-1H-pyrazole-4-carboxylic acid; |
| 24 | 1-[6-(4-tert-Butyl-phenylsulfanyl)-7-chloro-4-oxo-1,4-dihydro-quinazolin-2-yl]-1H-pyrazole-4-carboxylic acid; |
| 25 | 1-(7-Chloro-4-oxo-6-phenylsulfanyl-1,4-dihydro-quinazolin-2-yl)-1H-pyrazole-4-carboxylic acid; |
| 26 | 1-[7-Chloro-6-(3,4-dimethoxy-phenylsulfanyl)-4-oxo-1,4-dihydro-quinazolin-2-yl]-1H-pyrazole-4-carboxylic acid. |
| 27 | 1-[6-(2,6-Dimethyl-phenoxy)-7-methyl-4-oxo-3,4-dihydro-quinazolin-2-yl]-1H-pyrazole-4-carboxylic acid; |
| 28 | 1-[4-Oxo-6-(3,4,5-trimethoxy-phenoxy)-3,4-dihydro-quinazolin-2-yl]-1H-pyrazole-4-carboxylic acid; |
| 29 | 1-[6-(naphthalen-1-yloxy)-4-oxo-3,4-dihydro-quinazolin-2-yl]-1H-pyrazole-4-carboxylic acid; |
| 30 | 1-[6-(3-Chloro-phenoxy)-4-oxo-3,4-dihydro-quinazolin-2-yl]-1H-pyrazole-4-carboxylic acid; |
| 31 | 1-[6-(3-Methoxy-phenoxy)-4-oxo-3,4-dihydro-quinazolin-2-yl]-1H-pyrazole-4-carboxylic acid; |
| 32 | 1-[6-(4-Fluoro-phenoxy)-4-oxo-3,4-dihydro-quinazolin-2-yl]-1H-pyrazole-4-carboxylic acid; |
| 33 | 1-[6-(2-Fluoro-phenoxy)-4-oxo-3,4-dihydro-quinazolin-2-yl]-1H-pyrazole-4-carboxylic acid; |
| 34 | 1-[6-(3-Fluoro-phenoxy)-4-oxo-3,4-dihydro-quinazolin-2-yl]-1H-pyrazole-4-carboxylic acid; |
| 35 | 1-[6-(3,5-Di-tert-butyl-phenoxy)-4-oxo-3,4-dihydro-quinazolin-2-yl]-1H-pyrazole-4-carboxylic acid; |
| 36 | 1-(4-Oxo-6-m-tolyloxy-3,4-dihydro-quinazolin-2-yl)-1H-pyrazole-4-carboxylic acid; |
| 37 | 1-(4-Oxo-6-o-tolyloxy-3,4-dihydro-quinazolin-2-yl)-1H-pyrazole-4-carboxylic acid; |
| 38 | 1-[6-(2,6-Dichloro-phenoxy)-4-oxo-3,4-dihydro-quinazolin-2-yl]-1H-pyrazole-4-carboxylic acid; |
| 39 | 1-[6-(2,4-Dichloro-phenoxy)-4-oxo-3,4-dihydro-quinazolin-2-yl]-1H-pyrazole-4-carboxylic acid; |
| 40 | 1-[6-(2,5-Dichloro-phenoxy)-4-oxo-3,4-dihydro-quinazolin-2-yl]-1H-pyrazole-4-carboxylic acid; |
| 41 | 1-[6-(4-Methoxy-phenoxy)-4-oxo-3,4-dihydro-quinazolin-2-yl]-1H-pyrazole-4-carboxylic acid; |
| 42 | 1-[6-(2,6-Dimethyl-phenoxy)-4-oxo-3,4-dihydro-quinazolin-2-yl]-1H-pyrazole-4-carboxylic acid; |
| 43 | 1-[6-(Naphthalen-2-yloxy)-4-oxo-3,4-dihydro-quinazolin-2-yl]-1H-pyrazole-4-carboxylic acid; |
| 44 | 1-[4-Oxo-6-(5,6,7,8-tetrahydro-naphthalen-1-yloxy)-3,4-dihydro-quinazolin-2-yl]-1H-pyrazole-4-carboxylic acid; |
| 46 | 1-[6-(4-Chloro-phenoxy)-4-oxo-3,4-dihydro-quinazolin-2-yl]-1H-pyrazole-4-carboxylic acid; |
| 47 | 1-(4-Oxo-6-p-tolyloxy-3,4-dihydro-quinazolin-2-yl)-1H-pyrazole-4-carboxylic acid; |
| 48 | 1-[7-Chloro-6-(4-chloro-phenoxy)-4-oxo-3,4-dihydro-quinazolin-2-yl]-1H-pyrazole-4-carboxylic acid; |
| 49 | 1-[7-Chloro-6-(2,6-dimethyl-phenoxy)-4-oxo-3,4-dihydro-quinazolin-2-yl]-1H-pyrazole-4-carboxylic acid; |
| 50 | 1-[6-(2,6-Dichloro-phenoxy)-7-fluoro-4-oxo-3,4-dihydro-quinazolin-2-yl]-1H-pyrazole-4-carboxylic acid; |
| 51 | 1-[6-(2,6-Dimethyl-phenoxy)-7-fluoro-4-oxo-3,4-dihydro-quinazolin-2-yl]-1H-pyrazole-4-carboxylic acid; |
| 52 | 1-[7-Fluoro-6-(naphthalen-2-yloxy)-4-oxo-3,4-dihydro-quinazolin-2-yl]-1H-pyrazole-4-carboxylic acid; |
| 53 | 1-[7-Chloro-6-(naphthalen-1-yloxy)-4-oxo-3,4-dihydro-quinazolin-2-yl]-1H-pyrazole-4-carboxylic acid; |
| 54 | 1-[7-Chloro-6-(naphthalen-2-yloxy)-4-oxo-3,4-dihydro-quinazolin-2-yl]-1H-pyrazole-4-carboxylic acid; |
| 55 | 1-[7-Chloro-4-oxo-6-(5,6,7,8-tetrahydro-naphthalen-1-yloxy)-3,4-dihydro-quinazolin-2-yl]-1H-pyrazole-4-carboxylic acid; |
| 56 | 1-[7-Fluoro-6-(3-fluoro-phenoxy)-4-oxo-3,4-dihydro-quinazolin-2-yl]-1H-pyrazole-4-carboxylic acid; |
| 57 | 1-[7-Fluoro-6-(naphthalen-1-yloxy)-4-oxo-3,4-dihydro-quinazolin-2-yl]-1H-pyrazole-4-carboxylic acid; |
| 58 | 1-[7-Fluoro-6-(indan-5-yloxy)-4-oxo-3,4-dihydro-quinazolin-2-yl]-1H-pyrazole-4-carboxylic acid; |
| 59 | 1-(7-Methyl-4-oxo-6-phenoxy-3,4-dihydro-quinazolin-2-yl)-1H-pyrazole-4-carboxylic acid; |
| 60 | 1-[6-(2,3-dichloro-phenoxy)-4-oxo-3,4-dihydro-quinazolin-2-yl]-1H-pyrazole-4-carboxylic acid; |
| 61 | 1-[6-(2,6-Dimethyl-phenoxy)-7-methoxy-4-oxo-3,4-dihydro-quinazolin-2-yl]-1H-pyrazole-4-carboxylic acid; |
| 62 | 1-(7-Methoxy-4-oxo-6-phenoxy-3,4-dihydro-quinazolin-2-yl)-1H-pyrazole-4-carboxylic acid; |

| Ex. | Chemical Name |
|---|---|
| 63 | 1-[6-(2,6-Dimethyl-phenoxy)-5,7-difluoro-4-oxo-3,4-dihydro-quinazolin-2-yl]-1H-pyrazole-4-carboxylic acid; |
| 64 | 1-(5,7-Difluoro-4-oxo-6-phenoxy-3,4-dihydro-quinazolin-2-yl)-1H-pyrazole-4-carboxylic acid; |
| 65 | 1-[4-Oxo-6-(pyridin-3-yloxy)-3,4-dihydro-quinazolin-2-yl]-1H-pyrazole-4-carboxylic acid; |
| 66 | 1-(4-Oxo-7-phenoxy-3,4-dihydro-quinazolin-2-yl)-1H-pyrazole-4-carboxylic acid; |
| 67 | 1-[4-Oxo-7-(tetrahydro-pyran-4-yl)-3,4-dihydro-quinazolin-2-yl]-1H-pyrazole-4-carboxylic acid tris(hydroxymethyl)aminomethane salt; |
| 68 | 1-(7-Chloro-4-oxo-6-phenyl-3,4-dihydro-quinazolin-2-yl)-1H-pyrazole-4-carboxylic acid; |
| 69 | 1-(4-Oxo-6-o-tolyl-3,4-dihydro-quinazolin-2-yl)-1H-pyrazole-4-carboxylic acid; |
| 70 | 1-(6-Biphenyl-3-yl-4-oxo-3,4-dihydro-quinazolin-2-yl)-1H-pyrazole-4-carboxylic acid; |
| 71 | 1-[7-Chloro-6-(3,4-dimethoxy-benzenesulfonyl)-4-oxo-3,4-dihydro-quinazolin-2-yl]-1H-pyrazole-4-carboxylic acid; |
| 72 | 1-[6-(4-tert-Butyl-benzenesulfonyl)-7-chloro-4-oxo-3,4-dihydro-quinazolin-2-yl]-1H-pyrazole-4-carboxylic acid; |
| 73 | 1-(7,7-Dimethyl-4-oxo-3,7-dihydro-4H-8-oxa-1,3-diaza-anthracen-2-yl)-1H-pyrazole-4-carboxylic acid; |
| 74 | 1-(4-Oxo-6-phenoxymethyl-3,4-dihydro-quinazolin-2-yl)-1H-pyrazole-4-carboxylic acid; |
| 75 | 1-[6-(2,6-Dimethyl-phenoxymethyl)-4-oxo-3,4-dihydro-quinazolin-2-yl]-1H-pyrazole-4-carboxylic acid; |
| 76 | 1-(6-Ethynyl-4-oxo-3,4-dihydro-quinazolin-2-yl)-1H-pyrazole-4-carboxylic acid; |
| 77 | 1-[6-(1-Chloro-vinyl)-4-oxo-3,4-dihydro-quinazolin-2-yl]-1H-pyrazole-4-carboxylic acid; |
| 78 | 1-(4-Oxo-7-phenylsulfanyl-3,4-dihydro-quinazolin-2-yl)-1H-pyrazole-4-carboxylic acid; |
| 79 | 1-[7-(4-Chloro-phenylsulfanyl)-4-oxo-3,4-dihydro-quinazolin-2-yl]-1H-pyrazole-4-carboxylic acid; |
| 80 | 1-[7-(2-Chloro-phenylsulfanyl)-4-oxo-3,4-dihydro-quinazolin-2-yl]-1H-pyrazole-4-carboxylic acid; |
| 81 | 1-(7-Benzenesulfonyl-4-oxo-3,4-dihydro-quinazolin-2-yl)-1H-pyrazole-4-carboxylic acid; |
| 82 | 1-[7-(4-Chloro-benzenesulfonyl)-4-oxo-3,4-dihydro-quinazolin-2-yl]-1H-pyrazole-4-carboxylic acid; |
| 83 | 1-[7-(2-Chloro-benzenesulfonyl)-4-oxo-3,4-dihydro-quinazolin-2-yl]-1H-pyrazole-4-carboxylic acid; |
| 84 | 1-[7-Chloro-6-(3,4-dihydro-1H-isoquinolin-2-yl)-4-oxo-3,4-dihydro-quinazolin-2-yl]-1H-pyrazole-4-carboxylic acid; |
| 85 | 1-[6-(7-Bromo-3,4-dihydro-1H-isoquinolin-2-yl)-7-chloro-4-oxo-3,4-dihydro-quinazolin-2-yl]-1H-pyrazole-4-carboxylic acid; |
| 86 | (rac)-1-{7-Chloro-6-[3-(3-methoxy-phenyl)-piperidin-1-yl]-4-oxo-3,4-dihydro-quinazolin-2-yl}-1H-pyrazole-4-carboxylic acid; |
| 87 | 1-[6-(2,5-dichloro-phenoxy)-7-fluoro-4-oxo-3,4-dihydro-quinazolin-2-yl]-1H-pyrazole-4-carboxylic acid; |
| 88 | 1-[6-(3,4-dimethyl-phenoxy)-7-fluoro-4-oxo-3,4-dihydro-quinazolin-2-yl]-1H-pyrazole-4-carboxylic acid; |
| 89 | 1-[6-(3,5-dimethyl-phenoxy)-7-methyl-4-oxo-3,4-dihydro-quinazolin-2-yl]-1H-pyrazole-4-carboxylic acid; |
| 90 | 1-[6-(2,5-dichloro-phenoxy)-7-methyl-4-oxo-3,4-dihydro-quinazolin-2-yl]-1H-pyrazole-4-carboxylic acid; |
| 91 | 1-[6-(biphenyl-3-yloxy)-7-methyl-4-oxo-3,4-dihydro-quinazolin-2-yl]-1H-pyrazole-4-carboxylic acid; |
| 92 | 1-[6-(3,4-dimethyl-phenoxy)-7-methyl-4-oxo-3,4-dihydro-quinazolin-2-yl]-1H-pyrazole-4-carboxylic acid; |
| 93 | 1-[7-methyl-4-oxo-6-(3-trifluoromethyl-phenoxy)-3,4-dihydro-quinazolin-2-yl]-1H-pyrazole-4-carboxylic acid; |
| 94 | 1-[6-(3,5-dimethyl-phenoxy)-7-fluoro-4-oxo-3,4-dihydro-quinazolin-2-yl]-1H-pyrazole-4-carboxylic acid; |
| 95 | 1-[7-fluoro-4-oxo-6-(3-trifluoromethyl-phenoxy)-3,4-dihydro-quinazolin-2-yl]-1H-pyrazole-4-carboxylic acid; |
| 96 | 1-[6-(2-fluoro-3-trifluoromethyl-phenoxy)-4-oxo-3,4-dihydro-quinazolin-2-yl]-1H-pyrazole-4-carboxylic acid; |
| 97 | 1-[6-(3-fluoro-5-trifluoromethyl-phenoxy)-4-oxo-3,4-dihydro-quinazolin-2-yl]-1H-pyrazole-4-carboxylic acid; |
| 98 | 1-[6-(3,5-dimethyl-phenoxy)-4-oxo-3,4-dihydro-quinazolin-2-yl]-1H-pyrazole-4-carboxylic acid; |
| 99 | 1-[6-(biphenyl-3-yloxy)-4-oxo-3,4-dihydro-quinazolin-2-yl]-1H-pyrazole-4-carboxylic acid; |
| 100 | 1-[4-oxo-6-(3-trifluoromethyl-phenoxy)-3,4-dihydro-quinazolin-2-yl]-1H-pyrazole-4-carboxylic acid; |
| 101 | 1-[6-(2,6-dichloro-phenoxy)-5,7-difluoro-4-oxo-3,4-dihydro-quinazolin-2-yl]-1H-pyrazole-4-carboxylic acid; |
| 102 | 1-(6-cyclohexyloxy-4-oxo-3,4-dihydro-quinazolin-2-yl)-1H-pyrazole-4-carboxylic acid; |
| 103 | 1-[6-(4-methyl-piperazin-1-yl)-4-oxo-3,4-dihydro-quinazolin-2-yl]-1H-pyrazole-4-carboxylic acid; |
| 104 | 1-(6-isopropoxy-4-oxo-3,4-dihydro-quinazolin-2-yl)-1H-pyrazole-4-carboxylic acid; |
| 105 | 1-(6-benzyl-4-oxo-3,4-dihydro-quinazolin-2-yl)-1H-pyrazole-4-carboxylic acid; |
| 106 | 1-(4-oxo-6-phenyl-3,4-dihydro-quinazolin-2-yl)-1H-pyrazole-4-carboxylic acid; |
| 107 | 1-(6-morpholin-4-yl-4-oxo-3,4-dihydro-quinazolin-2-yl)-1H-pyrazole-4-carboxylic acid; |
| 108 | 1-[6-(1H-Indol-6-yl)-4-oxo-3,4-dihydro-quinazolin-2-yl]-1H-pyrazole-4-carboxylic acid |
| 109 | 1-(6-Cyclopropyl-4-oxo-3,4-dihydro-quinazolin-2-yl)-1H-pyrazole-4-carboxylic acid; |
| 110 | 1-(6-Cyclohexyl-7-fluoro-4-oxo-3,4-dihydro-quinazolin-2-yl)-1H-pyrazole-4-carboxylic acid; |
| 111 | 1-(Oxo-8-phenyl-3,4-dihydro-quinazolin-2-yl)-1H-pyrazole-4-carboxylic acid; |
| 112 | 1-(4-Oxo-8-phenoxy-3,4-dihydro-quinazolin-2-yl)-1H-pyrazole-4-carboxylic acid; |
| 113 | 1-(4-Oxo-8-phenylsulfanyl-3,4-dihydro-quinazolin-2-yl)-1H-pyrazole-4-carboxylic acid; |
| 114 | 1-(8-Isopropyl-4-oxo-3,4-dihydro-quinazolin-2-yl)-1H-pyrazole-4-carboxylic acid; |
| 115 | 1-(8-tert-Butyl-4-oxo-3,4-dihydro-quinazolin-2-yl)-1H-pyrazole-4-carboxylic acid; |
| 116 | 1-(5,8-Difluoro-4-oxo-3,4-dihydro-quinazolin-2-yl)-1H-pyrazole-4-carboxylic acid; |
| 117 | 1-(4-Oxo-8-trifluoromethoxy-3,4-dihydro-quinazolin-2-yl)-1H-pyrazole-4-carboxylic acid; |
| 118 | 1-(8-Fluoro-4-oxo-3,4-dihydro-quinazolin-2-yl)-1H-pyrazole-4-carboxylic acid; |
| 119 | 1-(6-Isopropyl-4-oxo-3,4-dihydro-quinazolin-2-yl)-1H-pyrazole-4-carboxylic acid; |
| 120 | 1-(6-sec-Butyl-4-oxo-3,4-dihydro-quinazolin-2-yl)-1H-pyrazole-4-carboxylic acid; |
| 121 | 1-(6-Ethoxy-4-oxo-3,4-dihydro-quinazolin-2-yl)-1H-pyrazole-4-carboxylic acid; |
| 122 | 1-(6-Methoxy-4-oxo-3,4-dihydro-quinazolin-2-yl)-1H-pyrazole-4-carboxylic acid; |
| 123 | 1-(4-Oxo-6-pyrrolidin-1-yl-3,4-dihydro-quinazolin-2-yl)-1H-pyrazole-4-carboxylic acid; |
| 124 | 1-(4-Oxo-6-piperidin-1-yl-3,4-dihydro-quinazolin-2-yl)-1H-pyrazole-4-carboxylic acid; |
| 125 | 1-(6-Dimethylamino-4-oxo-3,4-dihydro-quinazolin-2-yl)-1H-pyrazole-4-carboxylic acid; |
| 126 | 1-(4-Oxo-3,4-dihydro-quinazolin-2-yl)-1H-pyrazole-4-carboxylic acid; |
| 127 | 1-(6-Bromo-7-fluoro-4-oxo-3,4-dihydro-quinazolin-2-yl)-1H-pyrazole-4-carboxylic acid; |
| 128 | 1-(6-Ethyl-4-oxo-3,4-dihydro-quinazolin-2-yl)-1H-pyrazole-4-carboxylic acid; |
| 129 | 1-(4-Oxo-6-propyl-3,4-dihydro-quinazolin-2-yl)-1H-pyrazole-4-carboxylic acid; |
| 130 | 1-(6-Bromo-8-fluoro-4-oxo-3,4-dihydro-quinazolin-2-yl)-1H-pyrazole-4-carboxylic acid; |
| 131 | 1-(5,7-Difluoro-4-oxo-3,4-dihydro-quinazolin-2-yl)-1H-pyrazole-4-carboxylic acid; |
| 132 | 1-(5,7-Dichloro-4-oxo-3,4-dihydro-quinazolin-2-yl)-1H-pyrazole-4-carboxylic acid; |
| 133 | 1-(7-Fluoro-4-oxo-3,4-dihydro-quinazolin-2-yl)-1H-pyrazole-4-carboxylic acid; |
| 134 | 1-(7-Bromo-4-oxo-3,4-dihydro-quinazolin-2-yl)-1H-pyrazole-4-carboxylic acid; |
| 135 | 1-(7-Methoxy-4-oxo-3,4-dihydro-quinazolin-2-yl)-1H-pyrazole-4-carboxylic acid; |
| 136 | 1-(7-Benzyl-4-oxo-3,4-dihydro-quinazolin-2-yl)-1H-pyrazole-4-carboxylic acid; |
| 137 | 1-(4-Oxo-3,4,8,9-tetrahydro-7H-6,10-dioxa-1,3-diaza-cyclohepta[b]naphthalen-2-yl)-1H-pyrazole-4-carboxylic acid; |

| Ex. | Chemical Name |
|---|---|
| 138 | 1-(8-Oxo-2,3,7,8-tetrahydro-1,4-dioxa-5,7-diaza-phenanthren-6-yl)-1H-pyrazole-4-carboxylic acid; |
| 139 | 1-(4-Oxo-3,4,7,8-tetrahydro-[1,4]dioxino[2,3-g]quinazolin-2-yl)-1H-pyrazole-4-carboxylic acid; |
| 140 | 1-(4-Oxo-4,6,7,8-tetrahydro-3H-cyclopenta[g]quinazolin-2-yl)-1H-pyrazole-4-carboxylic acid; |
| 141 | 1-(6-Oxo-2,3,6,7-tetrahydro-1H-7,9-diaza-cyclopenta[a]naphthalen-8-yl)-1H-pyrazole-4-carboxylic acid; |
| 142 | 1-(4-Oxo-3,4,7,8,9,10-hexahydro-benzo[h]quinazolin-2-yl)-1H-pyrazole-4-carboxylic acid; |
| 143 | 1-(4-Oxo-3,4,6,7,8,9-hexahydro-benzo[g]quinazolin-2-yl)-1H-pyrazole-4-carboxylic acid; |
| 144 | 1-(1-Oxo-1,2,7,8,9,10-hexahydro-benzo[f]quinazolin-3-yl)-1H-pyrazole-4-carboxylic acid; |
| 145 | 1-(5,7-Dimethyl-4-oxo-3,4-dihydro-quinazolin-2-yl)-1H-pyrazole-4-carboxylic acid; |
| 146 | 1-(7-Isopropyl-4-oxo-3,4-dihydro-quinazolin-2-yl)-1H-pyrazole-4-carboxylic acid; |
| 147 | 1-(7-tert-Butyl-4-oxo-3,4-dihydro-quinazolin-2-yl)-1H-pyrazole-4-carboxylic acid; |
| 148 | 1-(4-Oxo-7-trifluoromethoxy-3,4-dihydro-quinazolin-2-yl)-1H-pyrazole-4-carboxylic acid; |
| 149 | 1-(7-Isopropoxy-4-oxo-3,4-dihydro-quinazolin-2-yl)-1H-pyrazole-4-carboxylic acid; |
| 150 | 1-(7-Dimethylamino-4-oxo-3,4-dihydro-quinazolin-2-yl)-1H-pyrazole-4-carboxylic acid; |
| 151 | 1-(5-Dimethylamino-4-oxo-3,4-dihydro-quinazolin-2-yl)-1H-pyrazole-4-carboxylic acid; |
| 152 | 1-(7-Ethoxy-4-oxo-3,4-dihydro-quinazolin-2-yl)-1H-pyrazole-4-carboxylic acid; |
| 153 | 1-(6-Chloro-4-oxo-3,4-dihydro-quinazolin-2-yl)-1H-pyrazole-4-carboxylic acid; |
| 154 | 1-(7-Hydroxy-4-oxo-3,4-dihydro-quinazolin-2-yl)-1H-pyrazole-4-carboxylic acid; |
| 155 | 1-(6-Methylsulfanyl-4-oxo-3,4-dihydro-quinazolin-2-yl)-1H-pyrazole-4-carboxylic acid; |
| 156 | 1-(4-Oxo-6-trifluoromethylsulfanyl-3,4-dihydro-quinazolin-2-yl)-1H-pyrazole-4-carboxylic acid; |
| 157 | 1-(6-Methanesulfonyl-4-oxo-3,4-dihydro-quinazolin-2-yl)-1H-pyrazole-4-carboxylic acid; |
| 158 | 1-(7-Chloro-6-methylsulfanyl-4-oxo-3,4-dihydro-quinazolin-2-yl)-1H-pyrazole-4-carboxylic acid; |
| 159 | 1-(7-Chloro-4-oxo-6-trifluoromethylsulfanyl-3,4-dihydro-quinazolin-2-yl)-1H-pyrazole-4-carboxylic acid; |
| 160 | 1-(7-Chloro-4-oxo-6-trifluoromethanesulfinyl-3,4-dihydro-quinazolin-2-yl)-1H-pyrazole-4-carboxylic acid; |
| 161 | 1-[4-Oxo-6-(pyrrolidine-1-sulfonyl)-3,4-dihydro-quinazolin-2-yl]-1H-pyrazole-4-carboxylic acid; |
| 162 | 1-[4-Oxo-6-(pyrrolidine-1-carbonyl)-3,4-dihydro-quinazolin-2-yl]-1H-pyrazole-4-carboxylic acid; |
| 163 | 1-[6-(2,6-Dimethyl-phenylcarbamoyl)-4-oxo-3,4-dihydro-quinazolin-2-yl]-1H-pyrazole-4-carboxylic acid; |
| 164 | 1-(6-Nitro-4-oxo-3,4-dihydro-quinazolin-2-yl)-1H-pyrazole-4-carboxylic acid |
| 165 | 1-(6-Benzoylamino-4-oxo-3,4-dihydro-quinazolin-2-yl)-1H-pyrazole-4-carboxylic acid; |
| 166 | 1-[6-(2,6-Dimethyl-benzoylamino)-4-oxo-3,4-dihydro-quinazolin-2-yl]-1H-pyrazole-4-carboxylic acid; |
| 167 | 1-(6-Acetylamino-4-oxo-3,4-dihydro-quinazolin-2-yl)-1H-pyrazole-4-carboxylic acid; |
| 168 | 1-[4-Oxo-6-(3-phenyl-ureido)-3,4-dihydro-quinazolin-2-yl]-1H-pyrazole-4-carboxylic acid; |
| 169 | 1-(6-Benzenesulfonylamino-4-oxo-3,4-dihydro-quinazolin-2-yl)-1H-pyrazole-4-carboxylic acid; |
| 170 | 1-(6-Methanesulfonylamino-4-oxo-3,4-dihydro-quinazolin-2-yl)-1H-pyrazole-4-carboxylic acid; |
| 171 | 1-(6-Benzylamino-4-oxo-3,4-dihydro-quinazolin-2-yl)-1H-pyrazole-4-carboxylic acid; |
| 172 | 1-(6-Ethylamino-4-oxo-3,4-dihydro-quinazolin-2-yl)-1H-pyrazole-4-carboxylic acid; |
| 173 | 1-[6-(2-Methyl-benzylamino)-4-oxo-3,4-dihydro-quinazolin-2-yl]-1H-pyrazole-4-carboxylic acid; |
| 174 | 1-[6-(2-Chloro-benzylamino)-4-oxo-3,4-dihydro-quinazolin-2-yl]-1H-pyrazole-4-carboxylic acid; |
| 175 | 1-[6-(2,6-Dimethyl-benzylamino)-4-oxo-3,4-dihydro-quinazolin-2-yl]-1H-pyrazole-4-carboxylic acid; |
| 176 | 1-[6-(2,6-Difluoro-benzylamino)-4-oxo-3,4-dihydro-quinazolin-2-yl]-1H-pyrazole-4-carboxylic acid; |
| 177 | 1-[6-(2-Cyano-benzylamino)-4-oxo-3,4-dihydro-quinazolin-2-yl]-1H-pyrazole-4-carboxylic acid; |
| 178 | 1-[6-(3-Cyano-benzylamino)-4-oxo-3,4-dihydro-quinazolin-2-yl]-1H-pyrazole-4-carboxylic acid; |
| 179 | 1-[6-(3-Carbamoyl-benzylamino)-4-oxo-3,4-dihydro-quinazolin-2-yl]-1H-pyrazole-4-carboxylic acid; |
| 180 | 1-[6-amino-4-oxo-3,4-dihydro-quinazolin-2-yl]-1H-pyrazole-4-carboxylic acid; |
| 181 | 1-[6-(2,6-Dichloro-benzylamino)-4-oxo-3,4-dihydro-quinazolin-2-yl]-1H-pyrazole-4-carboxylic acid; |
| 182 | 1-[6-(3-Chloro-benzylamino)-4-oxo-3,4-dihydro-quinazolin-2-yl]-1H-pyrazole-4-carboxylic acid; |
| 183 | 1-[6-(4-methyl-benzylamino)-4-oxo-3,4-dihydro-quinazolin-2-yl]-1H-pyrazole-4-carboxylic acid; |
| 184 | 1-(4-Oxo-7-phenyl-3,4-dihydro-quinazolin-2-yl)-1H-pyrazole-4-carboxylic acid; |
| 185 | 1-[7-(2-Chloro-phenyl)-4-oxo-3,4-dihydro-quinazolin-2-yl]-1H-pyrazole-4-carboxylic acid; |
| 186 | 1-[7-(3-Chloro-phenyl)-4-oxo-3,4-dihydro-quinazolin-2-yl]-1H-pyrazole-4-carboxylic acid; |
| 187 | 1-[7-(4-Chloro-phenyl)-4-oxo-3,4-dihydro-quinazolin-2-yl]-1H-pyrazole-4-carboxylic acid; |
| 188 | 1-(4-Oxo-7-o-tolyl-3,4-dihydro-quinazolin-2-yl)-1H-pyrazole-4-carboxylic acid; |
| 189 | 1-(4-Oxo-7-m-tolyl-3,4-dihydro-quinazolin-2-yl)-1H-pyrazole-4-carboxylic acid; |
| 190 | 1-(4-Oxo-6-m-tolyl-3,4-dihydro-quinazolin-2-yl)-1H-pyrazole-4-carboxylic acid; |
| 191 | 1-(4-Oxo-6-p-tolyl-3,4-dihydro-quinazolin-2-yl)-1H-pyrazole-4-carboxylic acid; |
| 192 | 1-[6-(2-Chloro-phenyl)-4-oxo-3,4-dihydro-quinazolin-2-yl]-1H-pyrazole-4-carboxylic acid; |
| 193 | 1-[6-(3-Chloro-phenyl)-4-oxo-3,4-dihydro-quinazolin-2-yl]-1H-pyrazole-4-carboxylic acid; |
| 194 | 1-[6-(4-Chloro-phenyl)-4-oxo-3,4-dihydro-quinazolin-2-yl]-1H-pyrazole-4-carboxylic acid; |
| 195 | 1-[6-(2-Fluoro-phenyl)-4-oxo-3,4-dihydro-quinazolin-2-yl]-1H-pyrazole-4-carboxylic acid; |
| 196 | 1-[6-(3-Fluoro-phenyl)-4-oxo-3,4-dihydro-quinazolin-2-yl]-1H-pyrazole-4-carboxylic acid; |
| 197 | 1-[6-(4-Fluoro-phenyl)-4-oxo-3,4-dihydro-quinazolin-2-yl]-1H-pyrazole-4-carboxylic acid; |
| 198 | 1-[6-(2-Methoxy-phenyl)-4-oxo-3,4-dihydro-quinazolin-2-yl]-1H-pyrazole-4-carboxylic acid; |
| 199 | 1-[6-(3-Methoxy-phenyl)-4-oxo-3,4-dihydro-quinazolin-2-yl]-1H-pyrazole-4-carboxylic acid; |
| 200 | 1-[6-(4-Methoxy-phenyl)-4-oxo-3,4-dihydro-quinazolin-2-yl]-1H-pyrazole-4-carboxylic acid; |
| 201 | 1-[4-Oxo-6-(2-trifluoromethyl-phenyl)-3,4-dihydro-quinazolin-2-yl]-1H-pyrazole-4-carboxylic acid; |
| 202 | 1-[4-Oxo-6-(2-trifluoromethoxy-phenyl)-3,4-dihydro-quinazolin-2-yl]-1H-pyrazole-4-carboxylic acid; |
| 203 | 1-[6-(2-Ethyl-phenyl)-4-oxo-3,4-dihydro-quinazolin-2-yl]-1H-pyrazole-4-carboxylic acid; |
| 204 | 1-[6-(2,3-Dihydro-benzo[1,4]dioxin-5-yl)-4-oxo-3,4-dihydro-quinazolin-2-yl]-1H-pyrazole-4-carboxylic acid; |
| 205 | 1-[4-Oxo-6-(3-trifluoromethoxy-phenyl)-3,4-dihydro-quinazolin-2-yl]-1H-pyrazole-4-carboxylic acid; |
| 206 | 1-[6-(3-Methanesulfonyl-phenyl)-4-oxo-3,4-dihydro-quinazolin-2-yl]-1H-pyrazole-4-carboxylic acid; |
| 207 | 1-(6-Benzo[1,3]dioxol-5-yl-4-oxo-3,4-dihydro-quinazolin-2-yl)-1H-pyrazole-4-carboxylic acid; |
| 208 | 1-(7-Iodo-4-oxo-3,4-dihydro-quinazolin-2-yl)-1H-pyrazole-4-carboxylic acid; |
| 209 | 1-(6-Benzenesulfinyl-7-chloro-4-oxo-3,4-dihydro-quinazolin-2-yl)-1H-pyrazole-4-carboxylic acid; |
| 210 | 1-(6-Benzenesulfonyl-7-chloro-4-oxo-3,4-dihydro-quinazolin-2-yl)-1H-pyrazole-4-carboxylic acid; and |
| 211 | 1-(4-Oxo-7-piperidin-1-yl-3,4-dihydro-quinazolin-2-yl)-1H-pyrazole-4-carboxylic acid. | and pharmaceutically acceptable salts thereof.

The invention includes also pharmaceutically acceptable salts of the compounds of Formula (I), preferably of those described above and of the specific compounds exemplified herein, and methods of treatment using such salts.

A "pharmaceutically acceptable salt" is intended to mean a salt of a free acid or base of a compound represented by Formula (I) that is non-toxic, biologically tolerable, or otherwise biologically suitable for administration to the subject. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methyl benzoates, di nitrobenzoates, hydroxybenzoates, methoxybenzoates, phthalates, sulfonates, xylenesulfonates, phenylacetates, phenyl propionates, phenylbutyrates, citrates, lactates, γ-hydroxybutyrates, glycolates, tartrates, methane-sulfonates, propane-sulfonates, naphthalene-1-sulfonates, naphthalene-2-sulfonates, and mandelates.

When the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acidor glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

Exemplary prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J Med Chem.* 1996, 39 (1), 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I), which may also be used in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, Design of Prodrugs (Elsevier Press, 1985); and Larsen, Design and Application of Prodrugs, Drug Design and Development (Krogsgaard-Larsen, et al., eds., Harwood Academic Publishers, 1991).

The compounds of Formula (I) and their pharmaceutically acceptable salts, pharmaceutically acceptable prodrugs, and pharmaceutically active metabolites of the present invention are useful as modulators of PHD in the methods of the invention. "Modulators" include both inhibitors and activators, where "inhibitors" refer to compounds that decrease, prevent, inactivate, desensitize or down-regulate PHD expression or activity, and "activators" are compounds that increase, activate, facilitate, sensitize, or up-regulate PHD expression or activity.

The term "treat" or "treating" as used herein is intended to refer to administration of an active agent or composition of the invention to a subject for the purpose of effecting a therapeutic or prophylactic benefit through modulation of prolyl hydroxylase activity. Treating includes reversing, ameliorating, alleviating, inhibiting the progress of, lessening the severity of, or preventing a disease, disorder, or condition, or one or more symptoms of such disease, disorder or condition mediated through modulation of PHD activity. The term "subject" refers to a mammalian patient in need of such treatment, such as a human.

Accordingly, the invention relates to methods of using the compounds described herein to treat subjects diagnosed with or suffering from a disease, disorder, or condition mediated by Prolyl Hydroxylase, such as: Anemia, vascular disorders, metabolic disorders, and wound healing. Symptoms or disease states are intended to be included within the scope of "medical conditions, disorders, or diseases."

As used herein the term "hypoxia" or "hypoxic disorder" refers to a condition where there is an insufficient level of oxygen provided in the blood or to tissues and organs. Hypoxic disorders can occur through a variety of mechanisms including where there is an insufficient capacity of the blood to carry oxygen (i.e. anemia), where there is an inadequate flow of blood to the tissue and/or organ caused by either heart failure or blockage of blood vessels and/or arteries (i.e. ischemia), where there is reduced barometric pressure (i.e. elevation sickness at high altitudes), or where dysfunctional cells are unable to properly make use of oxygen (i.e. hystotoxic conditions). Accordingly, one of skill in the art would readily appreciate the present invention to be useful in the treatment of a variety of hypoxic conditions including anemia, heart failure, coronary artery disease, thromboembolism, stroke, angina and the like.

In a preferred embodiment, molecules of the present invention are useful in the treatment or prevention of anemia comprising treatment of anemic conditions associated with chronic kidney disease, polycystic kidney disease, aplastic anemia, autoimmune hemolytic anemia, bone marrow transplantation anemia, Churg-Strauss syndrome, Diamond Blackfan anemia, Fanconi's anemia, Felty syndrome, graft versus host disease, hematopoietic stem cell transplantation, hemolytic uremic syndrome, myelodysplastic syndrome, nocturnal paroxysmal hemoglobinuria, osteomyelofibrosis, pancytopenia, pure red-cell aplasia, purpura Schoenlein-Henoch, refractory anemia with excess of blasts, rheumatoid arthritis, Shwachman syndrome, sickle cell disease, thalassemia major, thalassemia minor, thrombocytopenic purpura, anemic or non-anemic patients undergoing surgery, anemia associated with or secondary to trauma, sideroblastic anemia, anemic secondary to other treatment including: reverse transcriptase inhibitors to treat HIV, corticosteroid hormones, cyclic cisplatin or non-cisplatin-containing chemotherapeutics, vinca alkaloids, mitotic inhibitors, topoisomerase II inhibitors, anthracyclines, alkylating agents, particularly anemia secondary to inflammatory, aging and/or chronic diseases. PHD inhibition may also be used to treat symptoms of anemia including chronic fatigue, pallor and dizziness.

In another preferred embodiment, molecules of the present invention are useful for the treatment or prevention of diseases of metabolic disorders, including but not limited to diabetes and obesity. In another preferred embodiment, molecules of the present invention are useful for the treatment or prevention of vascular disorders. These include but are not limited to hypoxic or wound healing related diseases requiring pro-angiogenic mediators for vasculogenesis, angiogenesis, and arteriogenesis In treatment methods according to the invention, an effective amount of a pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the agents of the invention may be used in combination with additional active ingredients in the treatment of the above conditions. The additional compounds may be co-administered separately with an agent of Formula (I) or included with such an agent as an additional active ingredient in a pharmaceutical composition according to the invention. In an exemplary embodiment, additional active ingredients are those that are known or discovered to be effective in the treatment of conditions, disorders, or diseases mediated by PHD enzyme or that are active against another targets associated with the particular condition, disorder, or disease, such as an alternate PHD modulator. The combination may serve to increase efficacy (e.g., by including in the combination a compound potentiating the potency or effectiveness of a compound according to the invention), decrease one or more side effects, or decrease the required dose of the compound according to the invention.

The compounds of the invention are used, alone or in combination with one or more other active ingredients, to formulate pharmaceutical compositions of the invention. A pharmaceutical composition of the invention comprises: (a) an effective amount of a compound of Formula (I), or a pharmaceutically acceptable salt, pharmaceutically acceptable prodrug, or pharmaceutically active metabolite thereof; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a compound of the invention and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the compounds of the invention may be prepared using suitable pharmaceutical excipients and compounding techniques now or later known or available to those skilled in the art. The compositions may be administered in the inventive methods by oral, parenteral, rectal, topical, or ocular routes, or by inhalation. The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration. A preferred mode of use of the invention is local administration of PHD inhibitors particularly to sites where tissue has become or has been made ischemic. This may be achieved via a specialized catheter, angioplasty balloon or stent placement balloon.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Examples include lotions, creams, ointments and the like and can be formulated by known methods. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Abbreviations and acronyms used herein including the following:

| Term | Acronym |
| --- | --- |
| Diisopropylethylamine | DIEA |
| Tetrahydrofuran | THF |
| Dichloromethane | DCM |
| Dimethyl Sulfoxide | DMSO |
| Dimethylacetamide | DMA |
| 2-Chloromethoxy-ethyltrimethylsilane | SEMCI |
| 2-Methoxyethoxymethyl chloride | MEMCI |
| meta-Chloroperoxybenzoic acid | mCPBA |
| N,N-Dimethylformamide | DMF |
| Ethanol | EtOH |
| Acetonitrile | ACN |
| Ethyl Acetate | EtOAc |
| N-(3-Dimethylaminopropyl)-N-ethylcarbodiimide | EDCI |
| N,N'-Diisopropylcarbodiimide | DIC |
| N-(3-Dimethylaminopropyl)-N'-ethylcarbodiimide | EDAC |
| O-(7-Azabenzotriazol-1-yl)-N,N,N',N'-tetramethyluronium hexafluorophosphate | HATU |
| 1,8-diazabicyclo[5.4.0]undec-7-ene | DBU |
| Dichloroethane | DCE |

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may also be conducted in sealed pressure vessels above the normal reflux temperature of the solvent.

quinazolinones of formula (VI) is achieved using a suitable protecting group reagent such as 2-methoxyethoxymethyl chloride (MEMCl) in the presence of a base such as DIEA in a solvent such as THF to provide either (VII$^a$) or (VII$^b$) or a mixture of both. Displacement of the 2-chloro substituent of compounds of formula (VII$^a$ or VII$^b$) with various commercially available pyrazole-4-carboxylates of formula (IX), is accomplished in a polar aprotic solvent such as DMF, N,N-

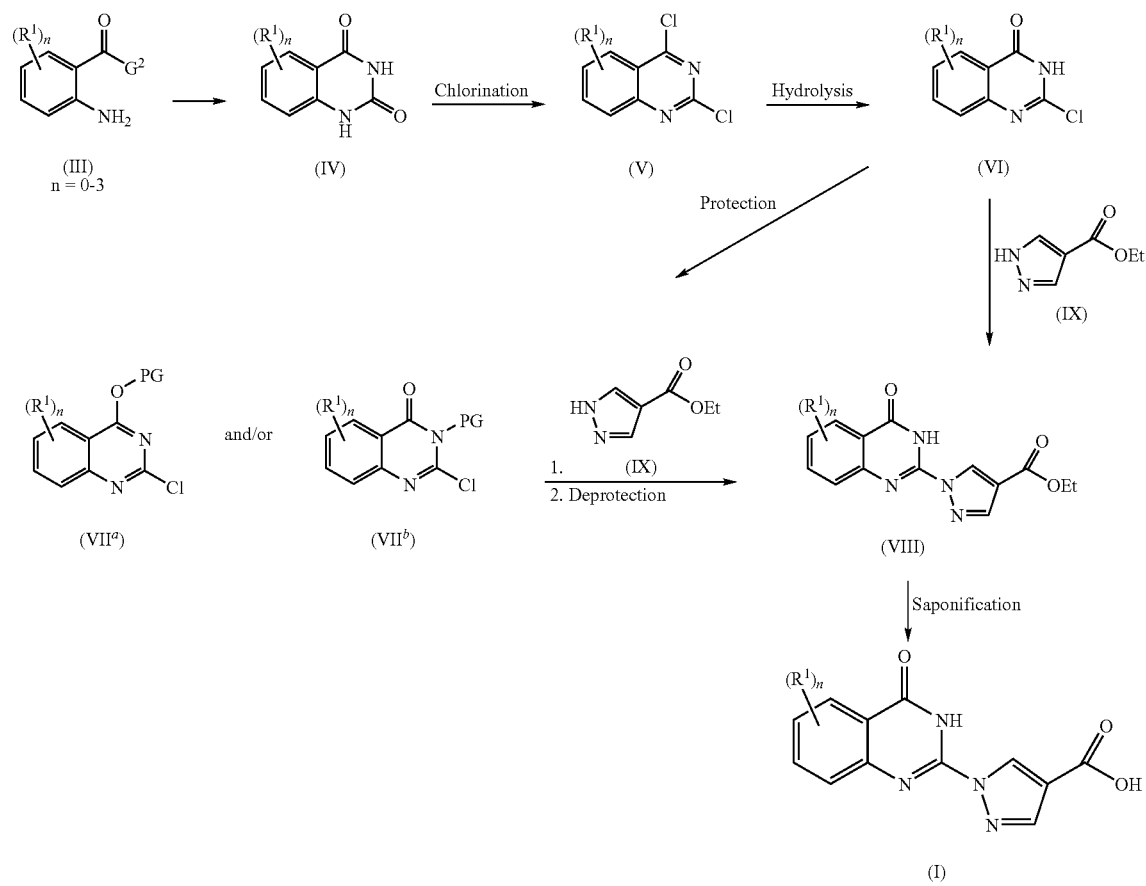

Scheme A

Referring to Scheme A, compounds of Formula (I) are prepared from anthranilic acid derivatives (III), where $G^2$ is —OH, —NH$_2$ or —OC$_{1-4}$alkyl and R$^1$ is independently H, halo, C$_{1-4}$alkyl, CF$_3$, trifluoroC$_{1-4}$alkoxy, —OC$_{1-4}$alkyl and —NO$_2$. Various anthranilic acid derivatives of formula (III) are commercially available or are prepared using known methods are reacted with urea and heated to provide quinazolin-2,4-diones of formula (IV). Chlorination of compounds of formula (IV) using methods as described in the art or methods as described in *Bioorganic & Medicinal Chemistry*, 2003, 11, 2439-2444, using phosphorus oxychloride (POCl$_3$) in a solvent such as acetonitrile (optional additives such as a tertiary amine base for example, alkylanilines or diisopropylethylamine (DIEA) may be employed), with heating, gives dichloroquinazolines of formula (V). Hydrolysis of compounds of formula (V) using known methods or methods as described in the *Journal of Medicinal Chemistry*, 2007, 50, 2297-2300, with a suitable base such as aq. NaOH, aq. LiOH or aq. KOH and the like, in a solvent such as THF provides chloroquinazolinones of formula (VI). Protection of chloro-dimethylacetamide (DMA), or THF, or a mixture thereof, in the presence of a suitable base such as Cs$_2$CO$_3$, K$_2$CO$_3$, Na$_2$CO$_3$, NaH, or a mixture thereof at elevated temperatures generally ranging between 80° C. and 120° C. Subsequent deprotection of PG using an acid such as HCl in an appropriate solvent such as EtOH provides compounds of formula (VIII). Saponification of compounds of formula (VIII) with a suitable base such as aq. NaOH, aq. LiOH or aq. KOH or a mixture thereof in a solvent such as THF provides compounds of Formula (I).

Alternatively, compounds of formula (VI) are reacted directly with various commercially available pyrazole-4-carboxylates of formula (IX), in a solvent such as xylenes, at elevated temperatures generally ranging between 100° C. and 130° C. to provide compounds of formula (VIII), eliminating the protection step. Subsequent saponification of compounds of formula (VIII) with a suitable base such as aq. NaOH, aq. LiOH or aq. KOH or a mixture thereof in a solvent such as THF provides compounds of Formula (I).

Scheme B

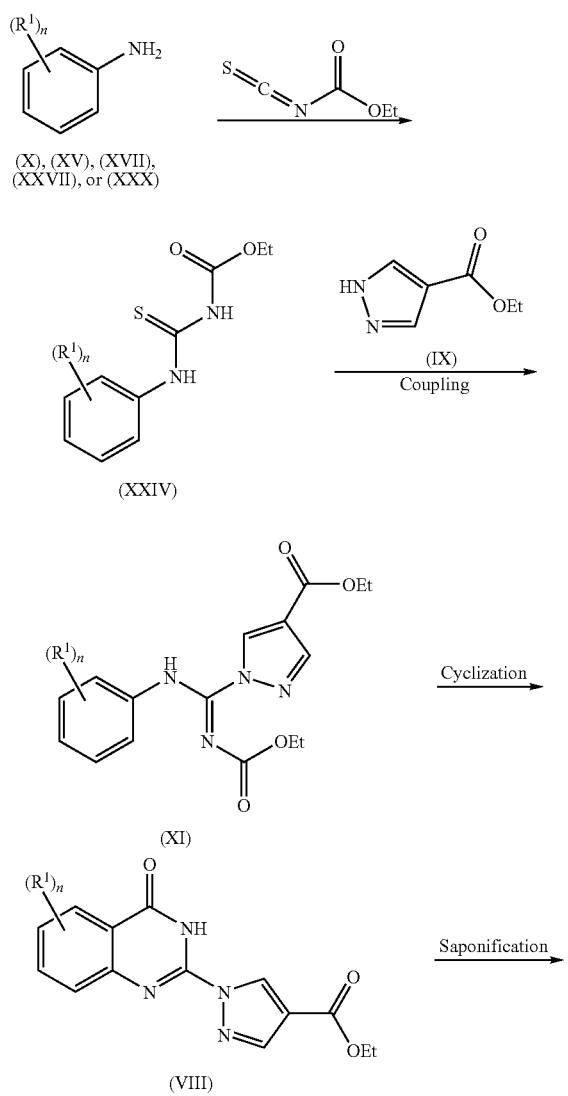

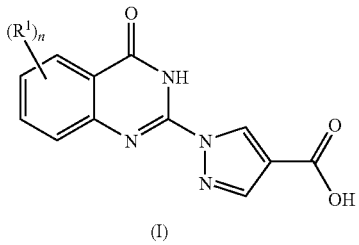

Compounds of Formula (I) are also prepared according to Scheme B from appropriately substituted commercially available or synthetically accessible anilines of formula (X), (XV), (XVII), (XXVII), or (XXX) prepared using known methods, methods described in Scheme C, or methods as described in the *Journal of Organic Chemistry*, 2008, 73 (6), 2473-75. Referring to Scheme B, functionalized anilines of formula (X), (XV), (XVII), (XXVII), or (XXX) are condensed with isothiocyanates such as ethyl isothiocyanatoformate in a solvent such as dichloromethane (DCM) at temperatures between room temperature and the reflux temperature of the solvent, to provide compounds of formula (XXIV). Subsequent coupling of compounds of formula (XXIV) with commercially available substituted pyrazole-4-carboxylates of formula (IX, in the presence of a coupling reagent such as EDCI, DIC and the like, with or without an amine base such as triethylamine provides compounds of formula (XI). Cyclization of compounds of formula (XI) with an appropriate Lewis acid such as chlorotrimethylsilane, titanium (IV) chloride, and the like, additives such as 2,6-di-tert-butylpyridine may or may not be used, in a solvent such as DCE or DMF, toluene and the like, at temperatures between room temperature and the reflux temperature of the solvent, provides compounds of formula (VIII). Saponification of compounds of formula (VIII) with a suitable base such as aq. NaOH, aq. LiOH or aq. KOH or a mixture thereof in a solvent such as THF provides compounds of Formula (I). There are an abundance of known and commercially available anilines that may be employed in the schemes herein. The schemes illustrated herein also provide guidance for synthesizing a variety of intermediates that are not readily available and are useful for making compounds of the present invention.

Scheme C

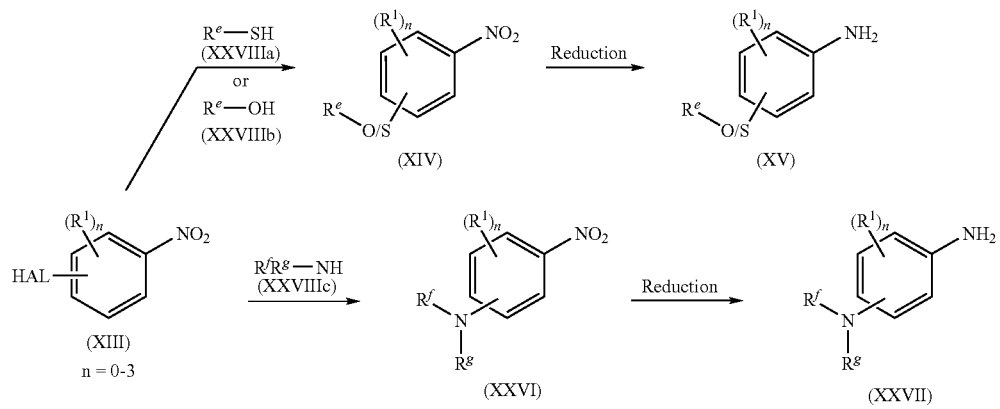

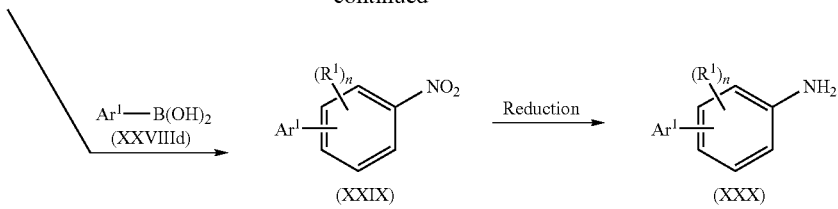

Thioether intermediates of formula (XV) are prepared according to Scheme C, where HAL is Cl, I, or F. Commercially available appropriately substituted halo-nitro-benzenes of formula (XIII) are reacted with substituted alkyl thiols or thiophenols of formula (XXVIIIa) in the presence of a base such as DBU, in a solvent such as DMF and the like, at temperatures between room temperature and the reflux temperature of the solvent, provides nitro intermediates of formula (XIV). Reduction of the nitro group, employing methods known to one skilled in the art, for example zinc powder in the presence of a saturated aqueous solution of $NH_4Cl$ in a solvent such as acetone, and the like, affords aniline intermediates of formula (XV).

Ether intermediates of formula (XVII) are also prepared according to Scheme C, where HAL is F, Cl. Commercially available appropriately substituted halo-nitro-benzenes of formula (XIII) are reacted with substituted phenols (XXVIIIb) in the presence of a base such as potassium carbonate, in a solvent such as DMSO, DMF, DMA, and the like, at temperatures between room temperature and the reflux temperature of the solvent, provides nitro intermediates of formula (XVI). Reduction of the nitro group, employing methods known to one skilled in the art, for example zinc powder in the presence of a saturated aqueous solution of $NH_4Cl$ in a solvent such as acetone, and the like, affords aniline intermediates of formula (XVII).

Amino intermediates of formula (XXVII) are also prepared according to Scheme C. Commercially available appropriately substituted halo-nitro-benzenes of formula (XIII), where HAL is Cl, are reacted with commercially available or synthetically accessible substituted heterocycloalkyl amines of formula (XXVIIIc) in the presence of a base such as potassium carbonate, in a solvent such as DMSO, DMF, DMA, and the like, at temperatures between room temperature and the reflux temperature of the solvent, provides nitro intermediates of formula (XXVI). Reduction of the nitro group, employing methods known to one skilled in the art, for example zinc powder in the presence of a saturated aqueous solution of $NH_4Cl$ in a solvent such as acetone, and the like, affords aniline intermediates of formula (XXVII).

Biaryl intermediates of formula (XXX) are also prepared according to Scheme C. Under Suzuki conditions, compounds of formula (XIII), where HAL is a suitable halogen, are reacted with monocyclic aryl or heteroaryl boronic acids or esters of formula (XXVIIId), in the presence of an organotransition metal catalyst such as $PdCl_2(dppf)$ and a suitable base such as CsF, in a solvent such as THF, provides biaryl intermediates of formula (XXIX). Reduction of the nitro group, employing methods known to one skilled in the art, for example zinc powder in the presence of a saturated aqueous solution of $NH_4Cl$ in a solvent such as acetone, and the like, affords aniline intermediates of formula (XXX).

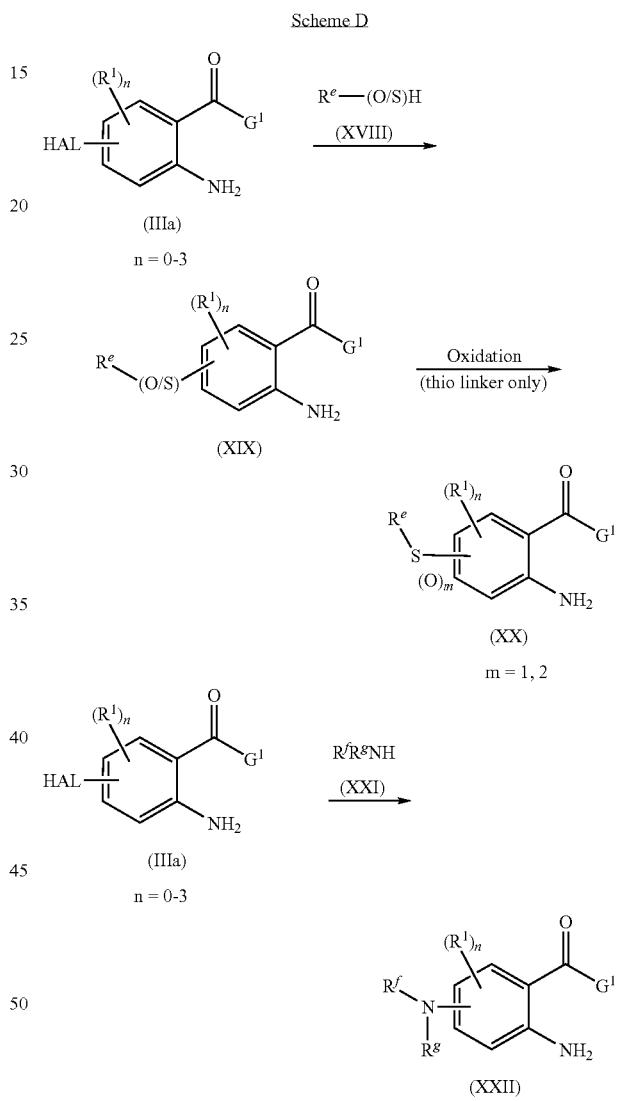

Intermediates of Formula (XIX) may be prepared according to Scheme D. Substituted 2-amino-4-halobenzoic acid derivatives of formula (IIIa), where $G^1$ is $-NH_2$ and HAL is Cl or F, are reacted with aromatic, heteroaromatic, benzyl, and alkyl thiols or alcohols of formula (XVIII) in the presence of a base such as $K_2CO_3$, NaH or the like, in a solvent such as DMF, may provide thioether or ether intermediates of formula (XIX). Where intermediates of formula (XIX) are thioethers, oxidation of the sulfur atom using oxone, mCPBA or other organic peroxides may provide sulfone and sulfoxide intermediates of formula (XX). It may also be advantageous to perform the oxidation at other stages in the synthesis route.

Racemic sulfoxides may be separated at this stage or at a subsequent stage using methods known to those skilled in the art, such as chiral chromatography or crystallization and the like. Intermediates of formula (XXII) may be prepared according to Scheme D. Substituted 2-amino-4-halobenzoic acid derivatives of formula (III), where G¹ is —NH₂ and HAL is Cl, Br, or F, are reacted with NHR'F$^g$ of formula (XXI), where is NHR'F$^g$ an aromatic, heteroaromatic, benzyl, alkyl and cycloalkyl amine, in the presence of a base such as K₂CO₃ or the like, in a solvent such as DMF or THF, to provide amino intermediates of formula (XXII).

the nitrogen of the quinazolinone, or a mixture of both oxygen and nitrogen protected species as indicated above by the dashed lines. Removal of the protecting group, after the coupling reaction (as described above), is affected using an acid such as HCl in an appropriate solvent such as EtOH provides compounds of formula (XXIII). Saponification of the carboxy group on the pyrazole ring of compounds of formula (XXIII), using a suitable base such as aq. NaOH, aq. LiOH or aq. KOH or a mixture thereof in a solvent such as THF, at temperatures between room temperature and the reflux temperature of the solvent provides compounds of Formula (I).

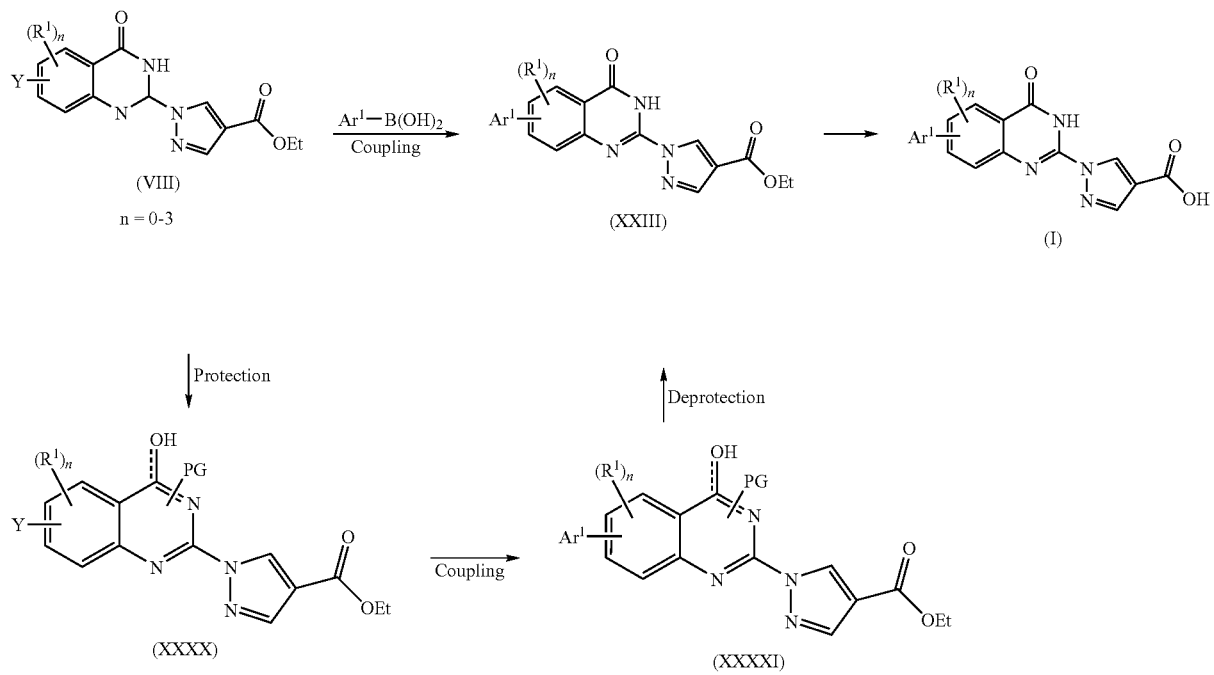

Compounds of Formula (I) are prepared according to Scheme E, where Ar¹ is an optionally substituted phenyl or monocyclic heteroaryl ring. Under Suzuki conditions, compounds of formula (VIII), where Y is a suitable halogen or triflate, are reacted with monocyclic aryl or heteroaryl boronic acids or esters, in the presence of an organotransition metal catalyst such as PdCl₂(dppf) and a suitable base such as CsF to provide biaryl intermediates of formula (XXIII). In addition to Suzuki conditions, other coupling reactions known in the art may be employed, for example, reaction with organozinc, organotin, organomagnesium reagents and the like. Saponification of the carboxy group on the pyrazole ring of compounds of formula (XXIII), using a suitable base such as aq. NaOH, aq. LiOH or aq. KOH or a mixture thereof in a solvent such as THF, at temperatures between room temperature and the reflux temperature of the solvent provides compounds of Formula (I).

Additionally, quinazolinones of formula (VIII) are also protected with a suitable protecting group before the coupling reaction, for example, 2-chloromethoxy-ethyltrimethylsilane (SEMCl) or 2-methoxyethoxymethyl chloride (MEMCl) in the presence of a base such as DIEA, and the like, in a solvent such as THF, and the like, to provide compounds of formula (XXXX). The protecting group, PG, protects the oxygen or

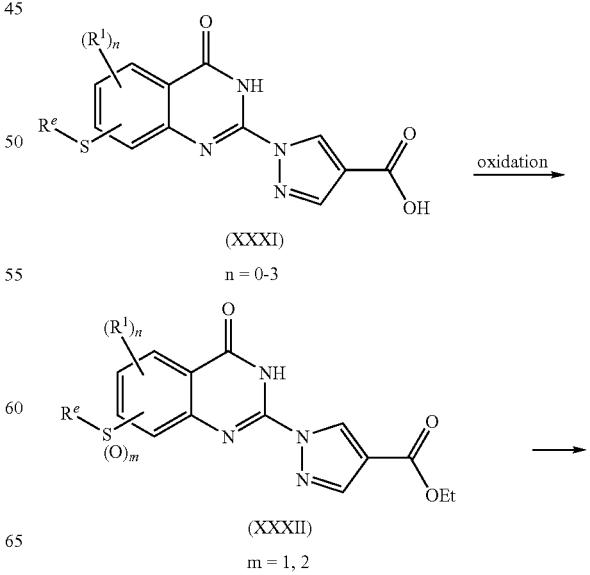

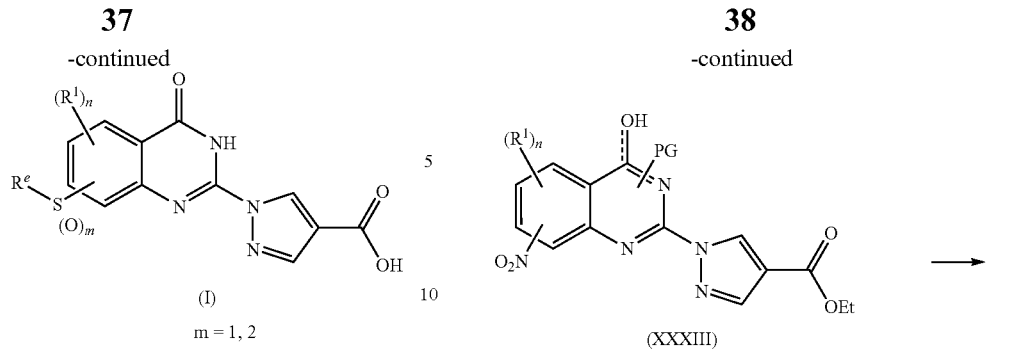

(I)

m = 1, 2

Compounds of Formula (I) may be prepared according to Scheme F. Compounds of formula (XXXI) are oxidized using known reagents such as meta-chloroperbenzoic acid or urea/hydrogen peroxide complex, and the like, in a suitable solvent such as DCE, and the like, to provide compounds of formula (XXXII). Sulfoxides and sufones formula (XXXII) are prepared, where m is one or two, depending on the stoichiometry, the oxidation reagent and/or the reactivity of the substrate. In the case of sulfoxide analogs, the resulting enantiomers may be separated using procedures known in the art, such as chiral chromatography or classical resolution. Saponification of the carboxy group on the pyrazole ring using a suitable base such as aq. NaOH, aq. LiOH or aq. KOH or a mixture thereof in a solvent such as THF, at temperatures between room temperature and the reflux temperature of the solvent provides compounds of Formula (I).

Scheme G

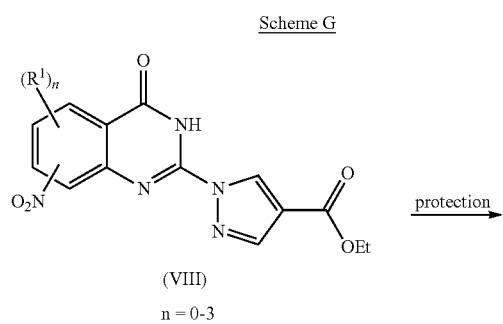

(VIII)

n = 0-3 protection

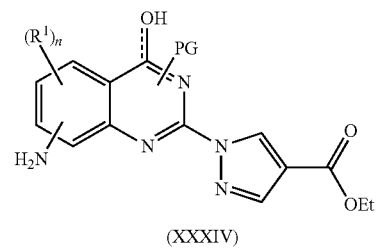

(XXXIII)

(XXXIV)

Compounds of formula (XXXIV) are prepared according to Scheme G. Quinazolinones of formula (VIII) are protected with a suitable protecting group such as 2-chloromethoxyethyltrimethylsilane (SEMCl) or 2-methoxyethoxymethyl chloride (MEMCl) in the presence of a base such as DIEA, and the like, in a solvent such as THF, and the like, to provide compounds of formula (XXXIII). The protecting group, PG, protects the oxygen or the nitrogen of the quinazolinone, or a mixture of both oxygen and nitrogen protected species as indicated above by the dashed lines. Reduction of the nitro group of compounds of formula (XXXIII), employing methods known to one skilled in the art, for example zinc powder in the presence of a saturated aqueous solution of $NH_4Cl$, in a solvent such as acetone, and the like, affords aniline intermediates of formula (XXXIV).

Scheme H

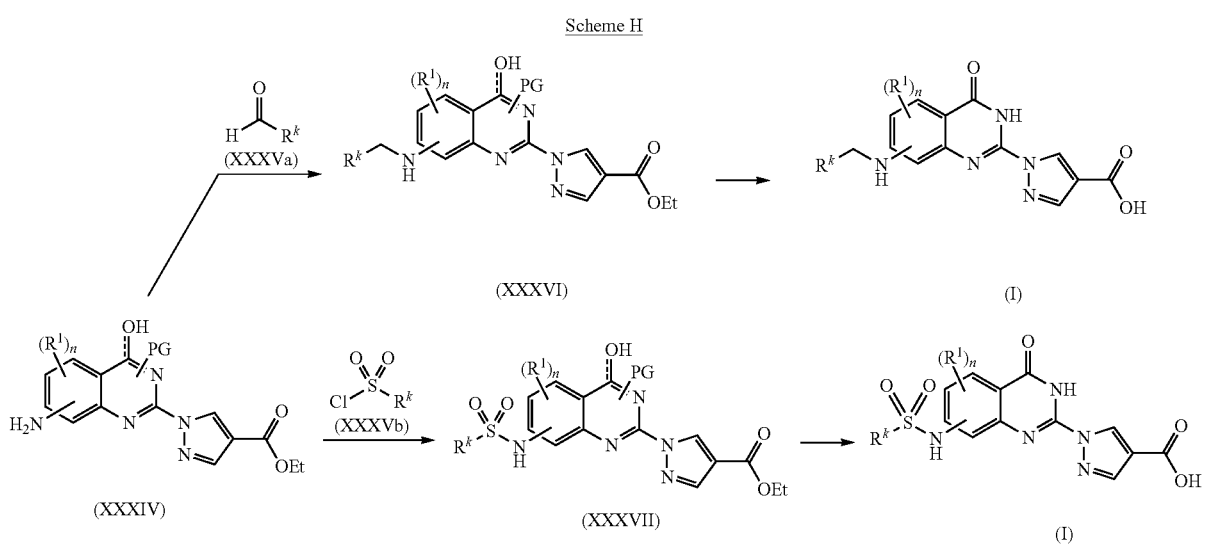

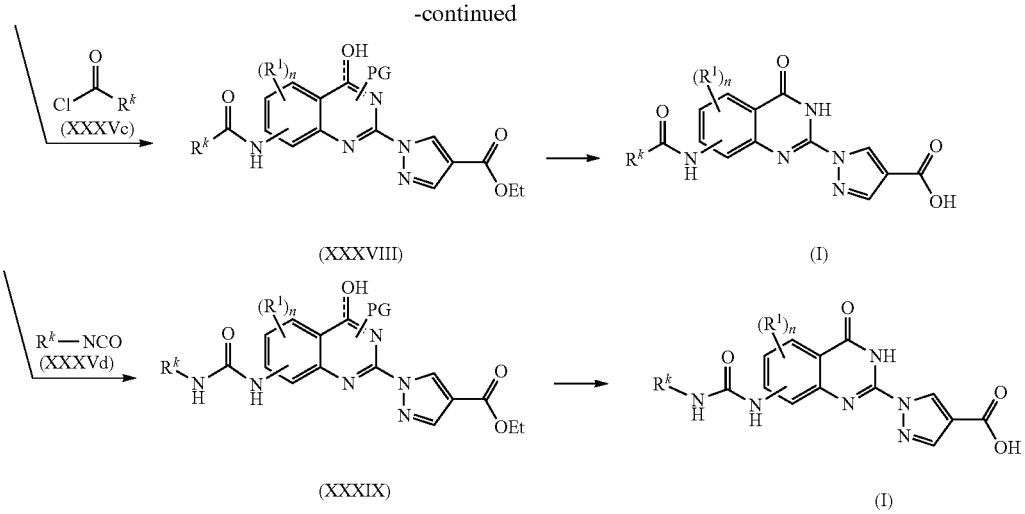

Compounds of the formula (XXXVI) are prepared according to Scheme G. Reductive amination of quinazolinones of formula (XXXIV), employing methods known to one skilled in the art, for example, reacting compounds of formula (XXXIV) with a suitable aldehyde of formula (XXXVa), in the presence of a reducing agent such as $NaBH(OAc)_3$, $NaBH_4$, or $NaCNBH_3$ in a solvent such as 1,2-dichloroethane (DCE), and the like, with optional additives such as acetic acid or an appropriate Lewis acid to provide quinazolinones of formula (XXXVI). Subsequent removal of the protecting group using an acid such as HCl in an appropriate solvent such as EtOH followed by saponification with a suitable base such as aq. NaOH, aq. LiOH or aq. KOH or a mixture thereof in a solvent such as THF provides compounds of Formula (I).

Compounds of the formulas (XXXVII), (XXXVIII) and (XXXIX) are prepared according to Scheme G. Quinazolinones of general formula (XXXIV) are coupled to commercially available or synthetically accessible sulfonyl chlorides of formula (XXXVb), acid chlorides of formula (XXXVc), or isocyanates of formula (XXXVd), in the presence of base such as DIEA, pyridine, and the like, in a solvent such as THF and the like, at temperatures ranging from 0° C. to 60° C., to provide compounds of formula (XXXVII), (XXXVIII) and (XXXIX). Subsequent deprotection of the protecting group using an acid such as HCl in an appropriate solvent such as EtOH followed by saponification with a suitable base such as aq. NaOH, aq. LiOH or aq. KOH or a mixture thereof in a solvent such as THF provides sulfonamides of Formula (I), amides of Formula (I) and ureas of Formula (I).

EXAMPLES

Chemistry

In obtaining the compounds described in the Examples below and the corresponding analytical data, the following experimental and analytical protocols were followed unless otherwise indicated.

Unless otherwise stated, reaction mixtures were magnetically stirred at room temperature (rt). Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure.

Thin-layer chromatography (TLC) was performed using Merck silica gel 60 $F_{254}$ 2.5 cm×7.5 cm 250 μm or 5.0 cm×10.0 cm 250 μm pre-coated silica gel plates. Preparative thin-layer chromatography was performed using EM Science silica gel 60 $F_{254}$ 20 cm×20 cm 0.5 mm pre-coated plates with a 20 cm×4 cm concentrating zone.

Normal-phase flash column chromatography (FCC) was performed on silica gel ($SiO_2$) eluting with hexanes/ethyl acetate, unless otherwise noted.

Reversed-phase HPLC was performed on a Hewlett Packard HPLC Series 1100, with a Eclipse XDB-$C_8$ (3.5 μm, 4.6×150 mm) column. Detection was done at $\lambda$=230, 254 and 280 nm. The gradient was 1 to 99% acetonitrile/water (0.05% trifluoroacetic acid) over 8.0 min with a flow rate of 0.75 mL/min. Alternately, preparative HPLC was performed on a Shimadzu automated HPLC system using a Gilson 215 liquid handler using LCMSsolution software with uv peak detection done at $\lambda$=254 nm and fitted with a reverse phase Inertsil ODS-3 (3 μm, 30×100 mm) column; mobile gradient of 5-99% of acetonitrile/water (0.05% trifluoroacetic acid) over 7 min and flow rates of 80 mL/min. The column was heated to 45° C. with a hot water bath. Alternately, preparative HPLC was performed on a Dionex APS automated HPLC system using Chromeleon software with uv peak detection done at $\lambda$=220 and 254 nm and fitted with a reverse phase Sunfire prep C18 OBD (5 μm, 30×150 mm) column; mobile gradient of 15-100% of acetonitrile/water (0.05% trifluoroacetic acid) over 10-20 min and flow rates of 20 mL/min.

Mass spectra (MS) were obtained on an Agilent series 1100 MSD equipped with a ESI/APCI positive and negative multimode source unless otherwise indicated.

Nuclear magnetic resonance (NMR) spectra were obtained on Bruker model DRX spectrometers. The format of the $^1$H NMR data below is: chemical shift in ppm downfield of the tetramethylsilane reference (apparent multiplicity, coupling constant J in Hz, integration).

Chemical names were generated using ChemDraw Version 6.0.2 (CambridgeSoft, Cambridge, Mass.) or ACD/Name Version 9 (Advanced Chemistry Development, Toronto, Ontario, Canada).

Example 1

1-(7-Chloro-4-oxo-3,4-dihydro-quinazolin-2-yl)-1H-pyrazole-4-carboxylic acid

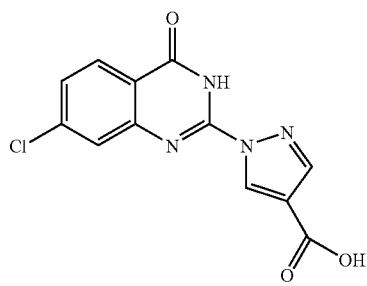 [SMILES: O=C(O)c1cnn(-c2nc3cc(Cl)ccc3c(=O)[nH]2)c1]

Step A: Preparation of 7-chloro-1H-quinazoline-2,4-dione. A mixture of 2-amino-4-chlorobenzoic acid (2.00 g, 11.6 mmol) and urea (2.80 g, 46.6 mmol) was heated to 200° C. for 1 h. The mixture was allowed to cool to room temperature and the resulting mass was triturated well with water. The product was collected by filtration (2.30 g, 100%). The MS and NMR data are in agreement with those that have been previously described: Organic Process Research & Development, 2003, 7, 700-706. $^1$H NMR (600 MHz, DMSO-$d_6$): 12.00 (br s, 2H), 8.59-8.53 (m, 1H), 7.93-7.80 (m, 2H).

Step B: Preparation of 2,4,7-trichloroquinazoline. A mixture of 7-chloro-1H-quinazoline-2,4-dione (2.0 g, 10 mmol) was suspended in ACN (50 mL), then POCl$_3$ (5.0 mL, 55 mmol) was added. This was followed by addition of DIEA (5.0 mL, 28 mmol). The resulting mixture was heated to reflux for 36 h, and then allowed to cool to rt and concentrated. The residue was carefully treated with ice and sodium bicarbonate. The resulting solid was collected by filtration and dried. Chromatographic purification (EtOAc/hexanes 0:100 to 10:90) provided the titled compound (2.1 g, 89%). The MS and NMR data are in agreement with those that have been previously described: Bioorganic & Medicinal Chemistry, 2003, 11, 2439-2444. $^1$H NMR (400 MHz, DMSO-$d_6$): 8.32 (d, J=8.7 Hz, 1H), 8.20 (d, J=1.9 Hz, 1H), 7.93 (dd, J=9.0, 2.1 Hz, 1H).

Step C: Preparation of 2,7-dichloro-4-oxoquinazoline. A 1.0 M aqueous solution of sodium hydroxide (19 mL, 19 mmol) was added to a mixture of 2,4,7-trichloroquinazoline (2.0 g, 8.5 mmol) and THF (30 mL) that had been cooled to 0° C. The reaction mixture was allowed to warm to rt and was stirred vigorously for 2 h. The mixture was concentrated to remove the THF, and the remaining aqueous phase was cooled to 0° C. and acidified by addition of 1.0 M aqueous HCl (25 mL). The resulting mixture was allowed to stand at 0° C. for 20 min, the solid was collected by filtration and dried to provide the titled compound (1.7 g, 92%). The MS and NMR data are in agreement with those that have been previously described: Journal of Medicinal Chemistry, 2007, 50, 2297-2300.

Step D: Preparation of 2,7-dichloro-4-(2-methoxy-ethoxymethoxy)-quinazoline. 2-methoxyethoxymethyl chloride (1.0 mL, 8.8 mmol) was added dropwise to a solution of 2,7-dichloro-4-oxoquinazoline (1.7 g, 7.8 mmol), DIEA (2.1 mL, 12 mmol), and THF (20 mL). The reaction was allowed to proceed at rt for 16 h, and then EtOAc was added (250 mL). The solution was washed with water (2×100 mL) and brine (100 mL). The organic layer was then dried and concentrated, and the resulting residue was triturated with EtOH to provide the titled compound (2.0 g, 83%). This material was used directly without further purification.

Step E: Preparation of 1-(7-chloro-4-oxo-3,4-dihydro-quinazolin-2-yl)-1H-pyrazole-4-carboxylic acid ethyl ester. A mixture of 2,7-dichloro-4-(2-methoxy-ethoxymethoxy)-quinazoline (0.68 g, 2.2 mmol), ethyl pyrazole-4-carboxylate (0.34 g, 2.4 mmol), Cs$_2$CO$_3$ (1.2 g, 3.6 mmol) and anhydrous DMF (10 mL) was heated to 120° C. for 20 min, and then was cooled to 0° C. The mixture was carefully diluted with 1 M aq. HCl (30 mL). The mixture was allowed to warm to rt and the precipitate was collected by filtration to provide the titled compound (0.35 g, 50%). MS (CI): mass calcd. for C$_{14}$H$_{11}$ClN$_4$O$_3$, 318.7; m/z found, 317.0 [M−H]$^-$. $^1$H NMR (400 MHz, DMSO-$d_6$): 13.04 (br s, 1H), 8.99 (s, 1H), 8.32 (s, 1H), 8.11 (d, J=8.5 Hz, 1H), 7.75 (s, 1H), 7.54 (dd, J=8.5, 2.1 Hz, 1H), 4.30 (q, J=7.1 Hz, 2H), 1.33 (t, J=7.1 Hz, 3H).

Step F: Preparation of 1-(7-chloro-4-oxo-3,4-dihydro-quinazolin-2-yl)-1H-pyrazole-4-carboxylic acid. A mixture of 1-(7-chloro-4-oxo-3,4-dihydro-quinazolin-2-yl)-1H-pyrazole-4-carboxylic acid ethyl ester (240 mg, 0.74 mmol), 1M aq. LiOH (4.0 mL), and THF (6 mL) was rapidly stirred for 6 h. The mixture was concentrated to remove the THF, and the aqueous residue was cooled to 0° C. and acidified to pH 2 with 1 M aq. HCl. The resulting precipitate was collected by filtration to provide the titled compound (205 mg, 71%). MS (CI): mass calcd. for C$_{12}$H$_7$ClN$_4$O$_3$, 290.7; m/z found, 289.0 [M−H]$^-$. $^1$H NMR (400 MHz, DMSO-$d_6$): 12.99 (br s, 2H), 8.93 (d, J=0.7 Hz, 1H), 8.27 (s, 1H), 8.11 (d, J=8.5 Hz, 1H), 7.74 (d, J=1.9 Hz, 1H), 7.54 (dd, J=8.5, 2.1 Hz, 1H).

The compounds in Examples 2-16 were prepared using methods analogous to those described in Example 1.

Example 2

1-(7-Trifluoromethyl-4-oxo-3,4-dihydro-quinazolin-2-yl)-1H-pyrazole-4-carboxylic acid

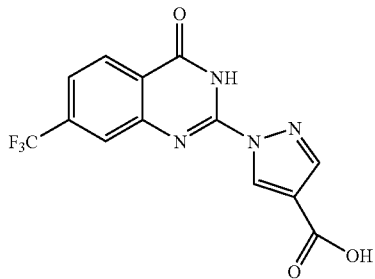 [SMILES: O=C(O)c1cnn(-c2nc3cc(C(F)(F)F)ccc3c(=O)[nH]2)c1]

The titled compound was prepared according to the methods described in Example 1 using 2-amino-4-trifluoromethylbenzoic acid in step A. MS (CI): mass calcd. for C$_{13}$H$_7$F$_3$N$_4$O$_3$, 324.2; m/z found, 323.0 [M−H]$^-$. $^1$H NMR (400 MHz, DMSO-$d_6$): 14.17-12.12 (br m, 2H), 8.98 (d, J=0.6 Hz, 1H), 8.32 (d, J=8.3 Hz, 1H), 8.29 (s, 1H), 8.02 (s, 1H), 7.80 (d, J=8.3 Hz, 1H).

Example 3

1-(6,7-Dichloro-4-oxo-3,4-dihydro-quinazolin-2-yl)-1H-pyrazole-4-carboxylic acid

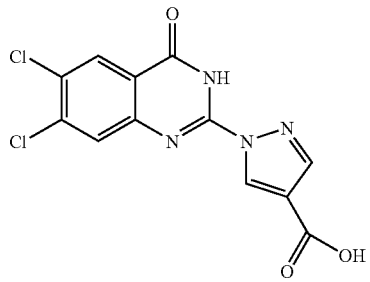 [SMILES: O=C(O)c1cnn(-c2nc3cc(Cl)c(Cl)cc3c(=O)[nH]2)c1]

The titled compound was prepared according to the methods described in Example 1 using 2-amino-4,5-dichlorobenzoic acid in step A. MS (CI): mass calcd. for $C_{12}H_6Cl_2N_4O_3$, 325.1; m/z found, 323.0 [M−H]⁻. ¹H NMR (500 MHz, DMSO-d₆): 13.58-12.82 (br m, 2H), 8.92 (s, 1H), 8.28 (s, 1H), 8.21 (s, 1H), 7.96 (s, 1H).

Example 4

1-(6-Fluoro-4-oxo-3,4-dihydro-quinazolin-2-yl)-1H-pyrazole-4-carboxylic acid

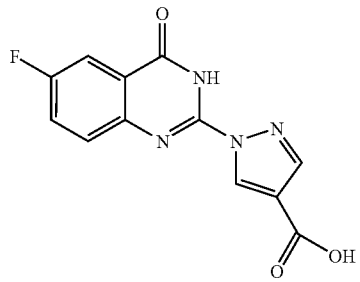 [SMILES: O=C(O)c1cnn(-c2nc3ccc(F)cc3c(=O)[nH]2)c1]

The titled compound was prepared in a manner analogous to Example 1 using 2-amino-5-fluorobenzoic acid in step A. MS (CI): mass calcd. for $C_{12}H_7FN_4O_3$, 274.2; m/z found, 273.0 [M−H]⁻. ¹H NMR (500 MHz, DMSO-d₆): 13.53-12.42 (br m, 2H), 8.93 (s, 1H), 8.26 (s, 1H), 7.87-7.65 (m, 3H).

Example 5

1-(6,7-Difluoro-4-oxo-3,4-dihydro-quinazolin-2-yl)-1H-pyrazole-4-carboxylic acid, trifluoroacetate salt

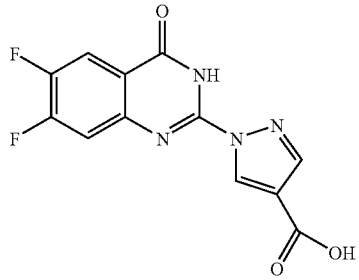 [SMILES: O=C(O)c1cnn(-c2nc3cc(F)c(F)cc3c(=O)[nH]2)c1]

The titled compound was prepared in a manner analogous to Example 1 using 2-amino-4,5-difluorobenzoic acid in step A. The titled compound was purified by preparative reverse-phase HPLC. MS (ESI): mass calcd. for $C_{12}H_6F_2N_4O_3$, 292.2; m/z found, 209.9 [M−H]⁻. ¹H NMR (500 MHz, DMSO-d₆): 13.79-12.30 (br m, 2H), 8.95-8.87 (br m, 1H), 8.26 (s, 1H), 8.04 (s, 1H), 7.76 (s, 1H).

Example 6

1-(5-Chloro-4-oxo-3,4-dihydro-quinazolin-2-yl)-1H-pyrazole-4-carboxylic acid

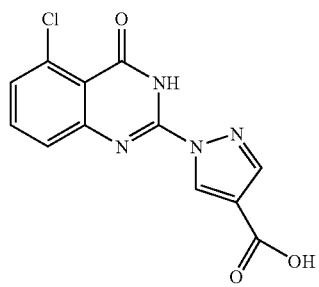 [SMILES: O=C(O)c1cnn(-c2nc3cccc(Cl)c3c(=O)[nH]2)c1]

The titled compound was prepared in a manner analogous to Example 1 using 2-amino-6-chlorobenzoic acid in step A. MS (ESI): mass calcd. for $C_{12}H_7ClN_4O_3$, 290.7; m/z found, 289.0 [M−H]⁻. ¹H NMR (500 MHz, DMSO-d₆): 13.39-12.49 (m, 2H), 8.94 (s, 1H), 8.27 (s, 1H), 7.75 (t, J=8.0 Hz, 1H), 7.63 (d, J=7.9 Hz, 1H), 7.51 (d, J=7.8 Hz, 1H).

Example 7

1-(8-Methoxy-4-oxo-3,4-dihydro-quinazolin-2-yl)-1H-pyrazole-4-carboxylic acid

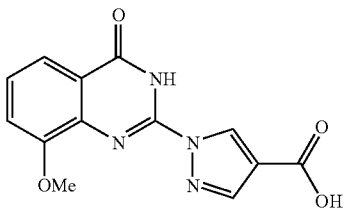 [SMILES: COc1cccc2c(=O)[nH]c(-n3cc(C(=O)O)cn3)nc12]

The titled compound was prepared in a manner analogous to Example 1 using 2-amino-3-methoxybenzoic acid in step A. MS (ESI): mass calcd. for $C_{13}H_{10}N_4O_4$, 286.2; m/z found, 287.2 [M+H]⁺. ¹H NMR (400 MHz, DMSO-d₆): 12.97 (br s, 1H), 12.85 (br s, 1H), 8.88 (s, 1H), 8.24 (s, 1H), 7.70 (d, J=7.6 Hz, 1H), 7.46 (t, J=6.9 Hz, 1H), 7.42 (d, J=6.5 Hz, 1H), 3.95 (s, 3H).

Example 8

1-(6-Methyl-4-oxo-3,4-dihydro-quinazolin-2-yl)-1H-pyrazole-4-carboxylic acid

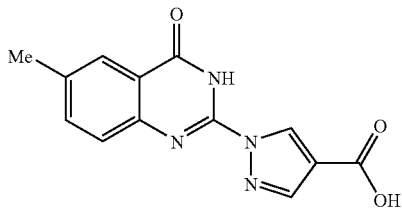 [SMILES: Cc1ccc2nc(-n3cc(C(=O)O)cn3)[nH]c(=O)c2c1]

The titled compound was prepared in a manner analogous to Example 1 using 2-amino-5-methylbenzoic acid in step A. MS (ESI/CI): mass calcd. for $C_{13}H_{10}N_4O_3$, 270.2; m/z found, 271.1 [M+H]$^+$. $^1$H NMR (400 MHz, DMSO-d$_6$): 13.14-12.84 (br s, 1H), 12.82-12.56 (br s, 1H), 8.93 (s, 1H), 8.24 (s, 1H), 7.94 (s, 1H), 7.68 (d, J=7.9 Hz, 1H), 7.60 (d, J=7.8 Hz, 1H), 2.46 (s, 3H).

Example 9

1-(8-Methyl-4-oxo-3,4-dihydro-quinazolin-2-yl)-1H-pyrazole-4-carboxylic acid

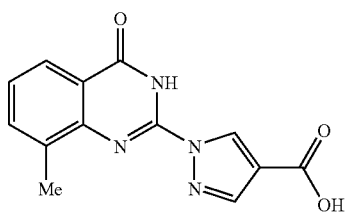 [SMILES: O=C(O)c1cnn(-c2nc3c(Br)cccc3c(=O)[nH]2)c1]

The titled compound was prepared in a manner analogous to Example 1 using 2-amino-3-methylbenzoic acid in step A. MS (ESI): mass calcd. for $C_{13}H_{10}N_4O_3$, 270.3; m/z found, 269.2 [M−H]$^−$. $^1$H NMR (500 MHz, DMSO-d$_6$): 13.29-12.58 (br m, 2H), 9.03 (s, 1H), 8.25 (s, 1H), 7.97 (d, J=7.9 Hz, 1H), 7.70 (d, J=7.2 Hz, 1H), 7.40 (t, J=7.6 Hz, 1H), 2.58 (s, 3H).

Example 10

1-(7-Methyl-4-oxo-3,4-dihydro-quinazolin-2-yl)-1H-pyrazole-4-carboxylic acid

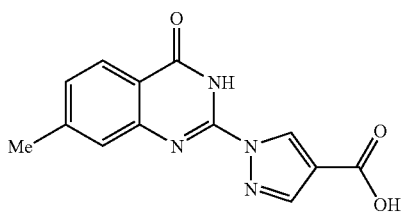

The titled compound was prepared in a manner analogous to Example 1 using 2-amino-4-methylbenzoic acid in step A. MS (ESI/CI): mass calcd. for $C_{13}H_{10}N_4O_3$, 270.3; m/z found, 271.1 [M−H]$^+$. $^1$H NMR (400 MHz, DMSO-d$_6$): 12.97 (br s, 1H), 12.70 (br s, 1H), 8.93 (s, 1H), 8.25 (s, 1H), 8.02 (d, J=8.0 Hz, 1H), 7.50 (s, 1H), 7.35 (d, J=7.9 Hz, 1H), 2.47 (s, 3H).

Example 11

1-(8-Bromo-4-oxo-3,4-dihydro-quinazolin-2-yl)-1H-pyrazole-4-carboxylic acid

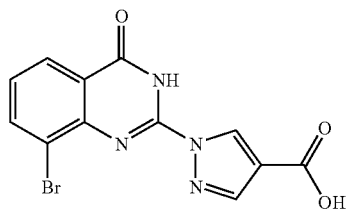

The titled compound was prepared in a manner analogous to Example 1 using 2-amino-3-bromobenzoic acid in step A. MS (CI): mass calcd. for $C_{12}H_7BrN_4O_3$, 335.1; m/z found, 333.0 [M−H]$^−$. $^1$H NMR (400 MHz, DMSO-d$_6$): 13.31-12.94 (br s, 2H), 8.91 (s, 1H), 8.28 (s, 1H), 8.22-8.07 (m, 2H), 7.41 (t, J=7.8 Hz, 1H).

Example 12

1-(6-Iodo-4-oxo-3,4-dihydro-quinazolin-2-yl)-1H-pyrazole-4-carboxylic acid

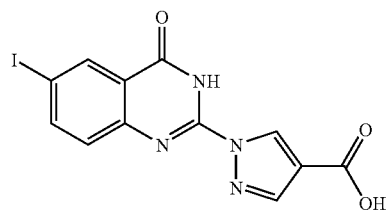 [SMILES: O=C(O)c1cnn(-c2nc3ccc(I)cc3c(=O)[nH]2)c1]

The titled compound was prepared in a manner analogous to Example 1 using 2-amino-5-iodobenzoic acid in step A. MS (CI): mass calcd. for $C_{12}H_7IN_4O_3$, 382.1; m/z found, 380.9 [M−H]$^−$. $^1$H NMR (400 MHz, DMSO-d$_6$): 13.00 (br s, 2H), 8.94 (s, 1H), 8.38 (s, 1H), 8.27 (s, 1H), 8.12 (d, J=8.6 Hz, 1H), 7.49 (d, J=8.5 Hz, 1H).

Example 13

1-(6-Bromo-4-oxo-3,4-dihydro-quinazolin-2-yl)-1H-pyrazole-4-carboxylic acid

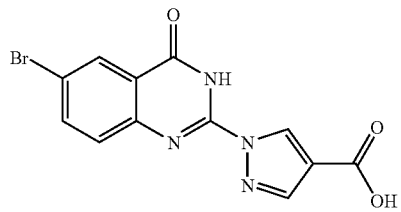 [SMILES: O=C(O)c1cnn(-c2nc3ccc(Br)cc3c(=O)[nH]2)c1]

The titled compound was prepared in a manner analogous to Example 1 using 2-amino-5-bromobenzoic acid in step A. MS (ESI/CI): mass calcd. for $C_{12}H_7BrN_4O_3$, 335.1; m/z found, 336.1 [M+H]$^+$. $^1$H NMR (400 MHz, DMSO-d$_6$): 12.87 (br s, 2H), 8.94 (s, 1H), 8.27 (s, 1H), 8.04 (d, J=8.5 Hz, 1H), 7.91 (s, 1H), 7.68 (dd, J=8.5, 1.9 Hz, 1H).

Example 14

1-(8-Chloro-4-oxo-3,4-dihydro-quinazolin-2-yl)-1H-pyrazole-4-carboxylic acid

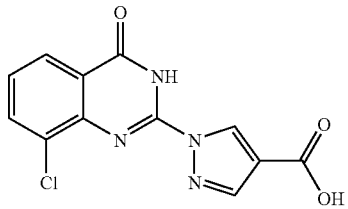 [SMILES: O=C(O)c1cnn(-c2nc3c(Cl)cccc3c(=O)[nH]2)c1]

The titled compound was prepared in a manner analogous to Example 1 using 2-amino-3-chlorobenzoic acid in step A. MS (CI): mass calcd. for $C_{12}H_7ClN_4O_3$, 290.7; m/z found, 292.0 [M+H]$^+$. $^1$H NMR (500 MHz, DMSO-d$_6$): 13.13 (br s, 2H), 8.92 (s, 1H), 8.29 (s, 1H), 8.09 (d, J=6.7 Hz, 1H), 8.00 (d, J=7.8 Hz, 1H), 7.49 (t, J=7.9 Hz, 1H).

Example 15

1-(4-Oxo-6-trifluoromethoxy-3,4-dihydro-quinazolin-2-yl)-1H-pyrazole-4-carboxylic acid

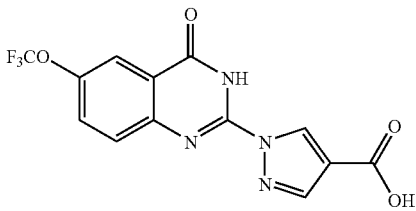 [SMILES: O=C(O)c1cnn(-c2nc3ccc(OC(F)(F)F)cc3c(=O)[nH]2)c1]

The titled compound was prepared in a manner analogous to Example 1 using 2-amino-5-trifluoromethoxybenzoic acid in step A. MS (CI): mass calcd. for $C_{13}H_7F_3N_4O_4$, 340.2; m/z found, 341.0 [M+H]$^+$. $^1$H NMR (400 MHz, DMSO-d$_6$): 13.00 (br s, 2H), 8.96 (s, 1H), 8.28 (s, 1H), 7.97 (s, 1H), 7.89-7.79 (br m, 2H).

Example 16

1-(4-Oxo-8-trifluoromethyl-3,4-dihydro-quinazolin-2-yl)-1H-pyrazole-4-carboxylic acid

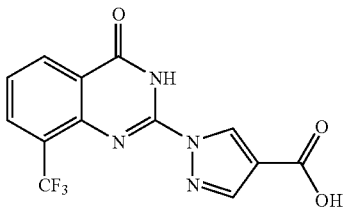

The titled compound was prepared in a manner analogous to Example 1 using 2-amino-3-trifluoromethylbenzoic acid in step A. MS (CI): mass calcd. for $C_{13}H_7F_3N_4O_3$, 324.2; m/z found, 325.0 [M+H]$^+$. $^1$H NMR (500 MHz, DMSO-d$_6$): 13.28 (br s, 1H), 13.15 (br s, 1H), 8.81 (s, 1H), 8.40 (d, J=6.9 Hz, 1H), 8.32 (s, 1H), 8.22 (d, J=7.5 Hz, 1H), 7.64 (t, J=7.8 Hz, 1H).

Example 17

1-(6,7-Dimethoxy-4-oxo-3,4-dihydro-quinazolin-2-yl)-1H-pyrazole-4-carboxylic acid

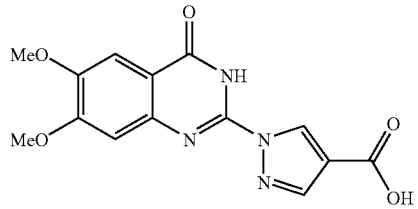 [SMILES: COc1cc2nc(-n3cc(C(=O)O)cn3)[nH]c(=O)c2cc1OC]

Step A: Preparation of 1-[(3,4-dimethoxy-phenylamino)-ethoxycarbonylimino-methyl]-1H-pyrazole-4-carboxylic acid ethyl ester. A solution of 3,4-dimethoxyaniline (0.15 g, 1.0 mmol), ethyl isothiocyanatoformate (0.14 mL, 1.2 mmol) and DCM (10 mL) was stirred at room temperature for 1 h. Triethylamine (0.42 mL, 3.0 mmol), ethyl pyrazole-4-carboxylate (0.17 g, 1.2 mmol), and EDCl (0.19 g, 1.2 mmol) were added and the solution was stirred at room temperature for 5 h. The mixture was concentrated, diluted with water, and extracted with DCM. The organic layer was dried and concentrated to provide the crude titled compound (390 mg, 100%). This material was used without purification: MS (ESI): mass calcd. for $C_{18}H_{22}N_4O_6$, 390.4; m/z found, 391.4 [M+H]$^+$.

Step B: Preparation of 1-(6,7-dimethoxy-4-oxo-3,4-dihydro-quinazolin-2-yl)-1H-pyrazole-4-carboxylic acid ethyl ester. Chlorotrimethylsilane (1.26 mL, 10.0 mmol) was added to a solution of 1-[(3,4-dimethoxy-phenylamino)-ethoxycarbonylimino-methyl]-1H-pyrazole-4-carboxylic acid ethyl ester (0.39 g, 1.0 mmol) and DMF (3 mL), and the resulting mixture was heated to 80° C. for 16 h in a sealed tube. The reaction mixture was cooled and water (2 mL) was added. The crude reaction mixture was concentrated under reduced pressure and the resulting aqueous mixture was adjusted to pH 7 using 2M aqueous NH$_4$OH. The residue was triturated well and collected by vacuum filtration. The titled compound was purified by preparative reverse-phase HPLC (0.28 g, 81%). MS (ESI): mass calcd. for $C_{16}H_{16}N_4O_5$, 344.4; m/z found, 345.7 [M+H]$^+$. $^1$H NMR (400 MHz, DMSO-d$_6$): 13.06-12.23 (br m, 1H), 8.97 (s, 1H), 8.28 (s, 1H), 7.47 (s, 1H), 7.21 (s, 1H), 4.29 (q, J=7.1 Hz, 2H), 3.93 (s, 3H), 3.89 (s, 3H), 1.32 (t, J=7.1 Hz, 3H).

Step C: Preparation of 1-(6,7-dimethoxy-4-oxo-3,4-dihydro-quinazolin-2-yl)-1H-pyrazole-4-carboxylic acid. A mixture of 1-(6,7-dimethoxy-4-oxo-3,4-dihydro-quinazolin-2-yl)-1H-pyrazole-4-carboxylic acid ethyl ester (0.28 g, 0.81 mmol), 1M aq. KOH (3.0 mL) and THF (3.0 mL) was stirred for 4 h. The mixture was concentrated to remove the THF and the aqueous residue was acidified to pH 2 with 1M aq. HCl. The resulting precipitate was collected by filtration to provide the titled compound (0.23 g, 89%). MS (ESI): mass calcd. for $C_{14}H_{12}N_4O_5$, 316.3; m/z found, 317.1 [M+H]$^+$. $^1$H NMR (400 MHz, DMSO-d$_6$): 13.32-12.29 (br m, 2H), 8.90 (s, 1H), 8.22 (s, 1H), 7.47 (s, 1H), 7.19 (s, 1H), 3.93 (s, 3H), 3.89 (s, 3H).

Example 18

1-(5,6,7-Trimethoxy-4-oxo-3,4-dihydro-quinazolin-2-yl)-1H-pyrazole-4-carboxylic acid

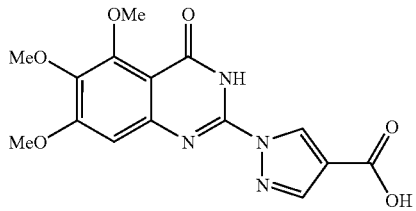 [SMILES: COc1cc2nc(-n3cc(C(=O)O)cn3)[nH]c(=O)c2c(OC)c1OC]

The titled compound was prepared in a manner analogous to Example 17 using 3,4,5-trimethoxy-aniline in step A. MS (ESI): mass calcd. for $C_{15}H_{15}N_4O_6$, 346.3; m/z found, 347.1 [M+H]$^+$. $^1$H NMR (500 MHz, DMSO-d$_6$): 13.16-12.82 (br m, 1H), 12.64-12.20 (br m, 1H), 8.90 (s, 1H), 8.24 (s, 1H), 7.04 (s, 1H), 3.94 (s, 3H), 3.83 (s, 3H), 3.79 (s, 3H).

Example 19

1-(6-tert-Butyl-4-oxo-3,4-dihydro-quinazolin-2-yl)-1H-pyrazole-4-carboxylic acid

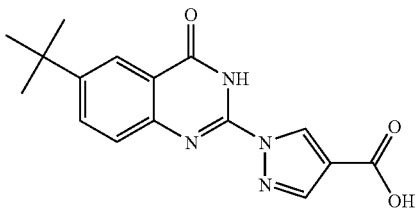 [SMILES: CC(C)(C)c1ccc2nc(-n3cc(C(=O)O)cn3)[nH]c(=O)c2c1]

The titled compound was prepared in a manner analogous to Example 17 using 4-tertbutylaniline in step A. MS (ESI): mass calcd. for $C_{16}H_{16}N_4O_3$, 312.3; m/z found, 313.2 [M+H]$^+$. $^1$H NMR (500 MHz, DMSO-d$_6$): 12.90 (br m, 2H), 8.94 (s, 1H), 8.25 (s, 1H), 8.07 (d, J=2.1 Hz, 1H), 7.94 (dd, J=8.6, 2.2 Hz, 1H), 7.66 (d, J=8.4 Hz, 1H), 1.36 (s, 9H).

Example 20

1-(4-Oxo-6-phenoxy-3,4-dihydro-quinazolin-2-yl)-1H-pyrazole-4-carboxylic acid

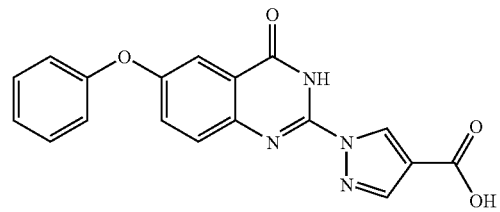 [SMILES: O=C(O)c1cnn(-c2nc3ccc(Oc4ccccc4)cc3c(=O)[nH]2)c1]

The titled compound was prepared in a manner analogous to Example 17 using 4-phenoxyaniline in step A. MS (ESI): mass calcd. for $C_{18}H_{12}N_4O_4$, 348.3; m/z found, 349.2 [M+H]$^+$. $^1$H NMR (400 MHz, DMSO-d$_6$): 13.16-12.96 (br m, 2H), 8.94 (s, 1H), 8.24 (s, 1H), 7.74 (s, 1H), 7.60 (dd, J=8.9 Hz, 2.9, 1H), 7.48 (t, J=8.0 Hz, 3H), 7.25 (t, J=7.4 Hz, 1H), 7.15 (d, J=7.8 Hz, 2H).

Example 21

1-(6-Cyclohexyl-4-oxo-3,4-dihydro-quinazolin-2-yl)-1H-pyrazole-4-carboxylic acid

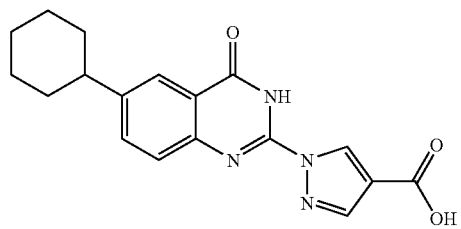 [SMILES: O=C(O)c1cnn(-c2nc3ccc(C4CCCCC4)cc3c(=O)[nH]2)c1]

The titled compound was prepared in a manner analogous to Example 17 using 4-cyclohexylaniline in step A. MS (ESI): mass calcd. for $C_{18}H_{18}N_4O_3$, 338.3; m/z found, 339.1 [M+H]$^+$. $^1$H NMR (400 MHz, DMSO-d$_6$): 12.95 (s, 1H), 12.78-12.59 (br m, 1H), 8.93 (s, 1H), 8.24 (s, 1H), 7.95 (s, 1H), 7.74 (d, J=7.3 Hz, 1H), 7.62 (d, J=8.0 Hz, 1H), 2.68 (s, 1H), 1.82 (d, J=12.7 Hz, 4H), 1.72 (d, J=12.7 Hz, 1H), 1.44 (dd, J=24.5, 12.6 Hz, 4H), 1.29 (s, 1H).

Example 22

1-(7-Chloro-4-oxo-6-trifluoromethoxy-3,4-dihydro-quinazolin-2-yl)-1H-pyrazole-4-carboxylic acid

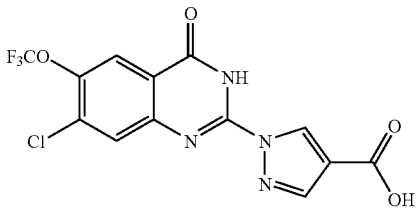 [SMILES: O=C(O)c1cnn(-c2nc3cc(Cl)c(OC(F)(F)F)cc3c(=O)[nH]2)c1]

The titled compound was prepared in a manner analogous to Example 17 using 3-chloro,4-trifluoromethoxyaniline in step A. MS (ESI): mass calcd. for $C_{13}H_6ClF_3N_4O_4$, 374.6; m/z found, 375.3 [M+H]$^+$. $^1$H NMR (500 MHz, DMSO-d$_6$): 13.49-13.16 (br m, 1H), 13.08 (s, 1H), 8.95 (s, 1H), 8.30 (s, 1H), 8.10 (s, 1H), 8.05 (s, 1H).

Example 23

1-(1-Oxo-2,7-dihydro-1H-pyrrolo[3,2-f]quinazolin-3-yl)-1H-pyrazole-4-carboxylic acid

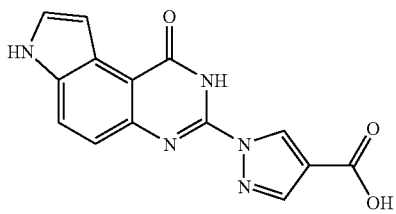 [SMILES: O=C(O)c1cnn(-c2nc3ccc4[nH]ccc4c3c(=O)[nH]2)c1]

The titled compound was prepared in a manner analogous to Example 17 using 5-aminoindole in step A. MS (ESI): mass calcd. for $C_{14}H_9N_5O_3$, 295.3; m/z found, 296.1 [M+H]$^+$. $^1$H NMR (500 MHz, DMSO-d$_6$): 11.79 (s, 1H), 8.97 (s, 1H), 8.24 (s, 1H), 7.93 (d, J=8.6 Hz, 1H), 7.62 (t, J=2.7 Hz, 1H), 7.45 (d, J=8.6 Hz, 1H), 7.30 (s, 1H).

Example 24

1-[6-(4-tert-Butyl-phenylsulfanyl)-7-chloro-4-oxo-1,4-dihydro-quinazolin-2-yl]-1H-pyrazole-4-carboxylic acid

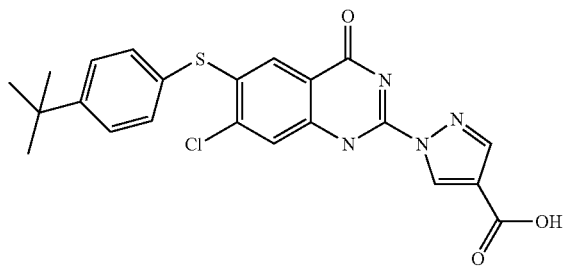 [SMILES: CC(C)(C)c1ccc(Sc2cc3c(=O)nc(-n4cc(C(=O)O)cn4)[nH]c3cc2Cl)cc1]

Step A: Preparation of 1-(4-tert-butyl-phenylsulfanyl)-2-chloro-4-nitro-benzene: Neat 1,8-diazabicyclo[5.4.0]undec-7-ene (DBU, 1.2 mL, 7.8 mmol) was added dropwise to a solution of 4-tert-butylthiophenol (0.95 g, 5.7 mmol), 3,4-dichloronitrobenzene (1.0 g, 5.2 mmol), and DMF (15 mL). The solution was stirred for 1 h at ambient temperature then 1 h at 60° C. The mixture was allowed to cool and was poured over ice. The resulting yellow precipitate was collected and dried. The crude product was used without further purification.

Step B: Preparation of 4-(4-tert-butyl-phenylsulfanyl)-3-chloroaniline: 1-(4-tert-butyl-phenylsulfanyl)-2-chloro-4-nitro-benzene was dissolved in acetone (15 mL), then saturated aqueous NH$_4$Cl (5 mL) was added and the mixture was cooled to 0° C. Solid zinc powder (3.7 g, 56 mmol) was added in portions over 10 min with rapid stirring. The mixture was allowed to warm to rt and was stirred 3 h. The mixture was diluted with EtOAc (250 mL), dried, and filtered through Celite®. Removal of solvent gave a yellow residue, which was used without further purification. MS (ESI): mass calcd. for $C_{16}H_{18}ClNS$, 291.1; m/z found 292.1 [M+H]$^+$. $^1$H NMR (500 MHz, DMSO-d$_6$): 7.33-7.21 (m, 3H), 6.95 (d, J=8.5, 2H), 6.77 (d, J=2.4, 1H), 6.55 (dd, J=8.4, 2.4, 1H), 5.80 (s, 2H), 1.22 (s, 9H).

Step C: Preparation of 1-[6-(4-tert-butyl-phenylsulfanyl)-7-chloro-4-oxo-1,4-dihydro-quinazolin-2-yl]-1H-pyrazole-4-carboxylic acid: The titled compound was prepared in a manner analogous to Example 17 using 4-(4-tert-butyl-phenylsulfanyl)-3-chloroaniline. MS (ESI): mass calcd. for $C_{22}H_{19}ClN_4O_3S$, 454.9; m/z found, 455.1 [M+H]$^+$. $^1$H NMR (500 MHz, DMSO-d$_6$): 13.01 (br s, 2H), 8.91 (s, 1H), 8.26 (s, 1H), 7.87 (s, 1H), 7.57 (d, J=8.5, 2H), 7.54 (s, 1H), 7.50 (d, J=8.4, 2H), 1.22 (s, 9H).

Example 25

1-(7-Chloro-4-oxo-6-phenylsulfanyl-1,4-dihydro-quinazolin-2-yl)-1H-pyrazole-4-carboxylic acid

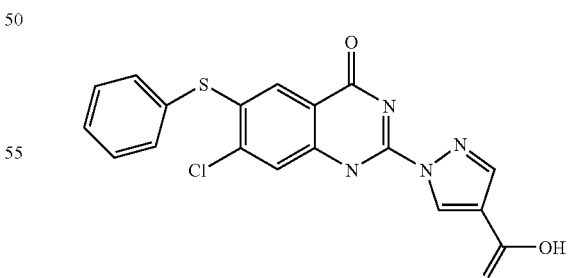

The titled compound was prepared in a manner analogous to Example 24 using thiophenol in step A. MS (ESI): mass calcd. for $C_{18}H_{11}ClN_4O_3S$, 398.0; m/z found, 399.0 [M+H]$^+$.

¹H NMR (500 MHz, DMSO-d₆): 13.04 (br s, 2H), 8.91 (s, 1H), 8.26 (s, 1H), 7.87 (s, 1H), 7.63-7.47 (m, 6H).

Example 26

1-[7-Chloro-6-(3,4-dimethoxy-phenylsulfanyl)-4-oxo-1,4-dihydro-quinazolin-2-yl]-1H-pyrazole-4-carboxylic acid

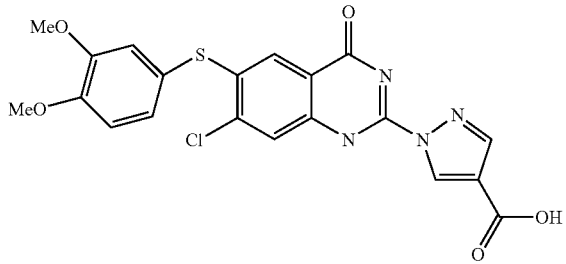 [SMILES: COc1ccc(Sc2cc3c(=O)nc(-n4cc(C(=O)O)cn4)[nH]c3cc2Cl)cc1OC]

The titled compound was prepared in a manner analogous to Example 24 using 3,4-dimethoxythiophenol in step A. MS (ESI): mass calcd. for $C_{20}H_{15}ClN_4O_5S$, 458.9 m/z found, 459.1 [M+H]⁺. ¹H NMR (500 MHz, DMSO-d₆): 13.02 (br s, 2H), 8.90 (s, 1H), 7.83 (s, 1H), 7.40 (s, 1H), 7.26-7.12 (m, 3H), 3.86 (s, 3H), 3.77 (s, 3H).

Example 27

1-[6-(2,6-Dimethyl-phenoxy)-7-methyl-4-oxo-3,4-dihydro-quinazolin-2-yl]-1H-pyrazole-4-carboxylic acid

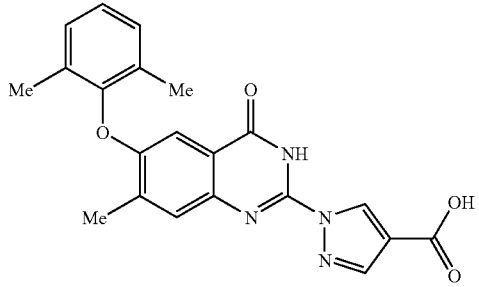 [SMILES: Cc1cc2nc(-n3cc(C(=O)O)cn3)[nH]c(=O)c2cc1Oc1c(C)cccc1C]

Step A: Preparation of 4-(2,6-dimethyl-phenoxy)-3-methyl-nitrobenzene. A solution of 2,6-dimethylphenol (0.87 g, 7.1 mmol), potassium carbonate (0.98 g, 7.1 mmol), 2-fluoro-5-nitrotoluene (1.0 g, 6.4 mmol) and DMF (20 mL) was stirred at 100° C. for 2 h. The reaction mixture was diluted with 100 mL water and extracted with 250 mL EtOAc. The organic layer was washed with brine, dried with sodium sulfate and concentrated to provide the crude titled compound (1.5 g, 92%). This material was used without purification: MS (ESI): mass calcd. for $C_{15}H_{15}NO_3$, 257.3; m/z found, 258.1 [M+H]⁺. ¹H NMR (400 MHz, CDCl₃): 8.16 (dd, J=2.8, 0.7 Hz, 1H), 7.92 (dd, J=9.1, 2.7 Hz, 1H), 7.18-7.07 (m, 3H), 6.33 (d, J=9.0 Hz, 1H), 2.50 (s, 3H), 2.09 (s, 6H).

Step B: Preparation of 4-(2,6-dimethyl-phenoxy)-3-methyl-aniline. Zinc dust (3.86 g, 59.1 mmol) was added to a stirred solution of 4-(2,6-dimethyl-phenoxy)-3-methyl-nitrobenzene (1.5 g, 5.9 mmol), acetone (20 mL) and saturated aqueous ammonium chloride (20 mL) at 0° C. The mixture was warmed to room temperature and stirred for 1 h. The reaction mixture was diluted with 200 mL EtOAc and filtered through diatomaceous earth. The organic layer was washed with brine, dried with sodium sulfate and concentrated to provide the crude titled compound (0.79 g, 59%). This material was used without purification: MS (ESI): mass calcd. for $C_{15}H_{17}NO$, 227.3; m/z found, 227.1 [M+H]⁺. ¹H NMR (500 MHz, CDCl₃): 7.07 (d, J=7.2 Hz, 2H), 7.01 (dd, J=8.3, 6.5 Hz, 1H), 6.60 (t, J=3.4 Hz, 1H), 6.31 (dd, J=8.5, 2.9 Hz, 1H), 6.06 (d, J=8.5 Hz, 1H), 3.36 (s, 2H), 2.34 (s, 3H), 2.11 (s, 6H).

Step C: Preparation of 1-{[4-(2,6-dimethyl-phenoxy)-3-methyl-phenylamino]-ethoxycarbonylimino-methyl}-1H-pyrazole-4-carboxylic acid ethyl ester. A solution of 4-(2,6-dimethyl-phenoxy)-3-methyl-aniline (0.80 g, 3.5 mmol), ethyl isothiocyanatoformate (0.40 mL, 3.5 mmol) and DCM (30 mL) was stirred at room temperature for 1 h. Ethyl pyrazole-4-carboxylate (0.54 g, 3.9 mmol) and DIC (0.54 mL, 3.5 mmol) were added, and the solution was stirred at room temperature for 16 h. The mixture was concentrated and purified by FCC (EtOAc/hexanes 0:100 to 50:50) to provide the titled compound (0.97 g, 60%). MS (ESI): mass calcd. for $C_{25}H_{28}N_4O_5$, 464.5; m/z found, 465.1 [M+H]⁺.

Step D: Preparation of 1-[6-(2,6-dimethyl-phenoxy)-7-methyl-4-oxo-3,4-dihydro-quinazolin-2-yl]-1H-pyrazole-4-carboxylic acid ethyl ester. Titanium (IV) chloride (0.25 mL, 2.3 mmol) was added to a solution of 1-{[4-(2,6-dimethyl-phenoxy)-3-methyl-phenylamino]-ethoxycarbonylimino-methyl}-1H-pyrazole-4-carboxylic acid ethyl ester (0.97 g, 2.1 mmol) and DCE (10 mL), and the resulting mixture was heated to 90° C. for 16 h. The reaction mixture was cooled to room temperature and poured into 50 mL EtOH. The mixture was stirred for 30 min and concentrated to dryness. The solid was and purified by FCC (CH₃CN/DCM, gradient 0:100 to 20:80) to provide the titled compound (0.28 g, 32%). MS (ESI): mass calcd. for $C_{23}H_{22}N_4O_4$, 418.4; m/z found, 419.2 [M+H]⁺. ¹H NMR (500 MHz, DMSO-d₆): 12.77 (s, 1H), 8.96 (s, 1H), 8.28 (s, 1H), 7.69 (s, 1H), 7.25 (d, J=7.4 Hz, 2H), 7.18 (dd, J=8.3, 6.7 Hz, 1H), 6.78 (s, 1H), 4.30 (q, J=7.1 Hz, 2H), 2.55 (s, 3H), 2.08 (s, 6H), 1.32 (t, J=7.1 Hz, 3H).

Step E: Preparation of 1-[6-(2,6-dimethyl-phenoxy)-7-methyl-4-oxo-3,4-dihydro-quinazolin-2-yl]-1H-pyrazole-4-carboxylic acid. A mixture of 1-[6-(2,6-dimethyl-phenoxy)-7-methyl-4-oxo-3,4-dihydro-quinazolin-2-yl]-1H-pyrazole-4-carboxylic acid ethyl ester (0.25 g, 0.60 mmol), 1M aq. KOH (5.0 mL) and THF (5.0 mL) was stirred for 4 h. The mixture was concentrated to remove the THF and the aqueous residue was acidified to pH 2 with 1M aq. HCl. The resulting precipitate was collected by filtration to provide the titled compound (0.22 g, 93%). MS (ESI): mass calcd. for $C_{21}H_{18}N_4O_4$, 390.1; m/z found, 391.1 [M+H]⁺. ¹H NMR (500 MHz, DMSO-d₆): 12.99 (s, 1H), 12.72 (s, 1H), 8.90 (d, J=13.2 Hz, 1H), 8.22 (s, 1H), 7.68 (s, 1H), 7.25 (d, J=7.4 Hz, 2H), 7.18 (dd, J=8.3, 6.7 Hz, 1H), 6.78 (s, 1H), 2.55 (s, 3H), 2.07 (d, J=8.2 Hz, 6H).

Example 28

1-[4-Oxo-6-(3,4,5-trimethoxy-phenoxy)-3,4-dihydro-quinazolin-2-yl]-1H-pyrazole-4-carboxylic acid

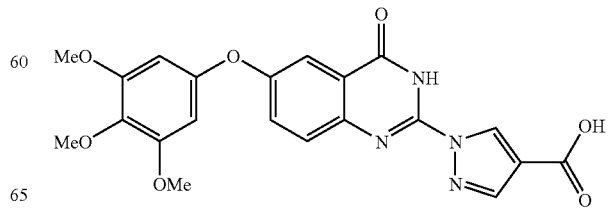

Step A: Preparation of 1-{[4-(3,4,5-trimethoxy-phenoxy)-phenylamino]-ethoxycarbonylimino-methyl}-1H-pyrazole-4-carboxylic acid ethyl ester. The titled compound was prepared in a manner analogous to Example 27, steps A-C using 3,4,5-trimethoxy-phenol and 4-fluoronitrobenzene in Step A. MS (ESI): mass calcd. for $C_{25}H_{28}N_4O_8$, 512.5; m/z found, 513.2 [M+FH]+.

Step B: Preparation of 1-[4-oxo-6-(3,4,5-trimethoxy-phenoxy)-3,4-dihydro-quinazolin-2-yl]-1H-pyrazole-4-carboxylic acid. The titled compound was prepared in a manner analogous to Example 27, steps D-E using chlorotrimethylsilane in place of titanium (IV) chloride in step D. MS (ESI): mass calcd. for $C_{21}H_{18}N_4O_7$, 438.1; m/z found, 439.1 [M+H]+. $^1$H NMR (500 MHz, DMSO-$d_6$): 12.99 (s, 1H), 12.89 (s, 1H), 8.94 (s, 1H), 8.24 (s, 1H), 7.73 (d, J=8.3 Hz, 1H), 7.57 (dd, J=8.8, 2.9 Hz, 1H), 7.48 (s, 1H), 6.50 (s, 2H), 3.74 (s, 6H), 3.68 (s, 3H).

Example 29

1-[6-(naphthalen-1-yloxy)-4-oxo-3,4-dihydro-quinazolin-2-yl]-1H-pyrazole-4-carboxylic acid

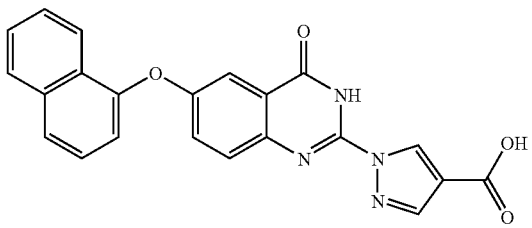 [SMILES: O=C(O)c1cnn(-c2nc3ccc(Oc4cccc5ccccc45)cc3c(=O)[nH]2)c1]

Step A: Preparation of 1-{Ethoxycarbonylimino-[4-(naphthalen-1-yloxy)-phenylamino]-methyl}-1H-pyrazole-4-carboxylic acid ethyl ester. The titled compound was prepared in a manner analogous to Example 27, steps A-C using 1-napthol and 4-fluoronitrobenzene in step A. MS (ESI): mass calcd. for $C_{26}H_{24}N_4O_5$, 472.2; m/z found, 473.2 [M+FH]+.

Step B: Preparation of 1-[6-(naphthalen-1-yloxy)-4-oxo-3,4-dihydro-quinazolin-2-yl]-1H-pyrazole-4-carboxylic acid ethyl ester. Titanium (IV) chloride (0.86 mL, 7.8 mmol) was added to a solution of 1-{ethoxycarbonylimino-[4-(naphthalen-1-yloxy)-phenylamino]methyl}-1H-pyrazole-4-carboxylic acid ethyl ester (0.74 g, 1.6 mmol) and DCE (10 mL), and the resulting mixture was heated to 90° C. for 16 h. The reaction mixture was cooled to room temperature and poured into 50 mL EtOH. The mixture was stirred for 30 min and the solid precipitate was collected by vacuum filtration (0.46 g, 69%). MS (ESI): mass calcd. for $C_{24}H_{18}N_4O_4$, 426.1; m/z found, 427.1 [M+H]+. $^1$H NMR (400 MHz, DMSO-$d_6$): 12.87 (s, 1H), 8.99 (s, 1H), 8.29 (s, 1H), 8.05 (d, J=7.5 Hz, 1H), 8.02 (d, J=8.3 Hz, 1H), 7.86 (d, J=8.3 Hz, 1H), 7.79 (d, J=7.6 Hz, 1H), 7.70 (dd, J=8.9, 2.9 Hz, 1H), 7.64-7.60 (m, 1H), 7.60-7.53 (m, 2H), 7.39 (d, J=2.8 Hz, 1H), 7.23 (d, J=7.4 Hz, 1H), 4.30 (q, J=7.1 Hz, 2H), 1.32 (t, J=7.1 Hz, 3H).

Step C: Preparation of 1-[6-(naphthalen-1-yloxy)-4-oxo-3,4-dihydro-quinazolin-2-yl]-1H-pyrazole-4-carboxylic acid. A mixture of 1-[6-(naphthalen-1-yloxy)-4-oxo-3,4-dihydro-quinazolin-2-yl]-1H-pyrazole-4-carboxylic acid ethyl ester (0.42 g, 0.99 mmol), 1M aq. KOH (5.0 mL) and THF (5.0 mL) was stirred for 4 h. The mixture was concentrated to remove the THF and the aqueous residue was acidified to pH 2 with 1M aq. HCl. The resulting precipitate was collected by filtration to provide the titled compound (0.34 g, 86%). MS (ESI): mass calcd. for $C_{22}H_{14}N_4O_4$, 398.1; m/z found, 399.1 [M+H]+. $^1$H NMR (500 MHz, DMSO-$d_6$): 12.99 (s, 1H), 12.86 (s, 1H), 8.94 (s, 1H), 8.24 (s, 1H), 8.06 (d, J=8.1 Hz, 1H), 8.02 (d, J=8.3 Hz, 1H), 7.87 (d, J=8.2 Hz, 1H), 7.78 (d, J=8.2 Hz, 1H), 7.71 (dd, J=8.9, 2.9 Hz, 1H), 7.62 (t, J=7.5 Hz, 1H), 7.60-7.54 (m, 2H), 7.38 (s, 1H), 7.24 (d, J=7.4 Hz, 1H).

Example 30

1-[6-(3-Chloro-phenoxy)-4-oxo-3,4-dihydro-quinazolin-2-yl]-1H-pyrazole-4-carboxylic acid

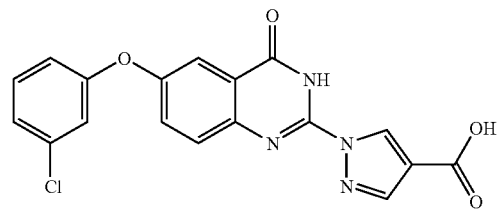

The titled compound was prepared in a manner analogous to Example 29 using 3-chlorophenol and 4-fluoronitrobenzene in step A. MS (ESI): mass calcd. for $C_{18}H_{11}ClN_4O_4$, 382.1; m/z found, 383.1 [M+H]+. $^1$H NMR (500 MHz, DMSO-$d_6$): 13.00 (s, 1H), 12.95 (s, 1H), 8.95 (s, 1H), 8.25 (s, 1H), 7.77 (d, J=8.6 Hz, 1H), 7.63 (dd, J=8.8, 2.9 Hz, 1H), 7.55 (s, 1H), 7.48 (t, J=8.2 Hz, 1H), 7.30 (d, J=8.0 Hz, 1H), 7.24 (s, 1H), 7.11 (d, J=8.2 Hz, 1H).

Example 31

1-[6-(3-Methoxy-phenoxy)-4-oxo-3,4-dihydro-quinazolin-2-yl]-1H-pyrazole-4-carboxylic acid

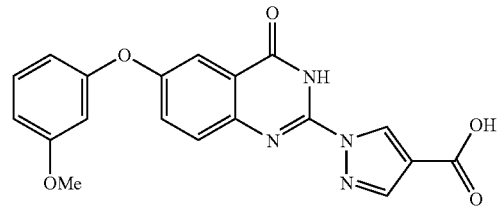 [SMILES: COc1cccc(Oc2ccc3nc(-n4cc(C(=O)O)cn4)[nH]c(=O)c3c2)c1]

The titled compound was prepared in a manner analogous to Example 28 using 3-methoxyphenol and 4-fluoronitrobenzene in step A. MS (ESI): mass calcd. for $C_{19}H_{14}N_4O_5$, 378.1; m/z found, 379.1 [M+H]+. $^1$H NMR (500 MHz, DMSO-$d_6$): 12.99 (s, 1H), 12.89 (s, 1H), 8.94 (s, 1H), 8.25 (s, 1H), 7.74 (d, J=8.7 Hz, 1H), 7.60 (dd, J=8.9, 2.9 Hz, 1H), 7.49 (s, 1H), 7.37 (t, J=8.2 Hz, 1H), 6.83 (dd, J=8.3, 1.9 Hz, 1H), 6.73 (s, 1H), 6.69 (d, J=7.8 Hz, 1H), 3.77 (s, 3H).

Example 32

1-[6-(4-Fluoro-phenoxy)-4-oxo-3,4-dihydro-quinazolin-2-yl]-1H-pyrazole-4-carboxylic acid

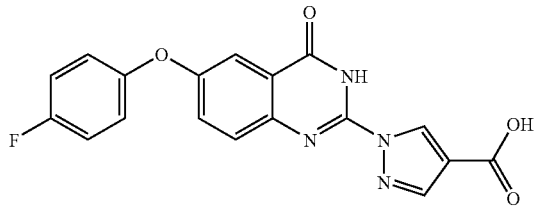 [SMILES: O=C(O)c1cnn(-c2nc3ccc(Oc4ccc(F)cc4)cc3c(=O)[nH]2)c1]

The titled compound was prepared in a manner analogous to Example 29 using 4-fluorophenol and 4-fluoronitrobenzene in step A. MS (ESI): mass calcd. for $C_{18}H_{11}FN_4O_4$, 366.1; m/z found, 367.1 [M+H]+. 1H NMR (500 MHz, DMSO-$d_6$): 12.89 (s, 2H), 8.94 (s, 1H), 8.25 (s, 1H), 7.76 (d, J=7.7 Hz, 1H), 7.59 (dd, J=8.9, 2.9 Hz, 1H), 7.43 (d, J=2.9 Hz, 1H), 7.35-7.28 (m, 2H), 7.25-7.19 (m, 2H).

Example 33

1-[6-(2-Fluoro-phenoxy)-4-oxo-3,4-dihydro-quinazolin-2-yl]-1H-pyrazole-4-carboxylic acid

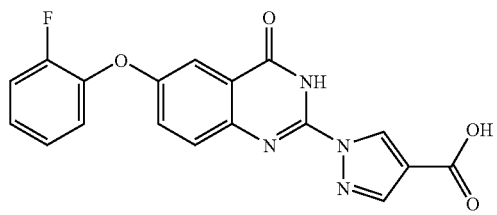 [SMILES: O=C(O)c1cnn(-c2nc3ccc(Oc4ccccc4F)cc3c(=O)[nH]2)c1]

The titled compound was prepared in a manner analogous to Example 29 using 2-fluorophenol and 4-fluoronitrobenzene in step A. MS (ESI): mass calcd. for $C_{18}H_{11}FN_4O_4$, 366.1; m/z found, 367.1 [M+H]+. 1H NMR (500 MHz, DMSO-$d_6$): 12.99 (s, 1H), 12.91 (s, 1H), 8.94 (s, 1H), 8.25 (s, 1H), 7.76 (d, J=8.3 Hz, 1H), 7.63 (dd, J=8.9, 3.0 Hz, 1H), 7.53-7.44 (m, 1H), 7.42-7.28 (m, 4H).

Example 34

1-[6-(3-Fluoro-phenoxy)-4-oxo-3,4-dihydro-quinazolin-2-yl]-1H-pyrazole-4-carboxylic acid

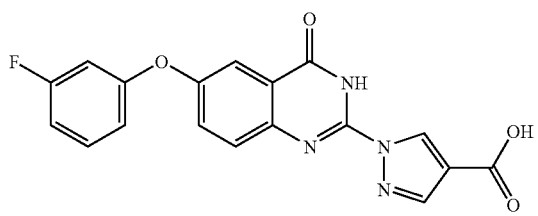 [SMILES: O=C(O)c1cnn(-c2nc3ccc(Oc4cccc(F)c4)cc3c(=O)[nH]2)c1]

The titled compound was prepared in a manner analogous to Example 29 using 3-fluorophenol and 4-fluoronitrobenzene in step A. MS (ESI): mass calcd. for $C_{18}H_{11}FN_4O_4$, 366.1; m/z found, 367.1 [M+H]+. 1H NMR (500 MHz, DMSO-$d_6$): 13.00 (s, 1H), 12.97-12.79 (m, 1H), 8.95 (s, 1H), 8.26 (s, 1H), 7.76 (s, 1H), 7.63 (dd, J=8.8, 2.9 Hz, 1H), 7.56 (s, 1H), 7.49 (dd, J=15.1, 8.2 Hz, 1H), 7.07 (dd, J=17.0, 9.2 Hz, 2H), 6.97 (d, J=8.0 Hz, 1H).

Example 35

1-[6-(3,5-Di-tert-butyl-phenoxy)-4-oxo-3,4-dihydro-quinazolin-2-yl]-1H-pyrazole-4-carboxylic acid

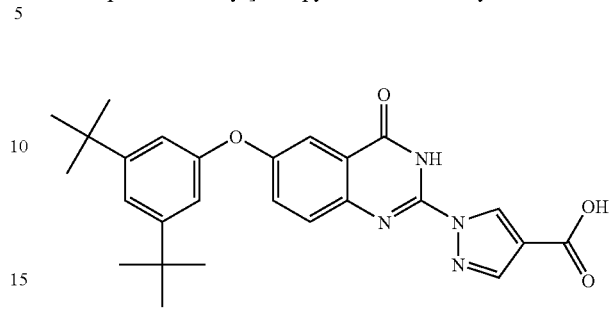

The titled compound was prepared in a manner analogous to Example 29 using 3,5-di-tert-butylphenol and 4-fluoronitrobenzene in step A. MS (ESI): mass calcd. for $C_{26}H_{28}N_4O_4$, 460.2; m/z found, 461.2 [M+H]+. 1H NMR (500 MHz, DMSO-$d_6$): 12.99 (s, 1H), 12.93-12.74 (m, 1H), 8.94 (s, 1H), 8.25 (s, 1H), 7.73 (s, 1H), 7.55 (dd, J=8.8, 2.8 Hz, 1H), 7.48 (s, 1H), 7.28 (s, 1H), 6.96 (d, J=1.2 Hz, 2H), 1.28 (s, 18H).

Example 36

1-(4-Oxo-6-m-tolyloxy-3,4-dihydro-quinazolin-2-yl)-1H-pyrazole-4-carboxylic acid

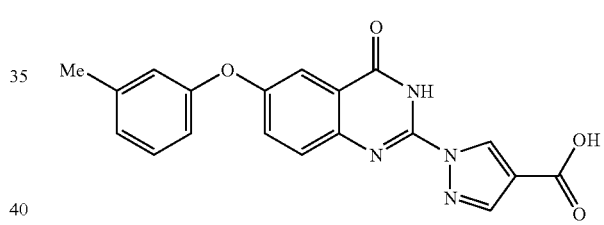

The titled compound was prepared in a manner analogous to Example 29 using 3-methylphenol and 4-fluoronitrobenzene in step A. MS (ESI): mass calcd. for $C_{19}H_{14}N_4O_4$, 362.1; m/z found, 363.1 [M+H]+. 1H NMR (400 MHz, DMSO-$d_6$): 12.96 (s, 1H), 12.84 (s, 1H), 8.94 (s, 1H), 8.24 (s, 1H), 7.74 (d, J=7.5 Hz, 1H), 7.58 (dd, J=8.9, 2.9 Hz, 1H), 7.46 (d, J=2.6 Hz, 1H), 7.35 (t, J=7.8 Hz, 1H), 7.06 (d, J=7.5 Hz, 1H), 6.97 (s, 1H), 6.93 (d, J=8.0 Hz, 1H), 2.33 (s, 3H).

Example 37

1-(4-Oxo-6-o-tolyloxy-3,4-dihydro-quinazolin-2-yl)-1H-pyrazole-4-carboxylic acid

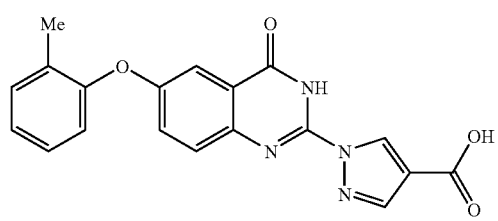 [SMILES: Cc1ccccc1Oc1ccc2nc(-n3cc(C(=O)O)cn3)[nH]c(=O)c2c1]

The titled compound was prepared in a manner analogous to Example 29 using 2-methylphenol and 4-fluoronitrobenzene in step A. MS (ESI): mass calcd. for $C_{19}H_{14}N_4O_4$, 362.1; m/z found, 363.1 [M+H]$^+$. $^1$H NMR (500 MHz, DMSO-d$_6$): 12.99 (s, 1H), 12.86 (s, 1H), 8.93 (s, 1H), 8.23 (s, 1H), 7.74 (d, J=9.0 Hz, 1H), 7.57 (dd, J=8.9, 3.0 Hz, 1H), 7.40 (d, J=7.4 Hz, 1H), 7.31 (t, J=7.1 Hz, 1H), 7.27 (s, 1H), 7.22 (t, J=7.0 Hz, 1H), 7.08 (d, J=7.9 Hz, 1H), 2.17 (s, 3H).

Example 38

1-[6-(2,6-Dichloro-phenoxy)-4-oxo-3,4-dihydro-quinazolin-2-yl]-1H-pyrazole-4-carboxylic acid

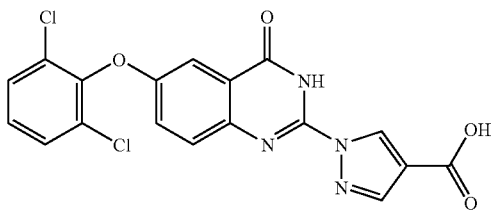 [SMILES: O=C(O)c1cnn(-c2nc3ccc(Oc4c(Cl)cccc4Cl)cc3c(=O)[nH]2)c1]

The titled compound was prepared in a manner analogous to Example 29 using 2,6-dichlorophenol and 4-fluoronitrobenzene in step A. MS (ESI): mass calcd. for $C_{18}H_{10}Cl_2N_4O_4$, 416.0; m/z found, 417.0 [M+H]$^+$. $^1$H NMR (400 MHz, DMSO-d$_6$): 12.94 (s, 2H), 8.93 (s, 1H), 8.23 (s, 1H), 7.75 (s, 1H), 7.72 (d, J=8.1 Hz, 2H), 7.60 (dd, J=8.9, 3.1 Hz, 1H), 7.45 (t, J=8.2 Hz, 1H), 7.17 (s, 1H).

Example 39

1-[6-(2,4-Dichloro-phenoxy)-4-oxo-3,4-dihydro-quinazolin-2-yl]-1H-pyrazole-4-carboxylic acid

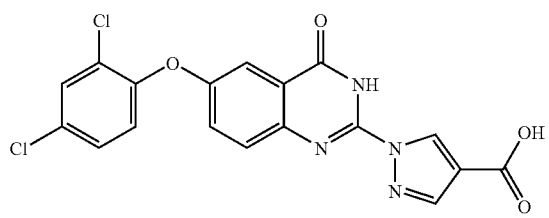 [SMILES: O=C(O)c1cnn(-c2nc3ccc(Oc4ccc(Cl)cc4Cl)cc3c(=O)[nH]2)c1]

The titled compound was prepared in a manner analogous to Example 29 using 2,4-dichlorophenol and 4-fluoronitrobenzene in step A. MS (ESI): mass calcd. for $C_{18}H_{10}Cl_2N_4O_4$, 416.0; m/z found, 417.0 [M+H]$^+$. $^1$H NMR (400 MHz, DMSO-d$_6$): 12.96 (s, 1H), 12.94-12.73 (m, 1H), 8.94 (s, 1H), 8.24 (s, 1H), 7.85 (d, J=2.5 Hz, 1H), 7.76 (d, J=8.2 Hz, 1H), 7.61 (dd, J=8.9, 3.0 Hz, 1H), 7.53 (dd, J=8.8, 2.5 Hz, 1H), 7.39 (s, 1H), 7.33 (d, J=8.8 Hz, 1H).

Example 40

1-[6-(2,5-Dichloro-phenoxy)-4-oxo-3,4-dihydro-quinazolin-2-yl]-1H-pyrazole-4-carboxylic acid

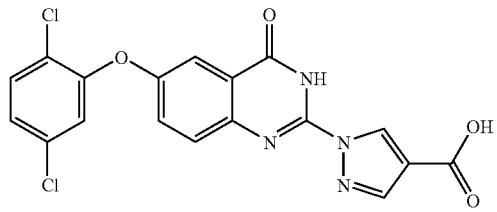

The titled compound was prepared in a manner analogous to Example 29 using 2,5-dichlorophenol and 4-fluoronitrobenzene in step A. MS (ESI): mass calcd. for $C_{18}H_{10}Cl_2N_4O_4$, 416.0; m/z found, 417.0 [M+H]$^+$. $^1$H NMR (400 MHz, DMSO-d$_6$): 12.95 (s, 2H), 8.94 (s, 1H), 8.25 (s, 1H), 7.78 (d, J=8.6 Hz, 1H), 7.71 (d, J=8.8 Hz, 1H), 7.63 (dd, J=8.9, 3.0 Hz, 1H), 7.42 (d, J=4.1 Hz, 2H), 7.39 (d, J=2.4 Hz, 1H).

Example 41

1-[6-(4-Methoxy-phenoxy)-4-oxo-3,4-dihydro-quinazolin-2-yl]-1H-pyrazole-4-carboxylic acid

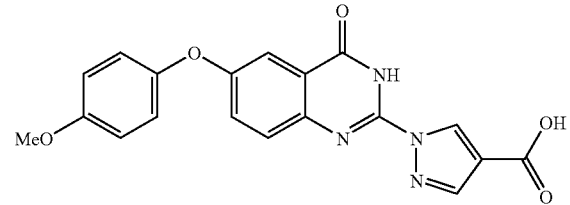 [SMILES: COc1ccc(Oc2ccc3nc(-n4cc(C(=O)O)cn4)[nH]c(=O)c3c2)cc1]

The titled compound was prepared in a manner analogous to Example 29 using 4-methoxyphenol and 4-fluoronitrobenzene in step A, and with the addition of 1.5 eq. of 2,6-di-tert-butylpyridine in step D. MS (ESI): mass calcd. for $C_{19}H_{14}N_4O_5$, 378.1; m/z found, 379.1 [M+H]$^+$. $^1$H NMR (400 MHz, DMSO-d$_6$): 12.93 (s, 1H), 12.88-12.67 (m, 1H), 8.93 (s, 1H), 8.23 (s, 1H), 7.72 (d, J=8.1 Hz, 1H), 7.55 (dd, J=8.9, 2.9 Hz, 1H), 7.36 (d, J=2.8 Hz, 1H), 7.17-7.08 (m, 2H), 7.08-6.99 (m, 2H), 3.79 (s, 3H).

Example 42

1-[6-(2,6-Dimethyl-phenoxy)-4-oxo-3,4-dihydro-quinazolin-2-yl]-1H-pyrazole-4-carboxylic acid

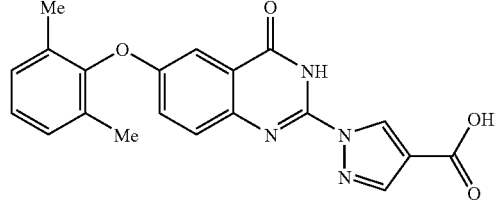 [SMILES: Cc1cccc(C)c1Oc1ccc2nc(-n3cc(C(=O)O)cn3)[nH]c(=O)c2c1]

The titled compound was prepared in a manner analogous to Example 29 using 2,6-dimethylphenol and 4-fluoronitrobenzene in step A. MS (ESI): mass calcd. for $C_{20}H_{16}N_4O_4$, 376.1; m/z found, 377.1 [M+H]+. 1H NMR (500 MHz, DMSO-d6): 12.82 (s, 2H), 8.92 (s, 1H), 8.23 (s, 1H), 7.74 (d, J=8.8 Hz, 1H), 7.54 (dd, J=8.9, 3.0 Hz, 1H), 7.24 (d, J=7.4 Hz, 2H), 7.18 (dd, J=8.3, 6.6 Hz, 1H), 7.08 (s, 1H), 2.09 (s, 6H).

Example 43

1-[6-(Naphthalen-2-yloxy)-4-oxo-3,4-dihydro-quinazolin-2-yl]-1H-pyrazole-4-carboxylic acid

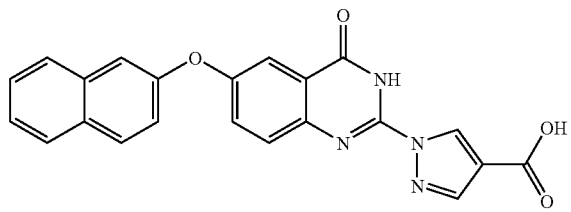

The titled compound was prepared in a manner analogous to Example 29 using 2-napthol and 4-fluoronitrobenzene in step A. MS (ESI): mass calcd. for C22H14N4O4, 398.1; m/z found, 399.1 [M+H]+. 1H NMR (500 MHz, DMSO-d6): 13.00 (s, 1H), 12.91 (s, 1H), 8.95 (s, 1H), 8.25 (s, 1H), 8.05 (d, J=8.9 Hz, 1H), 7.97 (d, J=7.9 Hz, 1H), 7.89 (d, J=8.0 Hz, 1H), 7.78 (d, J=8.1 Hz, 1H), 7.68 (dd, J=8.8, 2.9 Hz, 1H), 7.59 (s, 1H), 7.57-7.47 (m, 3H), 7.39 (dd, J=8.9, 2.4 Hz, 1H).

Example 44

1-[4-Oxo-6-(5,6,7,8-tetrahydro-naphthalen-1-yloxy)-3,4-dihydro-quinazolin-2-yl]-1H-pyrazole-4-carboxylic acid

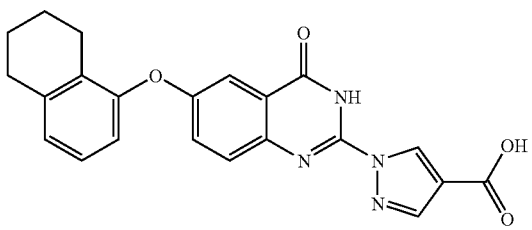 [SMILES: O=C(O)c1cnn(-c2nc3ccc(Oc4cccc5c4CCCC5)cc3c(=O)[nH]2)c1]

The titled compound was prepared in a manner analogous to Example 29 using 5,6,7,8-tetrahydro-naphthalen-1-ol and 4-fluoronitrobenzene in step A. MS (ESI): mass calcd. for C22H18N4O4, 402.1; m/z found, 403.1 [M+H]+. 1H NMR (500 MHz, DMSO-d6): 13.00 (s, 1H), 12.83 (s, 1H), 8.93 (s, 1H), 8.24 (s, 1H), 7.73 (d, J=8.6 Hz, 1H), 7.55 (dd, J=8.8, 2.8 Hz, 1H), 7.29 (s, 1H), 7.20 (t, J=7.8 Hz, 1H), 7.03 (d, J=7.6 Hz, 1H), 6.87 (d, J=7.9 Hz, 1H), 2.84-2.76 (m, 2H), 2.59-2.52 (m, 2H), 1.76-166 (m, 4H).

Example 46

1-[6-(4-Chloro-phenoxy)-4-oxo-3,4-dihydro-quinazolin-2-yl]-1H-pyrazole-4-carboxylic acid

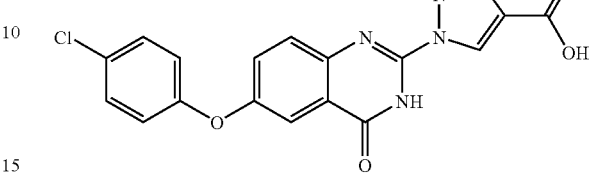

The titled compound was prepared in a manner analogous to Example 29 steps C-E using 4-(4-chloro-phenoxy)-phenylamine in step C. MS (ESI): mass calcd. for C18H11ClN4O4, 382.1; m/z found, 383.2 [M+H]+. 1H NMR (500 MHz, DMSO-d6): 13.00 (s, 1H), 12.93 (s, 1H), 8.95 (s, 1H), 8.25 (s, 1H), 7.76 (d, J=7.4 Hz, 1H), 7.62 (dd, J=8.8, 2.9 Hz, 1H), 7.51 (d, J=8.9 Hz, 3H), 7.18 (d, J=8.7 Hz, 2H).

Example 47

1-(4-Oxo-6-p-tolyloxy-3,4-dihydro-quinazolin-2-yl)-1H-pyrazole-4-carboxylic acid

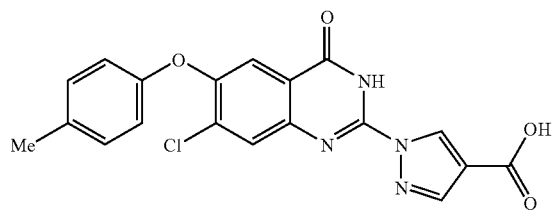 [SMILES: Cc1ccc(Oc2cc3c(=O)[nH]c(-n4cc(C(=O)O)cn4)nc3cc2Cl)cc1]

The titled compound was prepared in a manner analogous to Example 29 steps C-E using 4-p-tolyloxy-phenylamine in step C. MS (ESI): mass calcd. for C19H14N4O4, 362.1; m/z found, 363.1 [M+H]+. 1H NMR (500 MHz, DMSO-d6): 12.99 (s, 1H), 12.87 (s, 1H), 8.93 (s, 1H), 8.24 (s, 1H), 7.73 (d, J=8.9 Hz, 1H), 7.58 (dd, J=8.8, 2.9 Hz, 1H), 7.40 (s, 1H), 7.28 (d, J=8.2 Hz, 2H), 7.06 (d, J=8.3 Hz, 2H), 2.34 (s, 3H).

Example 48

1-[7-Chloro-6-(4-chloro-phenoxy)-4-oxo-3,4-dihydro-quinazolin-2-yl]-1H-pyrazole-4-carboxylic acid The titled compound was prepared in a manner analogous to Example 29 steps C-E using 3-chloro-4-(4-chloro-phenoxy)-phenylamine in step C. MS (ESI): mass calcd. for $C_{18}H_{10}Cl_2N_4O_4$, 416.0; m/z found, 417.0 [M+H]$^+$. $^1$H NMR (500 MHz, DMSO-d$_6$): 13.04 (s, 2H), 8.93 (s, 1H), 8.27 (s, 1H), 7.98 (s, 1H), 7.56 (s, 1H), 7.52 (d, J=8.9 Hz, 2H), 7.17 (d, J=8.8 Hz, 2H).

Example 49

1-[7-Chloro-6-(2,6-dimethyl-phenoxy)-4-oxo-3,4-dihydro-quinazolin-2-yl]-1H-pyrazole-4-carboxylic acid

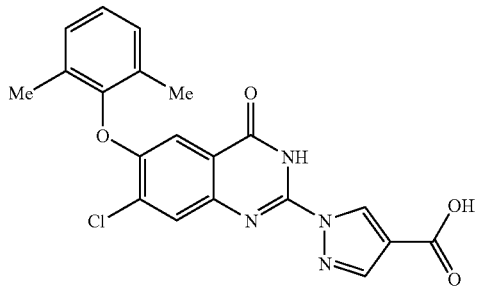

The titled compound was prepared in a manner analogous to Example 29 using 2,6-dimethylphenol and 2-chloro-1-fluoro-4-nitro-benzene in step A. MS (ESI): mass calcd. for $C_{20}H_{15}ClN_4O_4$, 410.1; m/z found, 411.1 [M+H]$^+$. $^1$H NMR (500 MHz, DMSO-d$_6$): 13.01 (s, 2H), 8.91 (s, 1H), 8.25 (s, 1H), 7.99 (s, 1H), 7.28 (d, J=7.3 Hz, 2H), 7.22 (dd, J=8.4, 6.5 Hz, 1H), 6.92 (s, 1H), 2.09 (s, 6H).

Example 50

1-[6-(2,6-Dichloro-phenoxy)-7-fluoro-4-oxo-3,4-dihydro-quinazolin-2-yl]-1H-pyrazole-4-carboxylic acid

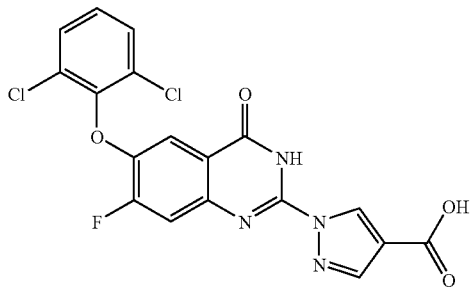 [SMILES: O=C(O)c1cnn(-c2nc3cc(F)c(Oc4c(Cl)cccc4Cl)cc3c(=O)[nH]2)c1]

The titled compound was prepared in a manner analogous to Example 29 using 2,6-dichlorophenol and 3,4-difluoronitrobenzene in step A. MS (ESI): mass calcd. for $C_{18}H_9Cl_2FN_4O_4$, 434.0; m/z found, 435.0 [M+H]$^+$. $^1$H NMR (400 MHz, DMSO-d$_6$): 12.98 (s, 2H), 8.91 (s, 1H), 8.25 (s, 1H), 7.80 (d, J=11.4 Hz, 1H), 7.75 (d, J=8.2 Hz, 2H), 7.49 (t, J=8.2 Hz, 1H), 7.07 (d, J=8.9 Hz, 1H).

Example 51

1-[6-(2,6-Dimethyl-phenoxy)-7-fluoro-4-oxo-3,4-dihydro-quinazolin-2-yl]-1H-pyrazole-4-carboxylic acid

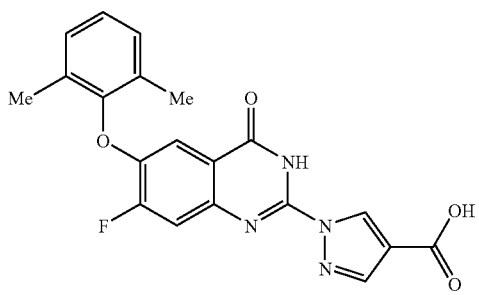 [SMILES: Cc1cccc(C)c1Oc1cc2c(=O)[nH]c(-n3cc(C(=O)O)cn3)nc2cc1F]

The titled compound was prepared in a manner analogous to Example 29 using 2,6-dimethylphenol and 3,4-difluoronitrobenzene in step A. MS (ESI): mass calcd. for $C_{20}H_{15}FN_4O_4$, 394.1; m/z found, 395.1 [M+H]$^+$. $^1$H NMR (400 MHz, DMSO-d$_6$): 12.92 (s, 2H), 8.90 (s, 1H), 8.23 (s, 1H), 7.74 (d, J=11.6 Hz, 1H), 7.27 (d, J=6.7 Hz, 2H), 7.21 (dd, J=8.7, 6.0 Hz, 1H), 6.97 (d, J=9.1 Hz, 1H), 2.11 (s, 6H).

Example 52

1-[7-Fluoro-6-(naphthalen-2-yloxy)-4-oxo-3,4-dihydro-quinazolin-2-yl]-1H-pyrazole-4-carboxylic acid

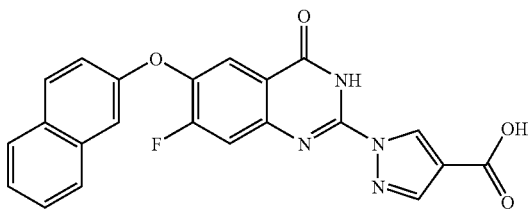 [SMILES: O=C(O)c1cnn(-c2nc3cc(F)c(Oc4ccc5ccccc5c4)cc3c(=O)[nH]2)c1]

The titled compound was prepared in a manner analogous to Example 29 using 2-napthol and 3,4-difluoronitrobenzene in step A. MS (ESI): mass calcd. for $C_{22}H_{13}FN_4O_4$, 416.1; m/z found, 417.1 [M+H]$^+$. $^1$H NMR (500 MHz, DMSO-d$_6$): 13.04 (s, 2H), 8.94 (s, 1H), 8.27 (s, 1H), 8.05 (d, J=8.9 Hz, 1H), 7.97 (d, J=8.0 Hz, 1H), 7.87 (d, J=8.1 Hz, 1H), 7.78 (d, J=11.3 Hz, 1H), 7.68 (d, J=8.8 Hz, 1H), 7.55 (s, 1H), 7.54-7.52 (m, 1H), 7.50 (dd, J=10.8, 4.1 Hz, 1H), 7.44 (dd, J=8.9, 2.5 Hz, 1H).

Example 53

1-[7-Chloro-6-(naphthalen-1-yloxy)-4-oxo-3,4-dihydro-quinazolin-2-yl]-1H-pyrazole-4-carboxylic acid

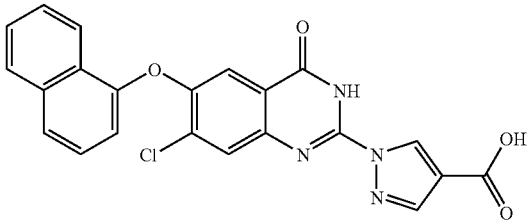 [SMILES: O=C(O)c1cnn(-c2nc3cc(Cl)c(Oc4cccc5ccccc45)cc3c(=O)[nH]2)c1]

The titled compound was prepared in a manner analogous to Example 29 using 1-napthol and 2-chloro-1-fluoro-4-nitro-benzene in step A. MS (ESI): mass calcd. for $C_{22}H_{13}ClN_4O_4$, 432.1; m/z found, 433.1 [M+H]$^+$. $^1$H NMR (500 MHz, DMSO-d$_6$): 13.03 (s, 2H), 8.93 (s, 1H), 8.26 (s, 1H), 8.07 (d, J=8.2 Hz, 1H), 8.01 (d, J=7.7 Hz, 2H), 7.88 (d, J=8.2 Hz, 1H), 7.60 (ddd, J=24.5, 15.4, 7.5 Hz, 3H), 7.37 (s, 1H), 7.19 (d, J=7.5 Hz, 1H).

Example 54

1-[7-Chloro-6-(naphthalen-2-yloxy)-4-oxo-3,4-dihydro-quinazolin-2-yl]-1H-pyrazole-4-carboxylic acid

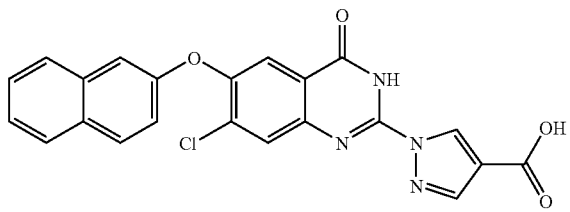 [SMILES: O=C(O)c1cnn(-c2nc3cc(Cl)c(Oc4ccc5ccccc5c4)cc3c(=O)[nH]2)c1]

The titled compound was prepared in a manner analogous to Example 29 using 2-napthol and 2-chloro-1-fluoro-4-nitro-benzene in step A. MS (ESI): mass calcd. for $C_{22}H_{13}ClN_4O_4$, 432.1; m/z found, 433.1 [M+H]$^+$. $^1$H NMR (500 MHz, DMSO-d$_6$): 13.05 (s, 2H), 8.94 (s, 1H), 8.27 (s, 1H), 8.06 (d, J=8.9 Hz, 1H), 8.01 (s, 1H), 7.98 (d, J=8.0 Hz, 1H), 7.88 (d, J=7.9 Hz, 1H), 7.58 (s, 1H), 7.57-7.48 (m, 3H), 7.42 (dd, J=8.9, 2.4 Hz, 1H).

Example 55

1-[7-Chloro-4-oxo-6-(5,6,7,8-tetrahydro-naphthalen-1-yloxy)-3,4-dihydro-quinazolin-2-yl]-1H-pyrazole-4-carboxylic acid

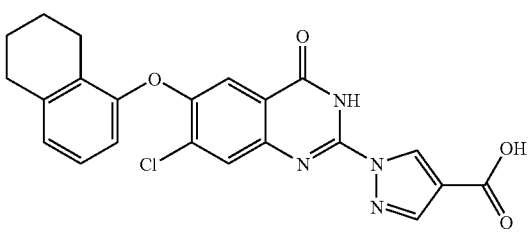 [SMILES: O=C(O)c1cnn(-c2nc3cc(Cl)c(Oc4cccc5c4CCCC5)cc3c(=O)[nH]2)c1]

The titled compound was prepared in a manner analogous to Example 29 using 5,6,7,8-tetrahydro-naphthalen-1-ol and 2-chloro-1-fluoro-4-nitro-benzene in step A. MS (ESI): mass calcd. for $C_{22}H_{17}ClN_4O_4$, 436.1; m/z found, 437.1 [M+H]$^+$. $^1$H NMR (500 MHz, DMSO-d$_6$): 13.04 (s, 2H), 8.92 (s, 1H), 8.25 (s, 1H), 7.96 (s, 1H), 7.27 (s, 1H), 7.21 (t, J=7.8 Hz, 1H), 7.05 (d, J=7.6 Hz, 1H), 6.86 (d, J=7.9 Hz, 1H), 2.84-2.78 (m, 2H), 2.59-2.52 (m, 2H), 1.77-1.67 (m, 4H).

Example 56

1-[7-Fluoro-6-(3-fluoro-phenoxy)-4-oxo-3,4-dihydro-quinazolin-2-yl]-1H-pyrazole-4-carboxylic acid

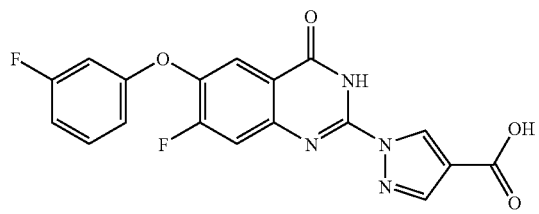 [SMILES: O=C(O)c1cnn(-c2nc3cc(F)c(Oc4cccc(F)c4)cc3c(=O)[nH]2)c1]

The titled compound was prepared in a manner analogous to Example 29 using 3-fluorophenol and 3,4-difluoronitrobenzene in step A. MS (ESI): mass calcd. for $C_{18}H_{10}F_2N_4O_4$, 384.1; m/z found, 385.1 [M+H]$^+$. $^1$H NMR (400 MHz, DMSO-d$_6$): 13.08 (s, 2H), 8.94 (s, 1H), 8.28 (s, 1H), 7.76 (d, J=11.4 Hz, 1H), 7.72 (d, J=8.8 Hz, 1H), 7.53-7.44 (m, 1H), 7.14-7.05 (m, 2H), 7.00-6.95 (m, 1H).

Example 57

1-[7-Fluoro-6-(naphthalen-1-yloxy)-4-oxo-3,4-dihydro-quinazolin-2-yl]-1H-pyrazole-4-carboxylic acid

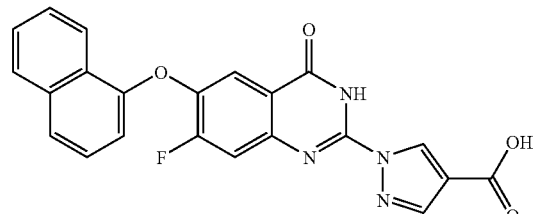

The titled compound was prepared in a manner analogous to Example 29 using 1-napthol and 3,4-difluoronitrobenzene in step A. MS (ESI): mass calcd. for $C_{22}H_{13}FN_4O_4$, 416.1; m/z found, 417.1 [M+H]$^+$. $^1$H NMR (400 MHz, DMSO-d$_6$): 13.05 (s, 2H), 8.93 (s, 1H), 8.26 (s, 1H), 8.08 (t, J=9.4 Hz, 2H), 7.86 (d, J=8.3 Hz, 1H), 7.80 (d, J=11.4 Hz, 1H), 7.63 (td, J=13.7, 5.9 Hz, 2H), 7.55 (t, J=7.9 Hz, 1H), 7.48 (d, J=8.9 Hz, 1H), 7.19 (d, J=7.5 Hz, 1H).

Example 58

1-[7-Fluoro-6-(indan-5-yloxy)-4-oxo-3,4-dihydro-quinazolin-2-yl]-1H-pyrazole-4-carboxylic acid

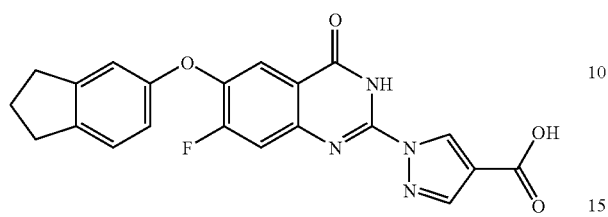

The titled compound was prepared in a manner analogous to Example 29 using 5-indanol and 3,4-difluoronitrobenzene in step A. MS (ESI): mass calcd. for $C_{21}H_{15}FN_4O_4$, 406.1; m/z found, 407.1 [M+H]$^+$. $^1$H NMR (400 MHz, DMSO-d$_6$): 13.04 (s, 2H), 8.92 (s, 1H), 8.26 (s, 1H), 7.71 (d, J=11.5 Hz, 1H), 7.48 (d, J=8.9 Hz, 1H), 7.30 (d, J=8.1 Hz, 1H), 7.04 (d, J=2.0 Hz, 1H), 6.93 (dd, J=8.1, 2.3 Hz, 1H), 2.88 (t, J=7.4 Hz, 4H), 2.06 (p, J=7.5 Hz, 2H).

Example 59

1-(7-Methyl-4-oxo-6-phenoxy-3,4-dihydro-quinazolin-2-yl)-1H-pyrazole-4-carboxylic acid

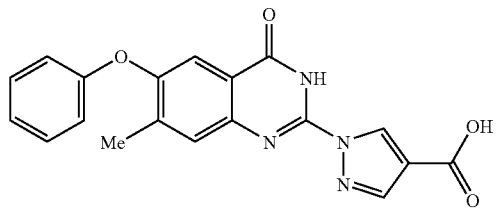 [SMILES: Cc1cc2nc(-n3cc(C(=O)O)cn3)[nH]c(=O)c2cc1Oc1ccccc1]

The titled compound was prepared in a manner analogous to Example 29 using phenol and 2-fluoro-5-nitrotoluene in step A. MS (ESI): mass calcd. for $C_{19}H_{14}N_4O_4$, 362.1; m/z found, 363.1 [M+H]$^+$. $^1$H NMR (500 MHz, DMSO-d$_6$): 13.01 (s, 1H), 12.79 (s, 1H), 8.91 (s, 1H), 8.24 (s, 1H), 7.67 (s, 1H), 7.46 (dd, J=8.6, 7.5 Hz, 2H), 7.32 (s, 1H), 7.23 (t, J=7.4 Hz, 1H), 7.10 (d, J=7.7 Hz, 2H), 2.41 (s, 3H).

Example 60

1-[6-(2,3-dichloro-phenoxy)-4-oxo-3,4-dihydro-quinazolin-2-yl]-1H-pyrazole-4-carboxylic acid

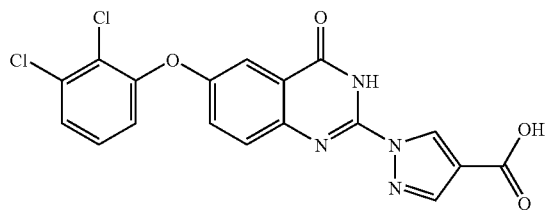 [SMILES: O=C(O)c1cnn(-c2nc3ccc(Oc4cccc(Cl)c4Cl)cc3c(=O)[nH]2)c1]

The titled compound was prepared in a manner analogous to Example 29 using 2,3-dichlorophenol and 4-fluoronitrobenzene in step A. MS (ESI): mass calcd. for $C_{18}H_{10}Cl_2N_4O_4$, 416.0; m/z found, 417.0 [M+H]$^+$. $^1$H NMR (500 MHz, DMSO-d$_6$): 13.00 (s, 1H), 12.97-12.67 (m, 1H), 8.95 (s, 1H), 8.25 (s, 1H), 7.77 (s, 1H), 7.64 (dd, J=8.9, 2.9 Hz, 1H), 7.59 (d, J=8.1 Hz, 1H), 7.47 (t, J=8.2 Hz, 1H), 7.40 (s, 1H), 7.28 (d, J=8.0 Hz, 1H).

Example 61

1-[6-(2,6-Dimethyl-phenoxy)-7-methoxy-4-oxo-3,4-dihydro-quinazolin-2-yl]-1H-pyrazole-4-carboxylic acid

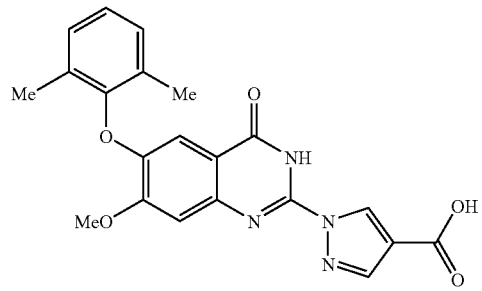 [SMILES: COc1cc2nc(-n3cc(C(=O)O)cn3)[nH]c(=O)c2cc1Oc1c(C)cccc1C]

The titled compound was prepared in a manner analogous to Example 29 using 2,6-dimethylphenol and 4-fluoro-3-methoxynitrobenzene in step A. MS (ESI): mass calcd. for $C_{21}H_{18}N_4O_5$, 406.1; m/z found, 407.1 [M+H]$^+$. $^1$H NMR (400 MHz, DMSO-d$_6$): 12.99 (s, 1H), 12.70 (s, 1H), 8.91 (s, 1H), 8.22 (s, 1H), 7.34 (s, 1H), 7.24 (d, J=7.4 Hz, 2H), 7.17 (dd, J=8.5, 6.3 Hz, 1H), 6.79 (s, 1H), 4.07 (s, 3H), 2.07 (s, 6H).

Example 62

1-(7-Methoxy-4-oxo-6-phenoxy-3,4-dihydro-quinazolin-2-yl)-1H-pyrazole-4-carboxylic acid

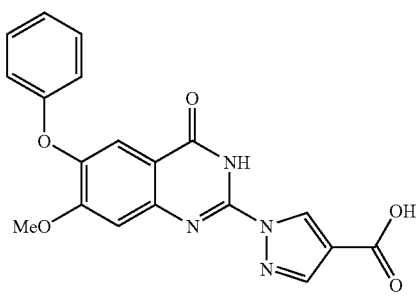 [SMILES: COc1cc2nc(-n3cc(C(=O)O)cn3)[nH]c(=O)c2cc1Oc1ccccc1]

The titled compound was prepared in a manner analogous to Example 29 using phenol and 4-fluoro-3-methoxynitrobenzene in step A. MS (ESI): mass calcd. for $C_{19}H_{14}N_4O_5$, 378.1; m/z found, 379.1 [M+H]$^+$. $^1$H NMR (400 MHz, DMSO-d$_6$): 13.01 (s, 1H), 12.79 (s, 1H), 8.93 (s, 1H), 8.25 (s, 1H), 7.45 (s, 1H), 7.41 (dd, J=8.6, 7.5 Hz, 2H), 7.35 (s, 1H), 7.17 (t, J=7.4 Hz, 1H), 7.03 (d, J=7.7 Hz, 2H), 3.95 (s, 3H).

Example 63

1-[6-(2,6-Dimethyl-phenoxy)-5,7-difluoro-4-oxo-3,4-dihydro-quinazolin-2-yl]-1H-pyrazole-4-carboxylic acid

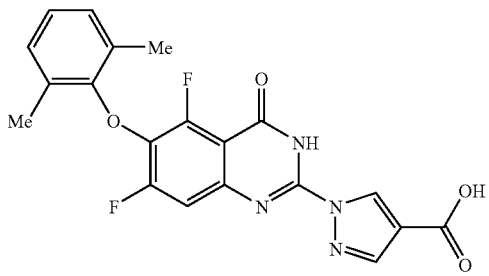 [SMILES: Cc1cccc(C)c1Oc1c(F)cc2nc(-n3cc(C(=O)O)cn3)[nH]c(=O)c2c1F]

The titled compound was prepared in a manner analogous to Example 29 using 2,6-dimethylphenol and 3,4,5-trifluoronitrobenzene in step A. MS (ESI): mass calcd. for $C_{20}H_{14}F_2N_4O_4$, 412.1; m/z found, 413.0 [M+H]$^+$. $^1$H NMR (400 MHz, DMSO-d$_6$): 13.07 (s, 2H), 8.91 (d, J=0.4 Hz, 1H), 8.27 (s, 1H), 7.52 (d, J=11.6 Hz, 1H), 7.12 (d, J=7.5 Hz, 2H), 7.06 (dd, J=8.5, 6.2 Hz, 1H), 2.16 (s, 6H).

Example 64

1-(5,7-Difluoro-4-oxo-6-phenoxy-3,4-dihydro-quinazolin-2-yl)-1H-pyrazole-4-carboxylic acid

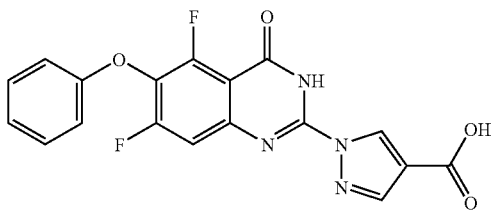 [SMILES: O=C(O)c1cnn(-c2nc3cc(F)c(Oc4ccccc4)c(F)c3c(=O)[nH]2)c1]

The titled compound was prepared in a manner analogous to Example 29 using phenol and 3,4,5-trifluoronitrobenzene in step A. MS (ESI): mass calcd. for $C_{18}H_{10}F_2N_4O_4$, 384.1; m/z found, 385.0 [M+H]$^+$. $^1$H NMR (400 MHz, DMSO-d$_6$): 13.10 (s, 2H), 8.94 (s, 1H), 8.30 (s, 1H), 7.61 (d, J=10.7 Hz, 1H), 7.39 (dd, J=8.6, 7.5 Hz, 2H), 7.14 (t, J=7.4 Hz, 1H), 7.04 (d, J=8.0 Hz, 2H).

Example 65

1-[4-Oxo-6-(pyridin-3-yloxy)-3,4-dihydro-quinazolin-2-yl]-1H-pyrazole-4-carboxylic acid

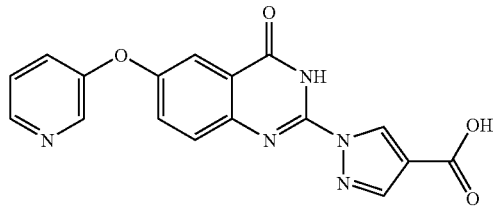

The titled compound was prepared in a manner analogous to Example 29 using 3-hydroxypyridine and 4-fluoronitrobenzene in step A. MS (ESI): mass calcd. for $C_{17}H_{11}N_5O_4$, 349.1; m/z found, 350.1 [M+H]$^+$. $^1$H NMR (500 MHz, DMSO-d$_6$): 13.00 (s, 1H), 12.96-12.70 (m, 1H), 8.95 (s, 1H), 8.51 (s, 1H), 8.48 (d, J=3.8 Hz, 1H), 8.26 (s, 1H), 7.78 (s, 1H), 7.66 (dd, J=8.8, 2.2 Hz, 1H), 7.62 (d, J=8.4 Hz, 1H), 7.56-7.48 (m, 2H).

Example 66

1-(4-Oxo-7-phenoxy-3,4-dihydro-quinazolin-2-yl)-1H-pyrazole-4-carboxylic acid

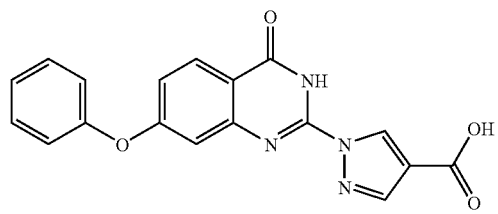 [SMILES: O=C(O)c1cnn(-c2nc3cc(Oc4ccccc4)ccc3c(=O)[nH]2)c1]

The titled compound was prepared in a manner analogous to Example 29 steps C-E using 3-phenoxyaniline in step C. MS (ESI): mass calcd. for $C_{18}H_{12}N_4O_4$, 348.1; m/z found, 349.1 [M+H]$^+$. $^1$H NMR (500 MHz, DMSO-d$_6$): 12.97 (s, 1H), 12.77 (s, 1H), 8.93 (s, 1H), 8.24 (s, 1H), 8.14 (d, J=7.9 Hz, 1H), 7.52 (t, J=7.9 Hz, 2H), 7.31 (t, J=7.4 Hz, 1H), 7.22 (d, J=7.7 Hz, 2H), 7.17 (d, J=8.5 Hz, 1H), 6.96 (s, 1H).

Example 67

1-[4-Oxo-7-(tetrahydro-pyran-4-yl)-3,4-dihydro-quinazolin-2-yl]-1H-pyrazole-4-carboxylic acid tris(hydroxymethyl)aminomethane salt

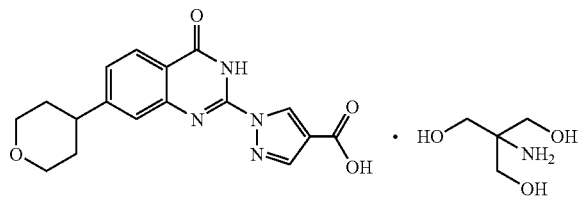

Step A: Preparation of [4-(4-hydroxy-tetrahydro-pyran-4-yl)-phenyl]carbamic acid tert-butyl ester. THF (50 mL) in an oven-dried 500 mL single neck flask was cooled in −78° C. bath under N$_2$. A solution of n-butyllithium in hexanes (15.4 mL, 2.5 M, 38.6 mmol) was added dropwise via syringe over 10 min. The clear solution was stirred at −78° C. for 30 min. N-Boc-4-bromoaniline (5.00 g, 18.4 mmol), dissolved in 10 mL THF, was added dropwise over 10 min with stirring then stirred a further 30 min at −78° C. Tetrahydro-4H-pyran-4-one (2.02 g, 20.2 mmol) in 5 mL THF added was dropwise over 10 min. After 150 min, the reaction mixture was allowed to warm to RT then added to 200 mL saturated NH$_4$Cl and extracted with ether (3×100 mL). The combined organic layers were washed with water (50 mL) and brine (50 mL) and dried over MgSO$_4$. Filtration and concentration provided the crude product that was recrystallized from 70 mL DCM to give the purified product as a white solid (2.29 g, 42%). MS (ESI): mass calcd. for $C_{16}H_{23}NO_4$, 293.3; m/z found, 276.1 [M−H$_2$O+H]$^+$. $^1$H NMR (500 MHz, CDCl$_3$): 7.46-7.38 (m, 2H), 7.36 (d, J=8.6 Hz, 2H), 6.48 (s, 1H), 3.90 (m, 4H), 2.30-1.98 (m, 2H), 1.68 (d, J=12.1 Hz, 2H), 1.52 (s, 9H).

Step B: Preparation of 4-(tetrahydro-pyran-4-yl)-phenylamine trifluoroacetic acid salt. 4-(4-Hydroxy-tetrahydro-pyran-4-yl)-phenyl]-carbamic acid tert-butyl ester (1.85 g, 6.31 mmol) was suspended in 40 mL DCM and 20 mL triethylsilane and sonicated for 2 min. TFA (40 mL) was added and a clear solution developed. Allowed to stand at RT for 16 h then concentrated in vacuo to give the product as an amorphous solid (2.40 g, 75%). MS (ESI): mass calcd. for $C_{11}H_{14}NO$, 177.2; m/z found, 178.1 [M+H]$^+$. $^1$H NMR (400 MHz, DMSO): 10.17 (s, 3H), 7.35 (d, J=8.4 Hz, 2H), 7.24 (d, J=8.4 Hz, 2H), 4.13-3.81 (m, 2H), 3.43 (td, J=11.2, 3.4 Hz, 2H), 2.97-2.64 (m, 1H), 1.91-1.35 (m, 3H).

Step C: Preparation of 1-[4-oxo-7-(tetrahydro-pyran-4-yl)-3,4-dihydro-quinazolin-2-yl]-1H-pyrazole-4-carboxylic acid. The title compound was prepared from 4-(tetrahydro-pyran-4-yl)-phenylamine trifluoroacetic acid salt using the procedures described in as described in EXAMPLE 27 steps C, D and E, replacing DIC with EDCl in step C. MS (ESI): mass calcd. for $C_{17}H_{16}N_4O_4$, 340.3; m/z found, 341.1 [M+H]$^+$, 379.1 [M+K]$^+$ $^1$H NMR (400 MHz, DMSO): 12.92 (s, 2H), 8.94 (s, 1H), 8.25 (s, 1H), 7.96 (s, 1H), 7.77 (s, 1H), 7.67 (s, 1H), 3.98 (m, 2H), 3.47 (m, 2H), 3.29 (m, 4H), 2.96 (m, 1H).

Step D: Preparation of 1-[4-oxo-7-(tetrahydro-pyran-4-yl)-3,4-dihydro-quinazolin-2-yl]-1H-pyrazole-4-carboxylic acid tris(hydroxymethyl)aminomethane salt. 1-[4-Oxo-7-(tetrahydro-pyran-4-yl)-3,4-dihydro-quinazolin-2-yl]-1H-pyrazole-4-carboxylic acid (0.158 g, 0.464 mmol), as the free acid, was suspended in 10 mL MeOH and 10 mL THF to which tris(hydroxymethyl)aminomethane (0.0562 g, 0.464 mmol) in 1 mL water was added. The resulting solution was stirred for 2 h then concentrated in vacuo and dried in a drying pistol (0.1 mmHg, 60° C.) to provide 214 mg of a white powder (99%). MS (ESI): mass calcd. for $C_{17}H_{16}N_4O_4$, 340.3; m/z found, 341.1 [M+H]$^+$.

Example 68

1-(7-Chloro-4-oxo-6-phenyl-3,4-dihydro-quinazolin-2-yl)-1H-pyrazole-4-carboxylic acid

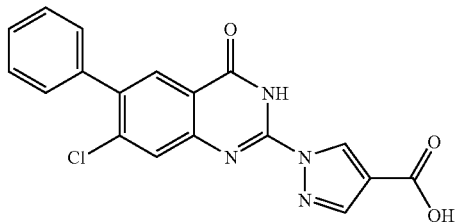 [SMILES: O=C(O)c1cnn(-c2nc3cc(Cl)c(-c4ccccc4)cc3c(=O)[nH]2)c1]

Step A: Preparation of 2-chloro-4-nitro-biphenyl. A mixture of potassium carbonate (1.48 g, 10.7 mmol), phenylboronic acid (645 mg, 5.29 mmol), 3-chloro-4-iodonitro benzene (1.00 g, 3.53 mmol), and THF (31 ml) was degassed with nitrogen in a sealable tube for 10 min. The dichloromethane adduct of 1,1'-bis(diphenylphosphino)ferrocene]dichloro palladium (351 mg, 0.429 mmol) was added to the reaction mixture and the pressure tube was sealed. The reaction mixture was stirred at 100° C. for 42 h. The mixture was cooled to 23° C., diluted with DCM (40 ml), and filtered. The filtrate was concentrated. The residue was purified by FCC (3-50% EtOAc/hexanes) to yield the titled compound (796 mg, 97%).

$^1$H NMR (600 MHz, DMSO-d$_6$): 8.42-8.41 (m, 1H), 8.26 (dd, J=8.5, 2.2, Hz 1H), 7.72 (d, J=8.5 Hz, 1H), 7.55-7.48 (m, 5H).

Step B: Preparation of 1-(7-chloro-4-oxo-6-phenyl-3,4-dihydro-quinazolin-2-yl)-1H-pyrazole-4-carboxylic acid. The titled compound was prepared in a manner analogous to Example 27, steps B-E, from 2-chloro-4-nitro-biphenyl. MS (ESI): mass calcd. for $C_{18}H_{11}ClN_4O_3$, 366.1; m/z found, 367.0 [M+H]$^+$. $^1$H NMR (600 MHz, DMSO-d$_6$): 13.04 (br s, 2H), 8.97 (s, 1H), 8.29 (s, 1H), 8.03 (s, 1H), 7.91 (s, 1H), 7.52 (d, J=4.4 Hz, 4H), 7.49-7.45 (m, 1H).

Example 69

1-(4-Oxo-6-o-tolyl-3,4-dihydro-quinazolin-2-yl)-1H-pyrazole-4-carboxylic acid

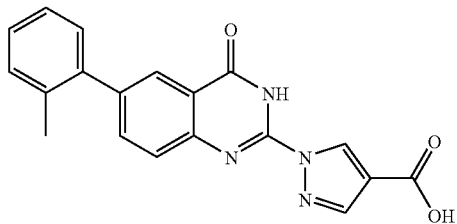 [SMILES: Cc1ccccc1-c1ccc2nc(-n3cc(C(=O)O)cn3)[nH]c(=O)c2c1]

Step A: Preparation of 1-(6-iodo-4-oxo-3,4-dihydro-quinazolin-2-yl)-1H-pyrazole-4-carboxylic acid ethyl ester. The titled compound was prepared in a manner analogous to Example 17, steps A and B, using 4-iodo-phenylamine in step A. MS (ESI): mass calcd. for $C_{14}H_{11}IN_4O_3$, 410.0; m/z found, 411.0 [M+H]$^+$. $^1$H NMR (600 MHz, DMSO-d$_6$): 9.01 (d, J=0.6 Hz, 1H), 8.39 (d, J=2.0 Hz, 1H), 8.34 (s, 1H), 8.14 (dd, J=8.5, 2.1 Hz, 1H), 7.52 (s, 1H), 4.30 (q, J=7.1 Hz, 2H), 1.32 (t, J=7.1 Hz, 3H).

Step B: Preparation of 1-[6-iodo-4-oxo-3-(2-trimethylsilanylethoxymethyl)-3,4-dihydro-quinazolin-2-yl]-1H-pyrazole-4-carboxylic acid ethyl ester. To a mixture of 1-(6-iodo-4-oxo-3,4-dihydro-quinazolin-2-yl)-1H-pyrazole-4-carboxylic acid ethyl ester (500 mg, 1.22 mmol) and THF (6 mL) was added DIPEA (0.425 mL, 2.44 mmol) followed by 2-(trimethylsilyl)-ethoxymethyl chloride (0.205 mL, 1.34 mmol) at 23° C. After stirring for 18 h, the reaction mixture was concentrated under reduced pressure. The residue was purified by FCC (5-45% EtOAc/hexanes to yield the titled compound (603 mg, 92%). MS (ESI): mass calcd. for $C_{20}H_{25}IN_4O_4Si$, 540.1; m/z found, 483.0 [M−CH$_2$OCH$_2$CH$_2$+H]$^+$. $^1$H NMR (600 MHz, DMSO-d$_6$): 8.91 (d, J=0.6 Hz, 1H), 8.50 (d, J=2.0 Hz, 1H), 8.30 (d, J=0.6 Hz, 1H), 8.24 (dd, J=8.5, 2.1 Hz, 1H), 7.55 (d, J=8.5 Hz, 1H), 5.61 (s, 2H), 4.29 (q, J=7.1 Hz, 2H), 3.41-3.37 (m, 2H), 1.30 (t, J=7.1 Hz, 3H), 0.72-0.69 (m, 2H), −0.12--0.13 (m, 9H).

Step C: Preparation of 1-[4-oxo-6-o-tolyl-3-(2-trimethylsilanyl-ethoxymethyl)-3,4-dihydro-quinazolin-2-yl]-1H-pyrazole-4-carboxylic acid ethyl ester. A mixture of potassium carbonate (85.4 mg 0.618 mmol), 2-methylphenylboronic acid (63.3 mg, 0.466 mmol), 1-[6-iodo-4-oxo-3-(2-trimethylsilanyl-ethoxymethyl)-3,4-dihydro-quinazolin-2-yl]-1H-pyrazole-4-carboxylic acid ethyl ester (110 mg, 0.204 mmol), and THF (1.5 ml) was degassed for 5 minutes with nitrogen in a sealable tube. The dichloromethane adduct of 1,1'-bis(diphenylphosphino)ferrocene] dichloro palladium (20.2 mg, 0.0246 mmol) was added to the reaction mixture and the pressure tube was sealed. The reaction mixture was stirred at 80° C. for 18 h. The reaction mixture was cooled to 23° C., diluted with DCM (10 ml), and filtered. The filtrate was concentrated. The residue was purified by FCC (3-40% EtOAc/hexanes) to yield the titled compound (92.0 mg, 90%). MS (ESI): mass calcd. for $C_{27}H_{32}N_4O_4Si$, 504.22; m/z found, 446.6 [M−CH$_2$OCH$_2$CH$_2$+H]$^+$. $^1$H NMR (600 MHz, CDCl$_3$): 8.68 (d, J=0.6 Hz, 1H), 8.31-8.30 (m, 1H), 8.18 (d, J=0.6 Hz, 1H), 7.79 (dd, J=8.3, 2.1 Hz, 1H), 7.76-7.74 (m, 1H), 7.33-7.28 (m, 4H), 5.91 (s, 2H), 4.39-4.35 (m, 2H), 4.37 (q, J=7.2 Hz, 2H), 2.31 (s, 3H), 1.39 (t, J=7.1 Hz, 3H), 0.83-0.79 (m, 2H), −0.08 (s, 9H).

Step D: Preparation of 1-(4-oxo-6-o-tolyl-3,4-dihydro-quinazolin-2-yl)-1H-pyrazole-4-carboxylic acid ethyl ester. A solution of HCl in dioxane (4M, 0.872 mL, 3.48 mmol) was added to 1-[4-oxo-6-o-tolyl-3-(2-trimethylsilanyl-ethoxymethyl)-3,4-dihydro-quinazolin-2-yl]-1H-pyrazole-4-carboxylic acid ethyl ester (88.0 mg, 0.174 mmol). The reaction mixture was stirred at 23° C. After 18 h, the reaction mixture was concentrated under reduced pressure. Et$_2$O was added (5 mL) and the resulting precipitate was collected by filtration and washed well with Et$_2$O to afford the titled compound (52.0 mg, 80%). MS (ESI): mass calcd. for $C_{21}H_{18}N_4O_3$, 374.1; m/z found 375.2 [M+H]$^+$. $^1$H NMR (600 MHz, CDCl$_3$): 9.05 (s, 1H), 8.35 (s, 1H), 8.02 (s, 1H), 7.86 (d, J=6.6 Hz, 1H), 7.78 (s, 1H), 7.37-7.28 (m, 4H), 4.31 (q, J=7.1 Hz, 2H), 2.28 (s, 3H), 1.33 (t, J=7.1 Hz, 3H).

Step E: Preparation of 1-(4-oxo-6-o-tolyl-3,4-dihydro-quinazolin-2-yl)-1H-pyrazole-4-carboxylic acid. A mixture of 1-(4-oxo-6-o-tolyl-3,4-dihydro-quinazolin-2-yl)-1H-pyrazole-4-carboxylic acid ethyl ester (40.0 mg, 1.07 mmol), 1M aq. KOH (0.5 mL) and THF (1 mL) was stirred for 16 h. The reaction mixture was concentrated under reduced pressure to remove the THF and the aqueous residue was acidified to pH 2 with 1 M aq. HCl. The resulting precipitate was collected by filtration to provide the titled compound (30.0 mg, 81%). MS (ESI): mass calcd. for $C_{19}H_{14}N_4O_3$, 346.1; m/z found 347.0 [M+H]$^+$. $^1$H NMR (600 MHz, DMSO-d$_6$): 13.04 (s, 1H), 12.93 (s, 1H), 8.99 (s, 1H), 8.28 (s, 1H), 8.02 (s, 1H), 7.86 (d, J=7.5 Hz, 1H), 7.76 (d, J=7.8 Hz, 1H), 7.37-7.29 (m, 4H), 2.28 (s, 3H).

Example 70

1-(6-Biphenyl-3-yl-4-oxo-3,4-dihydro-quinazolin-2-yl)-1H-pyrazole-4-carboxylic acid

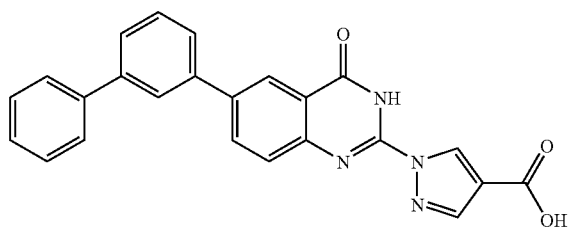 [SMILES: O=C(O)c1cnn(-c2nc3ccc(-c4cccc(-c5ccccc5)c4)cc3c(=O)[nH]2)c1]

The titled compound was prepared in a manner analogous to Example 69, steps C-E using 1-[6-iodo-4-oxo-3-(2-trimethylsilanyl-ethoxymethyl)-3,4-dihydro-quinazolin-2-yl]-1H-pyrazole-4-carboxylic acid ethyl ester (product from Example 69, step B) and biphenyl-3-boronic acid. MS (ESI): mass calcd. for $C_{24}H_{16}N_4O_3$, 408.1; m/z found, 409.1 [M+H]$^+$. $^1$H NMR (600 MHz, DMSO-d$_6$): 13.01 (s, 1H), 12.92 (s, 1H), 9.00 (s, 1H), 8.44 (s, 1H), 8.32-8.25 (m, 2H), 8.01 (s, 1H), 7.83-7.77 (m, 4H), 7.72 (d, J=7.8 Hz, 1H), 7.62 (t, J=7.7 Hz, 1H), 7.53-7.48 (m, 2H), 7.43-7.40 (m, 1H).

Example 71

1-[7-Chloro-6-(3,4-dimethoxy-benzenesulfonyl)-4-oxo-3,4-dihydro-quinazolin-2-yl]-1H-pyrazole-4-carboxylic acid

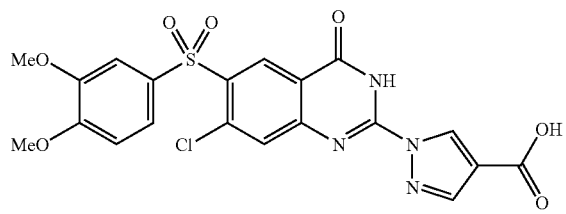 [SMILES: COc1ccc(S(=O)(=O)c2cc3c(=O)[nH]c(-n4cc(C(=O)O)cn4)nc3cc2Cl)cc1OC]

Step A: Preparation of 1-[7-chloro-6-(3,4-dimethoxy-benzenesulfonyl)-4-oxo-3,4-dihydro-quinazolin-2-yl]-1H-pyrazole-4-carboxylic acid ethyl ester. A suspension of urea•H$_2$O$_2$ (941 mg, 11.0 mmol) and DCM (8.6 mL) was cooled in an ice bath, then trifluoroacetic anhydride (2.4 mL, 17.0 mmol) was added dropwise. The resulting mixture was stirred for 1 h. A portion of this trifluoroperacetic acid solution (0.86 mL, 0.86 mmol) was added dropwise to a solution of 1-[7-chloro-6-(3,4-dimethoxy-phenylsulfanyl)-4-oxo-3,4-dihydro-quinazolin-2-yl]-1H-pyrazole-4-carboxylic acid ethyl ester (intermediate from Example 26, 140 mg, 0.28 mmol) and DMA (1 mL). After 16 h, a second aliquot of trifluoroperacetic acid solution (1 mL, 1 mmol) was added and the mixture was maintained for another 12 h. The mixture was cooled in an icebath, then water (15 mL) was added. The resulting precipitate was collected by filtration and used in subsequent steps without further purification.

Step B: Preparation of 1-[7-chloro-6-(3,4-dimethoxy-benzenesulfonyl)-4-oxo-3,4-dihydro-quinazolin-2-yl]-1H-pyrazole-4-carboxylic acid. 1-[7-Chloro-6-(3,4-dimethoxy-benzenesulfonyl)-4-oxo-3,4-dihydro-quinazolin-2-yl]-1H-pyrazole-4-carboxylic acid ethyl ester was combined with THF (5 mL), followed by the addition of a solution of aqueous 1M KOH (2.7 mL, 2.7 mmol), and the mixture was stirred for 16 h. The reaction mixture was cooled in an ice bath, then 1M aqueous HCl (5 mL) and water (5 mL) was added. The resulting precipitate was collected and purified by HPLC to furnish the titled compound (16 mg, 12%). MS (CI): mass calcd. for $C_{20}H_{15}ClN_4O_7S$, 490.0; m/z found, 489.0 [M−H]$^-$. $^1$H NMR (500 MHz, DMSO-d$_6$): 13.10 (s, 2H), 8.95 (s, 1H), 8.86 (s, 1H), 8.32 (s, 1H), 7.87 (s, 1H), 7.59 (dd, J=8.6, 1.8, 1H), 7.41 (d, J=2.0, 1H), 7.19 (d, J=8.6, 1H), 3.85 (s, 3H), 3.81 (s, 3H).

Example 72

1-[6-(4-tert-Butyl-benzenesulfonyl)-7-chloro-4-oxo-3,4-dihydro-quinazolin-2-yl]-1H-pyrazole-4-carboxylic acid

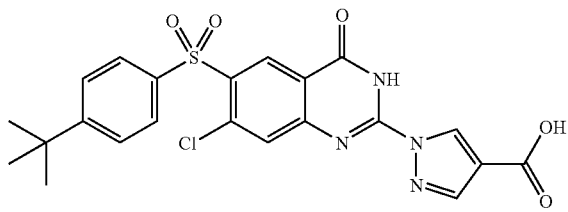 [SMILES: CC(C)(C)c1ccc(S(=O)(=O)c2cc3c(=O)[nH]c(-n4cc(C(=O)O)cn4)nc3cc2Cl)cc1]

The titled compound was prepared in a manner analogous to Example 71 using 1-[6-(4-tert-butyl-phenylsulfanyl)-7-chloro-4-oxo-1,4-dihydro-quinazolin-2-yl]-1H-pyrazole-4-carboxylic acid, ethyl ester (intermediate from EXAMPLE 24). MS (Cl): mass calcd. for $C_{22}H_{19}ClN_4O_5S$, 486.1; m/z found, 485.0 [M−H]⁻. ¹H NMR (500 MHz, DMSO-d₆): 12.97 (s, 1H), 12.77 (s, 1H), 8.93 (s, 1H), 8.24 (s, 1H), 8.14 (d, J=7.9 Hz, 1H), 7.52 (t, J=7.9 Hz, 2H), 7.31 (t, J=7.4 Hz, 1H), 7.22 (d, J=7.7 Hz, 2H), 7.17 (d, J=8.5 Hz, 1H), 6.96 (s, 1H). 13.09 (s, 1H), 8.95 (s, 1H), 8.88 (s, 1H), 8.31 (s, 1H), 7.90 (d, J=8.6, 2H), 7.87 (s, 1H), 7.67 (d, J=8.7, 2H), 1.29 (s, 9H).

Example 73

1-(7,7-Dimethyl-4-oxo-3,7-dihydro-4H-8-oxa-1,3-diaza-anthracen-2-yl)-1H-pyrazole-4-carboxylic acid

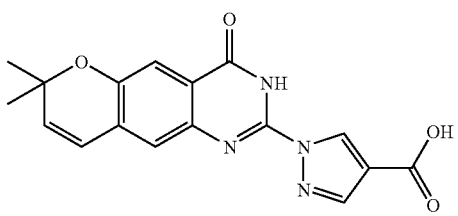 [SMILES: CC1(C)C=Cc2cc3nc(-n4cc(C(=O)O)cn4)[nH]c(=O)c3cc2O1]

The titled compound was prepared in a manner analogous to Example 27, steps C-E, using 2,2-dimethyl-6-amino-2H-1-benzopyran in step C, and with the addition of 4.0 equivalents of 2,6-di-tert-butylpyridine in step D. MS (ESI): mass calcd. for $C_{17}H_{14}N_4O_4$, 338.1; m/z found, 339.1 [M+H]⁺. ¹H NMR (500 MHz, DMSO-d₆): 12.94 (s, 2H), 8.88 (s, 1H), 8.23 (s, 1H), 7.44 (s, 1H), 7.31 (s, 1H), 6.64 (d, J=9.9 Hz, 1H), 6.10 (d, J=9.9 Hz, 1H), 1.43 (s, 6H).

Example 74

1-(4-Oxo-6-phenoxymethyl-3,4-dihydro-quinazolin-2-yl)-1H-pyrazole-4-carboxylic acid

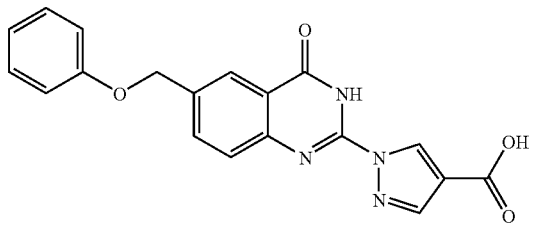 [SMILES: O=C(O)c1cnn(-c2nc3ccc(COc4ccccc4)cc3c(=O)[nH]2)c1]

The titled compound was prepared in a manner analogous to Example 27, steps C-E, using 4-phenoxymethylaniline in step C, and with the addition of 4.0 equivalents of 2,6-di-tert-butylpyridine in step D. MS (ESI): mass calcd. for $C_{19}H_{14}N_4O_4$, 362.1; m/z found, 363.1 [M+H]⁺. ¹H NMR (500 MHz, DMSO-d₆): 12.97 (s, 2H), 8.96 (s, 1H), 8.27 (s, 1H), 8.20 (s, 1H), 7.91 (dd, J=8.4, 1.9 Hz, 1H), 7.73 (d, J=8.2 Hz, 1H), 7.35-7.27 (m, 2H), 7.05 (dd, J=8.7, 0.9 Hz, 2H), 6.96 (t, J=7.3 Hz, 1H), 5.27 (s, 2H).

Example 75

1-[6-(2,6-Dimethyl-phenoxymethyl)-4-oxo-3,4-dihydro-quinazolin-2-yl]-1H-pyrazole-4-carboxylic acid

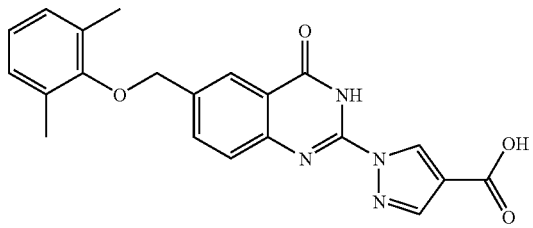 [SMILES: Cc1cccc(C)c1OCc1ccc2nc(-n3cc(C(=O)O)cn3)[nH]c(=O)c2c1]

The titled compound was prepared in a manner analogous to Example 27, steps C-E, using 4-(2,6-dimethyl)phenoxymethylaniline in step C, and with the addition of 4.0 equivalents of 2,6-di-tert-butylpyridine in step D. MS (ESI): mass calcd. for $C_{21}H_{18}N_4O_4$, 390.1; m/z found, 391.1 [M+H]⁺. ¹H NMR (500 MHz, DMSO-d₆): 12.99 (s, 2H), 8.96 (d, J=12.2 Hz, 1H), 8.26 (d, J=15.8 Hz, 2H), 7.97 (dd, J=8.4, 1.9 Hz, 1H), 7.76 (d, J=7.8 Hz, 1H), 7.11-7.04 (m, 2H), 7.01-6.93 (m, 1H), 4.95 (s, 2H), 2.28 (s, 6H).

Example 76

1-(6-Ethynyl-4-oxo-3,4-dihydro-quinazolin-2-yl)-1H-pyrazole-4-carboxylic acid

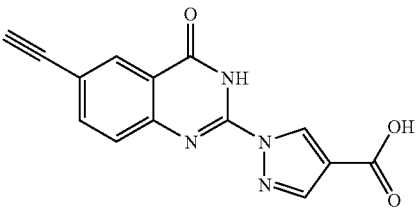 [SMILES: C#Cc1ccc2nc(-n3cc(C(=O)O)cn3)[nH]c(=O)c2c1]

Step A: Preparation of 1-(6-ethynyl-4-oxo-3,4-dihydro-quinazolin-2-yl)-1H-pyrazole-4-carboxylic acid, ethyl ester. The titled compound was prepared in a manner analogous to Example 27, steps C-D, using 4-ethynylaniline in step C, and with the addition of 4.0 equivalents of 2,6-di-tert-butylpyridine in step D. The crude product contained a 2.4:1 mixture of the titled product and 1-[6-(1-chloro-vinyl)-4-oxo-3,4-dihydro-quinazolin-2-yl]-1H-pyrazole-4-carboxylic acid, ethyl ester. A portion of this mixture was purified by HPLC to afford 1-(6-ethynyl-4-oxo-3,4-dihydro-quinazolin-2-yl)-1H-pyrazole-4-carboxylic acid, ethyl ester. MS (ESI): mass calcd. for $C_{16}H_{12}N_4O_3$, 308.1; m/z found, 309.1 [M+H]$^+$. $^1$H NMR (500 MHz, DMSO-d$_6$): 12.98 (br s, 1H), 8.95 (s, 1H), 8.27 (s, 1H), 8.07 (s, 1H), 7.82 (dd, J=8.4, 1.9 Hz, 1H), 7.72-7.54 (m, 1H), 4.31 (s, 1H), 4.23 (q, J=7.1 Hz, 2H), 1.26 (t, J=7.1 Hz, 3H).

Step B. Preparation of 1-(6-ethynyl-4-oxo-3,4-dihydro-quinazolin-2-yl)-1H-pyrazole-4-carboxylic acid. The titled compound was prepared in a manner analogous to Example 27, step E. MS (ESI): mass calcd. for $C_{14}H_8N_4O_3$, 280.1; m/z found, 281.1 [M+H]$^+$. $^1$H NMR (500 MHz, DMSO-d$_6$): 13.05 (s, 2H), 8.96 (s, 1H), 8.28 (br s, 1H), 8.13 (br s, 1H), 7.89 (dd, J=8.4, 2.0 Hz, 1H), 7.79-7.58 (m, 1H), 4.39 (s, 1H).

Example 77

1-[6-(1-Chloro-vinyl)-4-oxo-3,4-dihydro-quinazolin-2-yl]-1H-pyrazole-4-carboxylic acid

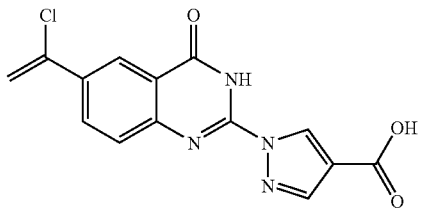 [SMILES: C=C(Cl)c1ccc2nc(-n3cc(C(=O)O)cn3)[nH]c(=O)c2c1]

The titled compound was prepared as described in Example 76. MS (ESI): mass calcd. for $C_{14}H_9ClN_4O_3$, 317.0; m/z found, 318.1 [M+H]$^+$. $^1$H NMR (500 MHz, DMSO-d$_6$): 13.05 (s, 3H), 8.97 (s, 1H), 8.41-8.24 (m, 2H), 8.19 (d, J=6.5 Hz, 1H), 7.80-7.64 (m, 1H), 6.29 (m, 1H), 5.77 (d, J=2.6 Hz, 1H).

Example 78

1-(4-Oxo-7-phenylsulfanyl-3,4-dihydro-quinazolin-2-yl)-1H-pyrazole-4-carboxylic acid

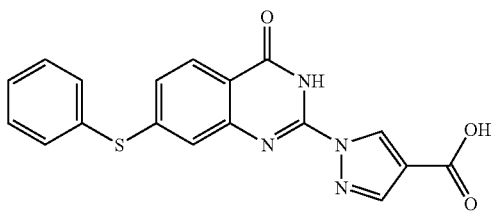 [SMILES: O=C(O)c1cnn(-c2nc3cc(Sc4ccccc4)ccc3c(=O)[nH]2)c1]

Step A: Preparation of 3-nitrophenyl phenyl sulfide. A mixture of thiophenol (1.0 g, 9.1 mmol), 3-iodonitrobenzene (1.9 g, 7.6 mmol), CuI (0.14 g, 0.76 mmol), K$_2$CO$_3$ (1.67 g, 12.1 mmol), and DMF (10 mL) was heated to 100° C. in a flame-dried sealed tube for 16 h. The mixture was allowed to cool and was poured over ice. The resulting mixture was extracted with EtOAc (2×), and the organic extracts were combined and washed sequentially with equal volumes of aqueous 1M HCl, water, and aqueous 1M NaOH. The solution was dried, concentrated, and the residue was purified by FCC (100:0 to 95:5 hexanes/EtOAc) to provide the titled compound, which was contaminated with ca. 10% thiophenol (1.43 g), and was taken on to subsequent steps without further purification.

Step B. Preparation of 3-phenylsulfanyl-phenylamine. 3-Nitrophenyl phenyl sulfide, mixture from step A (ca. 90% purity, 1.43 g, 6.2 mmol), was dissolved in acetone (20 mL) and was cooled in an ice bath. A saturated solution of NH$_4$Cl (5 mL) was added, followed by portionwise addition of zinc dust (3.7 g, 56 mmol) over 5 min with vigorous stirring. The ice bath was allowed to expire and the mixture was stirred 16 h. EtOAc (200 mL) was added followed by anhydrous sodium sulfate (20 g). The stirring was continued for 1 h, then the mixture was filtered through a pad of silica gel, eluting with additional EtOAc. The resulting clear solution was concentrated and the residue was purified by FCC (99:1 to 70:30 hexanes/EtOAc) to provide the titled compound (1.43 g, 69%). MS (ESI): mass calcd. for $C_{12}H_{11}NS$, 201.3; m/z found, 202.1 [M+H]$^{30}$.

Step C: Preparation of 1-(4-oxo-7-phenylsulfanyl-3,4-dihydro-quinazolin-2-yl)-1H-pyrazole-4-carboxylic acid, ethyl ester. The titled compound was prepared in a manner analogous to Example 27, steps C-D, using 3-thiophenylaniline in step C. MS (ESI): mass calcd. for $C_{20}H_{16}N_4O_3S$, 392.4; m/z found, 393.1 [M+H]$^+$. $^1$H NMR (500 MHz, DMSO-d$_6$): 12.94 (s, 1H), 8.97 (s, 1H), 8.30 (s, 1H), 8.03 (d, J=8.4, 1H), 7.66-7.58 (m, 2H), 7.58-7.51 (m, 3H), 7.29 (dd, J=8.4, 1.8, 1H), 7.22 (s, 1H), 4.28 (q, J=7.1, 2H), 1.31 (t, J=7.1, 3H).

Step D: Preparation of 1-(4-oxo-7-phenylsulfanyl-3,4-dihydro-quinazolin-2-yl)-1H-pyrazole-4-carboxylic acid. The titled compound was prepared in a manner analogous to Example 27, step E, using 1-(4-oxo-7-phenylsulfanyl-3,4-dihydro-quinazolin-2-yl)-1H-pyrazole-4-carboxylic acid in step E. MS (ESI): mass calcd. for $C_{18}H_{12}N_4O_3S$, 363.0; m/z found, 365.1 [M+H]$^+$. $^1$H NMR (500 MHz, DMSO-d$_6$): 13.09-12.70 (m, 2H), 8.90 (s, 1H), 8.24 (s, 1H), 8.03 (d, J=8.4, 1H), 7.64-7.59 (m, 2H), 7.57-7.52 (m, 3H), 7.28 (dd, J=8.4, 1.8, 1H), 7.21 (brs, 1H).

Example 79

1-[7-(4-Chloro-phenylsulfanyl)-4-oxo-3,4-dihydro-quinazolin-2-yl]-1H-pyrazole-4-carboxylic acid

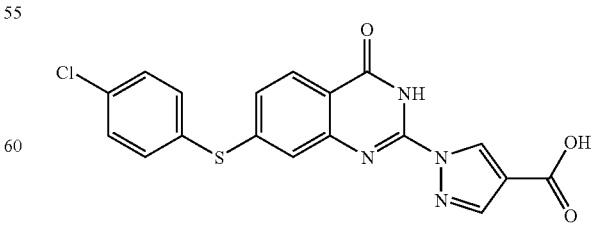

The titled compound was prepared in a manner analogous to Example 78, using 4-chlorothiophenol in step A. MS (ESI): mass calcd. for $C_{18}H_{11}ClN_4O_3S$, 398.0; m/z found, 399.1

[M+H]⁺. ¹H NMR (500 MHz, DMSO-d₆): 13.09-12.78 (m, 2H), 8.93 (s, 1H), 8.25 (s, 1H), 8.04 (d, J=8.2, 1H), 7.64-7.57 (m, 4H), 7.34-7.23 (m, 2H).

Example 80

1-[7-(2-Chloro-phenylsulfanyl)-4-oxo-3,4-dihydro-quinazolin-2-yl]-1H-pyrazole-4-carboxylic acid

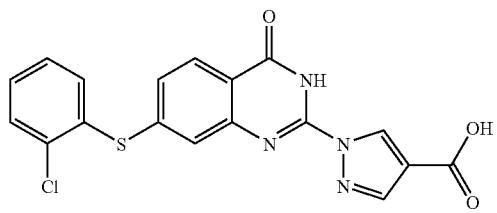

The titled compound was prepared in a manner analogous to Example 78, using 2-chlorothiophenol in step A. MS (ESI): mass calcd. for $C_{18}H_{11}ClN_4O_3S$, 398.0; m/z found, 399.1 [M+H]⁺. ¹H NMR (500 MHz, DMSO-d₆): 13.18-12.66 (m, 2H), 8.92 (s, 1H), 8.25 (s, 1H), 8.07 (d, J=8.3, 1H), 7.72 (dd, J=8.0, 1.3, 1H), 7.65 (dd, J=7.7, 1.6, 1H), 7.55 (td, J=7.7, 1.7, 1H), 7.48 (td, J=7.6, 1.4, 1H), 7.30 (dd, J=8.4, 1.8, 1H), 7.24 (s, 1H).

Example 81

1-(7-Benzenesulfonyl-4-oxo-3,4-dihydro-quinazolin-2-yl)-1H-pyrazole-4-carboxylic acid

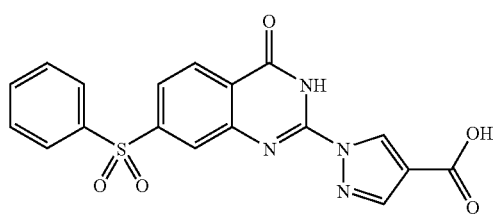 [SMILES: O=C(O)c1cnn(-c2nc3cc(S(=O)(=O)c4ccccc4)ccc3c(=O)[nH]2)c1]

Step A: Preparation of 1-(7-benzenesulfonyl-4-oxo-3,4-dihydro-quinazolin-2-yl)-1H-pyrazole-4-carboxylic acid, ethyl ester. Solid mCPBA (305 mg, 0.133 mmol) was added to solution of 1-(4-oxo-7-phenylsulfanyl-3,4-dihydro-quinazolin-2-yl)-1H-pyrazole-4-carboxylic acid, ethyl ester (Example 78, product from step C, 130 mg, 0.33 mmol) and DCM (10 mL). The reaction was allowed to proceed at rt for 16 h. The reaction mixture was diluted with DCM, washed with saturated aqueous sodium thiosulfate, saturated aqueous NaHCO₃, dried, and concentrated. The crude product was used without purification (52 mg, 37%). MS (ESI): mass calcd. for $C_{20}H_{16}N_4O_5S$, 424.1; m/z found, 425.1 [M+H]⁺.

Step B: Preparation of 1-(7-benzenesulfonyl-4-oxo-3,4-dihydro-quinazolin-2-yl)-1H-pyrazole-4-carboxylic acid. A mixture of 1-(7-benzenesulfonyl-4-oxo-3,4-dihydro-quinazolin-2-yl)-1H-pyrazole-4-carboxylic acid, ethyl ester (50 mg, 0.12 mmol), THF (2 mL) and aqueous 1M LiOH (0.6 mL, 0.6 mmol) was stirred for 16 h. The THF was removed under reduced pressure and aqueous 1M HCl (3 mL, 3 mmol) was added. The crude product was collected by filtration and purified by HPLC to afford the titled compound (7.0 mg, 14%). MS (ESI): mass calcd. for $C_{18}H_{12}N_4O_5S$, 396.1; m/z found, 397.1 [M+H]⁺. ¹H NMR (600 MHz, DMSO-d₆): 13.43-12.81 (m, 2H), 8.99 (s, 1H), 8.34-8.25 (m, 2H), 8.18 (s, 1H), 8.05 (d, J=7.6, 2H), 7.96 (dd, J=8.3, 1.5, 1H), 7.78-7.71 (m, 1H), 7.71-7.63 (m, 2H).

Example 82

1-[7-(4-Chloro-benzenesulfonyl)-4-oxo-3,4-dihydro-quinazolin-2-yl]-1H-pyrazole-4-carboxylic acid

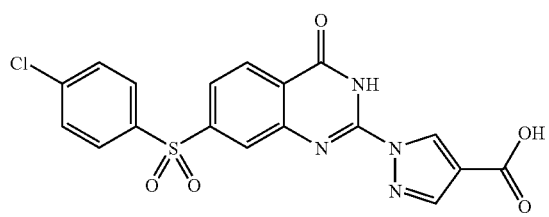 [SMILES: O=C(O)c1cnn(-c2nc3cc(S(=O)(=O)c4ccc(Cl)cc4)ccc3c(=O)[nH]2)c1]

The titled compound was prepared in a manner analogous to Example 81 using 1-[7-(4-chloro-phenylsulfanyl)-4-oxo-3,4-dihydro-quinazolin-2-yl]-1H-pyrazole-4-carboxylic acid, ethyl ester (intermediate from Example 79), in step A. MS (ESI): mass calcd. for $C_{18}H_{11}ClN_4O_5S$, 430.0; m/z found, 431.0 [M+H]⁺. ¹H NMR (600 MHz, DMSO-d₆): 13.06 (br s, 2H), 8.99 (s, 1H), 8.35-8.25 (m, 2H), 8.19 (s, 1H), 8.08 (d, J=8.4, 2H), 7.97 (dd, J=8.3, 1.7, 1H), 7.78-7.71 (m, 2H).

Example 83

1-[7-(2-Chloro-benzenesulfonyl)-4-oxo-3,4-dihydro-quinazolin-2-yl]-1H-pyrazole-4-carboxylic acid

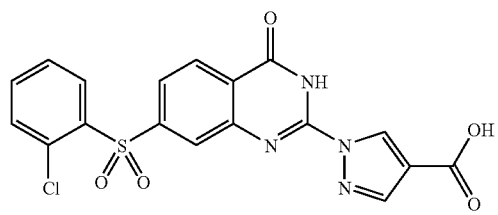 [SMILES: O=C(O)c1cnn(-c2nc3cc(S(=O)(=O)c4ccccc4Cl)ccc3c(=O)[nH]2)c1]

The titled compound was prepared in a manner analogous to Example 81 using 1-[7-(2-chloro-phenylsulfanyl)-4-oxo-3,4-dihydro-quinazolin-2-yl]-1H-pyrazole-4-carboxylic acid, ethyl ester (intermediate from Example 80). MS (ESI): mass calcd. for $C_{18}H_{11}ClN_4O_5S$, 430.0; m/z found, 431.0 [M+H]⁺. ¹H NMR (600 MHz, DMSO-d₆): 13.40-12.82 (m, 2H), 9.02 (s, 1H), 8.39 (d, J=7.8, 1H), 8.36-8.25 (m, 2H), 8.12 (s, 1H), 7.90 (d, J=8.3, 1H), 7.84-7.66 (m, 3H).

Example 84

1-[7-Chloro-6-(3,4-dihydro-1H-isoquinolin-2-yl)-4-oxo-3,4-dihydro-quinazolin-2-yl]-1H-pyrazole-4-carboxylic acid

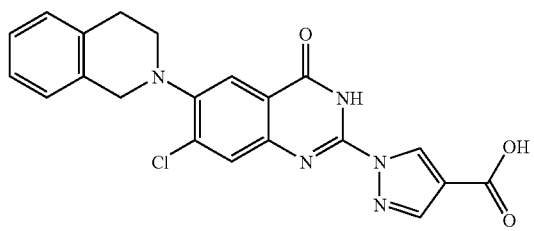 [SMILES: O=C(O)c1cnn(-c2nc3cc(Cl)c(N4CCc5ccccc5C4)cc3c(=O)[nH]2)c1]

Step A: Preparation of 2-(2-chloro-4-nitro-phenyl)-1,2,3,4-tetrahydro-isoquinoline. A mixture of 3,4-dichloronitrobenzene (1.0 g, 5.2 mmol), 1,2,3,4-tetrahydroisoquinoline (0.97 g, 7.3 mmol), $K_2CO_3$ (3.6 g, 26 mmol), and DMSO (20 mL) was heated to 80° C. for 16 h with stirring. The mixture was allowed to cool to rt, and was then poured over ice. The resulting precipitate was collected by filtration and dried to provide the titled compound (1.5 g, 98%). MS (ESI): mass calcd. for $C_{15}H_{13}ClN_2O_2$, 288.7; m/z found, 289.1 [M+H]$^+$.

Step B: Preparation of 2-(2-chloro-4-amino-phenyl)-1,2,3,4-tetrahydro-isoquinoline. A mixture of 2-(2-chloro-4-nitrophenyl)-1,2,3,4-tetrahydro-isoquinoline (1.4 g, 4.8 mmol), saturated aqueous ammonium chloride (5 mL), and acetone (20 mL) was cooled in an ice bath. Solid zinc powder (3.2 g, 48 mmol) was added in portions over 10 min with stirring. The ice bath was allowed to expire and the mixture was stirred for 16 h. EtOAc (200 mL) was then added, followed by anhydrous sodium sulfate (20 g). The mixture was stirred for 15 min, then filtered through a pad of silica gel, eluting with EtOAc. The resulting clear solution was concentrated to afford the titled compound (1.2 g, 96%). $^1$H NMR (500 MHz, CDCl$_3$): 7.20-7.11 (m, 3H), 7.11-7.04 (m, 1H), 6.95 (d, J=8.5 Hz, 1H), 6.78 (d, J=2.7 Hz, 1H), 6.56 (dd, J=8.5, 2.7 Hz, 1H), 4.17 (s, 2H), 3.55 (s, 2H), 3.27 (t, J=5.8 Hz, 2H), 3.00 (t, J=5.8 Hz, 2H).

Step C: Preparation of 1-{[4-chloro-3-(3,4-dihydro-1H-isoquinolin-2-yl)-benzoylamino]-ethoxycarbonylimino-methyl}-1H-pyrazole-4-carboxylic acid, ethyl ester. A solution of 2-(2-chloro-4-amino-phenyl)-1,2,3,4-tetrahydro-isoquinoline (1.2 g, 4.6 mmol) and ethyl isothiocyanatoformate (0.61 g, 4.6 mmol) and DCM (20 mL) was maintained at rt for 16 h. The reaction mixture was concentrated to dryness, and was then redissolved in DCM (20 mL). Ethyl pyrazole-4-carboxylate (0.98 g, 10 mmol), TEA (1.4 g, 14 mmol), EDCl (1.3 g, 7.0 mmol) were added and the reaction was allowed to proceed for 4 h. The mixture was diluted with EtOAc (200 mL), washed with equal volumes of water (2×), brine, dried, and concentrated. The residue was purified by FCC (1:99 to 30:70 EtOAc/hexanes) to provide a partially pure guanidine intermediate (1.2 g, 52%).

Step D: Preparation of 1-[7-chloro-6-(3,4-dihydro-1H-isoquinolin-2-yl)-4-oxo-3,4-dihydro-quinazolin-2-yl]-1H-pyrazole-4-carboxylic acid, ethyl ester. A solution of 1-{[4-chloro-3-(3,4-dihydro-1H-isoquinolin-2-yl)-benzoylamino]-ethoxycarbonylimino-methyl}-1H-pyrazole-4-carboxylic acid, ethyl ester (1.2 g, 2.4 mmol), DCE (5 mL) and chlorotrimethylsilane (2.8 mL, 22 mmol) was heated to 110° C. for 16 h in a sealed tube. The vessel was cooled in an ice bath for 1 h, and the resulting precipitate was collected by filtration, washed with cold DCE, and dried under vacuum to provide the titled compound (0.40 g, 19%). MS (ESI): mass calcd. for $C_{23}H_{20}ClN_5O_3$, 449.9; m/z found, 450.1 [M+H]$^+$.

Step E: Preparation of 1-[7-chloro-6-(3,4-dihydro-1H-isoquinolin-2-yl)-4-oxo-3,4-dihydro-quinazolin-2-yl]-1H-pyrazole-4-carboxylic acid. A mixture of 1-[7-chloro-6-(3,4-dihydro-1H-isoquinolin-2-yl)-4-oxo-3,4-dihydro-quinazolin-2-yl]-1H-pyrazole-4-carboxylic acid, ethyl ester (0.35 g, 0.78 mmol), THF (12 mL), and aqueous 1M LiOH (7.8 mL, 7.8 mmol) was stirred at rt for 16 h. The THF was removed, and the aqueous mixture was cooled in an ice bath. The pH was adjusted to ca. 5 using 1M aqueous HCl, and the resulting precipitate was collected, washed well with water, and dried to afford the titled compound (0.33 g, 99%). MS (ESI): mass calcd. for $C_{21}H_{16}ClN_5O_3$, 421.1; m/z found, 422.1 [M+H]$^+$. $^1$H NMR (500 MHz, DMSO-d$_6$): 13.22-12.69 (br m, 2H), 8.92 (s, 1H), 8.25 (s, 1H), 7.88-7.73 (m, 2H), 7.24-7.16 (m, 4H), 4.31 (s, 2H), 3.39 (t, J=5.6, 2H), 3.00 (t, J=5.5, 2H).

Example 85

1-[6-(7-Bromo-3,4-dihydro-1H-isoquinolin-2-yl)-7-chloro-4-oxo-3,4-dihydro-quinazolin-2-yl]-1H-pyrazole-4-carboxylic acid

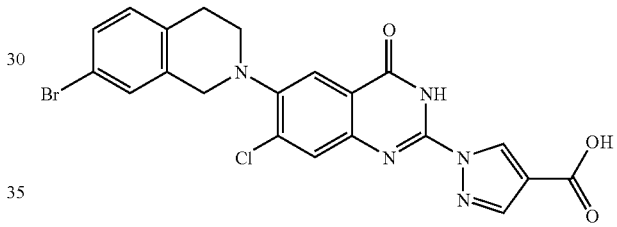

The titled compound was prepared in a manner analogous to Example 84 using 7-bromo-1,2,3,4-tetrahydro-isoquinoline and 2,3-dichloronitrobenzene, in step A. MS (ESI): mass calcd. for $C_{21}H_{15}BrClN_5O_3$, 499.0; m/z found, 500.0 [M+H]$^+$. $^1$H NMR (500 MHz, DMSO-d$_6$): 12.93 (s, 2H), 8.92 (s, 1H), 8.25 (s, 1H), 7.80 (s, 2H), 7.47 (s, 1H), 7.38 (d, J=8.1, 1H), 7.17 (d, J=8.2, 1H), 4.31 (s, 2H), 3.45-3.35 (m, 3H), 3.01-2.90 (m, 2H).

Example 86

(rac)-1-{7-Chloro-6-[3-(3-methoxy-phenyl)-piperidin-1-yl]-4-oxo-3,4-dihydro-quinazolin-2-yl}-1H-pyrazole-4-carboxylic acid

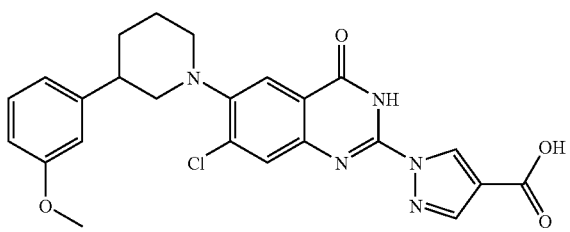 [SMILES: COc1cccc(C2CCCN(c3cc4c(=O)[nH]c(-n5cc(C(=O)O)cn5)nc4cc3Cl)C2)c1]

The titled compound was prepared in a manner analogous to Example 84 using 3-(3-methoxyphenyl)piperidine and 2,3-dichloronitrobenzene in step A. MS (ESI): mass calcd. for $C_{24}H_{22}ClN_5O_4$, 479.1; m/z found, 480.2 [M+H]$^+$. $^1$H NMR (500 MHz, DMSO-d$_6$): 13.32-12.61 (br m, 2H), 8.90 (s, 1H), 8.24 (s, 1H), 7.76 (s, 1H), 7.72 (s, 1H), 7.23 (t, J=7.9, 1H), 6.96-6.88 (m, 2H), 6.84-6.76 (m, 1H), 3.75 (s, 3H), 3.43-3.36 (m, 2H), 2.96 (t, J=11.3, 1H), 2.89-2.72 (m, 2H), 2.02-1.74 (m, 3H), 1.73-1.58 (m, 1H), Example 87

1-[6-(2,5-dichloro-phenoxy)-7-fluoro-4-oxo-3,4-dihydro-quinazolin-2-yl]-1H-pyrazole-4-carboxylic acid

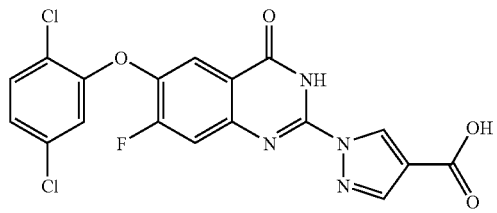 [SMILES: O=C(O)c1cnn(-c2nc3cc(F)c(Oc4cc(Cl)ccc4Cl)cc3c(=O)[nH]2)c1]

The titled compound was prepared in a manner analogous to Example 27 using 2,5-dichlorophenol and 3,4-difluoronitrobenzene in step A. MS (ESI): mass calcd. for $C_{18}H_9Cl_2FN_4O_4$, 434.0; m/z found, 434.9 [M+H]$^+$. $^1$H NMR (400 MHz, DMSO-d$_6$): 13.09 (s, 2H), 8.92 (s, 1H), 8.27 (s, 1H), 7.75 (d, J=11.4 Hz, 1H), 7.72 (d, J=8.6 Hz, 1H), 7.54 (d, J=8.8 Hz, 1H), 7.44 (d, J=2.4 Hz, 1H), 7.40 (dd, J=8.6, 2.4 Hz, 1H).

Example 88

1-[6-(3,4-dimethyl-phenoxy)-7-fluoro-4-oxo-3,4-dihydro-quinazolin-2-yl]-1H-pyrazole-4-carboxylic acid

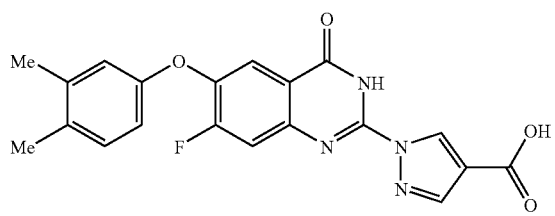 [SMILES: Cc1ccc(Oc2cc3c(=O)[nH]c(-n4cc(C(=O)O)cn4)nc3cc2F)cc1C]

The titled compound was prepared in a manner analogous to Example 27 using 3,4-dimethylphenol and 3,4-difluoronitrobenzene in step A. MS (ESI): mass calcd. for $C_{20}H_{15}FN_4O_4$, 394.1; m/z found, 395.0 [M+H]$^+$. $^1$H NMR (400 MHz, DMSO-d$_6$): 13.04 (s, 1H), 13.04-12.92 (m, 1H), 8.91 (s, 1H), 8.26 (s, 1H), 7.70 (d, J=11.5 Hz, 1H), 7.47 (d, J=8.9 Hz, 1H), 7.22 (d, J=8.2 Hz, 1H), 6.99 (d, J=2.7 Hz, 1H), 6.89 (dd, J=8.2, 2.7 Hz, 1H), 2.24 (s, 6H).

Example 89

1-[6-(3,5-dimethyl-phenoxy)-7-methyl-4-oxo-3,4-dihydro-quinazolin-2-yl]-1H-pyrazole-4-carboxylic acid

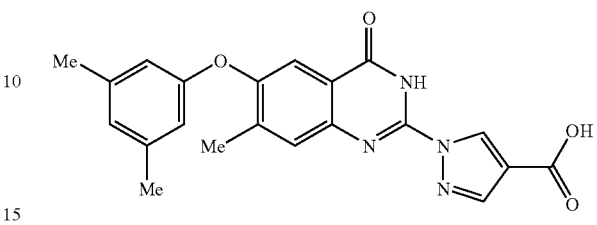

The titled compound was prepared in a manner analogous to Example 27 using 3,5-dimethylphenol and 4-fluoro-3-methylnitrobenzene in step A. MS (ESI): mass calcd. for $C_{21}H_{18}N_4O_4$, 390.1; m/z found, 391.1 [M+H]$^+$. $^1$H NMR (400 MHz, DMSO-d$_6$): 12.99 (s, 2H), 8.91 (s, 1H), 8.24 (s, 1H), 7.66 (s, 1H), 7.30 (s, 1H), 6.86 (s, 1H), 6.70 (s, 2H), 2.39 (s, 3H), 2.27 (s, 6H).

Example 90

1-[6-(2,5-dichloro-phenoxy)-7-methyl-4-oxo-3,4-dihydro-quinazolin-2-yl]-1H-pyrazole-4-carboxylic acid

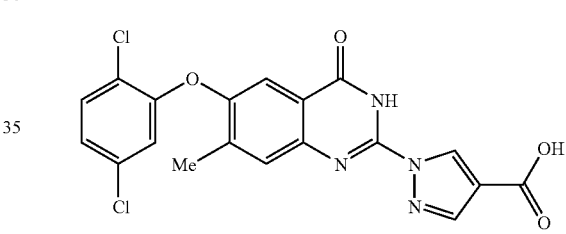

The titled compound was prepared in a manner analogous to Example 27 using 2,5-dichlorophenol and 4-fluoro-3-methylnitrobenzene in step A. MS (ESI): mass calcd. for $C_{19}H_{12}Cl_2N_4O_4$, 430.0; m/z found, 431.0 [M+H]$^+$. $^1$H NMR (400 MHz, DMSO-d$_6$): 13.02 (s, 1H), 12.87 (s, 1H), 8.92 (s, 1H), 8.25 (s, 1H), 7.72 (d, J=8.6 Hz, 2H), 7.40 (dd, J=8.6, 2.4 Hz, 1H), 7.35 (d, J=2.2 Hz, 1H), 7.23 (s, 1H), 2.43 (s, 3H).

Example 91

1-[6-(biphenyl-3-yloxy)-7-methyl-4-oxo-3,4-dihydro-quinazolin-2-yl]-1H-pyrazole-4-carboxylic acid

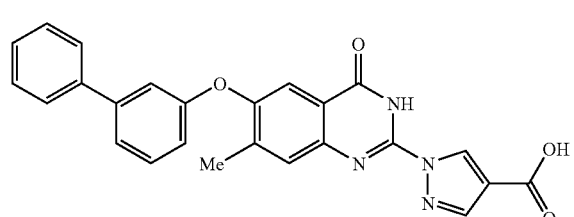

The titled compound was prepared in a manner analogous to Example 27 using 3-phenylphenol and 4-fluoro-3-methylnitrobenzene in step A. MS (ESI): mass calcd. for $C_{25}H_{18}N_4O_4$, 438.1; m/z found, 439.1 [M+H]$^+$. $^1$H NMR (400 MHz, DMSO-$d_6$): 12.91 (s, 2H), 8.91 (s, 1H), 8.22 (s, 1H), 7.72-7.65 (m, 3H), 7.54 (dd, J=3.8, 2.3 Hz, 2H), 7.46 (t, J=7.5 Hz, 2H), 7.41-7.37 (m, 3H), 7.10-7.03 (m, 1H), 2.43 (s, 3H).

Example 92

1-[6-(3,4-dimethyl-phenoxy)-7-methyl-4-oxo-3,4-dihydro-quinazolin-2-yl]-1H-pyrazole-4-carboxylic acid

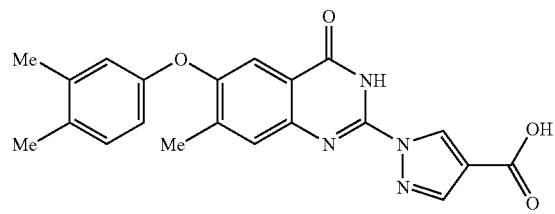 [SMILES: Cc1ccc(Oc2cc3c(=O)[nH]c(-n4cc(C(=O)O)cn4)nc3cc2C)cc1C]

The titled compound was prepared in a manner analogous to Example 27 using 3,4-dimethylphenol and 4-fluoro-3-methylnitrobenzene in step A. MS (ESI): mass calcd. for $C_{21}H_{18}N_4O_4$, 390.1; m/z found, 391.1 [M+H]$^+$. $^1$H NMR (400 MHz, DMSO-$d_6$): 13.01 (s, 1H), 12.77 (s, 1H), 8.90 (s, 1H), 8.24 (s, 1H), 7.65 (s, 1H), 7.23 (s, 1H), 7.21 (d, J=8.3 Hz, 1H), 6.93 (d, J=2.4 Hz, 1H), 6.83 (dd, J=8.1, 2.5 Hz, 1H), 2.41 (s, 3H), 2.23 (s, 6H).

Example 93

1-[7-methyl-4-oxo-6-(3-trifluoromethyl-phenoxy)-3,4-dihydro-quinazolin-2-yl]-1H-pyrazole-4-carboxylic acid

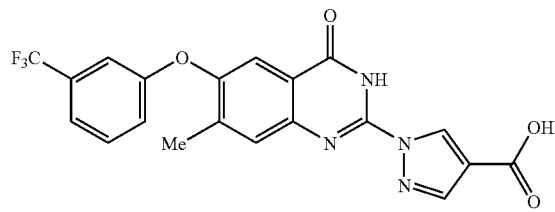 [SMILES: Cc1cc2nc(-n3cc(C(=O)O)cn3)[nH]c(=O)c2cc1Oc1cccc(C(F)(F)F)c1]

The titled compound was prepared in a manner analogous to Example 27 using 3-trifluoromethylphenol and 4-fluoro-3-methylnitrobenzene in step A. MS (ESI): mass calcd. for $C_{20}H_{13}F_3N_4O_4$, 430.0; m/z found, 431.0 [M+H]$^+$. $^1$H NMR (400 MHz, DMSO-$d_6$): 13.03 (s, 1H), 12.97-12.44 (m, 1H), 8.92 (s, 1H), 8.26 (s, 1H), 7.71 (d, J=5.1 Hz, 1H), 7.68 (t, J=8.0 Hz, 1H), 7.57 (d, J=7.8 Hz, 1H), 7.43 (s, 2H), 7.36 (d, J=8.2 Hz, 1H), 2.38 (s, 3H).

Example 94

1-[6-(3,5-dimethyl-phenoxy)-7-fluoro-4-oxo-3,4-dihydro-quinazolin-2-yl]-1H-pyrazole-4-carboxylic acid

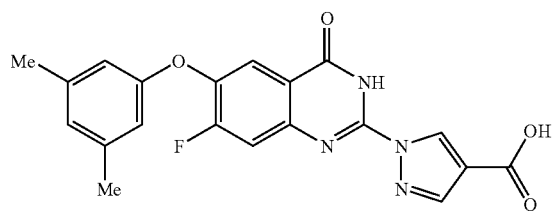 [SMILES: Cc1cc(C)cc(Oc2cc3c(=O)[nH]c(-n4cc(C(=O)O)cn4)nc3cc2F)c1]

The titled compound was prepared in a manner analogous to Example 27 using 3,5-dimethylphenol and 3,4-difluoronitrobenzene in step A. MS (ESI): mass calcd. for $C_{20}H_{15}FN_4O_4$, 394.1; m/z found, 395.0 [M+H]$^+$. $^1$H NMR (400 MHz, DMSO-$d_6$): 13.02 (s, 1H), 13.02-12.88 (m, 1H), 8.92 (s, 1H), 8.26 (s, 1H), 7.71 (d, J=11.4 Hz, 1H), 7.56 (d, J=8.9 Hz, 1H), 6.88 (s, 1H), 6.76 (s, 2H), 2.28 (s, 6H).

Example 95

1-[7-fluoro-4-oxo-6-(3-trifluoromethyl-phenoxy)-3,4-dihydro-quinazolin-2-yl]-1H-pyrazole-4-carboxylic acid

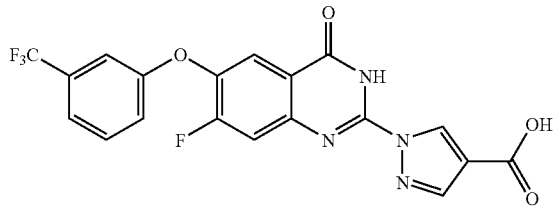 [SMILES: O=C(O)c1cnn(-c2nc3cc(F)c(Oc4cccc(C(F)(F)F)c4)cc3c(=O)[nH]2)c1]

The titled compound was prepared in a manner analogous to Example 27 using 3-trifluoromethylphenol and 3,4-difluoronitrobenzene in step A. MS (ESI): mass calcd. for $C_{19}H_{10}F_4N_4O_4$, 434.1; parent ion not observed. $^1$H NMR (400 MHz, DMSO-$d_6$): 13.07 (s, 2H), 8.93 (s, 1H), 8.28 (s, 1H), 7.75 (dd, J=10.1, 5.0 Hz, 2H), 7.69 (t, J=8.0 Hz, 1H), 7.60 (d, J=7.8 Hz, 1H), 7.52 (s, 1H), 7.44 (dd, J=8.2, 2.1 Hz, 1H).

Example 96

1-[6-(2-fluoro-3-trifluoromethyl-phenoxy)-4-oxo-3,4-dihydro-quinazolin-2-yl]-1H-pyrazole-4-carboxylic acid

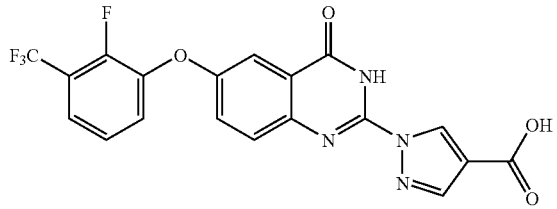 [SMILES: O=C(O)c1cnn(-c2nc3ccc(Oc4cccc(C(F)(F)F)c4F)cc3c(=O)[nH]2)c1]

The titled compound was prepared in a manner analogous to Example 27 using 2-fluoro-3-trifluoromethylphenol and 4-fluoronitrobenzene in step A. MS (ESI): mass calcd. for C$_{19}$H$_{10}$F$_4$N$_4$O$_4$, 434.1; parent ion not observed. $^1$H NMR (400 MHz, DMSO-d$_6$): 13.02 (s, 2H), 8.95 (s, 1H), 8.26 (s, 1H), 7.78 (s, 1H), 7.73-7.60 (m, 3H), 7.54 (s, 1H), 7.49 (t, J=8.2 Hz, 1H).

Example 97

1-[6-(3-fluoro-5-trifluoromethyl-phenoxy)-4-oxo-3,4-dihydro-quinazolin-2-yl]-1H-pyrazole-4-carboxylic acid

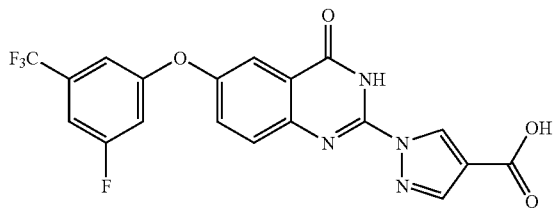

The titled compound was prepared in a manner analogous to Example 27 using 3-fluoro-5-trifluoromethylphenol and 4-fluoronitrobenzene in step A. MS (ESI): mass calcd. for C$_{19}$H$_{10}$F$_4$N$_4$O$_4$, 434.0; m/z found, 435.0 [M+H]$^+$. $^1$H-NMR (400 MHz, DMSO-d$_6$): 13.03 (s, 2H), 8.96 (s, 1H), 8.27 (s, 1H), 7.79 (s, 1H), 7.71-7.66 (m, 2H), 7.54 (d, J=8.4 Hz, 1H), 7.39 (d, J=9.9 Hz, 1H), 7.33 (s, 1H).

Example 98

1-[6-(3,5-dimethyl-phenoxy)-4-oxo-3,4-dihydro-quinazolin-2-yl]-1H-pyrazole-4-carboxylic acid

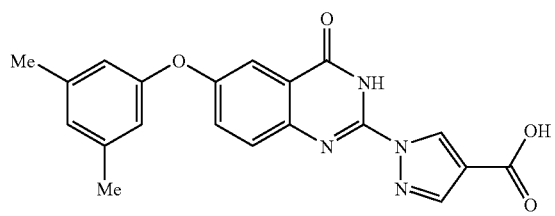 [SMILES: Cc1cc(C)cc(Oc2ccc3nc(-n4cc(C(=O)O)cn4)[nH]c(=O)c3c2)c1]

The titled compound was prepared in a manner analogous to Example 27 using 3,5-dimethylphenol and 4-fluoronitrobenzene in step A. MS (ESI): mass calcd. for C$_{20}$H$_{16}$N$_4$O$_4$, 376.1; m/z found, 377.1 [M+H]$^+$. $^1$H-NMR (400 MHz, DMSO-d$_6$): 13.01 (s, 1H), 12.91 (s, 1H), 8.94 (s, 1H), 8.25 (s, 1H), 7.73 (d, J=8.2 Hz, 1H), 7.57 (dd, J=8.9, 2.9 Hz, 1H), 7.43 (s, 1H), 6.89 (s, 1H), 6.75 (s, 2H), 2.28 (s, 6H).

Example 99

1-[6-(biphenyl-3-yloxy)-4-oxo-3,4-dihydro-quinazolin-2-yl]-1H-pyrazole-4-carboxylic acid

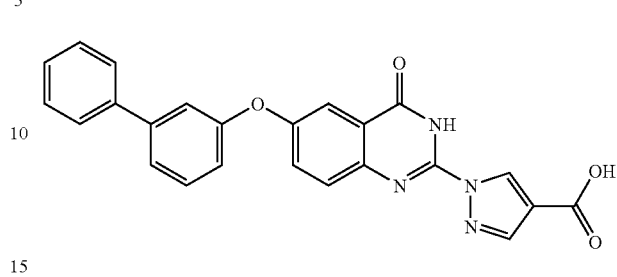

The titled compound was prepared in a manner analogous to Example 27 using 3-phenylphenol and 4-fluoronitrobenzene in step A. MS (ESI): mass calcd. for C$_{24}$H$_{16}$N$_4$O$_4$, 424.1; m/z found, 425.1 [M+H]$^+$. $^1$H-NMR (400 MHz, DMSO-d$_6$): 12.96 (s, 2H), 8.94 (s, 1H), 8.25 (s, 1H), 7.77 (d, J=8.9, 1H), 7.69 (d, J=7.7 Hz, 2H), 7.64 (dd, J=8.9, 2.7, 1H), 7.56 (d, J=4.7, 2H), 7.53 (d, J=2.8, 1H), 7.50-7.42 (m, 3H), 7.39 (t, J=7.3, 1H), 7.18-7.10 (m, 1H).

Example 100

1-[4-oxo-6-(3-trifluoromethyl-phenoxy)-3,4-dihydro-quinazolin-2-yl]-1H-pyrazole-4-carboxylic acid

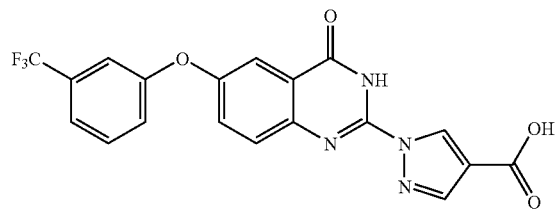

The titled compound was prepared in a manner analogous to Example 27 using 3-trifluoromethylphenol and 4-fluoronitrobenzene in step A. MS (ESI): mass calcd. for C$_{19}$H$_{11}$F$_3$N$_4$O$_4$, 416.0; m/z found, 417.0 [M+H]$^+$. $^1$H-NMR (400 MHz, DMSO-d$_6$): 13.02 (s, 2H), 8.95 (s, 1H), 8.27 (s, 1H), 7.79 (d, J=8.9, 1H), 7.69 (t, J=8.0, 1H), 7.65 (dd, J=8.9, 2.9, 1H), 7.60 (d, J=7.8, 1H), 7.57 (d, J=2.9, 1H), 7.49 (s, 1H), 7.44 (d, J=8.1, 1H).

Example 101

1-[6-(2,6-dichloro-phenoxy)-5,7-difluoro-4-oxo-3,4-dihydro-quinazolin-2-yl]-1H-pyrazole-4-carboxylic acid

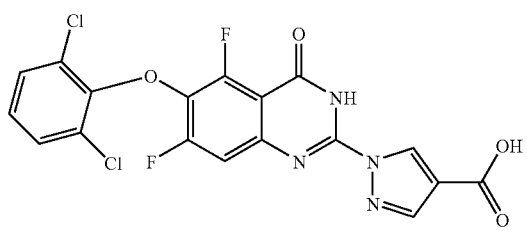 [SMILES: O=C(O)c1cnn(-c2nc3cc(F)c(Oc4c(Cl)cccc4Cl)c(F)c3c(=O)[nH]2)c1]

The titled compound was prepared in a manner analogous to Example 27 using 2,6-dichlorophenol and 3,4,5-trifluoronitrobenzene in step A. MS (ESI): mass calcd. for $C_{18}H_8Cl_2F_2N_4O_4$, 452.0; parent ion not observed. $^1$H-NMR (500 MHz, DMSO-d$_6$): 13.06 (s, 2H), 8.91 (s, 1H), 8.27 (s, 1H), 7.63 (d, J=8.2 Hz, 2H), 7.57 (d, J=11.6 Hz, 1H), 7.35 (t, J=8.2 Hz, 1H).

Example 102

1-(6-cyclohexyloxy-4-oxo-3,4-dihydro-quinazolin-2-yl)-1H-pyrazole-4-carboxylic acid

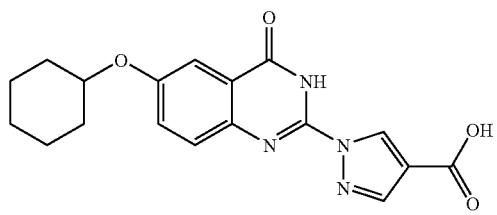 [SMILES: O=C(O)c1cnn(-c2nc3ccc(OC4CCCCC4)cc3c(=O)[nH]2)c1]

The titled compound was prepared in a manner analogous to Example 27 using cyclohexanol and 4-fluoronitrobenzene in step A. MS (ESI): mass calcd. for $C_{18}H_{18}N_4O_4$, 354.1; m/z found, 355.1 [M+H]$^+$. $^1$H-NMR (400 MHz, DMSO-d$_6$): 12.92 (s, 1H), 12.85-12.50 (m, 1H), 8.91 (s, 1H), 8.22 (s, 1H), 7.63 (d, J=8.0, 1H), 7.52 (d, J=2.7, 1H), 7.45 (dd, J=8.9, 2.8, 1H), 4.50 (s, 1H), 1.95 (s, 2H), 1.73 (s, 2H), 1.55-1.42 (m, 4H), 1.31-1.22 (m, 2H).

Example 103

1-[6-(4-methyl-piperazin-1-yl)-4-oxo-3,4-dihydro-quinazolin-2-yl]-1H-pyrazole-4-carboxylic acid

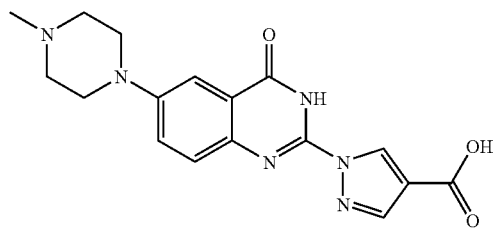 [SMILES: CN1CCN(c2ccc3nc(-n4cc(C(=O)O)cn4)[nH]c(=O)c3c2)CC1]

The titled compound was prepared in a manner analogous to Example 17 using 4-(4-methyl-piperazin-1-yl)-aniline in step A. MS (ESI): mass calcd. for $C_{17}H_{18}N_6O_3$, 354.1; m/z found, 355.2 [M+H]$^+$. $^1$H-NMR (400 MHz, DMSO-d$_6$): 12.88-11.90 (m, 2H), 8.79 (s, 1H), 7.91 (s, 1H), 7.64-7.20 (m, 3H), 3.15 (d, J=4.8, 4H), 2.24 (s, 3H).

Example 104

1-(6-isopropoxy-4-oxo-3,4-dihydro-quinazolin-2-yl)-1H-pyrazole-4-carboxylic acid

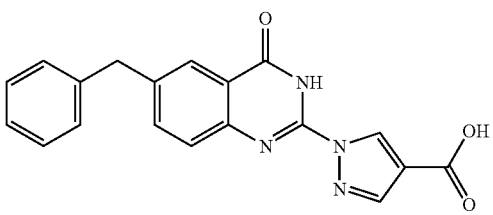 [SMILES: O=C(O)c1cnn(-c2nc3ccc(Cc4ccccc4)cc3c(=O)[nH]2)c1]

The titled compound was prepared in a manner analogous to Example 17 using 4-isopropoxyaniline in step A. MS (ESI): mass calcd. for $C_{15}H_{14}N_4O_4$, 314.1; m/z found, 315.1 [M+H]$^+$. $^1$H-NMR (500 MHz, DMSO-d$_6$): 12.96 (s, 1H), 12.76 (s, 1H), 8.92 (s, 1H), 8.23 (s, 1H), 7.63 (d, J=8.7 Hz, 1H), 7.51 (s, 1H), 7.43 (d, J=8.9 Hz, 1H), 4.90-4.61 (m, 1H), 1.32 (d, J=6.0 Hz, 6H).

Example 105

1-(6-benzyl-4-oxo-3,4-dihydro-quinazolin-2-yl)-1H-pyrazole-4-carboxylic acid

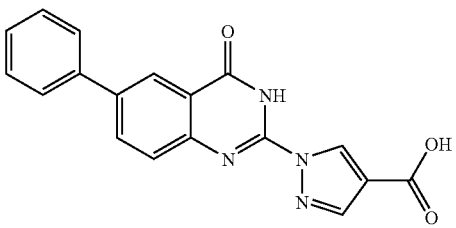 [SMILES: O=C(O)c1cnn(-c2nc3ccc(-c4ccccc4)cc3c(=O)[nH]2)c1]

The titled compound was prepared in a manner analogous to Example 17 using 4-benzylaniline in step A. MS (ESI): mass calcd. for $C_{19}H_{14}N_4O_3$, 346.1; m/z found, 347.1 [M+H]$^+$. $^1$H-NMR (500 MHz, DMSO-d$_6$): 12.99 (s, 1H), 12.77 (s, 1H), 8.93 (s, 1H), 8.24 (s, 1H), 7.96 (s, 1H), 7.73 (d, J=8.0 Hz, 1H), 7.62 (d, J=8.1 Hz, 1H), 7.34-7.28 (m, 4H), 7.21 (t, J=6.9 Hz, 1H), 4.11 (s, 2H).

Example 106

1-(4-oxo-6-phenyl-3,4-dihydro-quinazolin-2-yl)-1H-pyrazole-4-carboxylic acid

The titled compound was prepared in a manner analogous to Example 17 using 4-aminobiphenyl in step A. MS (ESI): mass calcd. for $C_{18}H_{12}N_4O_3$, 332.1; m/z found, 333.1 [M+H]$^+$. $^1$H-NMR (500 MHz, DMSO-d$_6$): 13.03 (s, 1H), 12.92 (s, 1H), 8.98 (s, 1H), 8.34 (s, 1H), 8.28 (s, 1H), 8.17 (d, J=8.3 Hz, 1H), 7.79 (d, J=7.4 Hz, 3H), 7.53 (t, J=7.7 Hz, 2H), 7.43 (t, J=7.4 Hz, 1H).

Example 107

1-(6-morpholin-4-yl-4-oxo-3,4-dihydro-quinazolin-2-yl)-1H-pyrazole-4-carboxylic acid

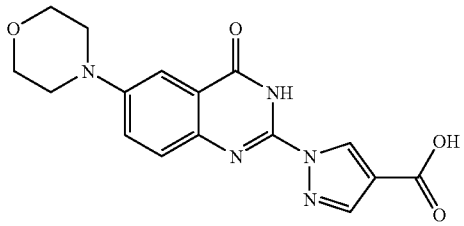 [SMILES: O=C(O)c1cnn(-c2nc3ccc(N4CCOCC4)cc3c(=O)[nH]2)c1]

The titled compound was prepared in a manner analogous to Example 17 using 4-(1-morpholino)-aniline in step A. MS (ESI): mass calcd. for $C_{16}H_{15}N_5O_4$, 341.1; m/z found, 342.1 [M+H]$^+$. $^1$H-NMR (500 MHz, DMSO-$d_6$): 12.95 (s, 1H), 12.63 (s, 1H), 8.90 (s, 1H), 8.22 (s, 1H), 7.60 (s, 2H), 7.43 (d, J=24.2 Hz, 1H), 3.84-3.72 (m, 4H), 3.27-3.21 (m, 4H).

Example 108

1-[6-(1H-Indol-6-yl)-4-oxo-3,4-dihydro-quinazolin-2-yl]-1H-pyrazole-4-carboxylic acid

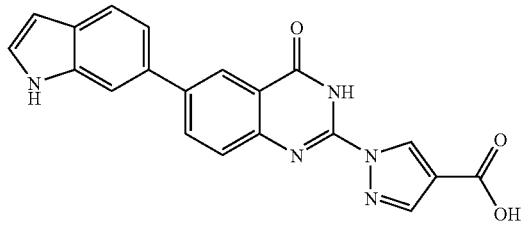 [SMILES: O=C(O)c1cnn(-c2nc3ccc(-c4ccc5cc[nH]c5c4)cc3c(=O)[nH]2)c1]

The titled compound was prepared in a manner analogous to Example 69, steps C-E, using 1-[6-iodo-4-oxo-3-(2-trimethylsilanyl-ethoxymethyl)-3,4-dihydro-quinazolin-2-yl]-1H-pyrazole-4-carboxylic acid ethyl ester (Example 69 product from step B) and indole-6-boronic acid in step C. MS (ESI): mass calcd. for $C_{20}H_{13}N_5O_3$, 371.1; m/z found, 372.1 [M+H]$^+$. $^1$H NMR (600 MHz, DMSO-$d_6$): 13.01 (s, 1H), 12.86 (s, 1H), 11.23 (s, 1H), 8.99 (s, 1H), 8.37 (s, 1H), 8.27 (s, 1H), 8.20 (s, 1H), 7.77 (s, 2H), 7.67 (d, J=8.2 Hz, 1H), 7.43 (s, 2H), 6.48 (s, 1H).

Example 109

1-(6-Cyclopropyl-4-oxo-3,4-dihydro-quinazolin-2-yl)-1H-pyrazole-4-carboxylic acid

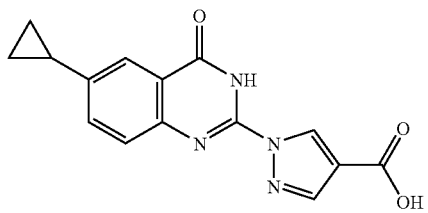 [SMILES: O=C(O)c1cnn(-c2nc3ccc(C4CC4)cc3c(=O)[nH]2)c1]

Step A: Preparation of 1-[(4-bromo-phenylimino)-ethoxycarbonylamino-methyl]-1H-pyrazole-4-carboxylic acid ethyl ester. Ethyl isothiocyanatoformate (1.44 mL, 12.2 mmol) was added to a solution of 4-bromo-phenylamine (1.91 g, 11.1 mmol) and DCM (37 mL). After 1 h, triethylamine (4.65 mL, 33.4 mmol) was added to the reaction mixture, followed by ethyl pyrazole-4-carboxylate (1.87 g, 13.3 mmol), and EDCl (3.20 g, 16.7 mmol). After 18 h, the reaction mixture was diluted with DCM (150 mL), washed with brine (50 mL), dried (MgSO$_4$), and concentrated. The residue was purified by FCC (5-40% EtOAc/hexanes) to yield the titled compound (1.84 g, 40% yield). MS (ESI/Cl): mass calcd. for $C_{16}H_{17}BrN_4O_4$, 408.1; m/z found, 409.1 [M+H]$^+$.

Step B: Preparation of 1-(6-bromo-4-oxo-3,4-dihydro-quinazolin-2-yl)-1H-pyrazole-4-carboxylic acid ethyl ester. Titanium (IV) chloride (2.47 mL, 22.5 mmol) was carefully added to a solution of 1-[(4-bromo-phenylimino)-ethoxycarbonylamino-methyl]-1H-pyrazole-4-carboxylic acid ethyl ester (1.84 g, 4.50 mmol) and DCE (45 mL), and the resulting solution was heated to 100° C. for 15 h. The reaction mixture was cooled to room temperature and poured into ice water (50 mL) and DCM (100 mL) was added. The biphasic mixture was stirred for 2 h, and the layers were separated. The aqueous layer was further extracted with DCM (2×50 mL). The combined organic layers were washed with brine (50 mL), dried (MgSO$_4$), and concentrated. The residue was triturated from EtOH to yield the titled compound (1.05 g, 64% yield). MS (ESI/Cl): mass calcd. for $C_{14}H_{11}BrN_4O_3$, 362.0; m/z found, 363.0 [M+H]$^+$. $^1$H NMR (600 MHz, DMSO-$d_6$): 13.15 (s, 1H), 9.01 (d, J=0.5 Hz, 1H), 8.33 (s, 1H), 8.20 (d, J=2.3 Hz, 1H), 7.99 (dd, J=8.7, 2.4 Hz, 1H), 7.66 (d, J=8.8 Hz, 1H), 4.30 (q, J=7.1 Hz, 2H), 1.32 (t, J=7.1 Hz, 3H).

Step C: Preparation of 1-[6-bromo-4-oxo-3-(2-trimethylsilanyl-ethoxymethyl)-3,4-dihydro-quinazolin-2-yl]-1H-pyrazole-4-carboxylic acid ethyl ester. DIEA (1.23 mL, 7.08 mmol) was added to 1-(6-bromo-4-oxo-3,4-dihydro-quinazolin-2-yl)-1H-pyrazole-4-carboxylic acid ethyl ester (0.980 g, 2.70 mmol) in THF (13.5 mL), followed by (2-chloromethoxy-ethyl)-trimethyl-silane (0.500 mL, 3.27 mmol). The reaction mixture was stirred at room temperature for 18 h, and concentrated. The residue was purified by FCC (0-20% EtOAc/hexanes) to yield the titled compound (1.27 g, 95% yield). MS (ESI/Cl): mass calcd. for $C_{20}H_{25}BrN_4O_4Si$, 492.1; m/z found, 435.1 [M−58+H]$^+$.

Step D: Preparation of 1-[6-cyclopropyl-4-oxo-3-(2-trimethylsilanylethoxymethyl)-3,4-dihydro-quinazolin-2-yl]-1H-pyrazole-4-carboxylic acid ethyl ester. A mixture of 1-[6-bromo-4-oxo-3-(2-trimethylsilanyl-ethoxymethyl)-3,4-dihydro-quinazolin-2-yl]-1H-pyrazole-4-carboxylic acid ethyl ester (0.500 g, 1.01 mmol), cyclopropylboronic acid (0.199 g, 2.32 mmol), dichloro(1,1'-bis(diphenylphosphino)ferrocene)palladium(II)dichloromethane adduct (0.100 g, 0.123 mmol), $K_2CO_3$ (0.420 g, 3.04 mmol) and THF (10 mL) were purged for 15 minutes with nitrogen and then heated to 80° C. for 15 h. The mixture was cooled to room temperature and filtered through a pad of CELITE®. The filtrate cake was washed with dichloromethane and concentrated. The residue was purified by FCC (0-20% EtOAc/hexanes) to yield the titled compound (0.120 g, 26% yield). MS (ESI/Cl): mass calcd. for $C_{23}H_{30}N_4O_4Si$, 454.2; m/z found, 455.2 [M+H]$^+$.

Step E: Preparation of 1-(6-cyclopropyl-4-oxo-3,4-dihydro-quinazolin-2-yl)-1H-pyrazole-4-carboxylic acid ethyl ester. HCl (4 M in dioxane, 1.32 mL, 5.28 mmol) was added to 1-[6-cyclopropyl-4-oxo-3-(2-trimethylsilanylethoxymethyl)-3,4-dihydro-quinazolin-2-yl]-1H-pyrazole-4-carboxylic acid ethyl ester (0.12 g, 0.264 mmol). The reaction mixture was stirred at room temperature for 1 h, and concentrated. The residue was triturated with ether (10 mL) and the precipitate was collected and dried to yield the titled compound (0.072 g, 84% yield). MS (ESI/Cl): mass calcd. for $C_{17}H_{16}N_4O_3$, 324.1; m/z found, 325.1 [M+H]$^+$. $^1$H NMR (600 MHz, DMSO-$d_6$): 12.81 (s, 1H), 8.99 (d, J=0.5 Hz, 1H), 8.30 (s, 1H), 7.81 (s, 1H), 7.65-7.50 (m, 2H), 4.30 (q, J=7.1 Hz, 2H), 2.17-2.03 (m, 1H), 1.32 (t, J=7.1 Hz, 3H), 1.09-0.99 (m, 2H), 0.81-0.72 (m, 2H).

Step F: 1-(6-Cyclopropyl-4-oxo-3,4-dihydro-quinazolin-2-yl)-1H-pyrazole-4-carboxylic acid. A mixture of 1-(6-cyclopropyl-4-oxo-3,4-dihydro-quinazolin-2-yl)-1H-pyrazole-4-carboxylic acid ethyl ester (0.045 g, 0.139 mmol), 1M aq. KOH (0.694 mL) and THF (0.694 mL) was stirred for 18 h. The mixture was concentrated to remove the THF and the aqueous residue was acidified with 6 M aq. HCl at 0° C. The resulting precipitate was collected by filtration to provide the titled compound (0.035 g, 85%). MS (ESI/Cl): mass calcd. for $C_{16}H_{12}N_4O_3$, 296.1; m/z found, 297.1 [M+H]$^+$. $^1$H NMR (600 MHz, DMSO-$d_6$): 12.92 (s, 2H), 8.93 (d, J=0.5 Hz, 1H), 8.24 (s, 1H), 7.81 (s, 1H), 7.65-7.50 (m, 2H), 2.22-2.04 (m, 1H), 1.14-0.94 (m, 2H), 0.85-0.68 (m, 2H).

Example 110

1-(6-Cyclohexyl-7-fluoro-4-oxo-3,4-dihydro-quinazolin-2-yl)-1H-pyrazole-4-carboxylic acid

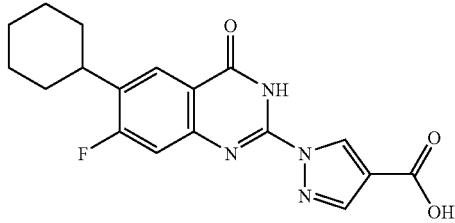 [SMILES: O=C(O)c1cnn(-c2nc3cc(F)c(C4CCCCC4)cc3c(=O)[nH]2)c1]

Step A: Preparation of 1-(6-bromo-7-fluoro-4-oxo-3,4-dihydro-quinazolin-2-yl)-1H-pyrazole-4-carboxylic acid ethyl ester. The titled compound was prepared in a manner analogous to Example 109, Steps A and B, using 4-bromo-3-fluorophenylamine in step A. MS (ESI/Cl): mass calcd. for $C_{14}H_{10}BrFN_4O_3$, 380.0; m/z found, 381.0 [M+H]$^+$. $^1$H NMR (400 MHz, CDCl$_3$): 10.29 (s, 1H), 8.99 (d, J=0.6 Hz, 1H), 8.51 (d, J=7.4 Hz, 1H), 8.15 (d, J=0.5 Hz, 1H), 7.40 (d, J=9.0 Hz, 1H), 4.38 (q, J=7.1 Hz, 2H), 1.40 (t, J=7.1 Hz, 3H).

Step B: Preparation of 1-(6-cyclohexyl-7-fluoro-4-oxo-3,4-dihydro-quinazolin-2-yl)-1H-pyrazole-4-carboxylic acid ethyl ester. To THF (5 mL), a 1M solution of $ZnCl_2$ in ether (5.00 mL, 5.00 mmol) was added followed by a 2M solution of cyclohexyl magnesium chloride in ether (2.50 mL, 5.00 mmol). The reaction mixture was stirred overnight at room temperature and the stirring was stopped until all of the precipitate settled to the bottom of the flask. In a different flask, THF (4 mL) was added to a mixture of palladium acetate (11.8 mg, 0.053 mmol), Ru-Phos (48.9 mg, 0.105 mmol) and 1-(6-bromo-7-fluoro-4-oxo-3,4-dihydro-quinazolin-2-yl)-1H-pyrazole-4-carboxylic acid ethyl ester (0.200 g, 0.525 mmol) and purged with nitrogen for 5 minutes. Then, a solution of cyclohexyl zinc chloride prepared as described above (5.25 mL, 2.62 mmol) was added and the mixture stirred for 18 h. The crude reaction mixture was poured into EtOH (10 mL) and acidified with 6 M aq. HCl (1 mL) slowly. The precipitated product was collected by filtration, triturated with EtOH and filtered again to provide the titled compound (0.110 g, 54%). MS (ESI/Cl): mass calcd. for $C_{20}H_{21}FN_4O_3$, 384.2; m/z found, 385.2 [M+H]$^+$.

Step C: Preparation of 1-(6-cyclohexyl-7-fluoro-4-oxo-3,4-dihydro-quinazolin-2-yl)-1H-pyrazole-4-carboxylic acid. The titled compound was prepared in a manner analogous to Example 109, Step F using 1-(6-cyclohexyl-7-fluoro-4-oxo-3,4-dihydro-quinazolin-2-yl)-1H-pyrazole-4-carboxylic acid ethyl ester. MS (ESI/Cl): mass calcd. for $C_{18}H_{17}FN_4O_3$, 356.1; m/z found, 357.1 [M+H]$^+$. $^1$H NMR (400 MHz, DMSO-$d_6$): 13.01 (s, 2H), 8.92 (d, J=0.6 Hz, 1H), 8.26 (s, 1H), 8.03 (d, J=8.1 Hz, 1H), 7.45 (d, J=11.2 Hz, 1H), 2.89 (t, J=11.7 Hz, 1H), 1.84 (d, J=8.4 Hz, 4H), 1.73 (d, J=12.7 Hz, 1H), 1.59-1.16 (m, 5H).

Example 111

1-(4-Oxo-8-phenyl-3,4-dihydro-quinazolin-2-yl)-1H-pyrazole-4-carboxylic acid

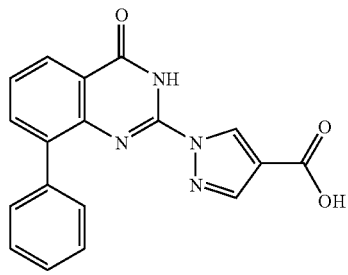 [SMILES: O=C(O)c1cnn(-c2nc3c(-c4ccccc4)cccc3c(=O)[nH]2)c1]

The titled compound was prepared in a manner analogous to Example 109, steps A, B and F, using biphenyl-2-yl-amine in step A. MS (ESI/Cl): mass calcd. for $C_{18}H_{12}N_4O_3$, 332.1; m/z found, 333.1 [M+H]$^+$. $^1$H NMR (500 MHz, DMSO-$d_6$): 13.00 (s, 2H), 8.58 (s, 1H), 8.24 (s, 1H), 8.18 (d, J=7.9 Hz, 1H), 7.89 (d, J=7.4 Hz, 1H), 7.70 (d, J=8.1 Hz, 2H), 7.60 (t, J=7.7 Hz, 1H), 7.52 (t, J=7.6 Hz, 2H), 7.46-7.43 (m, 1H).

Example 112

1-(4-Oxo-8-phenoxy-3,4-dihydro-quinazolin-2-yl)-1H-pyrazole-4-carboxylic acid

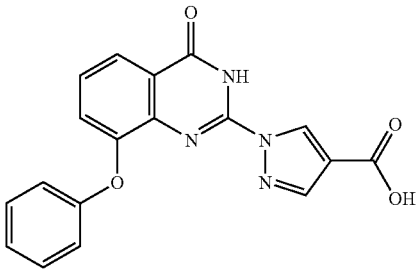 [SMILES: O=C(O)c1cnn(-c2nc3c(Oc4ccccc4)cccc3c(=O)[nH]2)c1]

The titled compound was prepared in a manner analogous to Example 109, steps A, B and F using 2-phenoxyphenylamine in step A. MS (ESI/Cl): mass calcd. for $C_{18}H_{12}N_4O_4$, 348.1; m/z found, 349.1 [M+H]$^+$. $^1$H NMR (500 MHz, DMSO-d$_6$): 12.97 (s, 2H), 8.41 (s, 1H), 8.21 (s, 1H), 8.02-7.88 (m, 1H), 7.51 (dd, J=7.4, 6.0 Hz, 2H), 7.39-7.36 (m, 2H), 7.11 (t, J=7.4 Hz, 1H), 7.02 (d, J=7.8 Hz, 2H).

Example 113

1-(4-Oxo-8-phenylsulfanyl-3,4-dihydro-quinazolin-2-yl)-1H-pyrazole-4-carboxylic acid

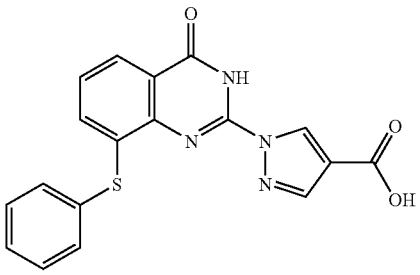

The titled compound was prepared in a manner analogous to Example 109, steps A, B and F using 2-phenylsulfanylphenylamine in step A. MS (ESI/Cl): mass calcd. for $C_{18}H_{12}N_4O_3S$, 364.1; m/z found, 365.1 [M+H]$^+$. $^1$H NMR (500 MHz, DMSO-d$_6$): 13.06 (s, 2H), 8.76 (d, J=0.6 Hz, 1H), 8.27 (d, J=0.6 Hz, 1H), 7.92 (dd, J=7.9 Hz, 1.3, 1H), 7.60-7.42 (m, 5H), 7.36 (t, J=7.8 Hz, 1H), 7.17 (d, J=7.7 Hz, 1H).

Example 114

1-(8-Isopropyl-4-oxo-3,4-dihydro-quinazolin-2-yl)-1H-pyrazole-4-carboxylic acid

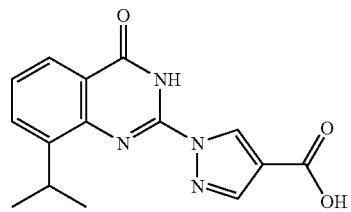 [SMILES: CC(C)c1cccc2c(=O)[nH]c(-n3cc(C(=O)O)cn3)nc12]

The titled compound was prepared in a manner analogous to Example 109, steps A, B and F using 2-isopropylphenylamine in step A. MS (ESI/Cl): mass calcd. for $C_{15}H_{14}N_4O_3$, 298.1; m/z found, 299.1 [M+H]$^+$. $^1$H NMR (400 MHz, DMSO-d$_6$): 12.92 (s, 2H), 9.00 (s, 1H), 8.26 (s, 1H), 8.00 (dd, J=7.9, 1.3 Hz, 1H), 7.76 (d, J=7.4 Hz, 1H), 7.48 (t, J=7.7 Hz, 1H), 4.03-3.93 (m, 1H), 1.30 (d, J=6.9 Hz, 6H).

Example 115

1-(8-tert-Butyl-4-oxo-3,4-dihydro-quinazolin-2-yl)-1H-pyrazole-4-carboxylic acid

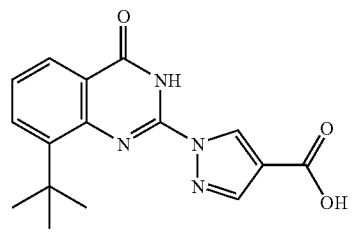 [SMILES: CC(C)(C)c1cccc2c(=O)[nH]c(-n3cc(C(=O)O)cn3)nc12]

The titled compound was prepared in a manner analogous to Example 109, steps A, B and F using 2-tert-butylphenylamine in step A. MS (ESI/Cl): mass calcd. for $C_{16}H_{16}N_4O_3$, 312.1; m/z found, 313.1 [M+H]$^+$. $^1$H NMR (500 MHz, DMSO-d$_6$): 13.01 (s, 2H), 8.82 (s, 1H), 8.28 (s, 1H), 8.06 (dd, J=7.9, 1.4 Hz, 1H), 7.79 (dd, J=7.7, 1.4 Hz, 1H), 7.45 (t, J=7.8 Hz, 1H), 1.58 (s, 9H).

Example 116

1-(5,8-Difluoro-4-oxo-3,4-dihydro-quinazolin-2-yl)-1H-pyrazole-4-carboxylic acid

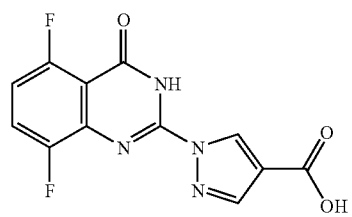 [SMILES: O=C(O)c1cnn(-c2nc3c(F)ccc(F)c3c(=O)[nH]2)c1]

The titled compound was prepared in a manner analogous to Example 109, steps A, B and F using 2,5-difluorophenylamine in step A. MS (ESI/Cl): mass calcd. for $C_{12}H_6F_2N_4O_3$, 292.0; m/z found, 293.0 [M+H]$^+$. $^1$H NMR (500 MHz, DMSO-d$_6$): 13.07 (s, 2H), 8.91 (s, 1H), 8.28 (s, 1H), 7.75 (td, J=9.5, 4.2 Hz, 1H), 7.28 (td, J=10.4, 3.6 Hz, 1H).

Example 117

1-(4-Oxo-8-trifluoromethoxy-3,4-dihydro-quinazolin-2-yl)-1H-pyrazole-4-carboxylic acid

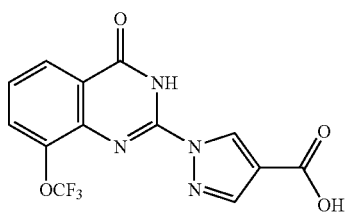 [SMILES: O=C(O)c1cnn(-c2nc3c(OC(F)(F)F)cccc3c(=O)[nH]2)c1]

The titled compound was prepared in a manner analogous to Example 109, steps A, B and F using 2-trifluoromethoxyphenylamine in step A. MS (ESI/Cl): mass calcd. for $C_{13}H_7F_3N_4O_4$, 340.1; m/z found, 341.1 $[M+H]^+$. $^1$H NMR (500 MHz, DMSO-$d_6$): 13.12 (s, 2H), 8.84 (d, J=0.6 Hz, 1H), 8.30 (d, J=0.6 Hz, 1H), 8.16 (dd, J=8.0, 1.4 Hz, 1H), 7.95-7.84 (m, 1H), 7.58 (t, J=8.0 Hz, 1H).

Example 118

1-(8-Fluoro-4-oxo-3,4-dihydro-quinazolin-2-yl)-1H-pyrazole-4-carboxylic acid

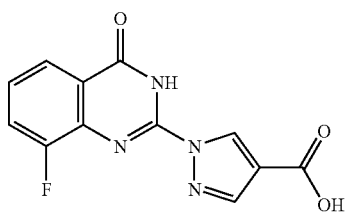 [SMILES: O=C(O)c1cnn(-c2nc3c(F)cccc3c(=O)[nH]2)c1]

The titled compound was prepared in a manner analogous to Example 109, steps A, B and F using 2-fluorophenylamine in step A. MS (ESI/Cl): mass calcd. for $C_{12}H_7FN_4O_3$, 274.0; m/z found, 275.1 $[M+H]^+$. $^1$H NMR (500 MHz, DMSO-$d_6$): 13.05 (s, 2H), 8.92 (s, 1H), 8.28 (s, 1H), 7.96 (d, J=7.6 Hz, 1H), 7.75-7.73 (m, 1H), 7.51 (td, J=8.0, 4.7 Hz, 1H).

Example 119

1-(6-Isopropyl-4-oxo-3,4-dihydro-quinazolin-2-yl)-1H-pyrazole-4-carboxylic acid

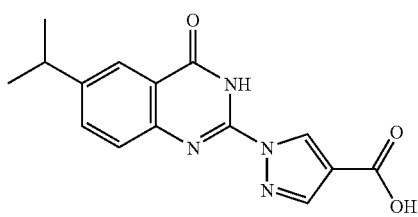 [SMILES: CC(C)c1ccc2nc(-n3cc(C(=O)O)cn3)[nH]c(=O)c2c1]

The titled compound was prepared in a manner analogous to Example 109, steps A, B and F using 4-isopropylphenylamine in step A. MS (ESI/Cl): mass calcd. for $C_{15}H_{14}N_4O_3$, 298.1; m/z found, 299.1 $[M+H]^+$. $^1$H NMR (600 MHz, DMSO-$d_6$): 12.90 (s, 2H), 8.94 (s, 1H), 8.25 (s, 1H), 7.97 (d, J=1.7 Hz, 1H), 7.77 (dd, J=8.4, 2.0 Hz, 1H), 7.65 (d, J=7.8 Hz, 1H), 3.1-3.04 (m, 1H), 1.27 (d, J=6.9 Hz, 6H).

Example 120

1-(6-sec-Butyl-4-oxo-3,4-dihydro-quinazolin-2-yl)-1H-pyrazole-4-carboxylic acid

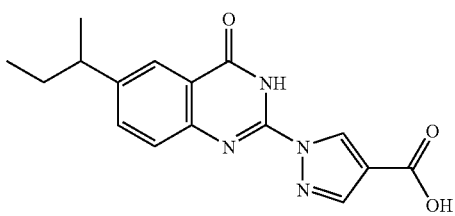 [SMILES: CCC(C)c1ccc2nc(-n3cc(C(=O)O)cn3)[nH]c(=O)c2c1]

The titled compound was prepared in a manner analogous to Example 109, steps A, B and F using 4-sec-butylphenylamine in step A. MS (ESI/Cl): mass calcd. for $C_{16}H_{16}N_4O_3$, 312.1; m/z found, 313.1 $[M+H]^+$. $^1$H NMR (500 MHz, DMSO-$d_6$): 12.91 (s, 2H), 8.94 (s, 1H), 8.25 (s, 1H), 7.93 (s, 1H), 7.72 (dd, J=8.4, 1.8 Hz, 1H), 7.65 (d, J=8.3 Hz, 1H), 2.82-2.77 (m, 1H), 1.76-1.50 (m, 2H), 1.26 (d, J=6.9 Hz, 3H), 0.79 (t, J=7.3 Hz, 3H).

Example 121

1-(6-Ethoxy-4-oxo-3,4-dihydro-quinazolin-2-yl)-1H-pyrazole-4-carboxylic acid

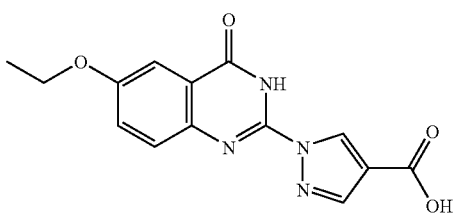 [SMILES: CCOc1ccc2nc(-n3cc(C(=O)O)cn3)[nH]c(=O)c2c1]

The titled compound was prepared in a manner analogous to Example 109, steps A, B and F using 4-ethoxyphenylamine in step A. MS (ESI/Cl): mass calcd. for $C_{14}H_{12}N_4O_4$, 300.1; m/z found, 301.1 $[M+H]^+$. $^1$H NMR (500 MHz, DMSO-$d_6$): 12.96 (s, 1H), 12.79 (s, 1H), 8.92 (s, 1H), 8.23 (s, 1H), 7.64 (d, J=7.8 Hz, 1H), 7.51 (d, J=2.3 Hz, 1H), 7.45 (dd, J=8.8, 2.8 Hz, 1H), 4.16 (q, J=6.9 Hz, 2H), 1.38 (t, J=6.9 Hz, 3H).

Example 122

1-(6-Methoxy-4-oxo-3,4-dihydro-quinazolin-2-yl)-1H-pyrazole-4-carboxylic acid

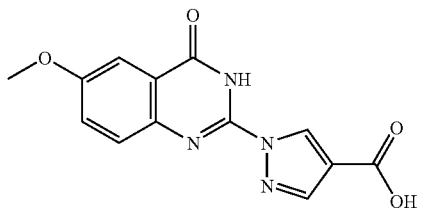

The titled compound was prepared in a manner analogous to Example 109, steps A, B and F using 4-methoxyphenylamine in step A. MS (ESI/Cl): mass calcd. for $C_{13}H_{10}N_4O_4$, 286.1; m/z found, 287.1 [M+H]$^+$. $^1$H NMR (500 MHz, DMSO-d$_6$): 12.95 (s, 2H), 8.92 (s, 1H), 8.24 (s, 1H), 7.65 (d, J=7.7 Hz, 1H), 7.53 (d, J=2.6 Hz, 1H), 7.46 (dd, J=8.9, 2.9 Hz, 1H), 3.89 (s, 3H).

Example 123

1-(4-Oxo-6-pyrrolidin-1-yl-3,4-dihydro-quinazolin-2-yl)-1H-pyrazole-4-carboxylic acid

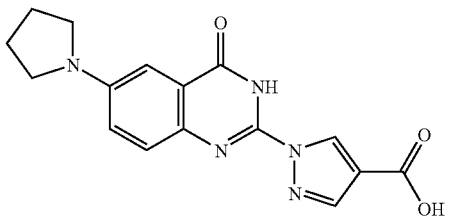 [SMILES: O=C(O)c1cnn(-c2nc3ccc(N4CCCC4)cc3c(=O)[nH]2)c1]

The titled compound was prepared in a manner analogous to Example 109, steps A, B and F using 4-pyrrolidin-1-yl-phenylamine in step A. MS (ESI/Cl): mass calcd. for $C_{16}H_{15}N_5O_3$, 325.1; m/z found, 326.1 [M+H]$^+$. $^1$H NMR (500 MHz, DMSO-d$_6$): 12.91 (s, 1H), 12.44 (s, 1H), 8.87 (d, J=0.6 Hz, 1H), 8.20 (s, 1H), 7.55 (d, J=8.9 Hz, 1H), 7.15 (dd, J=9.0, 2.9 Hz, 1H), 7.04 (d, J=2.8 Hz, 1H), 3.34 (t, J=6.4 Hz, 4H), 2.00 (t, J=6.5 Hz, 4H).

Example 124

1-(4-Oxo-6-piperidin-1-yl-3,4-dihydro-quinazolin-2-yl)-1H-pyrazole-4-carboxylic acid

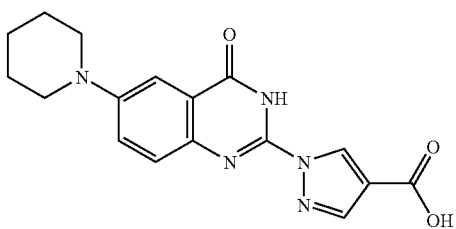 [SMILES: O=C(O)c1cnn(-c2nc3ccc(N4CCCCC4)cc3c(=O)[nH]2)c1]

The titled compound was prepared in a manner analogous to Example 109, steps A, B and F using 4-piperidin-1-yl-phenylamine in step A. MS (ESI/Cl): mass calcd. for $C_{17}H_{17}N_5O_3$, 339.1; m/z found, 340.2 [M+H]$^+$. $^1$H NMR (500 MHz, DMSO-d$_6$): 8.92 (s, 1H), 8.24 (s, 1H), 7.79 (br s, 2H), 7.67 (s, 1H), 4.31 (br s, 4H), 1.76 (s, 4H), 1.62 (s, 2H).

Example 125

1-(6-Dimethylamino-4-oxo-3,4-dihydro-quinazolin-2-yl)-1H-pyrazole-4-carboxylic acid

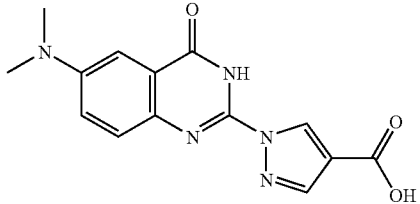

The titled compound was prepared in a manner analogous to Example 109, steps A, B and F using N,N-dimethyl-benzene-1,4-diamine in step A. MS (ESI/Cl): mass calcd. for $C_{14}H_{13}N_5O_3$, 299.1; m/z found, 300.1 [M+H]$^+$. $^1$H NMR (400 MHz, DMSO-d$_6$): 12.94 (s, 1H), 12.55 (s, 1H), 8.88 (d, J=0.5 Hz, 1H), 8.20 (s, 1H), 7.56 (d, J=9.0 Hz, 1H), 7.36 (dd, J=9.1, 3.0 Hz, 1H), 7.21 (d, J=2.8 Hz, 1H), 3.03 (s, 6H).

Example 126

1-(4-Oxo-3,4-dihydro-quinazolin-2-yl)-1H-pyrazole-4-carboxylic acid

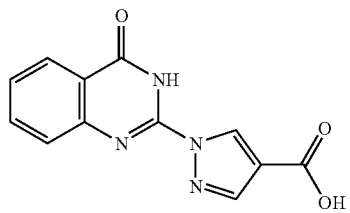 [SMILES: O=C(O)c1cnn(-c2nc3ccccc3c(=O)[nH]2)c1]

The titled compound was prepared in a manner analogous to Example 109, steps A, B and F using phenylamine in step A. MS (ESI/Cl): mass calcd. for $C_{12}H_8N_4O_3$, 256.1; m/z found, 257.1 [M+H]$^+$. $^1$H NMR (400 MHz, DMSO-d$_6$): 13.00 (s, 2H), 8.96 (s, 1H), 8.27 (s, 1H), 8.14 (d, J=7.6 Hz, 1H), 7.89-7.83 (m, 1H), 7.71 (d, J=7.7 Hz, 1H), 7.52 (dd, J=11.5, 4.5 Hz, 1H).

Example 127

1-(6-Bromo-7-fluoro-4-oxo-3,4-dihydro-quinazolin-2-yl)-1H-pyrazole-4-carboxylic acid

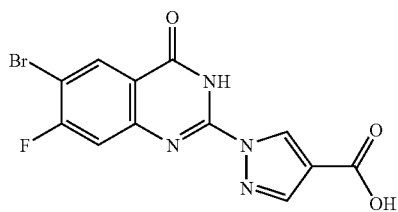 [SMILES: O=C(O)c1cnn(-c2nc3cc(F)c(Br)cc3c(=O)[nH]2)c1]

The titled compound was prepared in a manner analogous to Example 109, steps A, B and F using 4-bromo-3-fluorophenylamine in step A. MS (ESI/Cl): mass calcd. for $C_{12}H_6BrFN_4O_3$, 352.0; m/z found, 353.0 [M+H]$^+$. $^1$H NMR (400 MHz, DMSO-d$_6$): 13.08 (s, 2H), 8.93 (s, 1H), 8.35 (d, J=7.6 Hz, 1H), 8.29 (s, 1H), 7.69 (d, J=9.6 Hz, 1H).

Example 128

1-(6-Ethyl-4-oxo-3,4-dihydro-quinazolin-2-yl)-1H-pyrazole-4-carboxylic acid

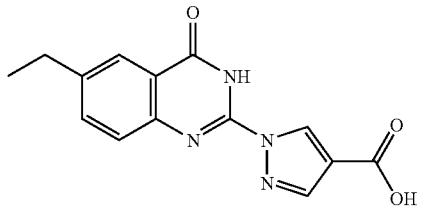 [SMILES: CCc1ccc2nc(-n3cc(C(=O)O)cn3)[nH]c(=O)c2c1]

The titled compound was prepared in a manner analogous to Example 109, steps A, B and F using 4-ethylphenylamine in step A. MS (ESI/Cl): mass calcd. for $C_{14}H_{12}N_4O_3$, 284.1; m/z found, 285.1 [M+H]$^+$. $^1$H NMR (400 MHz, DMSO-d$_6$): 12.89 (br s, 2H), 8.94 (s, 1H), 8.25 (s, 1H), 7.96 (s, 1H), 7.72 (d, J=7.0 Hz, 1H), 7.64 (s, 1H), 2.77 (q, J=7.5 Hz, 2H), 1.25 (t, J=7.6 Hz, 3H).

Example 129

1-(4-Oxo-6-propyl-3,4-dihydro-quinazolin-2-yl)-1H-pyrazole-4-carboxylic acid

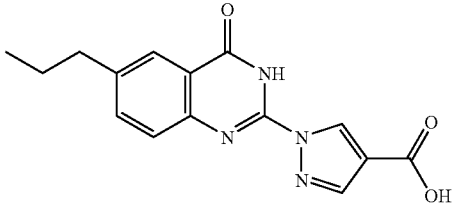 [SMILES: CCCc1ccc2nc(-n3cc(C(=O)O)cn3)[nH]c(=O)c2c1]

The titled compound was prepared in a manner analogous to Example 109, steps A, B and F using 4-propylphenylamine in step A. MS (ESI/Cl): mass calcd. for $C_{15}H_{14}N_4O_3$, 298.1; m/z found, 299.1 [M+H]$^+$. $^1$H NMR (400 MHz, DMSO-d$_6$): 12.97 (s, 2H), 8.94 (s, 1H), 8.26 (s, 1H), 7.93 (s, 1H), 7.70 (dd, J=8.3, 1.9 Hz, 1H), 7.63 (d, J=7.9 Hz, 1H), 2.71 (t, J=7.5 Hz, 2H), 1.70-1.61 (m, 2H), 0.91 (t, J=7.3 Hz, 3H).

Example 130

1-(6-Bromo-8-fluoro-4-oxo-3,4-dihydro-quinazolin-2-yl)-1H-pyrazole-4-carboxylic acid

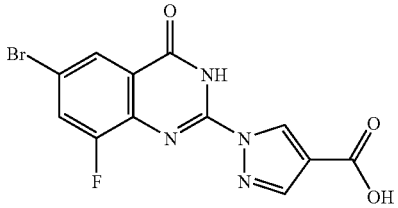 [SMILES: O=C(O)c1cnn(-c2nc3c(F)cc(Br)cc3c(=O)[nH]2)c1]

The titled compound was prepared in a manner analogous to Example 109, steps A, B and F using 4-bromo-2-fluorophenylamine in step A. MS (ESI/Cl): mass calcd. for $C_{12}H_6BrFN_4O_3$, 352.0; m/z found, 353.0 [M+H]$^+$. $^1$H NMR (400 MHz, DMSO-d$_6$): 13.30 (s, 1H), 13.08 (s, 1H), 8.91 (s, 1H), 8.29 (s, 1H), 8.08 (dd, J=9.7, 2.2 Hz, 1H), 8.04 (dd, J=2.1, 1.0 Hz, 1H).

Example 131

1-(5,7-Difluoro-4-oxo-3,4-dihydro-quinazolin-2-yl)-1H-pyrazole-4-carboxylic acid

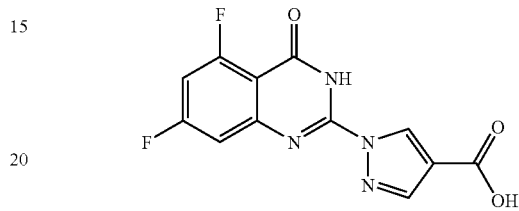

Step A: Preparation of 1-[(3,5-difluoro-phenylimino)-ethoxycarbonylamino-methyl]-1H-pyrazole-4-carboxylic acid ethyl ester. Ethyl isothiocyanatoformate (0.68 mL, 5.8 mmol) was added to a solution of 3,5-difluoroaniline (0.680 g, 5.27 mmol) and DCM (26 mL). After 3 h, triethylamine (2.20 mL, 15.8 mmol) was added to the reaction mixture, followed by ethyl pyrazole-4-carboxylate (0.812 g, 5.79 mmol), and EDCl (1.21 g, 6.32 mmol). After 1.5 h, the reaction mixture was diluted with DCM (25 mL), washed with water (3×30 mL) and with brine (50 mL), dried (MgSO$_4$), and concentrated. The residue was purified by FCC (3-45% EtOAc/hexanes) to yield the titled compound (0.323 g, 17% yield). MS (ESI/Cl): mass calcd. for $C_{16}H_{16}F_2N_4O_4$, 366.1; m/z found, 367.1 [M+H]$^+$.

Step B: Preparation of 1-(5,7-difluoro-4-oxo-3,4-dihydro-quinazolin-2-yl)-1H-pyrazole-4-carboxylic acid ethyl ester. Titanium (IV) chloride (0.39 mL, 3.5 mmol) was carefully added to a solution of 1-[(3,5-difluoro-phenylimino)-ethoxycarbonylamino-methyl]-1H-pyrazole-4-carboxylic acid ethyl ester (0.321 g, 0.876 mmol) and DCE (2.7 mL), and the resulting solution was heated to 110° C. for 1.5 h. The reaction mixture was cooled to room temperature and water (50 mL), methanol (1 mL), and DCM (40 mL) were added. The biphasic mixture was stirred for 30 min, and the layers were separated. The aqueous layer was further extracted with DCM (2×30 mL). The combined organic layers were washed with brine (40 mL), dried (MgSO$_4$), and concentrated. The residue was triturated from EtOH to yield the titled compound (0.172 g, 60% yield). MS (ESI/Cl): mass calcd. for $C_{14}H_{10}F_2N_4O_3$, 320.1; m/z found, 321.1 [M+H]$^+$. $^1$H NMR (400 MHz, DMSO-d$_6$): 13.09 (s, 1H), 8.99 (d, J=0.5 Hz, 1H), 8.35 (s, 1H), 7.42-7.32 (m, 2H), 4.30 (q, J=7.1 Hz, 2H), 1.32 (t, J=7.1 Hz, 3H).

Step C: Preparation of 1-(5,7-difluoro-4-oxo-3,4-dihydro-quinazolin-2-yl)-1H-pyrazole-4-carboxylic acid. Aqueous potassium hydroxide (1 M, 1.7 mL, 1.7 mmol) was added to 1-(5,7-difluoro-4-oxo-3,4-dihydro-quinazolin-2-yl)-1H-pyrazole-4-carboxylic acid ethyl ester (0.152 g, 0.475 mmol) in THF (1.7 mL). The reaction mixture was allowed to stir at room temperature for 18 h and was then concentrated. The residue was redissolved in water (5 mL) and brought to pH 1 with 1M aqueous HCl. The resulting precipitate was collected by filtration to yield the titled compound (0.137 g, 98% yield). MS (ESI/Cl): mass calcd. for $C_{12}H_6F_2N_4O_3$, 292.0; m/z found, 293.0 [M+H]+. 1H NMR (400 MHz, DMSO-d6): 13.07 (s, 2H), 8.93 (d, J=0.4 Hz, 1H), 8.28 (s, 1H), 7.44-7.27 (m, 2H).

Example 132

1-(5,7-Dichloro-4-oxo-3,4-dihydro-quinazolin-2-yl)-1H-pyrazole-4-carboxylic acid

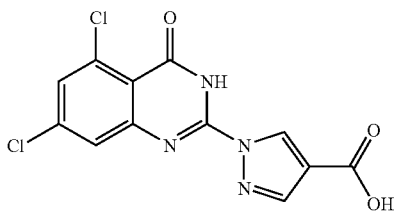 [SMILES: O=C(O)c1cnn(-c2nc3cc(Cl)cc(Cl)c3c(=O)[nH]2)c1]

The titled compound was prepared in a manner analogous to Example 131 using 3,5-dichloroaniline in step A. MS (ESI/Cl): mass calcd. for $C_{12}H_6Cl_2N_4O_3$, 324.0; m/z found, 325.0 [M+H]+. 1H NMR (600 MHz, DMSO-d6): 13.08 (s, 2H), 8.93 (s, 1H), 8.28 (s, 1H), 7.70 (s, 1H), 7.65 (d, J=2.0 Hz, 1H).

Example 133

1-(7-Fluoro-4-oxo-3,4-dihydro-quinazolin-2-yl)-1H-pyrazole-4-carboxylic acid

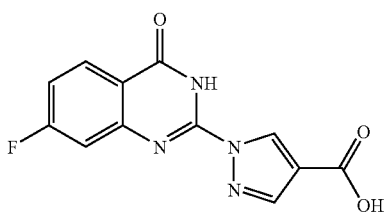

The titled compound was prepared in a manner analogous to Example 131 using 3-fluoroaniline in step A. MS (ESI/Cl): mass calcd. for $C_{12}H_7FN_4O_3$, 274.1; m/z found, 275.1 [M+H]+. 1H NMR (400 MHz, DMSO-d6): 13.04 (s, 2H), 8.94 (s, 1H), 8.28 (s, 1H), 8.19 (dd, J=8.7, 6.4 Hz, 1H), 7.49 (d, J=9.1 Hz, 1H), 7.38 (td, J=8.7, 2.5 Hz, 1H).

Example 134

1-(7-Bromo-4-oxo-3,4-dihydro-quinazolin-2-yl)-1H-pyrazole-4-carboxylic acid

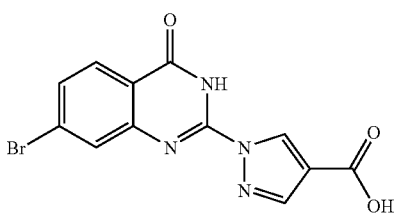 [SMILES: O=C(O)c1cnn(-c2nc3cc(Br)ccc3c(=O)[nH]2)c1]

The titled compound was prepared in a manner analogous to Example 131 using 3-bromoaniline in step A. MS (ESI/Cl): mass calcd. for $C_{12}H_7BrN_4O_3$, 334.0; m/z found, 335.0 [M+H]+. 1H NMR (400 MHz, DMSO-d6): 13.05 (s, 2H), 8.94 (d, J=0.5 Hz, 1H), 8.28 (s, 1H), 8.03 (d, J=8.5 Hz, 1H), 7.90 (s, 1H), 7.68 (dd, J=8.5, 1.9 Hz, 1H).

Example 135

1-(7-Methoxy-4-oxo-3,4-dihydro-quinazolin-2-yl)-1H-pyrazole-4-carboxylic acid

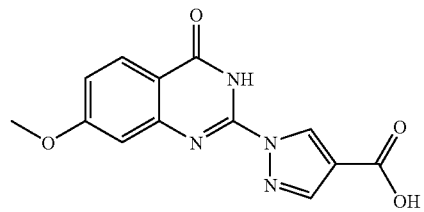

The titled compound was prepared in a manner analogous to Example 131 using 3-methoxyaniline in step A. MS (ESI/Cl): mass calcd. for $C_{13}H_{10}N_4O_4$, 286.1; m/z found, 287.1 [M+H]+. 1H NMR (400 MHz, DMSO-d6): 13.01 (s, 1H), 12.68 (s, 1H), 8.94 (s, 1H), 8.25 (s, 1H), 8.04 (d, J=8.8 Hz, 1H), 7.14 (s, 1H), 7.10 (dd, J=8.8, 2.2 Hz, 1H), 3.91 (s, 3H).

Example 136

1-(7-Benzyl-4-oxo-3,4-dihydro-quinazolin-2-yl)-1H-pyrazole-4-carboxylic acid

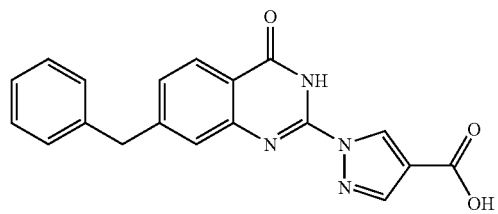 [SMILES: O=C(O)c1cnn(-c2nc3cc(Cc4ccccc4)ccc3c(=O)[nH]2)c1]

The titled compound was prepared in a manner analogous to Example 131 using 3-benzylaniline in step A. MS (ESI/Cl): mass calcd. for $C_{19}H_{14}N_4O_3$, 346.1; m/z found, 347.1 [M+H]+. 1H NMR (400 MHz, DMSO-d6): 13.00 (s, 1H), 12.75 (s, 1H), 8.93 (s, 1H), 8.25 (s, 1H), 8.05 (d, J=8.0 Hz, 1H), 7.52 (s, 1H), 7.41 (d, J=8.4 Hz, 1H), 7.36-7.26 (m, 4H), 7.26-7.18 (m, 1H), 4.12 (s, 2H).

Example 137

1-(4-Oxo-3,4,8,9-tetrahydro-7H-6,10-dioxa-1,3-diaza-cyclohepta[b]naphthalen-2-yl)-1H-pyrazole-4-carboxylic acid

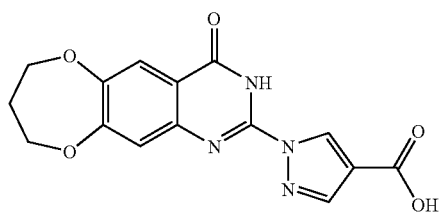 [SMILES: O=C(O)c1cnn(-c2nc3cc4c(cc3c(=O)[nH]2)OCCCO4)c1]

The titled compound was prepared in a manner analogous to Example 131 using 3,4-dihydro-2H-benzo[b][1,4]dioxepin-7-ylamine in step A. The titled compound was recovered as the potassium salt by triturating the residue in Step C with ethanol after concentrating the reaction mixture. MS (ESI/Cl): mass calcd. for $C_{15}H_{12}N_4O_5$, 328.1; m/z found, 329.1 [M+H]$^+$. $^1$H NMR (400 MHz, DMSO-d$_6$): 8.41 (d, J=0.8 Hz, 1H), 7.54 (d, J=0.8 Hz, 1H), 7.44 (s, 1H), 6.93 (s, 1H), 4.19-4.13 (m, 2H), 4.10 (t, J=5.4 Hz, 2H), 2.17-2.03 (m, 2H).

Example 138

1-(8-Oxo-2,3,7,8-tetrahydro-1,4-dioxa-5,7-diaza-phenanthren-6-yl)-1H-pyrazole-4-carboxylic acid

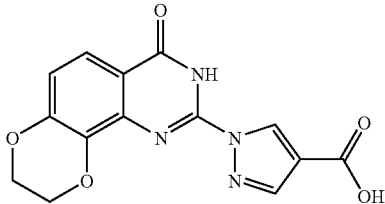 [SMILES: O=C(O)c1cnn(-c2nc3c4c(ccc3c(=O)[nH]2)OCCO4)c1]

Step A: Preparation of 1-[(2,3-dihydro-benzo[1,4]dioxin-5-ylimino)-ethoxycarbonylamino-methyl]-1H-pyrazole-4-carboxylic acid ethyl ester. The titled compound was prepared in a manner analogous to Example 131, step A, using 2,3-dihydro-benzo[1,4]dioxin-5-ylamine. MS (ESI/Cl): mass calcd. for $C_{18}H_{20}N_4O_6$, 388.1; m/z found, 389.2 [M+H]$^+$.

Step B: Preparation of 1-(8-oxo-2,3,7,8-tetrahydro-1,4-dioxa-5,7-diaza-phenanthren-6-yl)-1H-pyrazole-4-carboxylic acid ethyl ester. Titanium (IV) chloride (1.2 mL, 11 mmol) was carefully added to a solution of 1-[(2,3-dihydro-benzo[1,4]dioxin-5-ylimino)-ethoxycarbonylamino-methyl]-1H-pyrazole-4-carboxylic acid ethyl ester (1.39 g, 3.58 mmol) and DCE (11 mL), and the resulting solution was heated to 110° C. for 2 h. The reaction mixture was cooled to room temperature and ethanol (60 mL) was added. The resulting slurry was stirred at room temperature for 30 min; the precipitate was then collected to yield the titled compound (0.970 g, 78% yield). MS (ESI/Cl): mass calcd. for $C_{16}H_{14}N_4O_6$, 342.1; m/z found, 343.1 [M+H]$^+$. $^1$H NMR (400 MHz, DMSO-d$_6$): 12.78 (s, 1H), 8.90 (d, J=0.5 Hz, 1H), 8.31 (s, 1H), 7.62 (d, J=8.7 Hz, 1H), 7.06 (d, J=8.8 Hz, 1H), 4.48-4.35 (m, 4H), 4.30 (q, J=7.1 Hz, 2H), 1.33 (t, J=7.1 Hz, 3H).

Step C: Preparation of 1-(8-oxo-2,3,7,8-tetrahydro-1,4-dioxa-5,7-diaza-phenanthren-6-yl)-1H-pyrazole-4-carboxylic acid. Aqueous potassium hydroxide (1M, 2.6 mL, 2.6 mmol) was added to 1-(8-oxo-2,3,7,8-tetrahydro-1,4-dioxa-5,7-diaza-phenanthren-6-yl)-1H-pyrazole-4-carboxylic acid ethyl ester (0.298, 0.869 mmol) in THF (2.6 mL). The reaction mixture was allowed to stir at room temperature for 2 days and was then concentrated. The residue was redissolved in water (10 mL) and brought to pH 1 with 1M aqueous HCl. The resulting precipitate was collected by filtration to yield the titled compound (0.235 g, 85% yield). MS (ESI/Cl): mass calcd. for $C_{14}H_{10}N_4O_5$, 314.1; m/z found, 315.1 [M+H]$^+$. $^1$H NMR (400 MHz, DMSO-d$_6$): 13.01 (s, 1H), 12.73 (s, 1H), 8.86 (d, J=0.7 Hz, 1H), 8.24 (d, J=0.6 Hz, 1H), 7.61 (d, J=8.8 Hz, 1H), 7.05 (d, J=8.7 Hz, 1H), 4.40 (s, 4H).

Example 139

1-(4-Oxo-3,4,7,8-tetrahydro-[1,4]dioxino[2,3-g]quinazolin-2-yl)-1H-pyrazole-4-carboxylic acid

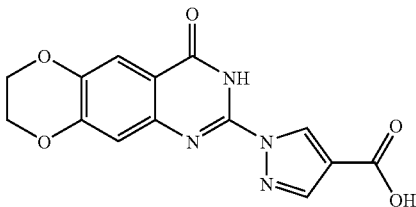 [SMILES: O=C(O)c1cnn(-c2nc3cc4c(cc3c(=O)[nH]2)OCCO4)c1]

Step A: Preparation of 1-(4-oxo-3,4,7,8-tetrahydro-[1,4]dioxino[2,3-g]quinazolin-2-yl)-1H-pyrazole-4-carboxylic acid ethyl ester. The titled compound was prepared in a manner analogous to Example 131, steps A-B, using 2,3-dihydro-benzo[1,4]dioxin-6-ylamine in step A. In step B, toluene was used as the solvent instead of DCE and the product was purified by FCC (0-10% DCM/MeOH). MS (ESI/Cl): mass calcd. for $C_{16}H_{14}N_4O_5$, 342.1; m/z found, 343.1 [M+H]$^+$. $^1$H NMR (400 MHz, DMSO-d$_6$): 12.69 (s, 1H), 8.95 (d, J=0.6 Hz, 1H), 8.27 (s, 1H), 7.48 (s, 1H), 7.13 (s, 1H), 4.42-4.33 (m, 4H), 4.29 (q, J=7.1 Hz, 2H), 1.32 (t, J=7.1 Hz, 3H).

Step B: Preparation of 1-(4-oxo-3,4,7,8-tetrahydro-[1,4]dioxino[2,3-g]quinazolin-2-yl)-1H-pyrazole-4-carboxylic acid. Lithium hydroxide monohydrate (28.7 mg, 0.684 mmol) and water (0.29 mL) were added to 1-(4-oxo-3,4,7,8-tetrahydro-[1,4]dioxino[2,3-g]quinazolin-2-yl)-1H-pyrazole-4-carboxylic acid ethyl ester (78.0 mg, 0.228 mmol) in THF (0.85 mL). The reaction mixture was stirred at room temperature for 18 h and was then concentrated and the residue re-dissolved in water (5 mL). This solution was brought to pH 1 with 1M aqueous HCl. The resulting precipitate was collected and dried to yield the titled compound (54.3 mg, 75% yield). MS (ESI/Cl): mass calcd. for $C_{14}H_{10}N_4O_5$, 314.1; m/z found, 315.0 [M+H]$^+$. $^1$H NMR (400 MHz, DMSO-d$_6$): 12.97 (s, 1H), 12.61 (s, 1H), 8.89 (d, J=0.6 Hz, 1H), 8.23 (s, 1H), 7.48 (s, 1H), 7.14 (s, 1H), 4.46-4.29 (m, 4H).

Example 140

1-(4-Oxo-4,6,7,8-tetrahydro-3H-cyclopenta[g]quinazolin-2-yl)-1H-pyrazole-4-carboxylic acid

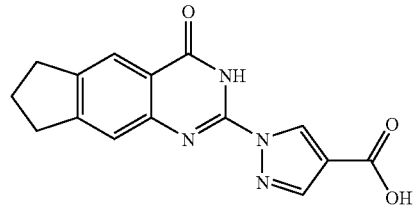 [SMILES: O=C(O)c1cnn(-c2nc3cc4c(cc3c(=O)[nH]2)CCC4)c1]

Step A: Preparation of 1-(4-oxo-4,6,7,8-tetrahydro-3H-cyclopenta[g]quinazolin-2-yl)-1H-pyrazole-4-carboxylic acid ethyl ester. The titled compound was prepared in a manner analogous to Example 131, steps A-B, using indan-5-ylamine in step A. Step B yielded a 10:1 mixture of the titled compound and 1-(1-oxo-2,7,8,9-tetrahydro-1H-cyclopenta[f]quinazolin-3-yl)-1H-pyrazole-4-carboxylic acid ethyl ester.

Data for 1-(4-oxo-4,6,7,8-tetrahydro-3H-cyclopenta[g]quinazolin-2-yl)-1H-pyrazole-4-carboxylic acid ethyl ester: MS (ESI/Cl): mass calcd. for $C_{17}H_{16}N_4O_3$, 324.1; m/z found, 325.1 [M+H]$^+$. $^1$H NMR (400 MHz, DMSO-$d_6$): 12.72 (s, 1H), 8.98 (d, J=0.6 Hz, 1H), 8.30 (s, 1H), 7.95 (s, 1H), 7.52 (s, 1H), 4.30 (q, J=7.1 Hz, 2H), 3.01 (t, J=7.3 Hz, 2H), 2.98 (t, J=7.3 Hz, 2H), 2.09 (p, J=7.5 Hz, 2H), 1.32 (t, J=7.1 Hz, 3H).

Step B: Preparation of 1-(4-oxo-4,6,7,8-tetrahydro-3H-cyclopenta[g]quinazolin-2-yl)-1H-pyrazole-4-carboxylic acid. Lithium hydroxide monohydrate (0.611 g, 14.6 mmol) and water (9.1 mL) were added to a 10:1 mixture of 1-(4-oxo-4,6,7,8-tetrahydro-3H-cyclopenta[g]quinazolin-2-yl)-1H-pyrazole-4-carboxylic acid ethyl ester and 1-(1-oxo-2,7,8,9-tetrahydro-1H-cyclopenta[f]quinazolin-3-yl)-1H-pyrazole-4-carboxylic acid ethyl ester (1.18 g, 0.228 mmol) in THF (13.6 mL) and the reaction mixture was stirred at room temperature for 18 h. The reaction mixture was concentrated and the residue was redissolved in water (20 mL). This solution was brought to pH 1 with 1M aqueous HCl. The resulting precipitate was collected and dried to yield a 10:1 mixture of the titled compound and 1-(1-oxo-2,7,8,9-tetrahydro-1H-cyclopenta[f]quinazolin-3-yl)-1H-pyrazole-4-carboxylic acid (1.05 g, 98% yield). A portion of the precipitate (0.511 g) was triturated twice from 10 mL DMSO to yield a pure sample of the titled compound (0.310 g, 61% recovery). MS (ESI/Cl): mass calcd. for $C_{15}H_{12}N_4O_3$, 296.1; m/z found, 297.1 [M+H]$^+$. $^1$H NMR (600 MHz, DMSO-$d_6$): 13.00 (s, 1H), 12.68 (s, 1H), 8.93 (s, 1H), 8.24 (s, 1H), 7.96 (s, 1H), 7.52 (s, 1H), 3.05-2.93 (m, 4H), 2.09 (p, J=7.4 Hz, 2H).

Step C: Preparation of 1-(4-oxo-4,6,7,8-tetrahydro-3H-cyclopenta[g]quinazolin-2-yl)-1H-pyrazole-4-carboxylic acid, potassium salt. Potassium carbonate (58.3 mg, 0.422 mmol) was added to 1-(4-oxo-4,6,7,8-tetrahydro-3H-cyclopenta[g]quinazolin-2-yl)-1H-pyrazole-4-carboxylic acid (0.250 g, 0.844 mmol) in methanol (4.2 mL) and the reaction mixture was heated to reflux for 3 h. The temperature was then lowered to 60° C. and stirring was continued for 18 h. The reaction mixture was cooled to room temperature and the precipitate was filtered and dried to yield the potassium salt of the titled compound (0.204 g, 71% yield). MS (ESI/Cl): mass calcd. for $C_{15}H_{12}N_4O_3$, 296.1; m/z found, 297.1 [M+H]$^+$. $^1$H NMR (600 MHz, DMSO-$d_6$): 12.63 (s, 1H), 8.81 (s, 1H), 7.92 (s, 1H), 7.80 (s, 1H), 7.29 (s, 1H), 2.96-2.89 (m, 4H), 2.04 (p, J=7.4 Hz, 2H).

Example 141

1-(6-Oxo-2,3,6,7-tetrahydro-1H-7,9-diaza-cyclopenta[a]naphthalen-8-yl)-1H-pyrazole-4-carboxylic acid

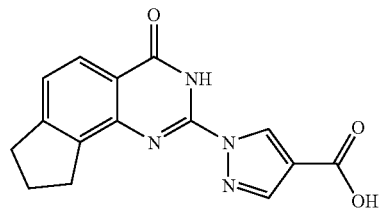 [SMILES: O=C(O)c1cnn(-c2nc3c4c(ccc3c(=O)[nH]2)CCC4)c1]

The titled compound was prepared in a manner analogous to Example 138 using indan-4-ylamine in step A and quenching the reaction mixture with a 50:1 ethanol/water solution instead of neat ethanol in Step B. MS (ESI/Cl): mass calcd. for $C_{15}H_{12}N_4O_3$, 296.1; m/z found, 297.1 [M+H]$^+$. $^1$H NMR (400 MHz, DMSO-$d_6$): 13.02 (s, 1H), 12.66 (s, 1H), 8.96 (d, J=0.7 Hz, 1H), 8.25 (d, J=0.6 Hz, 1H), 7.93 (d, J=7.9 Hz, 1H), 7.38 (d, J=8.0 Hz, 1H), 3.16 (t, J=7.5 Hz, 2H), 3.04 (t, J=7.5 Hz, 2H), 2.14 (p, J=7.6 Hz, 2H).

Example 142

1-(4-Oxo-3,4,7,8,9,10-hexahydro-benzo[h]quinazolin-2-yl)-1H-pyrazole-4-carboxylic acid

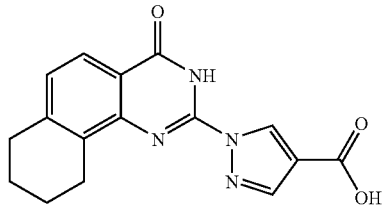 [SMILES: O=C(O)c1cnn(-c2nc3c4c(ccc3c(=O)[nH]2)CCCC4)c1]

The titled compound was prepared in a manner analogous to Example 131 using 5,6,7,8-tetrahydro-naphthalen-1-ylamine in step A and was recovered as the potassium salt by triturating the residue in Step C with ethanol after concentrating the reaction mixture. MS (ESI/Cl): mass calcd. for $C_{16}H_{14}N_4O_3$, 310.1; m/z found, 311.1 [M+H]$^+$. $^1$H NMR (400 MHz, DMSO-$d_6$): 8.50 (d, J=0.8 Hz, 1H), 7.66 (d, J=8.1 Hz, 1H), 7.55 (d, J=0.8 Hz, 1H), 6.78 (d, J=8.1 Hz, 1H), 2.97 (t, J=5.8 Hz, 2H), 2.75 (t, J=5.8 Hz, 2H), 1.89-1.68 (m, 4H).

Example 143

1-(4-Oxo-3,4,6,7,8,9-hexahydro-benzo[g]quinazolin-2-yl)-1H-pyrazole-4-carboxylic acid

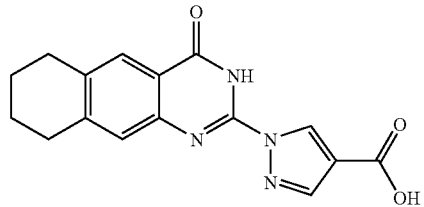 [SMILES: O=C(O)c1cnn(-c2nc3cc4c(cc3c(=O)[nH]2)CCCC4)c1]

Step A: Preparation of 1-(4-oxo-3,4,6,7,8,9-hexahydro-benzo[g]quinazolin-2-yl)-1H-pyrazole-4-carboxylic acid ethyl ester. The titled compound was prepared in a manner analogous to Example 131, steps A-B, using 5,6,7,8-tetrahydro-naphthalen-2-ylamine in step A. Step B yielded a 2:1 mixture of the titled compound and 1-(1-oxo-1,2,7,8,9,10-hexahydro-benzo[f]quinazolin-3-yl)-1H-pyrazole-4-carboxylic acid ethyl ester.

Data for 1-(4-oxo-3,4,6,7,8,9-hexahydro-benzo[g]quinazolin-2-yl)-1H-pyrazole-4-carboxylic acid ethyl ester: MS (ESI/Cl): mass calcd. for $C_{18}H_{18}N_4O_3$, 338.1; m/z found, 339.1 [M+H]$^+$. $^1$H NMR (400 MHz, DMSO-$d_6$): 12.66 (s, 1H), 8.98 (s, 1H), 8.30 (s, 1H), 7.84 (s, 1H), 7.40 (s, 1H), 4.30 (q, J=7.1 Hz, 2H), 2.97-2.77 (m, 4H), 1.87-1.68 (m, 4H), 1.33 (t, J=7.1 Hz, 3H).

Step B: Preparation of 1-[3-(2-methoxy-ethoxymethyl)-4-oxo-3,4,6,7,8,9-hexahydro-benzo[g]quinazolin-2-yl]-1H-pyrazole-4-carboxylic acid ethyl ester. DIEA (0.76 mL, 4.4 mmol) was added to a 2:1 mixture of 1-(4-oxo-3,4,6,7,8,9-hexahydro-benzo[g]quinazolin-2-yl)-1H-pyrazole-4-carboxylic acid ethyl ester and 1-(1-oxo-1,2,7,8,9,10-hexahydro-benzo[f]quinazolin-3-yl)-1H-pyrazole-4-carboxylic acid ethyl ester (0.500 g, 1.478 mmol) in THF (7.4 mL), followed by 1-chloromethoxy-2-methoxy-ethane (0.186 mL, 1.63 mmol). The reaction mixture was stirred at room temperature for 18 h, diluted with EtOAc (40 mL), and washed with water (30 mL). The aqueous layer was extracted with EtOAc (2×30 mL) and the combined organic layers were washed with brine (40 mL), dried (MgSO₄), and concentrated. The residue was purified by FCC (5-60% EtOAc/hexanes) to yield the titled compound (0.257 g, 41% yield) and 1-[2-(2-methoxy-ethoxymethyl)-1-oxo-1,2,7,8,9,10-hexahydro-benzo[t]quinazolin-3-yl]-1H-pyrazole-4-carboxylic acid ethyl ester (69.0 mg, 11% yield).

Data for 1-[3-(2-Methoxy-ethoxymethyl)-4-oxo-3,4,6,7,8,9-hexahydro-benzo[g]quinazolin-2-yl]-1H-pyrazole-4-carboxylic acid ethyl ester: $^1$H NMR (500 MHz, CDCl₃): 8.60 (s, 1H), 8.14 (s, 1H), 8.02 (s, 1H), 7.39 (s, 1H), 5.90 (s, 2H), 4.35 (q, J=7.1 Hz, 2H), 3.63-3.57 (m, 2H), 3.37-3.31 (m, 2H), 3.20 (s, 3H), 2.93 (s, 4H), 1.86 (t, J=3.2 Hz, 4H), 1.38 (t, J=7.1 Hz, 3H).

Step C: Preparation of 1-(4-oxo-3,4,6,7,8,9-hexahydro-benzo[g]quinazolin-2-yl)-1H-pyrazole-4-carboxylic acid ethyl ester. HCl (4M in dioxane, 2.1 mL, 8.3 mmol) was added to a solution of 1-[3-(2-methoxy-ethoxymethyl)-4-oxo-3,4,6,7,8,9-hexahydro-benzo[g]quinazolin-2-yl]-1H-pyrazole-4-carboxylic acid ethyl ester (0.254 g, 0.596 mmol) and ethanol (2.0 mL). The reaction mixture was stirred at room temperature for 4 h, at which point ether (2 mL) was added and the precipitate was collected. The precipitate was triturated three times with ethanol, once with ethanol/THF (1:1), and once with DMSO. The filter cake was rinsed with ethanol and dried to yield the titled compound (89.4 mg, 44% yield). MS (ESI/Cl): mass calcd. for C₁₈H₁₈N₄O₃, 338.1; m/z found, 339.1 [M+H]⁺. $^1$H NMR (600 MHz, DMSO-d₆): 12.66 (s, 1H), 8.98 (s, 1H), 8.30 (s, 1H), 7.84 (s, 1H), 7.40 (s, 1H), 4.30 (q, J=7.1 Hz, 2H), 2.95-2.83 (m, 4H), 1.82-1.74 (m, 4H), 1.32 (t, J=7.1 Hz, 3H).

Step D: Preparation of 1-(4-oxo-3,4,6,7,8,9-hexahydro-benzo[g]quinazolin-2-yl)-1H-pyrazole-4-carboxylic acid. Lithium hydroxide monohydrate (25.5 mg, 0.608 mmol) and water (0.45 mL) were added to 1-(4-oxo-3,4,6,7,8,9-hexahydro-benzo[g]quinazolin-2-yl)-1H-pyrazole-4-carboxylic acid ethyl ester (87.5 mg, 0.259 mmol) in THF (0.55 mL). The reaction mixture was stirred at room temperature for 18 h and was then concentrated. The residue was redissolved in water (5 mL) and this solution was brought to pH 1 with 1M aqueous HCl. The resulting precipitate was collected and dried to yield the titled compound (76.6 mg, 95% yield). MS (ESI/Cl): mass calcd. for C₁₆H₁₄N₄O₃, 310.1; m/z found, 311.1 [M+H]⁺. $^1$H NMR (400 MHz, DMSO-d₆): 13.00 (s, 1H), 12.61 (s, 1H), 8.91 (s, 1H), 8.24 (s, 1H), 7.83 (s, 1H), 7.40 (s, 1H), 2.89 (br d, J=4.7 Hz, 4H), 1.84-1.72 (m, 4H).

Example 144

1-(1-Oxo-1,2,7,8,9,10-hexahydro-benzo[f]quinazolin-3-yl)-1H-pyrazole-4-carboxylic acid

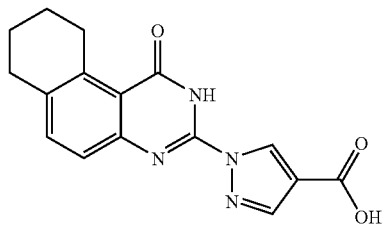 [SMILES: O=C(O)c1cnn(-c2nc3ccc4c(c3c(=O)[nH]2)CCCC4)c1]

Step A: Preparation of 1-(1-oxo-1,2,7,8,9,10-hexahydro-benzo[f]quinazolin-3-yl)-1H-pyrazole-4-carboxylic acid ethyl ester. The titled compound was prepared in a manner analogous to Example 131, steps A-B, using 5,6,7,8-tetrahydro-naphthalen-2-ylamine in step A. Step B yielded a 2:1 mixture of 1-(4-oxo-3,4,6,7,8,9-hexahydro-benzo[g]quinazolin-2-yl)-1H-pyrazole-4-carboxylic acid ethyl ester and the titled compound.

Data for 1-(1-oxo-1,2,7,8,9,10-hexahydro-benzo[f]quinazolin-3-yl)-1H-pyrazole-4-carboxylic acid ethyl ester: MS (ESI/Cl): mass calcd. for C₁₈H₁₈N₄O₃, 338.1; m/z found, 339.1 [M+H]⁺. $^1$H NMR (400 MHz, DMSO-d₆): 12.49 (s, 1H), 8.99 (s, 1H), 8.30 (s, 1H), 7.84 (d, J=8.2, 1H), 7.45-7.38 (m, 1H), 4.30 (q, J=7.1 Hz, 2H), 3.46-3.25 (m, 2H), 2.97-2.77 (m, 2H), 1.87-1.68 (m, 4H), 1.33 (t, J=7.1 Hz, 3H).

Step B: Preparation of 1-[2-(2-methoxy-ethoxymethyl)-1-oxo-1,2,7,8,9,10-hexahydro-benzo[f]quinazolin-3-yl]-1H-pyrazole-4-carboxylic acid ethyl ester. DIEA (0.76 mL, 4.4 mmol) was added to a 2:1 mixture of 1-(4-oxo-3,4,6,7,8,9-hexahydro-benzo[g]quinazolin-2-yl)-1H-pyrazole-4-carboxylic acid ethyl ester and 1-(1-oxo-1,2,7,8,9,10-hexahydro-benzo[f]quinazolin-3-yl)-1H-pyrazole-4-carboxylic acid ethyl ester (0.500 g, 1.478 mmol) in THF (7.4 mL), followed by 1-chloromethoxy-2-methoxy-ethane (0.186 mL, 1.63 mmol). The reaction mixture was stirred at room temperature for 18 h, diluted with EtOAc (40 mL), and washed with water (30 mL). The aqueous layer was extracted with EtOAc (2×30 mL) and the combined organic layers were washed with brine (40 mL), dried (MgSO₄), and concentrated. The residue was purified by FCC (5-60% EtOAc/hexanes) to yield 1-[3-(2-methoxy-ethoxymethyl)-4-oxo-3,4,6,7,8,9-hexahydro-benzo[g]quinazolin-2-yl]-1H-pyrazole-4-carboxylic acid ethyl ester (0.257 g, 41% yield) and the titled compound (69.0 mg, 11% yield).

Data for 1-[2-(2-methoxy-ethoxymethyl)-1-oxo-1,2,7,8,9,10-hexahydro-benzo[f]quinazolin-3-yl]-1H-pyrazole-4-carboxylic acid ethyl ester: $^1$H NMR (500 MHz, CDCl₃): 8.62 (s, 1H), 8.14 (s, 1H), 7.47 (d, J=8.4 Hz, 1H), 7.42 (d, J=8.3 Hz, 1H), 5.84 (s, 2H), 4.35 (q, J=7.2 Hz, 2H), 3.64-3.58 (m, 2H), 3.47 (t, J=6.1 Hz, 2H), 3.41-3.34 (m, 2H), 3.23 (s, 3H), 2.89 (t, J=6.1 Hz, 2H), 1.91-1.78 (m, 4H), 1.38 (t, J=7.1 Hz, 3H).

Step C: Preparation of 1-(1-oxo-1,2,7,8,9,10-hexahydro-benzo[f]quinazolin-3-yl)-1H-pyrazole-4-carboxylic acid ethyl ester. HCl (4M in dioxane, 0.57 mL, 2.3 mmol) was added to a solution of 1-[2-(2-methoxy-ethoxymethyl)-1-oxo-1,2,7,8,9,10-hexahydro-benzo[f]quinazolin-3-yl]-1H-pyrazole-4-carboxylic acid ethyl ester (70.0 mg, 0.164 mmol) and ethanol (0.57 mL). The reaction mixture was stirred at room temperature for 4 h, at which point ether (2 mL) was added and the precipitate was collected to yield the titled compound (27.0 mg, 49% yield). MS (ESI/Cl): mass calcd. for $C_{18}H_{18}N_4O_3$, 338.1; m/z found, 339.1 [M+H]$^+$.

Step D: Preparation of 1-(1-oxo-1,2,7,8,9,10-hexahydro-benzo[f]quinazolin-3-yl)-1H-pyrazole-4-carboxylic acid. Lithium hydroxide monohydrate (9.3 mg, 0.22 mmol) and water (0.19 mL) were added to 1-(1-oxo-1,2,7,8,9,10-hexahydro-benzo[f]quinazolin-3-yl)-1H-pyrazole-4-carboxylic acid ethyl ester (25.0 mg, 73.9 pmol) in THF (0.28 mL). The reaction mixture was stirred at room temperature for 18 h and was then concentrated. The residue was redissolved in water (3 mL) and this solution was brought to pH 1 with 1M aqueous HCl. The resulting precipitate was collected and dried to yield the titled compound (19.6 mg, 85% yield). MS (ESI/Cl): mass calcd. for $C_{16}H_{14}N_4O_3$, 310.1; m/z found, 311.1 [M+H]$^+$. $^1$H NMR (400 MHz, DMSO-d$_6$): 12.98 (s, 1H), 12.42 (s, 1H), 8.92 (s, 1H), 8.23 (s, 1H), 7.51 (d, J=8.5 Hz, 1H), 7.41 (d, J=8.3 Hz, 1H), 3.37 (t, J=5.8 Hz, 2H), 2.83 (t, J=5.3 Hz, 2H), 1.84-1.67 (m, 4H).

Example 145

1-(5,7-Dimethyl-4-oxo-3,4-dihydro-quinazolin-2-yl)-1H-pyrazole-4-carboxylic acid

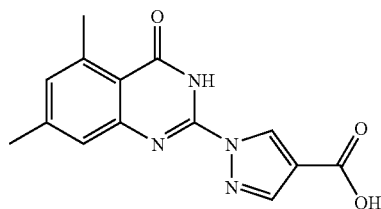 [SMILES: Cc1cc(C)c2c(=O)[nH]c(-n3cc(C(=O)O)cn3)nc2c1]

The titled compound was prepared in a manner analogous to Example 138 using 3,5-dimethylaniline in step A, and carefully pipetting the reaction mixture into ethanol instead of adding ethanol to the reaction mixture in Step B. MS (ESI/Cl): mass calcd. for $C_{14}H_{12}N_4O_3$, 284.1; m/z found, 285.1 [M+H]$^+$. $^1$H NMR (400 MHz, DMSO-d$_6$): 12.99 (s, 1H), 12.39 (s, 1H), 8.89 (d, J=0.5 Hz, 1H), 8.24 (s, 1H), 7.30 (s, 1H), 7.09 (s, 1H), 2.73 (s, 3H), 2.39 (s, 3H).

Example 146

1-(7-Isopropyl-4-oxo-3,4-dihydro-quinazolin-2-yl)-1H-pyrazole-4-carboxylic acid

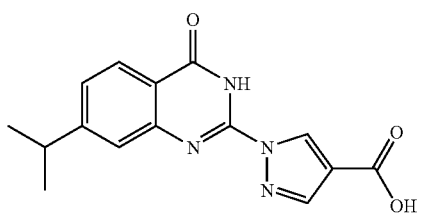 [SMILES: CC(C)c1ccc2c(=O)[nH]c(-n3cc(C(=O)O)cn3)nc2c1]

The titled compound was prepared in a manner analogous to Example 138 using 3-isopropylaniline in step A, and carefully pipetting the reaction mixture into ethanol instead of adding ethanol to the reaction mixture in Step B. MS (ESI/Cl): mass calcd. for $C_{15}H_{14}N_4O_3$, 298.1; m/z found, 299.1 [M+H]$^+$. $^1$H NMR (400 MHz, DMSO-d$_6$): 13.01 (s, 1H), 12.74 (s, 1H), 8.94 (s, 1H), 8.26 (s, 1H), 8.06 (d, J=8.1 Hz, 1H), 7.54 (s, 1H), 7.44 (d, J=8.2 Hz, 1H), 3.13-3.00 (m, 1H), 1.28 (d, J=6.9 Hz, 6H).

Example 147

1-(7-tert-Butyl-4-oxo-3,4-dihydro-quinazolin-2-yl)-1H-pyrazole-4-carboxylic acid

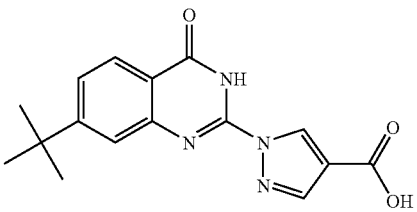 [SMILES: CC(C)(C)c1ccc2c(=O)[nH]c(-n3cc(C(=O)O)cn3)nc2c1]

The titled compound was prepared in a manner analogous to Example 138 using 3-tert-butylaniline in step A, and carefully pipetting the reaction mixture into ethanol instead of adding ethanol to the reaction mixture in Step B. MS (ESI/Cl): mass calcd. for $C_{16}H_{16}N_4O_3$, 312.1; m/z found, 313.1 [M+H]$^+$. $^1$H NMR (400 MHz, DMSO-d$_6$): 13.00 (s, 1H), 12.75 (s, 1H), 8.97 (s, 1H), 8.26 (s, 1H), 8.07 (d, J=8.3 Hz, 1H), 7.69-7.56 (m, 2H), 1.36 (s, 9H).

Example 148

1-(4-Oxo-7-trifluoromethoxy-3,4-dihydro-quinazolin-2-yl)-1H-pyrazole-4-carboxylic acid

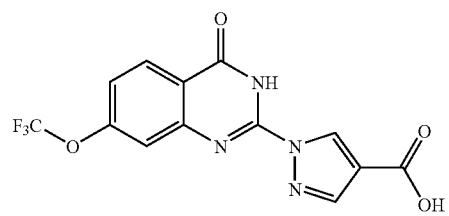 [SMILES: O=C(O)c1cnn(-c2nc3cc(OC(F)(F)F)ccc3c(=O)[nH]2)c1]

The titled compound was prepared in a manner analogous to Example 138 using 3-trifluoromethoxyaniline in step A, and carefully pipetting the reaction mixture into ethanol instead of adding ethanol to the reaction mixture in Step B. MS (ESI/Cl): mass calcd. for $C_{13}H_7F_3N_4O_4$, 340.0; m/z found, 341.1 [M+H]$^+$. $^1$H NMR (400 MHz, DMSO-d$_6$): 13.06 (s, 2H), 8.97 (s, 1H), 8.29 (s, 1H), 8.25 (d, J=8.8 Hz, 1H), 7.63 (s, 1H), 7.49 (d, J=8.8 Hz, 1H).

Example 149

1-(7-Isopropoxy-4-oxo-3,4-dihydro-quinazolin-2-yl)-1H-pyrazole-4-carboxylic acid

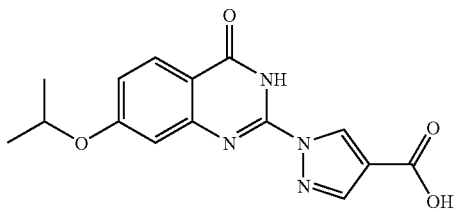 [SMILES: CC(C)Oc1ccc2c(=O)[nH]c(-n3cc(C(=O)O)cn3)nc2c1]

The titled compound was prepared in a manner analogous to Example 17 using 3-isopropylaniline in step A, omitting the purification by reverse-phase HPLC in step B. MS (ESI/Cl): mass calcd. for $C_{15}H_{14}N_4O_4$, 314.1; m/z found, 315.1 [M+H]$^+$. $^1$H NMR (600 MHz, DMSO-d$_6$): 12.99 (s, 1H), 12.61 (s, 1H), 8.94 (s, 1H), 8.25 (s, 1H), 8.02 (d, J=8.6 Hz, 1H), 7.11 (s, 1H), 7.05 (dd, J=8.8, 2.1 Hz, 1H), 4.83 (br s, 1H), 1.34 (d, J=6.0 Hz, 6H).

Example 150

1-(7-Dimethylamino-4-oxo-3,4-dihydro-quinazolin-2-yl)-1H-pyrazole-4-carboxylic acid

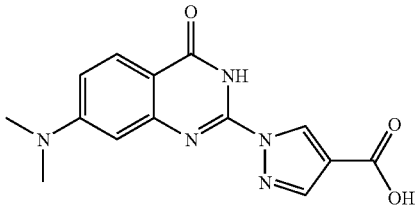 [SMILES: CN(C)c1ccc2c(=O)[nH]c(-n3cc(C(=O)O)cn3)nc2c1]

Step A: Preparation of 1-(7-dimethylamino-4-oxo-3,4-dihydro-quinazolin-2-yl)-1H-pyrazole-4-carboxylic acid ethyl ester. The titled compound was prepared in a manner analogous to Example 131, steps A-B, using 3-(N,N-dimethyl)aniline in step A. Step B yielded a 3:2 mixture of the titled compound and 1-(5-dimethylamino-4-oxo-3,4-dihydro-quinazolin-2-yl)-1H-pyrazole-4-carboxylic acid ethyl ester.

Data for 1-(7-dimethylamino-4-oxo-3,4-dihydro-quinazolin-2-yl)-1H-pyrazole-4-carboxylic acid ethyl ester: MS (ESI/Cl): mass calcd. for $C_{16}H_{17}N_5O_3$, 327.1; m/z found, 328.1 [M+H]$^+$. $^1$H NMR (600 MHz, DMSO-d$_6$): 12.22 (s, 1H), 8.98 (s, 1H), 8.28 (s, 1H), 7.90 (d, J=8.9 Hz, 1H), 6.93 (dd, J=8.9, 2.1 Hz, 1H), 6.73 (s, 1H), 4.29 (q, J=7.1 Hz, 2H), 3.07 (s, 6H), 1.32 (t, J=7.1 Hz, 3H).

Step B: Preparation of 1-(7-dimethylamino-4-oxo-3,4-dihydro-quinazolin-2-yl)-1H-pyrazole-4-carboxylic acid. Aqueous 1M KOH (3.8 mL, 3.8 mmol) was added to a 3:2 mixture of 1-(7-dimethylamino-4-oxo-3,4-dihydro-quinazolin-2-yl)-1H-pyrazole-4-carboxylic acid ethyl ester and 1-(5-dimethylamino-4-oxo-3,4-dihydro-quinazolin-2-yl)-1H-pyrazole-4-carboxylic acid ethyl ester (0.415 g, 1.27 mmol) in THF (3.8 mL). The reaction mixture was allowed to stir at room temperature for 18 h and was then concentrated. The residue was re-dissolved in water (10 mL) and acidified with 1M aqueous HCl (3 mL). The resulting precipitate was collected by filtration to yield a mixture of the titled compound and 1-(5-dimethylamino-4-oxo-3,4-dihydro-quinazolin-2-yl)-1H-pyrazole-4-carboxylic acid. The collected precipitate was triturated from DMSO and rinsed with ethanol to yield pure 1-(7-dimethylamino-4-oxo-3,4-dihydro-quinazolin-2-yl)-1H-pyrazole-4-carboxylic acid (0.113 mg, 29% yield). The filtrate was saved for further purification. MS (ESI/Cl): mass calcd. for $C_{14}H_{13}N_5O_3$, 299.1; m/z found, 300.1 [M+H]$^+$. $^1$H NMR (400 MHz, DMSO-d$_6$): 12.97 (s, 1H), 12.21 (s, 1H), 8.92 (s, 1H), 8.22 (s, 1H), 7.90 (d, J=8.9 Hz, 1H), 6.93 (dd, J=9.0, 2.3 Hz, 1H), 6.72 (s, 1H), 3.07 (s, 6H).

Example 151

1-(5-Dimethylamino-4-oxo-3,4-dihydro-quinazolin-2-yl)-1H-pyrazole-4-carboxylic acid

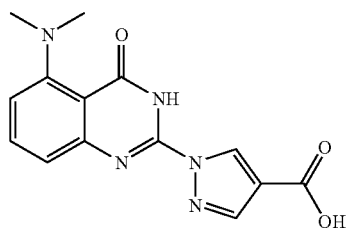 [SMILES: CN(C)c1cccc2nc(-n3cc(C(=O)O)cn3)[nH]c(=O)c12]

Step A: Preparation of 1-(5-dimethylamino-4-oxo-3,4-dihydro-quinazolin-2-yl)-1H-pyrazole-4-carboxylic acid ethyl ester. The titled compound was prepared in a manner analogous to Example 131, steps A-B, using 3-(N,N-dimethyl)aniline in step A. Step B yielded a 3:2 mixture of 1-(7-dimethylamino-4-oxo-3,4-dihydro-quinazolin-2-yl)-1H-pyrazole-4-carboxylic acid ethyl ester and the titled compound.

Data for 1-(5-dimethylamino-4-oxo-3,4-dihydro-quinazolin-2-yl)-1H-pyrazole-4-carboxylic acid ethyl ester: MS (ESI/Cl): mass calcd. for $C_{16}H_{17}N_5O_3$, 327.1; m/z found, 328.1 [M+H]$^+$. $^1$H NMR (600 MHz, DMSO-d$_6$): 12.22 (s, 1H), 8.98 (s, 1H), 8.20 (s, 1H), 8.01-7.39 (br m, 3H), 4.29 (q, J=7.1 Hz, 2H), 3.31 (s, 6H), 1.32 (t, J=7.1 Hz, 3H).

Step B: Preparation of 1-(5-dimethylamino-4-oxo-3,4-dihydro-quinazolin-2-yl)-1H-pyrazole-4-carboxylic acid. Aqueous 1M KOH (3.8 mL, 3.8 mmol) was added to a 3:2 mixture of 1-(7-dimethylamino-4-oxo-3,4-dihydro-quinazolin-2-yl)-1H-pyrazole-4-carboxylic acid ethyl ester and 1-(5-dimethylamino-4-oxo-3,4-dihydro-quinazolin-2-yl)-1H-pyrazole-4-carboxylic acid ethyl ester (0.415 g, 1.27 mmol) in THF (3.8 mL). The reaction mixture was allowed to stir at room temperature for 18 h and was then concentrated. The residue was re-dissolved in water (10 mL) and acidified with aqueous HCl (1 M, 3 mL). The resulting precipitate was collected by filtration to yield a mixture of the titled compound and 1-(7-dimethylamino-4-oxo-3,4-dihydro-quinazolin-2-yl)-1H-pyrazole-4-carboxylic acid. The collected precipitate was triturated from DMSO and rinsed with ethanol to yield pure 1-(7-dimethylamino-4-oxo-3,4-dihydro-quinazolin-2-yl)-1H-pyrazole-4-carboxylic acid. The filtrate from the trituration was purified by reverse-phase HPLC to yield the titled compound (49.7 mg, 13% yield). MS (ESI/Cl): mass calcd. for $C_{14}H_{13}N_5O_3$, 299.1; m/z found, 300.1 [M+H]$^+$. $^1$H NMR (400 MHz, DMSO-d$_6$): 12.99 (s, 2H), 8.96 (d, J=0.6 Hz, 1H), 8.25 (s, 1H), 7.84 (t, J=8.1 Hz, 1H), 7.67-7.48 (m, 2H), 3.12 (s, 6H).

Example 152

1-(7-Ethoxy-4-oxo-3,4-dihydro-quinazolin-2-yl)-1H-pyrazole-4-carboxylic acid

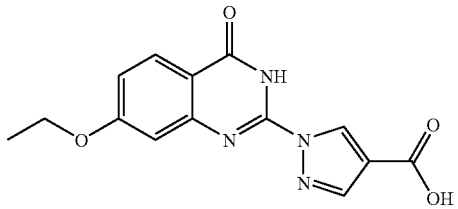 [SMILES: CCOc1ccc2c(=O)[nH]c(-n3cc(C(=O)O)cn3)nc2c1]

The titled compound was prepared in a manner analogous to Example 138 using 3-ethoxyaniline in step A, and carefully pipetting the reaction mixture into ethanol instead of adding ethanol to the reaction mixture in Step B. MS (ESI/Cl): mass calcd. for $C_{14}H_{12}N_4O_4$, 300.1; m/z found, 301.1 [M+H]$^+$. $^1$H NMR (400 MHz, DMSO-d$_6$): 13.01 (s, 1H), 12.66 (s, 1H), 8.93 (s, 1H), 8.25 (s, 1H), 8.02 (d, J=8.7 Hz, 1H), 7.21-7.02 (m, 2H), 4.19 (q, J=6.8 Hz, 2H), 1.39 (t, J=7.0 Hz, 3H).

Example 153

1-(6-Chloro-4-oxo-3,4-dihydro-quinazolin-2-yl)-1H-pyrazole-4-carboxylic acid

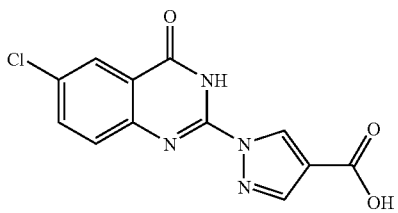 [SMILES: O=C(O)c1cnn(-c2nc3ccc(Cl)cc3c(=O)[nH]2)c1]

The titled compound was prepared in a manner analogous to Example 138 using 4-chloroaniline in step A, and carefully pipetting the reaction mixture into ethanol instead of adding ethanol to the reaction mixture in Step B. MS (ESI/Cl): mass calcd. for $C_{12}H_7ClN_4O_3$, 290.0; m/z found, 291.0 [M+H]$^+$. $^1$H NMR (400 MHz, DMSO-d$_6$): 13.05 (s, 2H), 8.95 (s, 1H), 8.28 (s, 1H), 8.06 (d, J=2.3 Hz, 1H), 7.88 (dd, J=8.7, 2.5 Hz, 1H), 7.72 (d, J=7.8 Hz, 1H).

Example 154

1-(7-Hydroxy-4-oxo-3,4-dihydro-quinazolin-2-yl)-1H-pyrazole-4-carboxylic acid

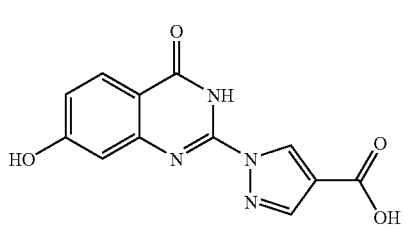 [SMILES: O=C(O)c1cnn(-c2nc3cc(O)ccc3c(=O)[nH]2)c1]

The titled compound was prepared in a manner analogous to Example 131 using 3-isopropylaniline in step A. In Step B, the product (1-(7-hydroxy-4-oxo-3,4-dihydro-quinazolin-2-yl)-1H-pyrazole-4-carboxylic acid ethyl ester) was collected by filtration from the water/DCM layers. MS (ESI/Cl): mass calcd. for $C_{12}H_8N_4O_4$, 272.1; m/z found, 273.0 [M+H]$^+$. $^1$H NMR (400 MHz, DMSO-d$_6$): 12.94 (s, 2H), 10.66 (s, 1H), 8.94 (s, 1H), 8.24 (s, 1H), 7.97 (d, J=8.8 Hz, 1H), 7.09-6.85 (m, 2H).

Example 155

1-(6-Methylsulfanyl-4-oxo-3,4-dihydro-quinazolin-2-yl)-1H-pyrazole-4-carboxylic acid

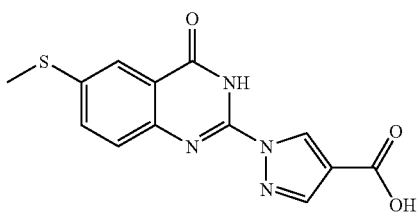 [SMILES: CSc1ccc2nc(-n3cc(C(=O)O)cn3)[nH]c(=O)c2c1]

Step A: Preparation of 1-(6-methylsulfanyl-4-oxo-3,4-dihydro-quinazolin-2-yl)-1H-pyrazole-4-carboxylic acid ethyl ester. The titled compound was prepared in a manner analogous to Example 131, steps A-B, using 4-methylsulfanylaniline in step A. MS (ESI/Cl): mass calcd. for $C_{15}H_{14}N_4O_3S$, 330.1; m/z found, 331.1 [M+H]$^+$. $^1$H NMR (400 MHz, DMSO-d$_6$): 12.95 (s, 1H), 9.00 (s, 1H), 8.31 (s, 1H), 7.86 (d, J=1.9 Hz, 1H), 7.74 (dd, J=8.6, 2.2 Hz, 1H), 7.64 (d, J=7.4 Hz, 1H), 4.30 (q, J=7.1 Hz, 2H), 2.59 (s, 3H), 1.32 (t, J=7.1 Hz, 3H).

Step B: Preparation of 1-(6-methylsulfanyl-4-oxo-3,4-dihydro-quinazolin-2-yl)-1H-pyrazole-4-carboxylic acid. The titled compound was prepared in a manner analogous to Example 131, step C, using 1-(6-methylsulfanyl-4-oxo-3,4-dihydro-quinazolin-2-yl)-1H-pyrazole-4-carboxylic acid ethyl ester. MS (ESI/Cl): mass calcd. for $C_{13}H_{10}N_4O_3S$, 302.1; m/z found, 303.1 [M+H]$^+$. $^1$H NMR (400 MHz, DMSO-d$_6$): 13.13-12.78 (m, 2H), 8.94 (s, 1H), 8.25 (s, 1H), 7.86 (s, 1H), 7.74 (dd, J=8.6, 2.3 Hz, 1H), 7.63 (d, J=8.3 Hz, 1H), 2.59 (s, 3H).

Example 156

1-(4-Oxo-6-trifluoromethylsulfanyl-3,4-dihydro-quinazolin-2-yl)-1H-pyrazole-4-carboxylic acid

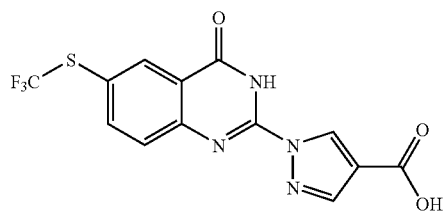 [SMILES: O=C(O)c1cnn(-c2nc3ccc(SC(F)(F)F)cc3c(=O)[nH]2)c1]

The titled compound was prepared in a manner analogous to Example 131 using 4-trifluoromethylsulfanylaniline in step A. MS (ESI/Cl): mass calcd. for $C_{13}H_7F_3N_4O_3S$, 356.0; m/z found, 357.0 [M+H]$^+$. $^1$H NMR (400 MHz, DMSO-d$_6$):

13.20 (s, 1H), 13.08 (s, 1H), 8.98 (s, 1H), 8.36 (s, 1H), 8.31 (s, 1H), 8.10 (dd, J=8.5, 2.2 Hz, 1H), 7.82 (br s, 1H).

Example 157

1-(6-Methanesulfonyl-4-oxo-3,4-dihydro-quinazolin-2-yl)-1H-pyrazole-4-carboxylic acid

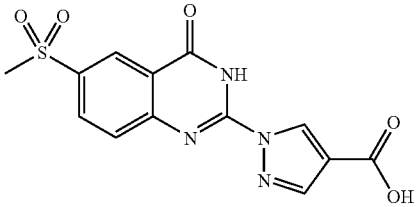 [SMILES: CS(=O)(=O)c1ccc2nc(-n3cc(C(=O)O)cn3)[nH]c(=O)c2c1]

Step A: Preparation of 1-(6-methanesulfonyl-4-oxo-3,4-dihydro-quinazolin-2-yl)-1H-pyrazole-4-carboxylic acid ethyl ester. 3-Chloroperoxybenzoic acid (91.2 mg, 0.407 mmol) was added to a solution of 1-(6-methylsulfanyl-4-oxo-3,4-dihydro-quinazolin-2-yl)-1H-pyrazole-4-carboxylic acid ethyl ester (Intermediate from Example 155, product from Step A) (64.0 mg, 0.194 mmol) and DCM (1.0 mL). The reaction mixture was stirred for 18 h and then concentrated. The residue was triturated from ethanol to yield the titled compound (63.0 mg, 90% yield). The filtrate was quenched with aqueous 0.5M sodium thiosulfate. MS (ESI/Cl): mass calcd. for $C_{15}H_{14}N_4O_5S$, 362.1; m/z found, 363.1 [M+H]$^+$. $^1$H NMR (400 MHz, DMSO-d$_6$): 13.39 (s, 1H), 9.07 (d, J=0.5 Hz, 1H), 8.57 (d, J=2.1 Hz, 1H), 8.38 (s, 1H), 8.30 (dd, J=8.6, 2.3 Hz, 1H), 7.91 (d, J=8.3 Hz, 1H), 4.31 (q, J=7.1 Hz, 2H), 3.33 (s, 3H), 1.33 (t, J=7.1 Hz, 3H).

Step B: Preparation of 1-(6-methanesulfonyl-4-oxo-3,4-dihydro-quinazolin-2-yl)-1H-pyrazole-4-carboxylic acid. The titled compound was prepared in a manner analogous to Example 131, step C, using 1-(6-methanesulfonyl-4-oxo-3,4-dihydro-quinazolin-2-yl)-1H-pyrazole-4-carboxylic acid ethyl ester. MS (ESI/Cl): mass calcd. for $C_{13}H_{10}N_4O_5S$, 334.0; m/z found, 335.0 [M+H]$^+$; 333.1, [M–H]$^-$. $^1$H NMR (400 MHz, DMSO-d$_6$): 13.35 (s, 1H), 13.09 (s, 1H), 9.01 (s, 1H), 8.57 (d, J=2.1 Hz, 1H), 8.32 (s, 1H), 8.29 (dd, J=8.6, 2.2 Hz, 1H), 7.90 (d, J=7.5 Hz, 1H), 3.33 (s, 3H).

Example 158

1-(7-Chloro-6-methylsulfanyl-4-oxo-3,4-dihydro-quinazolin-2-yl)-1H-pyrazole-4-carboxylic acid

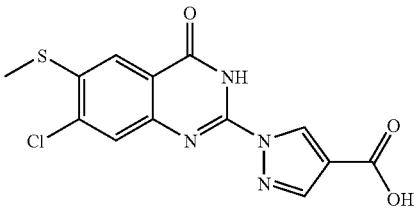 [SMILES: CSc1cc2c(=O)[nH]c(-n3cc(C(=O)O)cn3)nc2cc1Cl]

The titled compound was prepared in a manner analogous to Example 131 using 3-chloro-4-methylsulfanylaniline in step A. MS (ESI/Cl): mass calcd. for $C_{13}H_9ClN_4O_3S$, 336.0; m/z found, 337.0 [M+H]$^+$. $^1$H NMR (400 MHz, DMSO-d$_6$): 13.04 (s, 2H), 8.92 (d, J=0.6 Hz, 1H), 8.26 (s, 1H), 7.85 (s, 1H), 7.82 (s, 1H), 2.62 (s, 3H).

Example 159

1-(7-Chloro-4-oxo-6-trifluoromethylsulfanyl-3,4-dihydro-quinazolin-2-yl)-1H-pyrazole-4-carboxylic acid

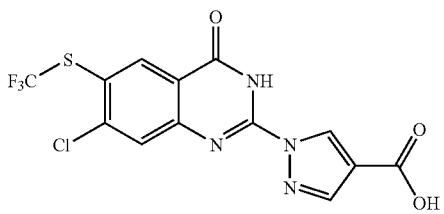

Step A: Preparation of 1-(7-chloro-4-oxo-6-trifluoromethylsulfanyl-3,4-dihydro-quinazolin-2-yl)-1H-pyrazole-4-carboxylic acid ethyl ester. The titled compound was prepared in a manner analogous to Example 131, steps A-B, using 3-chloro-4-trifluoromethylsulfanylaniline in step A. MS (ESI/Cl): mass calcd. for $C_{15}H_{10}ClF_3N_4O_3S$, 418.0; m/z found, 419.0 [M+H]$^+$. $^1$H NMR (400 MHz, DMSO-d$_6$): 13.38 (s, 1H), 9.02 (d, J=0.7 Hz, 1H), 8.46 (s, 1H), 8.38 (s, 1H), 8.05 (s, 1H), 4.31 (q, J=7.1 Hz, 2H), 1.32 (t, J=7.1 Hz, 3H).

Step B: Preparation of 1-(7-chloro-4-oxo-6-trifluoromethylsulfanyl-3,4-dihydro-quinazolin-2-yl)-1H-pyrazole-4-carboxylic acid. The titled compound was prepared in a manner analogous to Example 131, step C using 1-(7-chloro-4-oxo-6-trifluoromethylsulfanyl-3,4-dihydro-quinazolin-2-yl)-1H-pyrazole-4-carboxylic acid ethyl ester. MS (ESI/Cl): mass calcd. for $C_{13}H_6ClF_3N_4O_3S$, 390.0; m/z found, 389.0 [M–H]$^-$. $^1$H NMR (400 MHz, DMSO-d$_6$): 13.35 (s, 1H), 13.11 (s, 1H), 8.96 (d, J=0.6 Hz, 1H), 8.46 (s, 1H), 8.32 (s, 1H), 8.03 (s, 1H).

Example 160

1-(7-Chloro-4-oxo-6-trifluoromethanesulfinyl-3,4-dihydro-quinazolin-2-yl)-1H-pyrazole-4-carboxylic acid

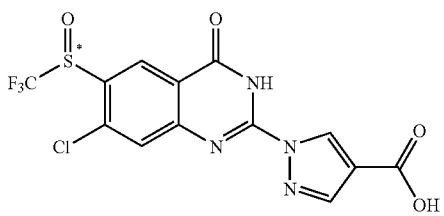 [SMILES: O=C(O)c1cnn(-c2nc3cc(Cl)c(S(=O)C(F)(F)F)cc3c(=O)[nH]2)c1]

The titled compound was prepared in a manner analogous to Example 157 using 1-(7-chloro-4-oxo-6-trifluoromethanesulfanyl-3,4-dihydro-quinazolin-2-yl)-1H-pyrazole-4-carboxylic acid (Intermediate from Example 159, product from Step A) for 1-(6-methylsulfanyl-4-oxo-3,4-dihydro-quinazolin-2-yl)-1H-pyrazole-4-carboxylic acid ethyl ester in step A. MS (ESI/Cl): mass calcd. for $C_{13}H_6ClF_3N_4O_4S$, 406.0; m/z found, 407.0 [M+H]$^+$; 405.0

[M–H]⁻. ¹H NMR (400 MHz, DMSO-d₆): 13.46 (br s, 1H), 13.12 (s, 1H), 8.97 (d, J=0.6 Hz, 1H), 8.54 (s, 1H), 8.33 (s, 1H), 8.03 (s, 1H).

Example 161

1-[4-Oxo-6-(pyrrolidine-1-sulfonyl)-3,4-dihydro-quinazolin-2-yl]-1H-pyrazole-4-carboxylic acid

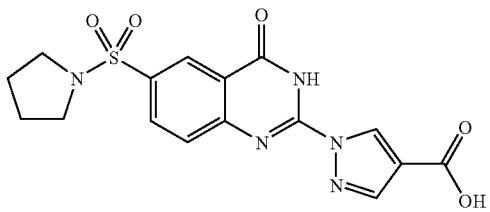 [SMILES: O=C(O)c1cnn(-c2nc3ccc(S(=O)(=O)N4CCCC4)cc3c(=O)[nH]2)c1]

The titled compound was prepared in a manner analogous to Example 17, using 4-(pyrrolidine-1-sulfonyl)aniline for 3,4-dimethoxyaniline in step A and omitting the purification by reverse-phase HPLC in step B. MS (ESI/Cl): mass calcd. for $C_{16}H_{15}N_5O_5S$, 389.1; m/z found, 390.1 [M+H]⁺. ¹H NMR (400 MHz, DMSO-d₆): 13.31 (s, 1H), 13.09 (s, 1H), 9.00 (s, 1H), 8.40 (d, J=1.9 Hz, 1H), 8.32 (s, 1H), 8.19 (dd, J=8.6, 2.2 Hz, 1H), 7.89 (s, 1H), 3.25-3.10 (m, 4H), 1.74-1.59 (m, 4H).

Example 162

1-[4-Oxo-6-(pyrrolidine-1-carbonyl)-3,4-dihydro-quinazolin-2-yl]-1H-pyrazole-4-carboxylic acid

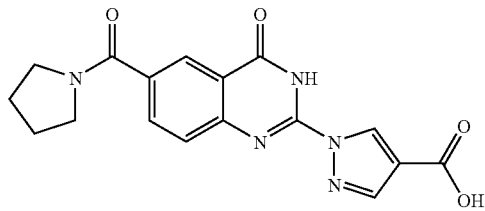 [SMILES: O=C(O)c1cnn(-c2nc3ccc(C(=O)N4CCCC4)cc3c(=O)[nH]2)c1]

Step A: Preparation of 1-{ethoxycarbonylamino-[4-(pyrrolidine-1-carbonyl)-phenylimino]-methyl}-1H-pyrazole-4-carboxylic acid ethyl ester. Ethyl isothiocyanatoformate (0.60 mL, 5.1 mmol) was added to a suspension of (4-aminophenyl)-pyrrolidin-1-yl-methanone (0.873 g, 4.59 mmol) in DCM (15 mL) and the reaction mixture was stirred at room temperature for 1 h. DIC (1.01 mL, 5.05 mmol) was then added, followed by ethyl pyrazole-4-carboxylate (0.707 g, 5.05 mmol). Stirring was continued for 18 h, at which point the reaction mixture was concentrated. Diethyl ether (25 mL) was added to the residue and the resulting suspension was cooled to 0° C. and filtered. The filtrate was concentrated and the residue was purified by FCC (2-100% EtOAc/hexanes) to yield the titled compound (1.502 g, 77% yield). MS (ESI/Cl): mass calcd. for $C_{21}H_{25}N_5O_5$, 427.2; m/z found, 428.2 [M+H]⁺.

Step B: Preparation of 1-[4-oxo-6-(pyrrolidine-1-carbonyl)-3,4-dihydro-quinazolin-2-yl]-1H-pyrazole-4-carboxylic acid ethyl ester. Titanium (IV) chloride (0.377 mL, 3.43 mmol) was carefully added to a solution of 1-{ethoxycarbonylamino-[4-(pyrrolidine-1-carbonyl)-phenylimino]-methyl}-1H-pyrazole-4-carboxylic acid ethyl ester (0.977 g, 2.29 mmol) and DCE (5.5 mL). The reaction mixture was heated to 100° C. for 2.5 h and was then cooled to room temperature and quenched with ethanol (10 mL). The resulting solution was concentrated and the residue was partitioned between DCM (30 mL) and water (30 mL). The two layers were filtered to remove a solid byproduct and then separated. The aqueous layer was washed with DCM (30 mL) and the combined organic layers were washed with brine (30 mL), dried (MgSO₄), and concentrated. The residue was triturated with diethyl ether and then with ethanol to yield the titled compound (18 mg, 2.0% yield). MS (ESI/Cl): mass calcd. for $C_{19}H_{19}N_5O_4$, 381.1; m/z found, 382.1 [M+H]⁺.

Step C: Preparation of 1-[4-oxo-6-(pyrrolidine-1-carbonyl)-3,4-dihydro-quinazolin-2-yl]-1H-pyrazole-4-carboxylic acid. Aqueous 1M KOH (0.13 mL, 0.13 mmol) was added to 1-[4-oxo-6-(pyrrolidine-1-carbonyl)-3,4-dihydro-quinazolin-2-yl]-1H-pyrazole-4-carboxylic acid (18.0 mg, 43.1 pmol) in THF (0.2 mL). The reaction mixture was allowed to stir at room temperature for 2 d and was then concentrated. The residue was redissolved in water (2 mL) and acidified with 1M aqueous HCl (0.5 mL). The resulting precipitate was collected by filtration to yield the titled compound (11 mg, 70% yield). MS (ESI/Cl): mass calcd. for $C_{17}H_{15}N_5O_4$, 353.1; m/z found, 354.1 [M+H]⁺. ¹H NMR (600 MHz, DMSO-d₆): 13.24-12.75 (m, 2H), 8.98 (s, 1H), 8.28 (s, 1H), 8.23 (s, 1H), 7.97 (d, J=8.3 Hz, 1H), 7.73 (s, 1H), 3.51 (t, J=6.8 Hz, 2H), 3.45 (t, J=6.5 Hz, 2H), 1.95-1.78 (m, 4H).

Example 163

1-[6-(2,6-Dimethyl-phenylcarbamoyl)-4-oxo-3,4-dihydro-quinazolin-2-yl]-1H-pyrazole-4-carboxylic acid

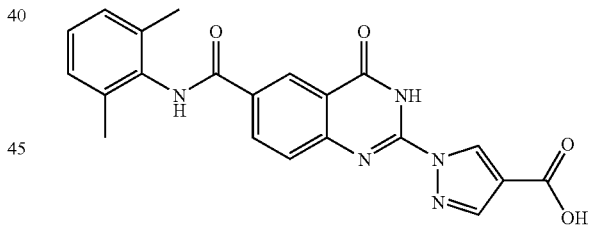

Step A: Preparation of 4-amino-N-(2,6-dimethyl-phenyl)-benzamide. Oxalyl chloride (1.9 mL, 22 mmol) was added dropwise to a solution of DMF (1.7 mL, 22 mmol) and DCM (22 mL) that was kept at 0° C. The resulting foamy white suspension was stirred for 30 min and allowed to warm to room temperature, then cooled again to 0° C. 4-Aminobenzoic acid (1.50 g, 10.9 mmol) was added and the reaction mixture was stirred at room temperature for 1 h. The flask was again cooled to 0° C. and DCM (11 mL) and pyridine (2.6 mL, 33 mmol) were added. Stirring was continued for 50 min and 2,6-dimethyl-phenylamine (1.33 g, 10.9 mmol) was then added. The reaction mixture was stirred at room temperature for 1.5 h and concentrated to dryness. The residue was dissolved in ethanol (30 mL) and 1,2-ethylenediamine (3.3 mL, 49 mmol) was added. The reaction mixture was heated at reflux for 2 h, allowed to cool to room temperature, stirred for 2 d, and concentrated. Water (50 mL) was added to the residue and the precipitate was collected, rinsed well with water, and dried to yield the titled compound (1.904 g, 70% yield). MS (ESI/Cl): mass calcd. for $C_{15}H_{16}N_2O$, 240.1; m/z found, 241.1 [M+H]$^+$. $^1$H NMR (400 MHz, CD$_3$OD): 7.76 (d, J=8.8 Hz, 2H), 7.10 (s, 3H), 6.72 (d, J=8.8 Hz, 2H), 2.24 (s, 6H).

Step B: Preparation of 1-[6-(2,6-dimethyl-phenylcarbamoyl)-4-oxo-3,4-dihydro-quinazolin-2-yl]-1H-pyrazole-4-carboxylic acid. The titled compound was prepared in a manner analogous to Example 162 using 4-amino-N-(2,6-dimethyl-phenyl)-benzamide (prepared according to procedure described in *J. Org. Chem.* 2008, 73, 8954-8959) in step A. MS (ESI/Cl): mass calcd. for $C_{21}H_{17}N_5O_4$, 403.1; m/z found, 404.1 [M+H]$^+$. $^1$H NMR (400 MHz, DMSO-d$_6$): 13.07 (s, 2H), 10.08 (s, 1H), 9.01 (s, 1H), 8.81 (s, 1H), 8.39 (d, J=7.7 Hz, 1H), 8.30 (s, 1H), 7.81 (d, J=7.6 Hz, 1H), 7.14 (s, 3H), 2.21 (s, 6H).

Example 164

1-(6-Nitro-4-oxo-3,4-dihydro-quinazolin-2-yl)-1H-pyrazole-4-carboxylic acid

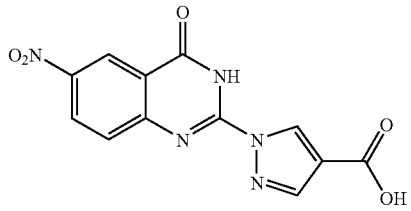 [SMILES: O=C(O)c1cnn(-c2nc3ccc([N+](=O)[O-])cc3c(=O)[nH]2)c1]

Step A: Preparation of 6-nitro-1H-quinazoline-2,4-dione. Urea (9.89 g, 0.165 mol) and 5-nitroanthranilic acid (6.00 g, 32.9 mmol) were heated to 200° C. with vigorous stirring for 1 h. The melt was allowed to cool to 150° C., and water (150 mL) was slowly added. The resulting slurry was sonicated for 1 h and stirred vigorously for an additional 2 h. It was then cooled to 0° C., and the precipitate was collected and rinsed with water to yield the titled compound (6.43 g, 94% yield). This material was dried in a vacuum oven and used without further purification. This compound did not yield MS data.

Step B: Preparation of 2,4-dichloro-6-nitro-quinazoline. Phosphorus oxychloride (6.64 mL, 72.6 mmol) was added to a suspension of 6-nitro-1H-quinazoline-2,4-dione (5.01 g, 24.2 mmol) in toluene (100 mL) and the reaction mixture was heated to 55° C. Tri-n-propylamine (12.1 mL, 63.9 mmol) was added dropwise from an addition funnel over 25 minutes. The reaction mixture was heated to 110° C. for 6 h, stirred at room temperature for 4 d, and then pipetted into water (75 mL) and vigorously stirred for 1 h. The two layers were filtered and separated. The organic layer was washed with brine (30 mL), dried (MgSO$_4$), and concentrated to yield the titled compound (3.79 g, 67% yield, 95% pure) after 24 h under high vacuum. This compound did not yield MS data. $^1$H NMR (600 MHz, CDCl$_3$): 9.18 (d, J=2.4 Hz, 1H), 8.75 (dd, J=9.2, 2.5 Hz, 1H), 8.18 (d, J=9.2 Hz, 1H).

Step C: Preparation of 2-chloro-6-nitro-3H-quinazolin-4-one. Aqueous 2M NaOH (22.2 mL, 44.4 mmol) was added to 2,4-dichloro-6-nitro-quinazoline (3.61 g, 14.8 mmol). The mixture was sonicated, stirred at room temperature for 3 h, and filtered, rinsing with water (60 mL). Acetic acid (3.81 mL, 66.6 mmol) was added to the filtrate to yield a precipitate, which was collected and dried in a vacuum oven to yield the titled compound (2.99 g, 90% yield). This compound did not yield MS data. $^1$H NMR (400 MHz, CDCl$_3$): 9.07 (s, 1H), 8.56 (d, J=8.9 Hz, 1H), 7.78 (d, J=8.8 Hz, 1H).

Step D: Preparation of 1-(6-nitro-4-oxo-3,4-dihydro-quinazolin-2-yl)-1H-pyrazole-4-carboxylic acid ethyl ester. Ethyl pyrazole-4-carboxylate (1.83 g, 13.1 mmol) was added to a suspension of 2-chloro-6-nitro-3H-quinazolin-4-one (2.95 g, 13.1 mmol) in xylenes (52 mL). The reaction mixture was heated to 130° C. for 1 h, allowed to cool, and stirred at room temperature for 18 h. The precipitate was collected and rinsed with ether (20 mL) to yield the titled compound (4.22 g, 98%). MS (ESI/Cl): mass calcd. for $C_{14}H_{11}N_5O_5$, 329.1; m/z found, 330.1 [M+H]$^+$.

Step E: Preparation of 1-(6-nitro-4-oxo-3,4-dihydro-quinazolin-2-yl)-1H-pyrazole-4-carboxylic acid. The titled compound was prepared in a manner analogous to Example 1, Step C. The final compound was triturated from DMSO. MS (ESI/Cl): mass calcd. for $C_{12}H_7N_5O_5$, 301.0; m/z found, 302.2 [M+H]$^+$, 300.1 [M−H]$^1$NMR (400 MHz, DMSO-d$_6$): 13.47 (s, 1H), 13.11 (s, 1H), 9.02 (s, 1H), 8.80 (d, J=2.7 Hz, 1H), 8.58 (dd, J=9.0, 2.7 Hz, 1H), 8.33 (s, 1H), 7.88 (d, J=8.7 Hz, 1H).

Example 165

1-(6-Benzoylamino-4-oxo-3,4-dihydro-quinazolin-2-yl)-1H-pyrazole-4-carboxylic acid

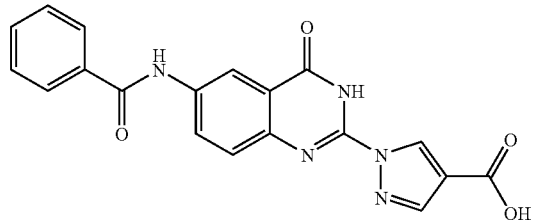 [SMILES: O=C(O)c1cnn(-c2nc3ccc(NC(=O)c4ccccc4)cc3c(=O)[nH]2)c1]

Step A: Preparation of 1-[6-nitro-4-oxo-3-(2-trimethylsilanyl-ethoxymethyl)-3,4-dihydro-quinazolin-2-yl]-1H-pyrazole-4-carboxylic acid ethyl ester. DIEA (4.41 mL, 25.6 mmol) was added to a suspension of 1-(6-nitro-4-oxo-3,4-dihydro-quinazolin-2-yl)-1H-pyrazole-4-carboxylic acid ethyl ester (Intermediate from Example 164, product from Step D) (4.21 g, 12.8 mmol) in THF (64 mL), followed by (2-chloromethoxy-ethyl)-trimethylsilane (2.49 mL, 14.1 mmol). The reaction mixture was stirred at room temperature for 18 h and then concentrated. The residue was partitioned between water (75 mL) and EtOAc (75 mL), and the organic layer was washed with water (2×75 mL) and brine (50 mL), dried (MgSO$_4$), and concentrated to yield the titled compound (5.92 g, 86% yield, 85% pure). This material was carried on to the next step without further purification. MS (ESI/Cl): mass calcd. for $C_{20}H_{25}N_5O_6Si$, 459.2; m/z found, 402.1 [M+H−58]$^+$.

Step B: Preparation of 1-[6-amino-4-oxo-3-(2-trimethylsilanyl-ethoxymethyl)-3,4-dihydro-quinazolin-2-yl]-1H-pyrazole-4-carboxylic acid ethyl ester. Ammonium chloride (4.10 g, 76.6 mmol) and water (9.1 mL) were added to a solution of 1-[6-nitro-4-oxo-3-(2-trimethylsilanyl-ethoxymethyl)-3,4-dihydro-quinazolin-2-yl]-1H-pyrazole-4-carboxylic acid ethyl ester (5.92 g, 85% pure, 10.9 mmol) in acetone (46 mL). Zinc dust (5.01 g, 76.6 mmol) was then added in portions with vigorous stirring. Stirring was continued for 45 min, at which point the reaction mixture was filtered through diatomaceous earth. The filter cake was rinsed thoroughly with EtOAc (100 mL). The filtrate was concentrated and the residue was dissolved in EtOAc (75 mL), decanting from the remaining salts. The organic layer was washed with brine (45 mL), dried (MgSO$_4$), and concentrated. The residue was purified by FCC (2-70% EtOAc/hexanes) to yield the titled compound (4.19 g, 89% yield). MS (ESI/Cl): mass calcd. for C$_{20}$H$_{27}$N$_5$O$_4$Si, 430.2; m/z found, 429.2 [M+H]$^+$. $^1$H NMR (400 MHz, CDCl$_3$): 8.56 (d, J=0.6 Hz, 1H), 8.15 (d, J=0.6 Hz, 1H), 7.53 (d, J=8.6 Hz, 1H), 7.49 (d, J=2.6 Hz, 1H), 7.13 (dd, J=8.6, 2.8 Hz, 1H), 5.78 (s, 2H), 4.35 (q, J=7.1 Hz, 2H), 4.09 (s, 2H), 3.57-3.43 (m, 2H), 1.37 (t, J=7.1 Hz, 3H), 0.86-0.74 (m, 2H), -0.08 (s, 9H).

Step C: Preparation of 1-[6-benzoylamino-4-oxo-3-(2-trimethylsilanyl-ethoxymethyl)-3,4-dihydro-quinazolin-2-yl]-1H-pyrazole-4-carboxylic acid ethyl ester. Benzoyl chloride (81.1 µL, 0.698 mmol) was added dropwise to a solution of 1-[6-amino-4-oxo-3-(2-trimethylsilanyl-ethoxymethyl)-3,4-dihydro-quinazolin-2-yl]-1H-pyrazole-4-carboxylic acid ethyl ester (0.200 g, 0.466 mmol), TEA (0.162 mL, 1.16 mmol), and DCM (2.3 mL). The reaction mixture was stirred at room temperature for 1.5 h and was then diluted with DCM (25 mL) and quenched with water (15 mL). The organic layer was washed with water (20 mL) and brine (20 mL), dried (MgSO$_4$), and concentrated. The residue was purified by FCC (10-70% EtOAc/hexanes) to yield the titled compound (0.240 g, 97% yield). MS (ESI/Cl): mass calcd. for C$_{27}$H$_{31}$N$_5$O$_5$Si, 533.2; m/z found, 476.2 [M+H−58]$^+$.

Step D: Preparation of 1-(6-benzoylamino-4-oxo-3,4-dihydro-quinazolin-2-yl)-1H-pyrazole-4-carboxylic acid ethyl ester. Hydrochloric acid (4M in dioxane, 2.0 mL, 8.0 mmol) was added to a solution of 1-[6-benzoylamino-4-oxo-3-(2-trimethylsilanyl-ethoxymethyl)-3,4-dihydro-quinazolin-2-yl]-1H-pyrazole-4-carboxylic acid ethyl ester (0.239 g, 0.488 mmol) and dioxane (2.0 mL). The reaction mixture was stirred at room temperature for 18 h, at which point ether (10 mL) was added and the precipitate was collected to yield the titled compound (0.157 g, 86% yield). MS (ESI/Cl): mass calcd. for C$_{21}$H$_{17}$N$_5$O$_4$, 403.1; m/z found, 404.1 [M+H]$^+$. $^1$H NMR (400 MHz, DMSO-d$_6$): 12.87 (s, 1H), 10.62 (s, 1H), 9.01 (s, 1H), 8.69 (s, 1H), 8.32 (s, 1H), 8.23 (dd, J=8.9, 2.4 Hz, 1H), 8.06-7.96 (m, 2H), 7.84-7.49 (m, 4H), 4.31 (q, J=7.1 Hz, 2H), 1.33 (t, J=7.1 Hz, 3H).

Step E: Preparation of 1-(6-benzoylamino-4-oxo-3,4-dihydro-quinazolin-2-yl)-1H-pyrazole-4-carboxylic acid. Aqueous 1M KOH (1.06 mL, 1.06 mmol) was added to 1-(6-benzoylamino-4-oxo-3,4-dihydro-quinazolin-2-yl)-1H-pyrazole-4-carboxylic acid ethyl ester (0.142 g, 0.343 mmol) in THF (1.0 mL). The reaction mixture was allowed to stir at room temperature for 18 h and was then concentrated. The residue was redissolved in water (5 mL) and brought to pH 1 with aqueous 1M HCl (3 mL). The resulting precipitate was collected by filtration to yield the titled compound (0.110 g, 82% yield). MS (ESI/Cl): mass calcd. for C$_{19}$H$_{13}$N$_5$O$_4$, 375.1; m/z found, 376.1 [M+H]$^+$. $^1$H NMR (600 MHz, DMSO-d$_6$): 12.99 (s, 1H), 12.79 (s, 1H), 10.60 (s, 1H), 8.95 (s, 1H), 8.68 (s, 1H), 8.26 (s, 1H), 8.23 (dd, J=8.8, 2.4 Hz, 1H), 8.04-7.99 (m, 2H), 7.71 (d, J=7.8 Hz, 1H), 7.65-7.60 (m, 1H), 7.59-7.54 (m, 2H).

Example 166

1-[6-(2,6-Dimethyl-benzoylamino)-4-oxo-3,4-dihydro-quinazolin-2-yl]-1H-pyrazole-4-carboxylic acid

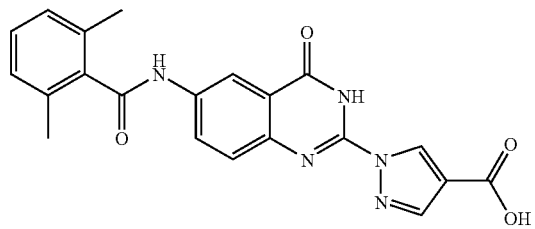 [SMILES: Cc1cccc(C)c1C(=O)Nc1ccc2nc(-n3cc(C(=O)O)cn3)[nH]c(=O)c2c1]

Step A: Preparation of 2,6-dimethylbenzoyl chloride. DMF (2 drops) was added to 2,6-dimethylbenzoic acid (0.100 g, 0.666 mmol) in thionyl chloride (0.50 mL, 6.9 mmol). The reaction mixture was stirred for 2 h and concentrated to yield the titled compound, which was used in the next step without further purification.

Step B: Preparation of 1-[6-(2,6-dimethyl-benzoylamino)-4-oxo-3,4-dihydro-quinazolin-2-yl]-1H-pyrazole-4-carboxylic acid. The titled compound was prepared in a manner analogous to Example 165, Steps C-E, substituting 2,6-dimethylbenzoyl chloride for benzoyl chloride in Step C. MS (ESI/Cl): mass calcd. for C$_{21}$H$_{17}$N$_5$O$_4$, 403.1; m/z found, 404.1 [M+H]$^+$. $^1$H NMR (400 MHz, DMSO-d$_6$): 13.00 (s, 1H), 12.83 (s, 1H), 10.78 (s, 1H), 8.95 (s, 1H), 8.72 (s, 1H), 8.25 (s, 1H), 8.03 (dd, J=8.8, 2.4 Hz, 1H), 7.69 (d, J=8.8 Hz, 1H), 7.29-7.23 (m, 1H), 7.14 (d, J=7.5 Hz, 2H), 2.30 (s, 6H).

Example 167

1-(6-Acetylamino-4-oxo-3,4-dihydro-quinazolin-2-yl)-1H-pyrazole-4-carboxylic acid

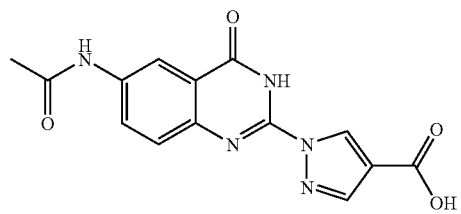 [SMILES: CC(=O)Nc1ccc2nc(-n3cc(C(=O)O)cn3)[nH]c(=O)c2c1]

The titled compound was prepared in a manner analogous to Example 165, substituting acetyl chloride for benzoyl chloride in Step C. MS (ESI/Cl): mass calcd. for C$_{14}$H$_{11}$N$_5$O$_4$, 313.1; m/z found, 314.1 [M+H]$^+$. $^1$H NMR (600 MHz, DMSO-d$_6$): 12.97 (s, 1H), 12.73 (s, 1H), 10.30 (s, 1H), 8.92 (d, J=0.6 Hz, 1H), 8.48 (s, 1H), 8.25 (s, 1H), 7.94 (dd, J=8.8, 2.5 Hz, 1H), 7.65 (d, J=8.6 Hz, 1H), 2.10 (s, 3H).

Example 168

1-[4-Oxo-6-(3-phenyl-ureido)-3,4-dihydro-quinazolin-2-yl]-1H-pyrazole-4-carboxylic acid

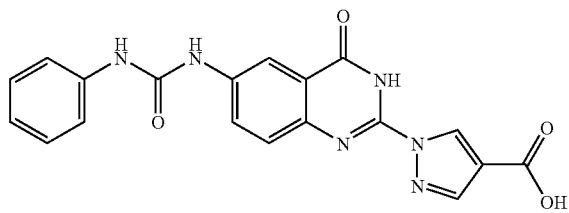 [SMILES: O=C(Nc1ccccc1)Nc1ccc2nc(-n3cc(C(=O)O)cn3)[nH]c(=O)c2c1]

Step A: Preparation of 1-[4-oxo-6-(3-phenyl-ureido)-3-(2-trimethylsilanyl-ethoxymethyl)-3,4-dihydro-quinazolin-2-yl]-1H-pyrazole-4-carboxylic acid ethyl ester. Benzyl isocyanate (79.2 µL, 0.729 mmol) was added dropwise to 1-[6-amino-4-oxo-3-(2-trimethylsilanyl-ethoxymethyl)-3,4-dihydro-quinazolin-2-yl]-1H-pyrazole-4-carboxylic acid ethyl ester (0.240 g, 0.559 mmol) in THF (11.2 mL). The reaction mixture was stirred at room temperature for 24 h, then at 50° C. for 18 h. Another aliquot of benzyl isocyanate (60.9 µL, 0.561 mmol) was added and heating was continued for another 6 h. The reaction mixture was concentrated and the residue was partitioned between EtOAc (30 mL) and water (30 mL). The aqueous layer was further extracted with EtOAc (30 mL), and the combined organic layers were washed with brine (30 mL), dried (MgSO$_4$), and concentrated. The residue was purified by FCC (EtOAc/hexanes) to yield the titled compound (0.287 g, 94% yield). MS (ESI/Cl): mass calcd. for $C_{27}H_{32}N_6O_5Si$, 548.2; m/z found, 491.2 [M+H−58]$^+$.

Step B: Preparation of 1-[4-oxo-6-(3-phenyl-ureido)-3,4-dihydro-quinazolin-2-yl]-1H-pyrazole-4-carboxylic acid. The titled compound was prepared in a manner analogous to Example 165, Steps D-E. MS (ESI/Cl): mass calcd. for $C_{19}H_{14}N_6O_4$, 390.1; m/z found, 391.1 [M+H]$^+$. $^1$H NMR (400 MHz, DMSO-d$_6$): 13.22-12.51 (m, 2H), 9.12 (s, 1H), 8.93 (d, J=0.7 Hz, 1H), 8.80 (s, 1H), 8.37 (d, J=2.5 Hz, 1H), 8.25 (s, 1H), 7.81 (dd, J=8.9, 2.6 Hz, 1H), 7.65 (d, J=8.8 Hz, 1H), 7.49 (dd, J=8.6, 1.1 Hz, 2H), 7.31 (dd, J=10.7, 5.2 Hz, 2H), 7.04-6.96 (m, 1H).

Example 169

1-(6-Benzenesulfonylamino-4-oxo-3,4-dihydro-quinazolin-2-yl)-1H-pyrazole-4-carboxylic acid

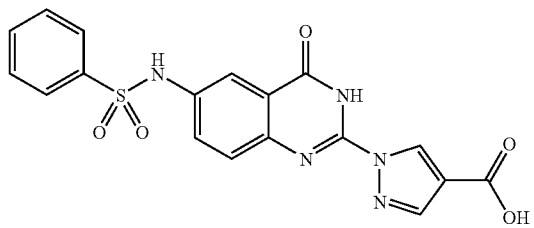 [SMILES: O=C(O)c1cnn(-c2nc3ccc(NS(=O)(=O)c4ccccc4)cc3c(=O)[nH]2)c1]

Step A: Preparation of 1-[6-benzenesulfonylamino-4-oxo-3-(2-trimethylsilanyl-ethoxymethyl)-3,4-dihydro-quinazolin-2-yl]-1H-pyrazole-4-carboxylic acid ethyl ester. Benzenesulfonyl chloride (0.131 mL, 1.02 mmol) was added dropwise to a solution of 1-[6-amino-4-oxo-3-(2-trimethylsilanyl-ethoxymethyl)-3,4-dihydro-quinazolin-2-yl]-1H-pyrazole-4-carboxylic acid ethyl ester (0.200 g, 0.466 mmol) in pyridine (2.3 mL). The reaction mixture was stirred for 2 h, then quenched with water (15 mL) and extracted with EtOAc (30 mL). The organic layer was washed with water (15 mL) and brine (15 mL), dried (MgSO$_4$), and concentrated. The residue was purified by FCC (5-50% EtOAc/hexanes) to yield the titled compound (0.253 mg, 95% yield). MS (ESI/Cl): mass calcd. for $C_{26}H_{31}N_5O_6SSi$, 569.2; m/z found, 512.1 [M+H−58]$^+$.

Step B: Preparation of 1-(6-benzenesulfonylamino-4-oxo-3,4-dihydro-quinazolin-2-yl)-1H-pyrazole-4-carboxylic acid. The titled compound was prepared in a manner analogous to Example 165, Steps D-E. MS (ESI/Cl): mass calcd. for $C_{18}H_{13}N_5O_5S$, 411.1; m/z found, 412.0 [M+H]$^+$. $^1$H NMR (600 MHz, DMSO-d$_6$): 12.97 (s, 1H), 12.80 (s, 1H), 10.71 (s, 1H), 8.88 (s, 1H), 8.22 (s, 1H), 7.81 (s, 1H), 7.79 (d, J=7.3 Hz, 2H), 7.64-7.53 (m, 5H).

Example 170

1-(6-Methanesulfonylamino-4-oxo-3,4-dihydro-quinazolin-2-yl)-1H-pyrazole-4-carboxylic acid

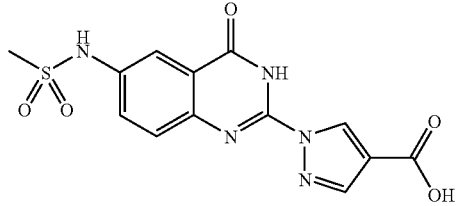 [SMILES: CS(=O)(=O)Nc1ccc2nc(-n3cc(C(=O)O)cn3)[nH]c(=O)c2c1]

The titled compound was synthesized in a manner analogous to Example 169, substituting methanesulfonyl chloride for benzenesulfonyl chloride in step A. MS (ESI/Cl): mass calcd. for $C_{13}H_{11}N_5O_5S$, 349.1; m/z found, 350.0 [M+H]$^+$. $^1$H NMR (400 MHz, DMSO-d$_6$): 13.00 (s, 1H), 12.88 (s, 1H), 10.18 (s, 1H), 8.93 (s, 1H), 8.25 (s, 1H), 7.95 (s, 1H), 7.75-7.62 (m, 2H), 3.06 (s, 3H).

Example 171

1-(6-Benzylamino-4-oxo-3,4-dihydro-quinazolin-2-yl)-1H-pyrazole-4-carboxylic acid

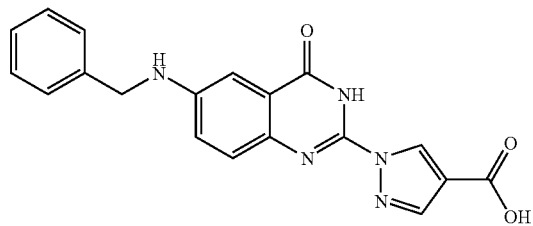

Step A: Preparation of 1-[6-benzylamino-4-oxo-3-(2-trimethylsilanyl-ethoxymethyl)-3,4-dihydro-quinazolin-2-yl]-1H-pyrazole-4-carboxylic acid ethyl ester. A vial was charged with 1-[6-amino-4-oxo-3-(2-trimethylsilanyl-ethoxymethyl)-3,4-dihydro-quinazolin-2-yl]-1H-pyrazole-4-carboxylic acid ethyl ester (0.250 g, 0.582 mmol), benzaldehyde (59.2 µL, 0.582 mmol), and 4 Å MS (0.25 g). DCE was added (1.9 mL) and the reaction mixture was stirred at room temperature for 18 h. Sodium triacetoxyborohydride (0.308 g, 1.46 mmol) was added and the reaction mixture was stirred for a further 24 h. The reaction was quenched with saturated aqueous sodium bicarbonate (10 mL) and was then extracted with DCM (3×15 mL). The combined organic layers were washed with brine (20 mL), dried (MgSO$_4$), and concentrated. The residue was purified by FCC (2-40% EtOAc/hexanes) to yield the titled compound (0.273 g, 90% yield). MS (ESI/Cl): mass calcd. for $C_{27}H_{33}N_5O_4Si$, 519.2; m/z found, 520.2 [M+H]$^+$.

Step B: Preparation of 1-(6-benzylamino-4-oxo-3,4-dihydro-quinazolin-2-yl)-1H-pyrazole-4-carboxylic acid. The titled compound was prepared in a manner analogous to Example 165, Steps D-E. In Step D, the dioxane was evaporated before the product was triturated from ether. MS (ESI/Cl): mass calcd. for $C_{19}H_{15}N_5O_3$, 361.1; m/z found, 362.1 [M+H]$^+$. $^1$H NMR (600 MHz, DMSO-d$_6$): 12.93 (s, 1H), 12.44 (s, 1H), 8.85 (d, J=0.6 Hz, 1H), 8.19 (s, 1H), 7.46 (d, J=8.7 Hz, 1H), 7.39 (d, J=7.7 Hz, 2H), 7.34 (t, J=7.7 Hz, 2H), 7.28-7.19 (m, 2H), 7.09 (d, J=2.7 Hz, 1H), 6.92 (s, 1H), 4.38 (s, 2H).

Example 172

1-(6-Ethylamino-4-oxo-3,4-dihydro-quinazolin-2-yl)-1H-pyrazole-4-carboxylic acid

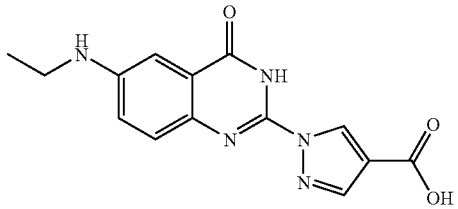 [SMILES: CCNc1ccc2nc(-n3cc(C(=O)O)cn3)[nH]c(=O)c2c1]

Step A: Preparation of 1-[6-ethylamino-4-oxo-3-(2-trimethylsilanyl-ethoxymethyl)-3,4-dihydro-quinazolin-2-yl]-1H-pyrazole-4-carboxylic acid ethyl ester. Acetaldehyde (1 mL) was added to 1-[6-amino-4-oxo-3-(2-trimethylsilanyl-ethoxymethyl)-3,4-dihydro-quinazolin-2-yl]-1H-pyrazole-4-carboxylic acid ethyl ester (0.250 g, 0.582 mol) and 4 Å molecular sieves (0.35 g) in ethanol (1.9 g). The reaction mixture was stirred at room temperature for 18 h and was then filtered. Ethanol and acetaldehyde were removed under high vacuum. The residue was redissolved in DCE (1.5 mL) and sodium triacetoxyborohydride (0.308 g, 1.46 mmol) was added. The reaction mixture was stirred at room temperature for 6 d, then diluted with EtOAc (30 mL) and washed with saturated aqueous sodium bicarbonate (20 mL). The aqueous layer was extracted with EtOAc (30 mL) and the combined organic layers were washed with brine (20 mL), dried (MgSO$_4$), and concentrated. The residue was purified via FCC (5-65% EtOAc/hexanes) to yield the titled compound (87.0 mg, 33% yield). MS (ESI/Cl): mass calcd. for $C_{22}H_{31}N_5O_4Si$, 457.2; m/z found, 458.2 [M+H]$^+$.

Step B: Preparation of 1-(6-ethylamino-4-oxo-3,4-dihydro-quinazolin-2-yl)-1H-pyrazole-4-carboxylic acid. The titled compound was prepared in a manner analogous to Example 165, Steps D-E. In Step D, the dioxane was evaporated before the product was triturated from ether. MS (ESI/Cl): mass calcd. for $C_{14}H_{13}N_5O_3$, 299.1; m/z found, 300.1 [M+H]$^+$. $^1$H NMR (400 MHz, DMSO-d$_6$): 13.04-12.24 (m, 2H), 8.85 (d, J=0.7 Hz, 1H), 8.19 (s, 1H), 7.46 (d, J=8.8 Hz, 1H), 7.16 (dd, J=8.8, 2.7 Hz, 1H), 7.06 (d, J=2.7 Hz, 1H), 6.23 (s, 1H), 3.12 (br q, J=7.0 Hz, 2H), 1.21 (t, J=7.1 Hz, 3H).

Example 173

1-[6-(2-Methyl-benzylamino)-4-oxo-3,4-dihydro-quinazolin-2-yl]-1H-pyrazole-4-carboxylic acid

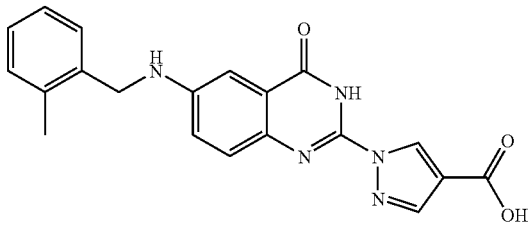 [SMILES: Cc1ccccc1CNc1ccc2nc(-n3cc(C(=O)O)cn3)[nH]c(=O)c2c1]

The titled compound was prepared in a manner analogous to Example 171, substituting 2-methylbenzaldehyde for benzaldehyde in step A. MS (ESI/Cl): mass calcd. for $C_{20}H_{17}N_5O_3$, 375.1; m/z found, 376.1 [M+H]$^+$. $^1$H NMR (600 MHz, DMSO-d$_6$): 12.92 (s, 1H), 12.46 (s, 1H), 8.86 (d, J=0.5 Hz, 1H), 8.19 (s, 1H), 7.46 (d, J=8.8 Hz, 1H), 7.28 (d, J=7.1 Hz, 1H), 7.26-7.12 (m, 4H), 7.09 (s, 1H), 6.74 (s, 1H), 4.31 (d, J=5.2 Hz, 2H), 2.36 (s, 3H).

Example 174

1-[6-(2-Chloro-benzylamino)-4-oxo-3,4-dihydro-quinazolin-2-yl]-1H-pyrazole-4-carboxylic acid

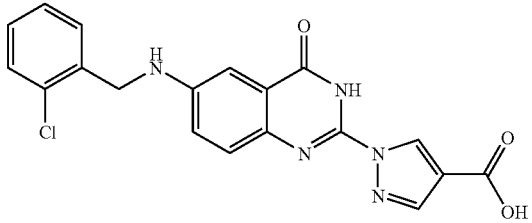 [SMILES: O=C(O)c1cnn(-c2nc3ccc(NCc4ccccc4Cl)cc3c(=O)[nH]2)c1]

The titled compound was prepared in a manner analogous to Example 171, substituting 2-chlorobenzaldehyde for benzaldehyde in step A. MS (ESI/Cl): mass calcd. for $C_{19}H_{14}ClN_5O_3$, 395.1; m/z found, 396.1 [M+H]$^+$. $^1$H NMR (600 MHz, DMSO-d$_6$): 12.93 (s, 1H), 12.48 (s, 1H), 8.86 (d, J=0.6 Hz, 1H), 8.19 (s, 1H), 7.53-7.46 (m, 2H), 7.40 (dd, J=5.9, 3.5 Hz, 1H), 7.33-7.28 (m, 2H), 7.23 (d, J=9.0 Hz, 1H), 7.03 (d, J=2.2 Hz, 1H), 6.95 (s, 1H), 4.44 (d, J=4.6 Hz, 2H).

Example 175

1-[6-(2,6-Dimethyl-benzylamino)-4-oxo-3,4-dihydro-quinazolin-2-yl]-1H-pyrazole-4-carboxylic acid

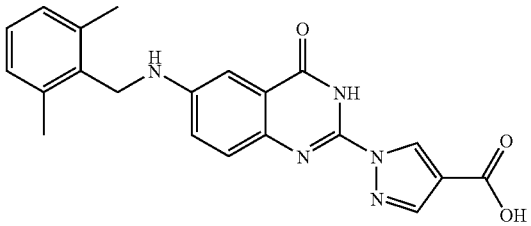 [SMILES: Cc1cccc(C)c1CNc1ccc2nc(-n3cc(C(=O)O)cn3)[nH]c(=O)c2c1]

The titled compound was prepared in a manner analogous to Example 171, substituting 2,6-dimethylbenzaldehyde for benzaldehyde in step A. MS (ESI/Cl): mass calcd. for $C_{21}H_{19}N_5O_3$, 389.2; m/z found, 390.2 [M+H]$^+$. $^1$H NMR (400 MHz, DMSO-d$_6$): 12.92 (s, 1H), 12.49 (s, 1H), 8.88 (d, J=0.7 Hz, 1H), 8.20 (s, 1H), 7.47 (d, J=8.8 Hz, 1H), 7.30 (dd, J=8.7, 2.7 Hz, 1H), 7.23 (d, J=2.5 Hz, 1H), 7.17-7.05 (m, 3H), 6.23 (t, J=3.9 Hz, 1H), 4.21 (d, J=4.1 Hz, 2H), 2.35 (s, 6H).

Example 176

1-[6-(2,6-Difluoro-benzylamino)-4-oxo-3,4-dihydro-quinazolin-2-yl]-1H-pyrazole-4-carboxylic acid

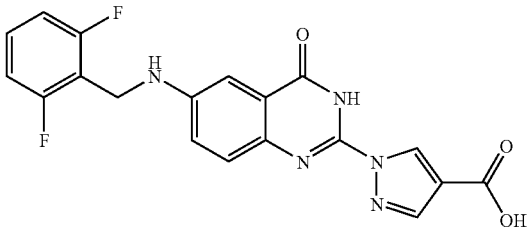 [SMILES: O=C(O)c1cnn(-c2nc3ccc(NCc4c(F)cccc4F)cc3c(=O)[nH]2)c1]

The titled compound was prepared in a manner analogous to Example 171, substituting 2,6-difluorobenzaldehyde for benzaldehyde in step A. MS (ESI/Cl): mass calcd. for $C_{19}H_{13}F_2N_5O_3$, 397.1; m/z found, 398.1 [M+H]$^+$. $^1$H NMR (600 MHz, DMSO-d$_6$): 12.94 (s, 1H), 12.49 (s, 1H), 8.86 (d, J=0.6 Hz, 1H), 8.21 (s, 1H), 7.48 (d, J=8.6 Hz, 1H), 7.46-7.39 (m, 1H), 7.25 (dt, J=8.7, 2.7 Hz, 2H), 7.18-7.11 (m, 2H), 6.69 (s, 1H), 4.37 (s, 2H).

Example 177

1-[6-(2-Cyano-benzylamino)-4-oxo-3,4-dihydro-quinazolin-2-yl]-1H-pyrazole-4-carboxylic acid

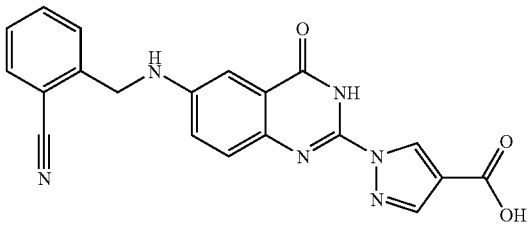 [SMILES: N#Cc1ccccc1CNc1ccc2nc(-n3cc(C(=O)O)cn3)[nH]c(=O)c2c1]

The titled compound was prepared in a manner analogous to Example 171, substituting 2-cyanobenzaldehyde for benzaldehyde in step A and purifying the titled compound by reverse-phase HPLC. MS (ESI/Cl): mass calcd. for $C_{20}H_{14}N_6O_3$, 386.1; m/z found, 387.1 [M+H]$^+$. $^1$H NMR (600 MHz, DMSO-d$_6$): 13.23 (s, 1H), 13.09 (s, 1H), 10.18 (s, 1H), 9.30 (s, 1H), 9.02 (s, 1H), 8.44 (s, 1H), 8.32 (d, J=7.8 Hz, 2H), 8.10 (d, J=9.2 Hz, 1H), 7.94 (s, 1H), 7.89 (dd, J=11.3, 4.7 Hz, 1H), 7.84 (d, J=7.7 Hz, 1H), 7.75 (t, J=7.7 Hz, 1H), 5.36 (s, 2H).

Example 178

1-[6-(3-Cyano-benzylamino)-4-oxo-3,4-dihydro-quinazolin-2-yl]-1H-pyrazole-4-carboxylic acid

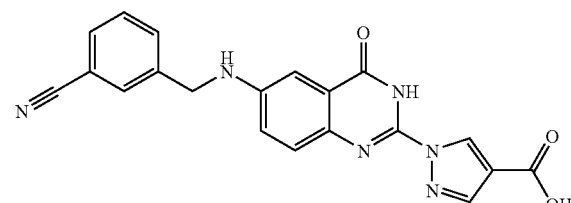

The titled compound was prepared in a manner analogous to Example 171, substituting 3-cyanobenzaldehyde for benzaldehyde in step A. Step C yielded a mixture of the titled compound, 1-[6-(3-carbamoyl-benzylamino)-4-oxo-3,4-dihydro-quinazolin-2-yl]-1H-pyrazole-4-carboxylic acid, and 1-[6-amino-4-oxo-3,4-dihydro-quinazolin-2-yl]-1H-pyrazole-4-carboxylic acid, which was separated by reverse-phase HPLC.

Data for 1-[6-(3-cyano-benzylamino)-4-oxo-3,4-dihydro-quinazolin-2-yl]-1H-pyrazole-4-carboxylic acid: MS (ESI/Cl): mass calcd. for $C_{20}H_{14}N_6O_3$, 386.1; m/z found, 387.1 [M+H]$^+$. $^1$H NMR (600 MHz, DMSO-d$_6$): 12.93 (s, 1H), 12.48 (s, 1H), 8.85 (d, J=0.5 Hz, 1H), 8.19 (s, 1H), 7.83 (s, 1H), 7.73 (dd, J=7.8, 1.2 Hz, 2H), 7.57 (t, J=7.8 Hz, 1H), 7.47 (d, J=8.8 Hz, 1H), 7.23 (d, J=6.5 Hz, 1H), 7.08 (d, J=2.1 Hz, 1H), 6.99 (t, J=5.9 Hz, 1H), 4.46 (d, J=5.9 Hz, 2H).

Example 179

1-[6-(3-Carbamoyl-benzylamino)-4-oxo-3,4-dihydro-quinazolin-2-yl]-1H-pyrazole-4-carboxylic acid

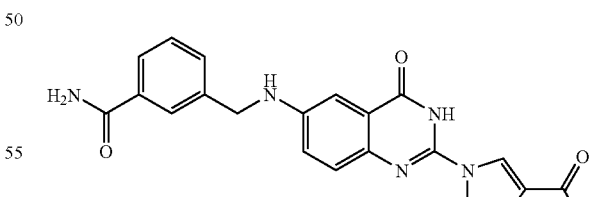

The titled compound was prepared in a manner analogous to Example 171, substituting 3-cyanobenzaldehyde for benzaldehyde in step A. Step C yielded a mixture of 1-[6-(3-cyano-benzylamino)-4-oxo-3,4-dihydro-quinazolin-2-yl]-1H-pyrazole-4-carboxylic acid, the titled compound, and 1-[6-amino-4-oxo-3,4-dihydro-quinazolin-2-yl]-1H-pyrazole-4-carboxylic acid, which was separated by reverse-phase HPLC.

Data for 1-[6-(3-carbamoyl-benzylamino)-4-oxo-3,4-dihydro-quinazolin-2-yl]-1H-pyrazole-4-carboxylic acid: MS (ESI/Cl): mass calcd. for $C_{20}H_{16}N_6O_4$, 404.1; m/z found, 405.1 [M+H]$^+$. $^1$H NMR (600 MHz, DMSO-d$_6$): 12.92 (s, 1H), 12.45 (s, 1H), 8.85 (d, J=0.6 Hz, 1H), 8.18 (s, 1H), 7.96 (s, 1H), 7.92 (s, 1H), 7.75 (d, J=7.8 Hz, 1H), 7.53 (d, J=7.6 Hz, 1H), 7.46 (d, J=8.8 Hz, 1H), 7.42 (t, J=7.7 Hz, 1H), 7.36 (s, 1H), 7.28-7.19 (m, 1H), 7.08 (d, J=2.4 Hz, 1H), 6.96 (t, J=5.8 Hz, 1H), 4.42 (d, J=5.7 Hz, 2H).

Example 180

1-[6-amino-4-oxo-3,4-dihydro-quinazolin-2-yl]-1H-pyrazole-4-carboxylic acid

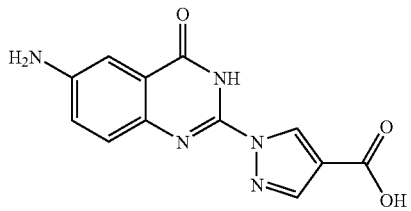

The titled compound was prepared in a manner analogous to Example 171, substituting 3-cyanobenzaldehyde for benzaldehyde in step A. Step C yielded a mixture of 1-[6-(3-cyano-benzylamino)-4-oxo-3,4-dihydro-quinazolin-2-yl]-1H-pyrazole-4-carboxylic acid, 1-[6-(3-carbamoyl-benzylamino)-4-oxo-3,4-dihydro-quinazolin-2-yl]-1H-pyrazole-4-carboxylic acid, and the titled compound. The mixture was separated by reverse-phase HPLC; the titled compound was recovered as the trifluoroacetate salt.

Data for 1-[6-amino-4-oxo-3,4-dihydro-quinazolin-2-yl]-1H-pyrazole-4-carboxylic acid, trifluoroacetate salt: MS (ESI/Cl): mass calcd. for $C_{12}H_9N_5O_3$, 271.1; m/z found, 272.1 [M+H]$^+$. $^1$H NMR (600 MHz, DMSO-d$_6$): 12.93 (s, 1H), 12.40 (s, 1H), 8.85 (d, J=0.6 Hz, 1H), 8.20 (s, 1H), 7.43 (d, J=8.7 Hz, 1H), 7.24 (d, J=2.5 Hz, 1H), 7.12 (dd, J=8.7, 2.6 Hz, 1H), 5.84 (s, 3H).

Example 181

1-[6-(2,6-Dichloro-benzylamino)-4-oxo-3,4-dihydro-quinazolin-2-yl]-1H-pyrazole-4-carboxylic acid

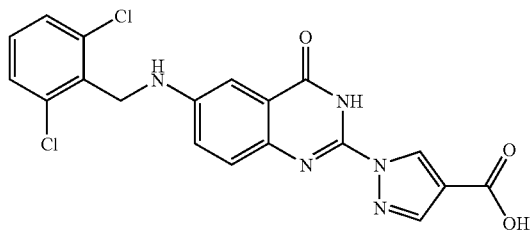

The titled compound was prepared in a manner analogous to Example 171, substituting 2,6-dichlorobenzaldehyde for benzaldehyde in step A. MS (ESI/Cl): mass calcd. for $C_{20}H_{13}Cl_2N_5O_3$, 429.0; m/z found, 430.2.1 [M+H]$^+$. $^1$H NMR DMSO-d$_6$): 12.93 (s, 1H), 12.50 (s, 1H), 8.87 (d, J=0.6 Hz, 1H), 8.20 (s, 1H), 7.55 (d, J=8.1 Hz, 2H), 7.48 (d, J=8.6 Hz, 1H), 7.41 (dd, J=8.5, 7.8 Hz, 1H), 7.28 (d, J=8.6 Hz, 1H), 7.26 (s, 1H), 6.50 (s, 1H), 4.49 (d, J=4.5 Hz, 2H).

Example 182

1-[6-(3-Chloro-benzylamino)-4-oxo-3,4-dihydro-quinazolin-2-yl]-1H-pyrazole-4-carboxylic acid

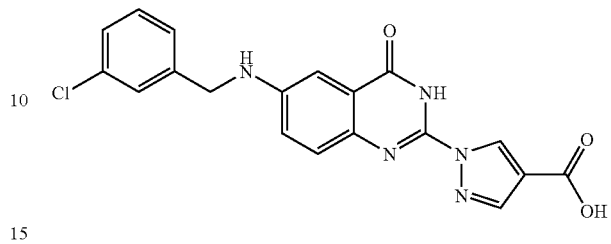

The titled compound was prepared in a manner analogous to Example 171, substituting 3-chlorobenzaldehyde for benzaldehyde in step A. MS (ESI/Cl): mass calcd. for $C_{19}H_{14}ClN_5O_3$, 395.1; m/z found, 396.2 [M+H]$^+$. $^1$H NMR (400 MHz, DMSO-d$_6$): 8.86 (d, J=0.6 Hz, 1H), 8.20 (d, J=0.5 Hz, 1H), 7.48 (d, J=8.8 Hz, 1H), 7.44 (s, 1H), 7.42-7.29 (m, 3H), 7.24 (dd, J=8.8, 2.8 Hz, 1H), 7.09 (d, J=2.7 Hz, 1H), 4.41 (s, 2H).

Example 183

1-[6-(4-methyl-benzylamino)-4-oxo-3,4-dihydro-quinazolin-2-yl]-1H-pyrazole-4-carboxylic acid

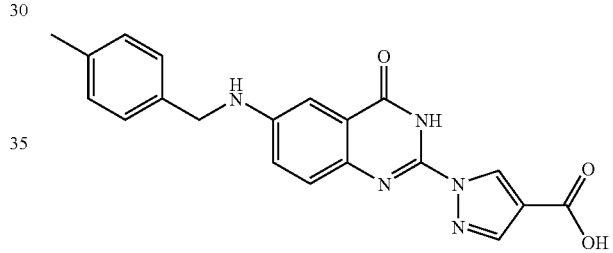

The titled compound was prepared in a manner analogous to Example 171, substituting 4-methylbenzaldehyde for benzaldehyde in step A. MS (ESI/Cl): mass calcd. for $C_{20}H_{17}N_5O_3$, 375.1; m/z found, 376.3 [M+H]$^+$. $^1$H NMR (400 MHz, DMSO-d$_6$) 12.90 (s, 1H), 12.46 (s, 1H), 8.85 (s, 1H), 8.19 (s, 1H), 7.45 (d, J=8.7 Hz, 1H), 7.27 (d, J=8.0 Hz, 2H), 7.21 (dd, J=8.9, 2.7 Hz, 1H), 7.15 (d, J=7.9 Hz, 2H), 7.07 (d, J=2.6 Hz, 1H), 6.87 (t, J=4.8 Hz, 1H), 4.32 (d, J=5.5 Hz, 2H), 2.27 (s, 3H).

Example 184

1-(4-Oxo-7-phenyl-3,4-dihydro-quinazolin-2-yl)-1H-pyrazole-4-carboxylic acid

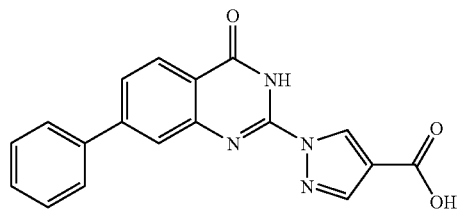 [SMILES: O=C(O)c1cnn(-c2nc3cc(-c4ccccc4)ccc3c(=O)[nH]2)c1]

Step A: Preparation of 1-(7-iodo-4-oxo-3,4-dihydro-quinazolin-2-yl)-1H-pyrazole-4-carboxylic acid ethyl ester.

The titled compound was prepared in a manner analogous to Example 27, steps C-D using 3-iodoaniline in step C. MS (ESI): mass calcd. for $C_{14}H_{11}IN_4O_3$, 410.0; m/z found, 411.0 [M+H]+. 1H NMR (600 MHz, DMSO-d6): 13.04 (s, 1H), 9.00 (d, J=0.6 Hz, 1H), 8.34 (s, 1H), 8.11 (s, 1H), 7.85 (s, 2H), 4.30 (q, J=7.1 Hz, 2H), 1.32 (t, J=7.1 Hz, 3H).

Step B: Preparation of 1-[7-iodo-3-(2-methoxy-ethoxymethyl)-4-oxo-3,4-dihydro-quinazolin-2-yl]-1H-pyrazole-4-carboxylic acid ethyl ester. To a mixture of 1-(7-iodo-4-oxo-3,4-dihydro-quinazolin-2-yl)-1H-pyrazole-4-carboxylic acid ethyl ester (1.65 g, 4.02 mmol) and THF (20 mL) was added DIPEA (2.10 mL, 12.1 mmol) followed by 1-chloromethoxy-2-methoxy-ethane (1.01 mL, 8.85 mmol) at 23° C. After stirring for 18 h, the reaction mixture was concentrated under reduced pressure. The residue was used in subsequent reactions without further purification (1.89 g, 94%). MS (ESI): mass calcd. for $C^{18}H_{19}IN_4O_5$, 498.0; m/z found, 499.0 [M+H]+. 1H NMR (600 MHz, DMSO-d6): 8.85 (d, J=0.6 Hz, 1H), 8.30 (d, J=0.6 Hz, 1H), 8.17 (d, J=1.4 Hz, 1H), 8.00 (dd, J=8.3, 1.6 Hz, 1H), 7.95 (d, J=8.3 Hz, 1H), 5.65 (s, 2H), 4.30 (q, J=7.1 Hz, 2H), 3.50-3.48 (m, 2H), 3.26-3.23 (m, 2H), 3.05 (s, 3H), 1.31 (t, J=7.1 Hz, 3H).

Step C: Preparation of 1-[3-(2-methoxy-ethoxymethyl)-4-oxo-7-phenyl-3,4-dihydro-quinazolin-2-yl]-1H-pyrazole-4-carboxylic acid ethyl ester. A mixture of potassium carbonate (210 mg 1.52 mmol), phenylboronic acid (156 mg, 1.28 mmol), 1-[7-iodo-3-(2-methoxy-ethoxymethyl)-4-oxo-3,4-dihydro-quinazolin-2-yl]-1H-pyrazole-4-carboxylic acid ethyl ester (250 mg, 0.502 mmol), and THF (4.4 ml) was degassed with nitrogen for 10 min in a sealable tube. The dichloromethane adduct of 1,1'-bis(diphenylphosphino)ferrocene]dichloro palladium (48.9 mg, 0.0610 mmol) was added to the reaction mixture and the pressure tube was sealed. The reaction mixture was stirred at 80° C. for 18 h. The reaction mixture was cooled to 23° C., diluted with DCM (15 mL), and filtered. The filtrate was concentrated. The residue was purified by FCC (5-45% EtOAc/hexanes) to yield the titled compound (192 mg, 85%). MS (ESI): mass calcd. for $C_{24}H_{24}N_4O_5$, 448.2; m/z found, 449.2 [M+H]+. 1H NMR (400 MHz, DMSO-d6): 8.88 (d, J=0.6 Hz, 1H), 8.30 (d, J=0.6 Hz, 1H), 8.04 (d, J=1.5 Hz, 1H), 8.00 (dd, J=8.3, 1.8 Hz, 1H), 7.88-7.84 (m, 2H), 7.78 (dd, J=8.0, 1.5 Hz, 1H), 7.58-7.52 (m, 2H), 7.51-7.46 (m, 1H), 5.67 (s, 2H), 4.30 (q, J=7.1 Hz, 2H), 3.54-3.50 (m, 2H), 3.29-3.25 (m, 2H), 3.08 (s, 3H), 1.32 (t, J=7.1 Hz, 3H).

Step D: Preparation of 1-(4-oxo-7-phenyl-3,4-dihydro-quinazolin-2-yl)-1H-pyrazole-4-carboxylic acid ethyl ester. A solution of 4M HCl and dioxane (3.00 mL, 12.0 mmol) was added to 1-[3-(2-methoxy-ethoxymethyl)-4-oxo-7-phenyl-3,4-dihydro-quinazolin-2-yl]-1H-pyrazole-4-carboxylic acid ethyl ester (90.0 mg, 0.201 mmol). The reaction mixture was stirred at 23° C. After 18 h, the reaction mixture was concentrated under reduced pressure. Et2O was added (5 mL) and the resulting precipitate was collected by filtration and washed well with Et2O to afford the titled compound (38.0 mg, 53%). MS (ESI): mass calcd. for $C_{20}H_{16}N_4O_3$, 360.1; m/z found, 361.1 [M+H]+. 1H NMR (600 MHz, DMSO-d6): 12.93 (s, 1H), 9.04 (s, 1H), 8.34 (s, 1H), 8.20 (d, J=8.2 Hz, 1H), 7.98 (s, 1H), 7.84 (dd, J=10.5, 4.2 Hz, 3H), 7.55 (t, J=7.6 Hz, 2H), 7.49-7.46 (m, 1H), 4.31 (q, J=7.1 Hz, 2H), 1.33 (t, J=7.1 Hz, 3H).

Step E: Preparation of 1-(4-oxo-7-phenyl-3,4-dihydro-quinazolin-2-yl)-1H-pyrazole-4-carboxylic acid. Potassium hydroxide (37.4 mg, 0.666 mmol) was added to a mixture of 1-(4-oxo-7-phenyl-3,4-dihydro-quinazolin-2-yl)-1H-pyrazole-4-carboxylic acid ethyl ester (48.0 mg, 0.133 mmol), water (0.8 mL) and THF (0.8 mL). The mixture was stirred for 16 h at 23° C. The reaction mixture was concentrated under reduced pressure to remove the THF and the aqueous residue was acidified to pH 2 with 1M aq. HCl. The resulting precipitate was collected by filtration to provide the titled compound (42.0 mg, 85%). MS (ESI): mass calcd. for $C_{18}H_{12}N_4O_3$, 332.1; m/z found, 333.1 [M+H]+. 1H NMR (400 MHz, DMSO-d6): 8.45 (d, J=0.8 Hz, 1H), 7.99 (d, J=8.2 Hz, 1H), 7.78-7.72 (m, 2H), 7.62 (d, J=1.5 Hz, 1H), 7.55 (d, J=0.8 Hz, 1H), 7.49 (t, J=7.6 Hz, 2H), 7.41-7.36 (m, 2H).

Example 185

1-[7-(2-Chloro-phenyl)-4-oxo-3,4-dihydro-quinazolin-2-yl]-1H-pyrazole-4-carboxylic acid

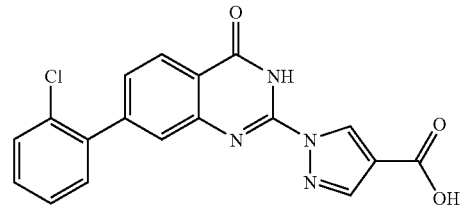

The titled compound was prepared in a manner analogous to Example 184, steps C-E using 1-[7-iodo-3-(2-methoxy-ethoxymethyl)-4-oxo-3,4-dihydro-quinazolin-2-yl]-1H-pyrazole-4-carboxylic acid ethyl ester (Intermediate from Example 184, product from step B) and 2-chlorophenylboronic acid in step C. MS (ESI): mass calcd. for $C_{18}H_{11}ClN_4O_3$, 366.1; m/z found, 367.0 [M+H]+. 1H NMR (500 MHz, DMSO-d6): 13.02 (br s, 1H), 12.92 (br s, 1H), 8.97 (s, 1H), 8.28 (s, 1H), 8.22 (d, J=6.6 Hz, 1H), 7.71 (s, 1H), 7.67-7.62 (m, 1H), 7.58 (d, J=7.3 Hz, 1H), 7.55-7.47 (m, 3H).

Example 186

1-[7-(3-Chloro-phenyl)-4-oxo-3,4-dihydro-quinazolin-2-yl]-1H-pyrazole-4-carboxylic acid

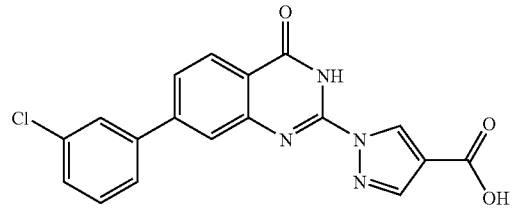 [SMILES: O=C(O)c1cnn(-c2nc3cc(-c4cccc(Cl)c4)ccc3c(=O)[nH]2)c1]

The titled compound was prepared in a manner analogous to Example 184, steps C-E using 1-[7-iodo-3-(2-methoxy-ethoxymethyl)-4-oxo-3,4-dihydro-quinazolin-2-yl]-1H-pyrazole-4-carboxylic acid ethyl ester (Intermediate from Example 184, product from step B) and 3-chlorophenylboronic acid in step C. MS (ESI): mass calcd. for $C_{18}H_{11}ClN_4O_3$, 366.1; m/z found, 367.0 [M+H]+. 1H NMR (400 MHz, DMSO-d6): 13.04 (br s, 1H), 12.94 (br s, 1H), 8.97

(s, 1H), 8.28 (s, 1H), 8.21 (d, J=8.0 Hz, 1H), 8.00 (s, 1H), 7.91 (s, 1H), 7.87 (d, J=8.4 Hz, 1H), 7.82 (d, J=6.7 Hz, 1H), 7.60-7.52 (m, 2H).

Example 187

1-[7-(4-Chloro-phenyl)-4-oxo-3,4-dihydro-quinazolin-2-yl]-1H-pyrazole-4-carboxylic acid

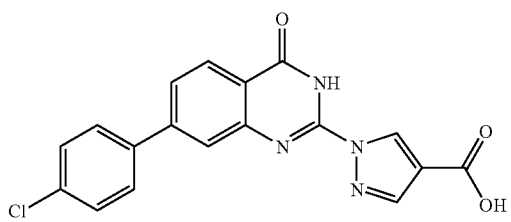 [SMILES: O=C(O)c1cnn(-c2nc3cc(-c4ccc(Cl)cc4)ccc3c(=O)[nH]2)c1]

The titled compound was prepared in a manner analogous to Example 184, steps C-E using 1-[7-iodo-3-(2-methoxy-ethoxymethyl)-4-oxo-3,4-dihydro-quinazolin-2-yl]-1H-pyrazole-4-carboxylic acid ethyl ester (Intermediate from Example 184, product from step B) and 4-chlorophenylboronic acid in step C. MS (ESI): mass calcd. for $C_{18}H_{11}ClN_4O_3$, 366.1; m/z found, 367.0 [M+H]$^+$. $^1$H NMR (400 MHz, DMSO-d$_6$): 12.99 (br s, 2H), 8.97 (d, J=0.6 Hz, 1H), 8.28 (s, 1H), 8.20 (d, J=8.3 Hz, 1H), 7.97 (s, 1H), 7.87 (d, J=8.5 Hz, 2H), 7.83 (dd, J=8.3, 1.7 Hz, 1H), 7.63-7.58 (m, 2H).

Example 188

1-(4-Oxo-7-o-tolyl-3,4-dihydro-quinazolin-2-yl)-1H-pyrazole-4-carboxylic acid

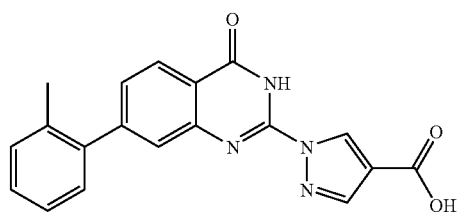 [SMILES: Cc1ccccc1-c1ccc2c(=O)[nH]c(-n3cc(C(=O)O)cn3)nc2c1]

The titled compound was prepared in a manner analogous to Example 184, steps C-E using 1-[7-iodo-3-(2-methoxy-ethoxymethyl)-4-oxo-3,4-dihydro-quinazolin-2-yl]-1H-pyrazole-4-carboxylic acid ethyl ester (Intermediate from Example 184, product from step B) and 2-methylphenylboronic acid in step C. MS (ESI): mass calcd. for $C_{19}H_{14}N_4O_3$, 346.1; m/z found, 347.1 [M+H]$^+$. $^1$H NMR (600 MHz, DMSO-d$_6$): 12.82 (br s, 1H), 8.92 (s, 1H), 8.10 (s, 1H), 8.08 (d, J=8.1 Hz, 1H), 7.47 (s, 1H), 7.36-7.27 (m, 5H), 2.28 (s, 3H).

Example 189

1-(4-Oxo-7-m-tolyl-3,4-dihydro-quinazolin-2-yl)-1H-pyrazole-4-carboxylic acid

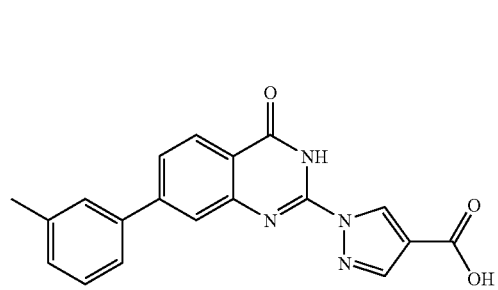 [SMILES: Cc1cccc(-c2ccc3c(=O)[nH]c(-n4cc(C(=O)O)cn4)nc3c2)c1]

The titled compound was prepared in a manner analogous to Example 184, steps C-E using 1-[7-iodo-3-(2-methoxy-ethoxymethyl)-4-oxo-3,4-dihydro-quinazolin-2-yl]-1H-pyrazole-4-carboxylic acid ethyl ester (Intermediate from Example 184, product from step B) and 3-methylphenylboronic acid in step C. MS (ESI): mass calcd. for $C_{19}H_{14}N_4O_3$, 346.1; m/z found, 347.1 [M+H]$^+$. $^1$H NMR (600 MHz, DMSO-d$_6$): 13.04 (s, 1H), 12.87 (s, 1H), 8.98 (s, 1H), 8.28 (s, 1H), 8.20 (d, J=8.2 Hz, 1H), 7.94 (s, 1H), 7.83 (d, J=8.1 Hz, 1H), 7.67 (s, 1H), 7.62 (d, J=7.0 Hz, 1H), 7.43 (t, J=7.6 Hz, 1H), 7.29 (d, J=7.5 Hz, 1H), 2.42 (s, 3H).

Example 190

1-(4-Oxo-6-m-tolyl-3,4-dihydro-quinazolin-2-yl)-1H-pyrazole-4-carboxylic acid

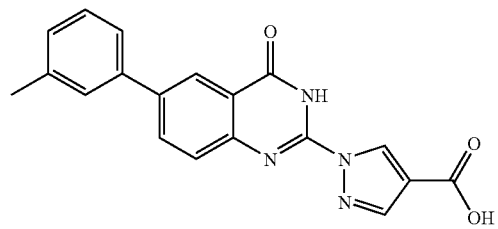 [SMILES: Cc1cccc(-c2ccc3nc(-n4cc(C(=O)O)cn4)[nH]c(=O)c3c2)c1]

The titled compound was prepared in a manner analogous to Example 69, steps C-E, using 1-[6-iodo-4-oxo-3-(2-trimethylsilanyl-ethoxymethyl)-3,4-dihydro-quinazolin-2-yl]-1H-pyrazole-4-carboxylic acid ethyl ester (Example 69 product from step B) and 3-methylphenylboronic acid in step C. MS (ESI): mass calcd. for $C_{19}H_{14}N_4O_3$, 346.1; m/z found, 347.1 [M+H]$^+$. $^1$H NMR (500 MHz, DMSO-d$_6$): 13.02 (s, 1H), 12.91 (s, 1H), 8.98 (s, 1H), 8.34 (s, 1H), 8.27 (s, 1H), 8.17 (d, J=7.9 Hz, 1H), 7.78 (d, J=6.3 Hz, 1H), 7.62 (s, 1H), 7.58 (d, J=7.3 Hz, 1H), 7.41 (t, J=7.6 Hz, 1H), 7.24 (d, J=7.0 Hz, 1H), 2.42 (s, 3H).

Example 191

1-(4-Oxo-6-p-tolyl-3,4-dihydro-quinazolin-2-yl)-1H-pyrazole-4-carboxylic acid

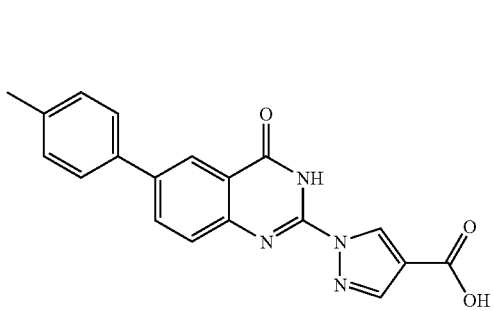 [SMILES: Cc1ccc(-c2ccc3nc(-n4cc(C(=O)O)cn4)[nH]c(=O)c3c2)cc1]

The titled compound was prepared in a manner analogous to Example 69, steps C-E, using 1-[6-iodo-4-oxo-3-(2-trimethylsilanyl-ethoxymethyl)-3,4-dihydro-quinazolin-2-yl]-1H-pyrazole-4-carboxylic acid ethyl ester (Example 69 product from step B) and 4-methylphenylboronic acid in step C. MS (ESI): mass calcd. for $C_{19}H_{14}N_4O_3$, 346.1; m/z found, 347.1 [M+H]$^+$. $^1$H NMR (600 MHz, DMSO-$d_6$): 13.03 (s, 1H), 12.92 (s, 1H), 8.98 (s, 1H), 8.33 (s, 1H), 8.27 (s, 1H), 8.16 (d, J=7.9 Hz, 1H), 7.77 (s, 1H), 7.69 (d, J=8.0 Hz, 2H), 7.33 (d, J=7.9 Hz, 2H), 2.37 (s, 3H).

Example 192

1-[6-(2-Chloro-phenyl)-4-oxo-3,4-dihydro-quinazolin-2-yl]-1H-pyrazole-4-carboxylic acid

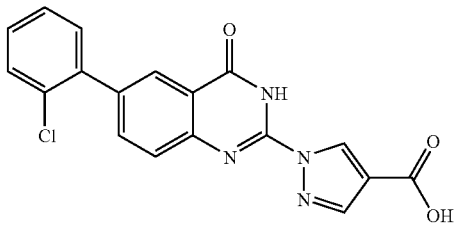 [SMILES: O=C(O)c1cnn(-c2nc3ccc(-c4ccccc4Cl)cc3c(=O)[nH]2)c1]

The titled compound was prepared in a manner analogous to Example 69, steps C-E, using 1-[6-iodo-4-oxo-3-(2-trimethylsilanyl-ethoxymethyl)-3,4-dihydro-quinazolin-2-yl]-1H-pyrazole-4-carboxylic acid ethyl ester (Example 69 product from step B) and 2-chlorophenylboronic acid in step C. MS (ESI): mass calcd. for $C_{18}H_{11}ClN_4O_3$, 366.1; m/z found, 367.0 [M+H]$^+$. $^1$H NMR (600 MHz, DMSO-$d_6$): 12.99 (s, 2H), 8.98 (d, J=0.6 Hz, 1H), 8.27 (s, 1H), 8.13 (d, J=2.1 Hz, 1H), 7.91 (dd, J=8.4, 2.1 Hz, 1H), 7.78 (d, J=8.4 Hz, 1H), 7.64-7.61 (m, 1H), 7.55-7.52 (m, 1H), 7.47 (pd, J=7.4, 1.8 Hz, 2H).

Example 193

1-[6-(3-Chloro-phenyl)-4-oxo-3,4-dihydro-quinazolin-2-yl]-1H-pyrazole-4-carboxylic acid

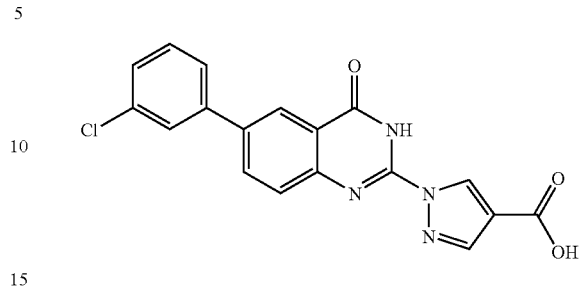

The titled compound was prepared in a manner analogous to Example 69, steps C-E, using 1-[6-iodo-4-oxo-3-(2-trimethylsilanyl-ethoxymethyl)-3,4-dihydro-quinazolin-2-yl]-1H-pyrazole-4-carboxylic acid ethyl ester (Example 69 product from step B) and 3-chlorophenylboronic acid in step C. MS (ESI): mass calcd. for $C_{18}H_{11}ClN_4O_3$, 366.1; m/z found, 367.0 [M+H]$^+$. $^1$H NMR (600 MHz, DMSO-$d_6$): 13.00 (br s, 2H), 8.98 (s, 1H), 8.36 (d, J=2.2 Hz, 1H), 8.28 (s, 1H), 8.20 (dd, J=8.5, 2.3 Hz, 1H), 7.85 (t, J=1.9 Hz, 1H), 7.81-7.75 (m, 2H), 7.55 (t, J=7.9 Hz, 1H), 7.49 (ddd, J=8.0, 2.0, 1.0 Hz, 1H).

Example 194

1-[6-(4-Chloro-phenyl)-4-oxo-3,4-dihydro-quinazolin-2-yl]-1H-pyrazole-4-carboxylic acid

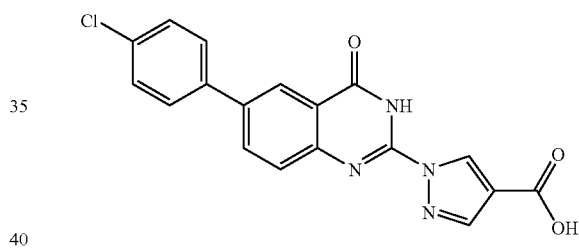

The titled compound was prepared in a manner analogous to Example 69, steps C-E, using 1-[6-iodo-4-oxo-3-(2-trimethylsilanyl-ethoxymethyl)-3,4-dihydro-quinazolin-2-yl]-1H-pyrazole-4-carboxylic acid ethyl ester (Example 69 product from step B) and 4-chlorophenylboronic acid in step C. MS (ESI): mass calcd. for $C_{18}H_{11}ClN_4O_3$, 366.1; m/z found, 367.0 [M+H]$^+$. $^1$H NMR (600 MHz, DMSO-$d_6$): 13.02 (s, 1H), 12.95 (s, 1H), 8.99 (s, 1H), 8.28 (s, 2H), 8.05 (d, J=8.5 Hz, 1H), 7.81 (s, 1H), 7.67 (t, J=7.9 Hz, 1H), 7.49 (tdd, J=7.1, 5.1, 1.7 Hz, 1H), 7.40-7.34 (m, 2H).

Example 195

1-[6-(2-Fluoro-phenyl)-4-oxo-3,4-dihydro-quinazolin-2-yl]-1H-pyrazole-4-carboxylic acid

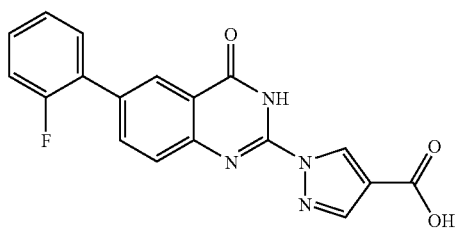 [SMILES: O=C(O)c1cnn(-c2nc3ccc(-c4ccccc4F)cc3c(=O)[nH]2)c1]

The titled compound was prepared in a manner analogous to Example 69, steps C-E, using 1-[6-iodo-4-oxo-3-(2-trimethylsilanyl-ethoxymethyl)-3,4-dihydro-quinazolin-2-yl]-1H-pyrazole-4-carboxylic acid ethyl ester (Example 69 product from step B) and 2-fluorophenylboronic acid in step C. MS (ESI): mass calcd. for $C_{18}H_{11}FN_4O_3$, 350.1; m/z found, 351.1 [M+H]$^+$. $^1$H NMR (600 MHz, DMSO-d$_6$): 13.02 (br s, 1H), 12.95 (br s, 1H), 8.99 (s, 1H), 8.28 (s, 2H), 8.05 (d, J=8.5 Hz, 1H), 7.81 (s, 1H), 7.67 (t, J=7.9, 1H), 7.49 (tdd, J=7.1, 5.1, 1.7, 1H), 7.40-7.34 (m, 2H).

Example 196

1-[6-(3-Fluoro-phenyl)-4-oxo-3,4-dihydro-quinazolin-2-yl]-1H-pyrazole-4-carboxylic acid

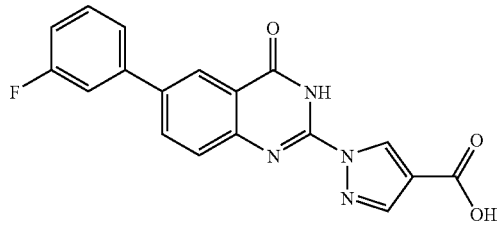 [SMILES: O=C(O)c1cnn(-c2nc3ccc(-c4cccc(F)c4)cc3c(=O)[nH]2)c1]

The titled compound was prepared in a manner analogous to Example 69, steps C-E, using 1-[6-iodo-4-oxo-3-(2-trimethylsilanyl-ethoxymethyl)-3,4-dihydro-quinazolin-2-yl]-1H-pyrazole-4-carboxylic acid ethyl ester (Example 69 product from step B) and 3-fluorophenylboronic acid in step C. MS (ESI): mass calcd. for $C_{18}H_{11}FN_4O_3$, 350.1; m/z found, 351.1 [M+H]$^+$. $^1$H NMR (600 MHz, DMSO-d$_6$): 13.01 (br s, 2H), 8.98 (s, 1H), 8.38 (d, J=2.0 Hz, 1H), 8.29 (s, 1H), 8.22-8.20 (m, 1H), 7.80 (d, J=8.0 Hz, 1H), 7.68-7.64 (m, 2H), 7.58-7.54 (m, 1H), 7.28-7.24 (m, 1H).

Example 197

1-[6-(4-Fluoro-phenyl)-4-oxo-3,4-dihydro-quinazolin-2-yl]-1H-pyrazole-4-carboxylic acid

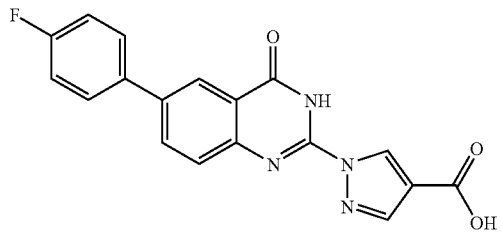 [SMILES: O=C(O)c1cnn(-c2nc3ccc(-c4ccc(F)cc4)cc3c(=O)[nH]2)c1]

The titled compound was prepared in a manner analogous to Example 69, steps C-E, using 1-[6-iodo-4-oxo-3-(2-trimethylsilanyl-ethoxymethyl)-3,4-dihydro-quinazolin-2-yl]-1H-pyrazole-4-carboxylic acid ethyl ester (Example 69 product from step B) and 4-fluorophenylboronic acid in step C. MS (ESI): mass calcd. for $C_{18}H_{11}FN_4O_3$, 350.1; m/z found, 351.1 [M+H]$^+$. $^1$H NMR (600 MHz, DMSO-d$_6$): 13.01 (br s, 1H), 12.92 (br s, 1H), 8.98 (s, 1H), 8.32 (s, 1H), 8.28 (s, 1H), 8.16 (dd, J=8.5, 2.2 Hz, 1H), 7.88-7.82 (m, 2H), 7.79 (s, 1H), 7.37-7.32 (m, 2H).

Example 198

1-[6-(2-Methoxy-phenyl)-4-oxo-3,4-dihydro-quinazolin-2-yl]-1H-pyrazole-4-carboxylic acid

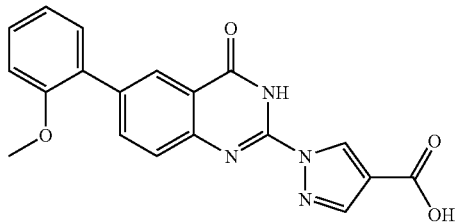 [SMILES: COc1ccccc1-c1ccc2nc(-n3cc(C(=O)O)cn3)[nH]c(=O)c2c1]

The titled compound was prepared in a manner analogous to Example 69, steps C-E, using 1-[6-iodo-4-oxo-3-(2-trimethylsilanyl-ethoxymethyl)-3,4-dihydro-quinazolin-2-yl]-1H-pyrazole-4-carboxylic acid ethyl ester (Example 69 product from step B) and 2-methoxyphenylboronic acid in step C. MS (ESI): mass calcd. for $C_{19}H_{14}N_4O_4$, 362.1; m/z found, 363.1 [M+H]$^+$. $^1$H NMR (600 MHz, DMSO-d$_6$): 13.00 (br s, 1H), 12.84 (br s, 1H), 8.98 (s, 1H), 8.28 (s, 1H), 8.21 (d, J=1.7 Hz, 1H), 7.97 (dd, J=8.4, 2.1 Hz, 1H), 7.74 (d, J=7.0 Hz, 1H), 7.43-7.39 (m, 2H), 7.19-7.16 (m, 1H), 7.09 (td, J=7.5, 1.0 Hz, 1H), 3.81 (s, 3H).

Example 199

1-[6-(3-Methoxy-phenyl)-4-oxo-3,4-dihydro-quinazolin-2-yl]-1H-pyrazole-4-carboxylic acid

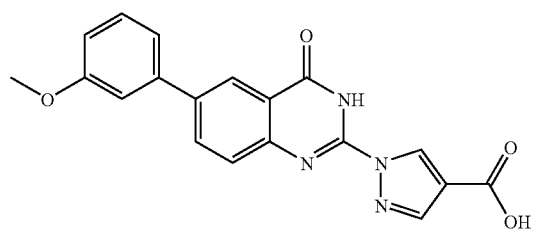 [SMILES: COc1cccc(-c2ccc3nc(-n4cc(C(=O)O)cn4)[nH]c(=O)c3c2)c1]

The titled compound was prepared in a manner analogous to Example 69, steps C-E, using 1-[6-iodo-4-oxo-3-(2-trimethylsilanyl-ethoxymethyl)-3,4-dihydro-quinazolin-2-yl]-1H-pyrazole-4-carboxylic acid ethyl ester (Example 69 product from step B) and 3-methoxyphenylboronic acid in step C. MS (ESI): mass calcd. for $C_{19}H_{14}N_4O_4$, 362.1; m/z found, 363.1 [M+H]$^+$. $^1$H NMR (600 MHz, DMSO-d$_6$): 13.01 (br s, 1H), 12.91 (br s, 1H), 8.98 (s, 1H), 8.34 (s, 1H), 8.28 (s, 1H), 8.18 (d, J=6.7 Hz, 1H), 7.78 (s, 1H), 7.44 (t, J=7.9 Hz, 1H), 7.35 (d, J=7.8 Hz, 1H), 7.29 (s, 1H), 7.00 (dd, J=8.2, 1.8 Hz, 1H), 3.86 (s, 3H).

Example 200

1-[6-(4-Methoxy-phenyl)-4-oxo-3,4-dihydro-quinazolin-2-yl]-1H-pyrazole-4-carboxylic acid

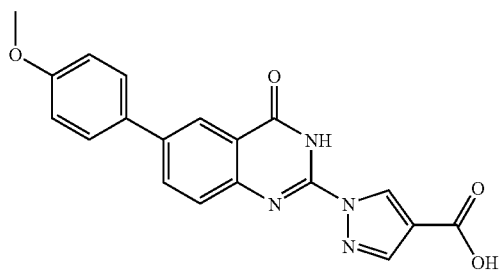 [SMILES: COc1ccc(-c2ccc3nc(-n4cc(C(=O)O)cn4)[nH]c(=O)c3c2)cc1]

The titled compound was prepared in a manner analogous to Example 69, steps C-E, using 1-[6-iodo-4-oxo-3-(2-trimethylsilanyl-ethoxymethyl)-3,4-dihydro-quinazolin-2-yl]-1H-pyrazole-4-carboxylic acid ethyl ester (Example 69 product from step B) and 4-methoxyphenylboronic acid in step C. MS (ESI): mass calcd. for $C_{19}H_{14}N_4O_4$, 362.1; m/z found, 363.1 [M+H]+. 1H NMR (600 MHz, DMSO-d6): 12.99 (br s, 1H), 12.88 (br s, 1H), 8.97 (s, 1H), 8.28 (d, J=13.9 Hz, 2H), 8.13 (d, J=8.4 Hz, 1H), 7.78-7.72 (m, 3H), 7.09-7.06 (m, 2H), 3.82 (s, 3H).

Example 201

1-[4-Oxo-6-(2-trifluoromethyl-phenyl)-3,4-dihydro-quinazolin-2-yl]-1H-pyrazole-4-carboxylic acid

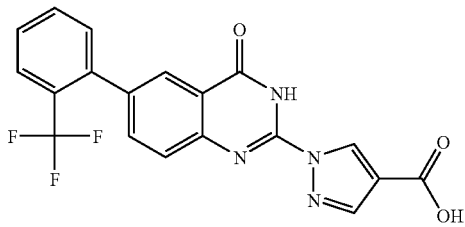 [SMILES: O=C(O)c1cnn(-c2nc3ccc(-c4ccccc4C(F)(F)F)cc3c(=O)[nH]2)c1]

The titled compound was prepared in a manner analogous to Example 69, steps C-E, using 1-[6-iodo-4-oxo-3-(2-trimethylsilanyl-ethoxymethyl)-3,4-dihydro-quinazolin-2-yl]-1H-pyrazole-4-carboxylic acid ethyl ester (Example 69 product from step B) and 2-trifluoromethylphenylboronic acid in step C. MS (ESI): mass calcd. for $C_{19}H_{11}F_3N_4O_3$, 400.1; m/z found, 401.1 [M+H]+. 1H NMR (600 MHz, DMSO-d6): 13.01 (br s, 2H), 8.99 (s, 1H), 8.42 (d, J=1.6 Hz, 1H), 8.31-8.25 (m, 2H), 8.13 (d, J=7.6 Hz, 1H), 8.10 (s, 1H), 7.83 (s, 1H), 7.77 (dt, J=15.3, 7.8 Hz, 2H).

Example 202

1-[4-Oxo-6-(2-trifluoromethoxy-phenyl)-3,4-dihydro-quinazolin-2-yl]-1H-pyrazole-4-carboxylic acid

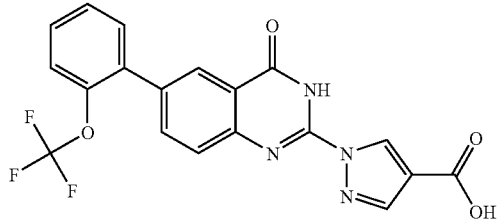 [SMILES: O=C(O)c1cnn(-c2nc3ccc(-c4ccccc4OC(F)(F)F)cc3c(=O)[nH]2)c1]

The titled compound was prepared in a manner analogous to Example 69, steps C-E, using 1-[6-iodo-4-oxo-3-(2-trimethylsilanyl-ethoxymethyl)-3,4-dihydro-quinazolin-2-yl]-1H-pyrazole-4-carboxylic acid ethyl ester (Example 69 product from step B) and 2-trifluoromethoxyphenylboronic acid in step C. MS (ESI): mass calcd. for $C_{19}H_{11}F_3N_4O_4$, 416.1; m/z found, 417.1 [M+H]+. 1H NMR (600 MHz, DMSO-d6): 13.02 (s, 1H), 12.95 (s, 1H), 8.99 (s, 1H), 8.28 (s, 1H), 8.20 (s, 1H), 7.96 (d, J=7.5 Hz, 1H), 7.69-7.66 (m, 1H), 7.61-7.53 (m, 3H).

Example 203

1-[6-(2-Ethyl-phenyl)-4-oxo-3,4-dihydro-quinazolin-2-yl]-1H-pyrazole-4-carboxylic acid

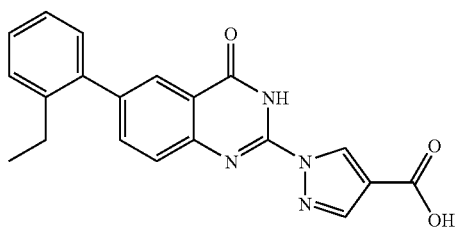 [SMILES: CCc1ccccc1-c1ccc2nc(-n3cc(C(=O)O)cn3)[nH]c(=O)c2c1]

The titled compound was prepared in a manner analogous to Example 69, steps C-E, using 1-[6-iodo-4-oxo-3-(2-trimethylsilanyl-ethoxymethyl)-3,4-dihydro-quinazolin-2-yl]-1H-pyrazole-4-carboxylic acid ethyl ester (Example 69 product from step B) and 2-ethylphenylboronic acid in step C. MS (ESI): mass calcd. for $C_{20}H_{16}N_4O_3$, 360.1; m/z found, 361.1 [M+H]+. 1H NMR (600 MHz, DMSO-d6): 13.01 (br s, 1H), 12.91 (br s, 1H), 8.99 (s, 1H), 8.28 (s, 1H), 7.99 (s, 1H), 7.81 (dd, J=8.2, 1.8 Hz, 1H), 7.77 (s, 1H), 7.40-7.36 (m, 2H), 7.32-7.29 (m, 1H), 7.25 (d, J=7.2 Hz, 1H), 2.59 (q, J=7.5 Hz, 2H), 1.05 (t, J=7.5 Hz, 3H).

Example 204

1-[6-(2,3-Dihydro-benzo[1,4]dioxin-5-yl)-4-oxo-3,4-dihydro-quinazolin-2-yl]-1H-pyrazole-4-carboxylic acid

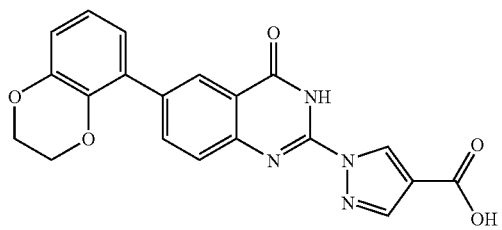 [SMILES: O=C(O)c1cnn(-c2nc3ccc(-c4cccc5c4OCCO5)cc3c(=O)[nH]2)c1]

The titled compound was prepared in a manner analogous to Example 69, steps C-E, using 1-[6-iodo-4-oxo-3-(2-trimethylsilanyl-ethoxymethyl)-3,4-dihydro-quinazolin-2-yl]-1H-pyrazole-4-carboxylic acid ethyl ester (Example 69 product from step B) and 1,4-benzodioxan-5-boronic acid in step C. MS (ESI): mass calcd. for $C_{20}H_{14}N_4O_5$, 390.1; m/z found, 391.1 [M+H]$^+$. $^1$H NMR (600 MHz, DMSO-d$_6$): 13.00 (s, 1H), 12.87 (s, 1H), 8.97 (s, 1H), 8.25 (s, 2H), 8.10 (d, J=7.8 Hz, 1H), 7.73 (s, 1H), 7.28-7.24 (m, 2H), 6.99 (d, J=8.4 Hz, 1H), 4.30 (s, 4H).

Example 205

1-[4-Oxo-6-(3-trifluoromethoxy-phenyl)-3,4-dihydro-quinazolin-2-yl]-1H-pyrazole-4-carboxylic acid

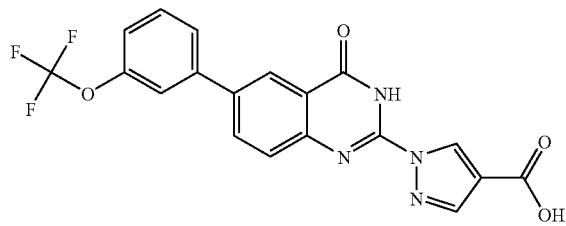 [SMILES: O=C(O)c1cnn(-c2nc3ccc(-c4cccc(OC(F)(F)F)c4)cc3c(=O)[nH]2)c1]

The titled compound was prepared in a manner analogous to Example 69, steps C-E, using 1-[6-iodo-4-oxo-3-(2-trimethylsilanyl-ethoxymethyl)-3,4-dihydro-quinazolin-2-yl]-1H-pyrazole-4-carboxylic acid ethyl ester (Example 69 product from step B) and 3-trifluoromethoxyphenylboronic acid in step C. MS (ESI): mass calcd. for $C_{19}H_{11}F_3N_4O_4$, 416.1; m/z found, 417.1 [M+H]$^+$. $^1$H NMR (600 MHz, DMSO-d$_6$): 13.06-12.92 (m, 2H), 8.99 (s, 1H), 8.39 (s, 1H), 8.28 (s, 1H), 8.22 (dd, J=8.4, 1.8 Hz, 1H), 7.86 (d, J=8.0 Hz, 1H), 7.79 (s, 2H), 7.66 (t, J=8.0 Hz, 1H), 7.46-7.40 (m, 1H).

Example 206

1-[6-(3-Methanesulfonyl-phenyl)-4-oxo-3,4-dihydro-quinazolin-2-yl]-1H-pyrazole-4-carboxylic acid

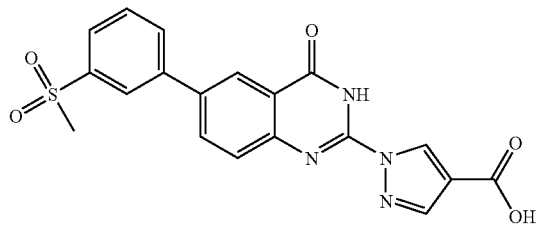 [SMILES: CS(=O)(=O)c1cccc(-c2ccc3nc(-n4cc(C(=O)O)cn4)[nH]c(=O)c3c2)c1]

The titled compound was prepared in a manner analogous to Example 69, steps C-E, using 1-[6-iodo-4-oxo-3-(2-trimethylsilanyl-ethoxymethyl)-3,4-dihydro-quinazolin-2-yl]-1H-pyrazole-4-carboxylic acid ethyl ester (Example 69 product from step B) and 3-(methylsulfonyl)phenylboronic acid in step C. MS (ESI): mass calcd. for $C_{19}H_{14}N_4O_5S$, 410.1; m/z found, 411.1 [M+H]$^+$. $^1$H NMR (600 MHz, DMSO-d$_6$): 13.01 (br s, 2H), 8.99 (s, 1H), 8.47 (d, J=2.1 Hz, 1H), 8.31- 8.27 (m, 3H), 8.18 (d, J=8.5 Hz, 1H), 7.97 (ddd, J=7.8, 1.7, 1.0 Hz, 1H), 7.85 (d, J=7.7 Hz, 1H), 7.80 (t, J=7.8 Hz, 1H), 3.34 (s, 3H).

Example 207

1-(6-Benzo[1,3]dioxol-5-yl-4-oxo-3,4-dihydro-quinazolin-2-yl)-1H-pyrazole-4-carboxylic acid

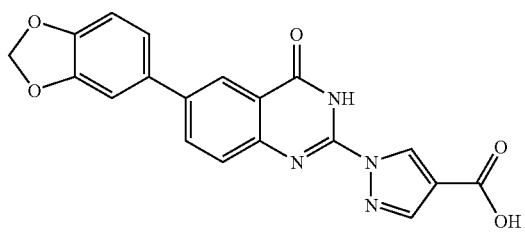 [SMILES: O=C(O)c1cnn(-c2nc3ccc(-c4ccc5c(c4)OCO5)cc3c(=O)[nH]2)c1]

The titled compound was prepared in a manner analogous to Example 69, steps C-E, using 1-[6-iodo-4-oxo-3-(2-trimethylsilanyl-ethoxymethyl)-3,4-dihydro-quinazolin-2-yl]-1H-pyrazole-4-carboxylic acid ethyl ester (Example 69 product from step B) and 3,4-methylenedioxyphenylboronic acid in step C. (ESI): mass calcd. for $C_{19}H_{12}N_4O_5$, 376.1; m/z found, 377.1 [M+H]$^+$. $^1$H NMR (500 MHz, DMSO-d$_6$): 12.96 (br s, 2H), 8.97 (s, 1H), 8.29-8.25 (m, 2H), 8.11 (dd, J=8.5, 2.2 Hz, 1H), 7.75 (d, J=8.5 Hz, 1H), 7.38 (d, J=1.7 Hz, 1H), 7.27 (dd, J=8.1, 1.8 Hz, 1H), 7.05 (d, J=8.1 Hz, 1H), 6.10 (s, 2H).

Example 208

1-(7-Iodo-4-oxo-3,4-dihydro-quinazolin-2-yl)-1H-pyrazole-4-carboxylic acid

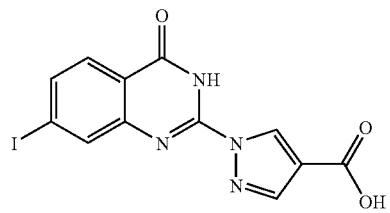 [SMILES: O=C(O)c1cnn(-c2nc3cc(I)ccc3c(=O)[nH]2)c1]

The titled compound was prepared in a manner analogous to Example 184, step E, from 1-(7-iodo-4-oxo-3,4-dihydro-quinazolin-2-yl)-1H-pyrazole-4-carboxylic acid ethyl ester (Example 184, product from step A). MS (ESI): mass calcd. for $C_{12}H_7IN_4O_3$, 382.0; m/z found, 382.9 [M+H]$^+$. $^1$H NMR (600 MHz, DMSO-d$_6$): 13.06 (s, 1H), 12.99 (s, 1H), 8.94 (s, 1H), 8.27 (s, 1H), 8.09 (s, 1H), 7.85 (s, 2H).

The following prophetic Examples may be synthesized using the general schemes provided above.

Example 209

1-(6-Benzenesulfinyl-7-chloro-4-oxo-3,4-dihydroquinazolin-2-yl)-1H-pyrazole-4-carboxylic acid

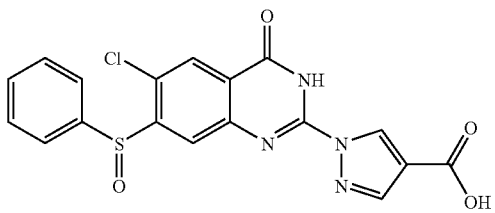 [SMILES: O=C(O)c1cnn(-c2nc3cc(S(=O)c4ccccc4)c(Cl)cc3c(=O)[nH]2)c1]

MS (ESI/Cl): predicted mass $C_{18}H_{11}ClN_4O_4S$, 414.8.

Example 210

1-(6-Benzenesulfonyl-7-chloro-4-oxo-3,4-dihydroquinazolin-2-yl)-1H-pyrazole-4-carboxylic acid

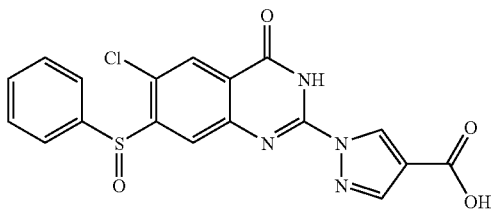 [SMILES: O=C(O)c1cnn(-c2nc3cc(S(=O)c4ccccc4)c(Cl)cc3c(=O)[nH]2)c1]

MS (ESI/Cl): predicted mass for $C_{18}H_{11}ClN_4O_5S$, 430.8.

Example 211

1-(4-Oxo-7-piperidin-1-yl-3,4-dihydro-quinazolin-2-yl)-1H-pyrazole-4-carboxylic acid

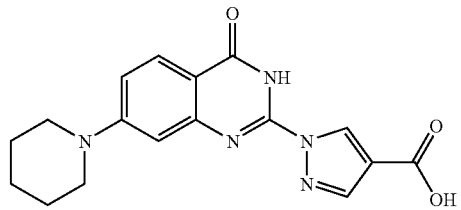 [SMILES: O=C(O)c1cnn(-c2nc3cc(N4CCCCC4)ccc3c(=O)[nH]2)c1]

The above compound may be made according to scheme B using 3-piperidin-1-yl-phenylamine. MS (ESI/Cl): predicted mass for $C_{17}H_{17}N_5O_3$, 339.1.

Biological Protocols:

Expression and Purification of $PHD2_{181-417}$

The human PHD2 expression construct containing amino acids 181-417 of GenBank Accession ID NM_022051 was cloned into a pBAD vector (Invitrogen), by Ulp1. Protein production was achieved by expression in BL21 cells grown in Terrific Broth containing 100 µg/ml ampicillin. Cell cultures were inoculated at 37° C. and grown to an $OD_{600}$ of 0.8. Cultures were induced with 0.1% arabinose and grown overnight at 20° C. with continuous shaking at 225 rpm. Cells were then harvested by centrifugation and stored at −80° C. Cell pellets were suspended in Buffer A (50 mM Tris-HCl pH 7.2, 100 mM NaCl, 100 mM L-arginine, 1 mM TCEP, 0.05% (w/v) NP-40, 50 mM imidazole) followed by the addition of lysozyme and benzonase. Cells were lysed by sonication and the lysate was cleared by centrifugation (15,000 rpm, 90 min, 4° C.). The protein was purified by nickel affinity chromatography using a HisTrap Crude FF column (GE Healthcare). Samples were eluted in Buffer A with a 50-200 mM imidazole gradient. Cleavage of the Smt tag with Ulp1 protease was achieved via overnight incubation with dialyzing against Buffer A. The $PHD2_{181-417}$ sample was then passed over a second HisTrap Crude FF column (GE Healthcare) to remove uncleaved protein. The flow-through was then dialyzed into 50 mM MES pH 6.0, 1 mM TCEP, 5 mM NaCl for ion exchange chromatography on a HiTrap SP Cation Exchange column (GE Healthcare). The $PHD2_{181-417}$ protein was eluted with a 0-0.2 M NaCl gradient. Fractions were pooled for further purification by size exclusion chromatography over a Superdex 75 Size Exclusion Column (GE Healthcare). Final protein was concentrated to 4 mg/ml and dialyzed in 10 mM PIPES pH 7.0, 100 mM NaCl, 0.5 mM TCEP. The protein was determined to have a purity of >95% by gel electrophoresis.

Enzyme Activity Assay

The PHD enzymatic assay was performed in 0.5 ml of reaction mixture containing the following: purified $PHD2_{181-417}$ polypeptide (3 µg), synthetic HIF-1α peptide comprising residues [KNPFSTGDTDLDLEMLAPYIPMDDDFQL-RSFDQLS] (10 µM, California Peptide Research Inc., Napa, Calif.), and [5-$^{14}$C]-2-oxoglutaric acid (50 mCi/mmol, Moravek Chemicals, Brea, Calif.) in reaction buffer (40 mM Tris-HCl, pH 7.5, 0.4 mg/ml catalase, 0.5 mM DTT, 1 mM ascorbate) for 10 minutes. The reaction was stopped by addition of 50 µl of 70 mM $H_3PO_4$ and 50 µl of 500 mM $NaH_2PO_4$, pH 3.2. Detection of [$^{14}$C]-succinic acid was achieved by separating from [5-$^{14}$C]-2-oxoglutaric acid by incubating the reaction mixture with 100 µl of 0.16 M DNP prepared in 30% perchloric acid. Next, 50 µl of unlabeled 20 mM 2-oxoglutaric acid/20 mM succinic acid, serving as carrier for the radioactivity, was added to the mixture, and was allowed to proceed for 30 minutes at room temperature. The reaction was then incubated with 50 µl of 1 M 2-oxoglutaric acid for 30 additional minutes at room temperature to precipitate the excess DNP. The reaction was then centrifuged at 2800×g for 10 minutes at room temperature to separate [$^{14}$C]-succinic acid in the supernatant from the precipitated [$^{14}$C]-dinitrophenylhydrazone. Fractions of the supernatant (400 µl) were counted using a beta counter (Beckman Coulter, Fullerton, Calif.). Inhibition of $PHD2_{181-417}$ activity was measured as a decrease in [$^{14}$C]-succinic acid production. The $IC_{50}$ values were estimated by fitting the data to a three-parameter logistic function using GraphPad Prism, version 4.02 (Graph Pad Software, San Diego, Calif.).

Cellular Assay

Hep-3B cells (ATCC, Manassas, Va.) were plated in 96-well plates at 20,000 cells per well in 100 µl of DMEM containing 10% fetal bovine serum, 1% non-essential amino acids, 50 IU/mL of penicillin and 50 µg/mL of streptomycin (all cell culture reagents from Invitrogen, Carlsbad, Calif.). Twenty-four hours after plating, compounds were added and incubated for an additional 24 hours. All compounds were tested under saturating conditions with final compound concentrations at 100 µM. Fifty microliters of the supernatant was then transferred to a human Hypoxia assay kit (Meso-Scale Discovery, Gaithersburg, Md.). Erythropoietin in the supernatant was detected according to the manufacturer's instructions as follows. EPO detection plates were blocked with 3% BSA in PBS overnight and 50 µl of the supernatant was incubated at room temperature in an orbital shaker for 2 h. Twenty-five microliters of 0.5 µg/ml anti-EPO detection antibody was added for 2 hours at room temperature in an orbital shaker. After 3 washes in PBS, 150 µl of 1× read buffer is added and the plate is then read on the MSD SECTOR instrument. Data was analyzed by determining the percent of EPO secretion in the presence of 100 µM compound relative to an assay control compound, 7-[(4-Chloro-phenyl)-(5-methyl-isoxazol-3-ylamino)-methyl]-quinolin-8-ol.

Results for the compounds tested in these assays are presented in Table 1 as an average of results obtained (NT=not tested). Compounds were tested in free base (*), hydrochloride salt (^), or trifluoroacetic acid (") form. Where activity is shown as greater than (>) a particular value, the value is the highest concentration tested.

TABLE 1

| Ex. | Chemical Name | Enzyme pIC50 | Cellular % EPO Stimulation |
|---|---|---|---|
| 1 | 1-(7-Chloro-4-oxo-3,4-dihydro-quinazolin-2-yl)-1H-pyrazole-4-carboxylic acid; | 7.3 | 37 |
| 2 | 1-(7-Trifluoromethyl-4-oxo-3,4-dihydro-quinazolin-2-yl)-1H-pyrazole-4-carboxylic acid; | 6.8 | 21 |
| 3 | 1-(6,7-Dichloro-4-oxo-3,4-dihydro-quinazolin-2-yl)-1H-pyrazole-4-carboxylic acid; | 7.6 | 37 |
| 4 | 1-(6-Fluoro-4-oxo-3,4-dihydro-quinazolin-2-yl)-1H-pyrazole-4-carboxylic acid; | 7.4 | 15 |
| 5 | 1-(6,7-Difluoro-4-oxo-3,4-dihydro-quinazolin-2-yl)-1H-pyrazole-4-carboxylic acid; | 7.7 | 21 |
| 6 | 1-(5-Chloro-4-oxo-3,4-dihydro-quinazolin-2-yl)-1H-pyrazole-4-carboxylic acid; | 6.8 | 19 |
| 7 | 1-(8-Methoxy-4-oxo-3,4-dihydro-quinazolin-2-yl)-1H-pyrazole-4-carboxylic acid; | 6.8 | 25 |
| 8 | 1-(6-Methyl-4-oxo-3,4-dihydro-quinazolin-2-yl)-1H-pyrazole-4-carboxylic acid; | 7.4 | 14 |
| 9 | 1-(8-Methyl-4-oxo-3,4-dihydro-quinazolin-2-yl)-1H-pyrazole-4-carboxylic acid; | 7.1 | 49 |
| 10 | 1-(7-Methyl-4-oxo-3,4-dihydro-quinazolin-2-yl)-1H-pyrazole-4-carboxylic acid; | 7.3 | 32 |
| 11 | 1-(8-Bromo-4-oxo-3,4-dihydro-quinazolin-2-yl)-1H-pyrazole-4-carboxylic acid; | 6.8 | 40 |
| 12 | 1-(6-Iodo-4-oxo-3,4-dihydro-quinazolin-2-yl)-1H-pyrazole-4-carboxylic acid; | 7.6 | 50 |
| 13 | 1-(6-Bromo-4-oxo-3,4-dihydro-quinazolin-2-yl)-1H-pyrazole-4-carboxylic acid; | 7.2 | 35 |
| 14 | 1-(8-Chloro-4-oxo-3,4-dihydro-quinazolin-2-yl)-1H-pyrazole-4-carboxylic acid; | 6.6 | 8 |
| 15 | 1-(4-Oxo-6-trifluoromethoxy-3,4-dihydro-quinazolin-2-yl)-1H-pyrazole-4-carboxylic acid; | 7.8 | 19 |
| 16 | 1-(4-Oxo-8-trifluoromethyl-3,4-dihydro-quinazolin-2-yl)-1H-pyrazole-4-carboxylic acid; | 6.6 | 16 |
| 17 | 1-(6,7-Dimethoxy-4-oxo-3,4-dihydro-quinazolin-2-yl)-1H-pyrazole-4-carboxylic acid; | 6.7 | 33 |
| 18 | 1-(5,6,7-Trimethoxy-4-oxo-3,4-dihydro-quinazolin-2-yl)-1H-pyrazole-4-carboxylic acid | 6.5 | 42 |
| 19 | 1-(6-tert-Butyl-4-oxo-3,4-dihydro-quinazolin-2-yl)-1H-pyrazole-4-carboxylic acid; | 7.4 | 45 |
| 20 | 1-(4-Oxo-6-phenoxy-3,4-dihydro-quinazolin-2-yl)-1H-pyrazole-4-carboxylic acid; | 7.6 | 104 |
| 21 | 1-(6-Cyclohexyl-4-oxo-3,4-dihydro-quinazolin-2-yl)-1H-pyrazole-4-carboxylic acid; | 7.6 | 84 |
| 22 | 1-(7-Chloro-4-oxo-6-trifluoromethoxy-3,4-dihydro-quinazolin-2-yl)-1H-pyrazole-4-carboxylic acid; | 7.5 | 61 |
| 23 | 1-(1-Oxo-2,7-dihydro-1H-pyrrolo[3,2-f]quinazolin-3-yl)-1H-pyrazole-4-carboxylic acid; | 6.8 | 33 |
| 24 | 1-[6-(4-tert-Butyl-phenylsulfanyl)-7-chloro-4-oxo-1,4-dihydro-quinazolin-2-yl]-1H-pyrazole-4-carboxylic acid; | 7.6 | 50 |
| 25 | 1-(7-Chloro-4-oxo-6-phenylsulfanyl-1,4-dihydro-quinazolin-2-yl)-1H-pyrazole-4-carboxylic acid; | 7.4 | 68 |
| 26 | 1-[7-Chloro-6-(3,4-dimethoxy-phenylsulfanyl)-4-oxo-1,4-dihydro-quinazolin-2-yl]-1H-pyrazole-4-carboxylic acid. | 7.5 | 55 |
| 27 | 1-[6-(2,6-Dimethyl-phenoxy)-7-methyl-4-oxo-3,4-dihydro-quinazolin-2-yl]-1H-pyrazole-4-carboxylic acid; | 7.7 | 10 |
| 28 | 1-[4-Oxo-6-(3,4,5-trimethoxy-phenoxy)-3,4-dihydro-quinazolin-2-yl]-1H-pyrazole-4-carboxylic acid; | 7.7 | 9 |
| 29 | 1-[6-(naphthalen-1-yloxy)-4-oxo-3,4-dihydro-quinazolin-2-yl]-1H-pyrazole-4-carboxylic acid; | 7.6 | 124 |
| 30 | 1-[6-(3-Chloro-phenoxy)-4-oxo-3,4-dihydro-quinazolin-2-yl]-1H-pyrazole-4-carboxylic acid; | 7.6 | 15 |

TABLE 1-continued

| Ex. | Chemical Name | Enzyme pIC50 | Cellular % EPO Stimulation |
|---|---|---|---|
| 31 | 1-[6-(3-Methoxy-phenoxy)-4-oxo-3,4-dihydro-quinazolin-2-yl]-1H-pyrazole-4-carboxylic acid; | 7.7 | 129 |
| 32 | 1-[6-(4-Fluoro-phenoxy)-4-oxo-3,4-dihydro-quinazolin-2-yl]-1H-pyrazole-4-carboxylic acid; | 7.6 | 68 |
| 33 | 1-[6-(2-Fluoro-phenoxy)-4-oxo-3,4-dihydro-quinazolin-2-yl]-1H-pyrazole-4-carboxylic acid; | 7.5 | 56 |
| 34 | 1-[6-(3-Fluoro-phenoxy)-4-oxo-3,4-dihydro-quinazolin-2-yl]-1H-pyrazole-4-carboxylic acid; | 7.6 | 73 |
| 35 | 1-[6-(3,5-Di-tert-butyl-phenoxy)-4-oxo-3,4-dihydro-quinazolin-2-yl]-1H-pyrazole-4-carboxylic acid; | 7.5 | 8 |
| 36 | 1-(4-Oxo-6-m-tolyloxy-3,4-dihydro-quinazolin-2-yl)-1H-pyrazole-4-carboxylic acid; | 7.4 | 22 |
| 37 | 1-(4-Oxo-6-o-tolyloxy-3,4-dihydro-quinazolin-2-yl)-1H-pyrazole-4-carboxylic acid; | 7.6 | 78 |
| 38 | 1-[6-(2,6-Dichloro-phenoxy)-4-oxo-3,4-dihydro-quinazolin-2-yl]-1H-pyrazole-4-carboxylic acid; | 7.7 | 91 |
| 39 | 1-[6-(2,4-Dichloro-phenoxy)-4-oxo-3,4-dihydro-quinazolin-2-yl]-1H-pyrazole-4-carboxylic acid; | 7.6 | 77 |
| 40 | 1-[6-(2,5-Dichloro-phenoxy)-4-oxo-3,4-dihydro-quinazolin-2-yl]-1H-pyrazole-4-carboxylic acid; | 7.6 | 77 |
| 41 | 1-[6-(4-Methoxy-phenoxy)-4-oxo-3,4-dihydro-quinazolin-2-yl]-1H-pyrazole-4-carboxylic acid; | 7.7 | 112 |
| 42 | 1-[6-(2,6-Dimethyl-phenoxy)-4-oxo-3,4-dihydro-quinazolin-2-yl]-1H-pyrazole-4-carboxylic acid; | 7.6 | 117 |
| 43 | 1-[6-(Naphthalen-2-yloxy)-4-oxo-3,4-dihydro-quinazolin-2-yl]-1H-pyrazole-4-carboxylic acid; | 7.6 | 76 |
| 44 | 1-[4-Oxo-6-(5,6,7,8-tetrahydro-naphthalen-1-yloxy)-3,4-dihydro-quinazolin-2-yl]-1H-pyrazole-4-carboxylic acid; | 7.6 | 52 |
| 46 | 1-[6-(4-Chloro-phenoxy)-4-oxo-3,4-dihydro-quinazolin-2-yl]-1H-pyrazole-4-carboxylic acid; | 7.5 | 126 |
| 47 | 1-(4-Oxo-6-p-tolyloxy-3,4-dihydro-quinazolin-2-yl)-1H-pyrazole-4-carboxylic acid; | 7.5 | 95 |
| 48 | 1-[7-Chloro-6-(4-chloro-phenoxy)-4-oxo-3,4-dihydro-quinazolin-2-yl]-1H-pyrazole-4-carboxylic acid; | 7.5 | 51 |
| 49 | 1-[7-Chloro-6-(2,6-dimethyl-phenoxy)-4-oxo-3,4-dihydro-quinazolin-2-yl]-1H-pyrazole-4-carboxylic acid; | 7.5 | 55 |
| 50 | 1-[6-(2,6-Dichloro-phenoxy)-7-fluoro-4-oxo-3,4-dihydro-quinazolin-2-yl]-1H-pyrazole-4-carboxylic acid; | 7.5 | 67 |
| 51 | 1-[6-(2,6-Dimethyl-phenoxy)-7-fluoro-4-oxo-3,4-dihydro-quinazolin-2-yl]-1H-pyrazole-4-carboxylic acid; | 7.6 | 100 |
| 52 | 1-[7-Fluoro-6-(naphthalen-2-yloxy)-4-oxo-3,4-dihydro-quinazolin-2-yl]-1H-pyrazole-4-carboxylic acid; | 7.4 | 76 |
| 53 | 1-[7-Chloro-6-(naphthalen-1-yloxy)-4-oxo-3,4-dihydro-quinazolin-2-yl]-1H-pyrazole-4-carboxylic acid; | 7.5 | 45 |
| 54 | 1-[7-Chloro-6-(naphthalen-2-yloxy)-4-oxo-3,4-dihydro-quinazolin-2-yl]-1H-pyrazole-4-carboxylic acid; | 7.4 | 90 |
| 55 | 1-[7-Chloro-4-oxo-6-(5,6,7,8-tetrahydro-naphthalen-1-yloxy)-3,4-dihydro-quinazolin-2-yl]-1H-pyrazole-4-carboxylic acid; | 7.5 | 25 |
| 56 | 1-[7-Fluoro-6-(3-fluoro-phenoxy)-4-oxo-3,4-dihydro-quinazolin-2-yl]-1H-pyrazole-4-carboxylic acid; | 7.7 | 68 |
| 57 | 1-[7-Fluoro-6-(naphthalen-1-yloxy)-4-oxo-3,4-dihydro-quinazolin-2-yl]-1H-pyrazole-4-carboxylic acid; | 7.7 | 135 |
| 58 | 1-[7-Fluoro-6-(indan-5-yloxy)-4-oxo-3,4-dihydro-quinazolin-2-yl]-1H-pyrazole-4-carboxylic acid; | 7.5 | 62 |
| 59 | 1-(7-Methyl-4-oxo-6-phenoxy-3,4-dihydro-quinazolin-2-yl)-1H-pyrazole-4-carboxylic acid; | 7.6 | 80 |
| 60 | 1-[6-(2,3-dichloro-phenoxy)-4-oxo-3,4-dihydro-quinazolin-2-yl]-1H-pyrazole-4-carboxylic acid; | 7.5 | 70 |
| 61 | 1-[6-(2,6-Dimethyl-phenoxy)-7-methoxy-4-oxo-3,4-dihydro-quinazolin-2-yl]-1H-pyrazole-4-carboxylic acid; | 7.7 | 86 |
| 62 | 1-(7-Methoxy-4-oxo-6-phenoxy-3,4-dihydro-quinazolin-2-yl)-1H-pyrazole-4-carboxylic acid; | 7.4 | 7 |

TABLE 1-continued

| Ex. | Chemical Name | Enzyme pIC50 | Cellular % EPO Stimulation |
|---|---|---|---|
| 63 | 1-[6-(2,6-Dimethyl-phenoxy)-5,7-difluoro-4-oxo-3,4-dihydro-quinazolin-2-yl]-1H-pyrazole-4-carboxylic acid; | 7.7 | 14 |
| 64 | 1-(5,7-Difluoro-4-oxo-6-phenoxy-3,4-dihydro-quinazolin-2-yl)-1H-pyrazole-4-carboxylic acid; | 7.6 | 22 |
| 65 | 1-[4-Oxo-6-(pyridin-3-yloxy)-3,4-dihydro-quinazolin-2-yl]-1H-pyrazole-4-carboxylic acid; | 7.6 | 42 |
| 66 | 1-(4-Oxo-7-phenoxy-3,4-dihydro-quinazolin-2-yl)-1H-pyrazole-4-carboxylic acid; | 7.2 | 41 |
| 67 | 1-[4-Oxo-7-(tetrahydro-pyran-4-yl)-3,4-dihydro-quinazolin-2-yl]-1H-pyrazole-4-carboxylic acid tris(hydroxymethyl)aminomethane salt; | 7.8 | 18 |
| 68 | 1-(7-Chloro-4-oxo-6-phenyl-3,4-dihydro-quinazolin-2-yl)-1H-pyrazole-4-carboxylic acid; | 7.7 | 59 |
| 69 | 1-(4-Oxo-6-o-tolyl-3,4-dihydro-quinazolin-2-yl)-1H-pyrazole-4-carboxylic acid; | 8.1 | 57 |
| 70 | 1-(6-Biphenyl-3-yl-4-oxo-3,4-dihydro-quinazolin-2-yl)-1H-pyrazole-4-carboxylic acid; | 7.5 | 41 |
| 71 | 1-[7-Chloro-6-(3,4-dimethoxy-benzenesulfonyl)-4-oxo-3,4-dihydro-quinazolin-2-yl]-1H-pyrazole-4-carboxylic acid; | 7.8 | 16 |
| 72 | 1-[6-(4-tert-Butyl-benzenesulfonyl)-7-chloro-4-oxo-3,4-dihydro-quinazolin-2-yl]-1H-pyrazole-4-carboxylic acid; | 7.3 | 22 |
| 73 | 1-(7,7-Dimethyl-4-oxo-3,7-dihydro-4H-8-oxa-1,3-diaza-anthracen-2-yl)-1H-pyrazole-4-carboxylic acid; | 7.7 | 88 |
| 74 | 1-(4-Oxo-6-phenoxymethyl-3,4-dihydro-quinazolin-2-yl)-1H-pyrazole-4-carboxylic acid; | 7.5 | 35 |
| 75 | 1-[6-(2,6-Dimethyl-phenoxymethyl)-4-oxo-3,4-dihydro-quinazolin-2-yl]-1H-pyrazole-4-carboxylic acid; | 7.7 | 20 |
| 76 | 1-(6-Ethynyl-4-oxo-3,4-dihydro-quinazolin-2-yl)-1H-pyrazole-4-carboxylic acid; | 7.5 | 16 |
| 77 | 1-[6-(1-Chloro-vinyl)-4-oxo-3,4-dihydro-quinazolin-2-yl]-1H-pyrazole-4-carboxylic acid; | 7.6 | 27 |
| 78 | 1-(4-Oxo-7-phenylsulfanyl-3,4-dihydro-quinazolin-2-yl)-1H-pyrazole-4-carboxylic acid; | 7.4 | 5 |
| 79 | 1-[7-(4-Chloro-phenylsulfanyl)-4-oxo-3,4-dihydro-quinazolin-2-yl]-1H-pyrazole-4-carboxylic acid; | 7.4 | 6 |
| 80 | 1-[7-(2-Chloro-phenylsulfanyl)-4-oxo-3,4-dihydro-quinazolin-2-yl]-1H-pyrazole-4-carboxylic acid; | 7.5 | 5 |
| 81 | 1-(7-Benzenesulfonyl-4-oxo-3,4-dihydro-quinazolin-2-yl)-1H-pyrazole-4-carboxylic acid; | 7.1 | 26 |
| 82 | 1-[7-(4-Chloro-benzenesulfonyl)-4-oxo-3,4-dihydro-quinazolin-2-yl]-1H-pyrazole-4-carboxylic acid; | 7.2 | 15 |
| 83 | 1-[7-(2-Chloro-benzenesulfonyl)-4-oxo-3,4-dihydro-quinazolin-2-yl]-1H-pyrazole-4-carboxylic acid; | 7 | 11 |
| 84 | 1-[7-Chloro-6-(3,4-dihydro-1H-isoquinolin-2-yl)-4-oxo-3,4-dihydro-quinazolin-2-yl]-1H-pyrazole-4-carboxylic acid; | 7.7 | 101 |
| 85 | 1-[6-(7-Bromo-3,4-dihydro-1H-isoquinolin-2-yl)-7-chloro-4-oxo-3,4-dihydro-quinazolin-2-yl]-1H-pyrazole-4-carboxylic acid; | 7.6 | 49 |
| 86 | (rac)-1-{7-Chloro-6-[3-(3-methoxy-phenyl)-piperidin-1-yl]-4-oxo-3,4-dihydro-quinazolin-2-yl}-1H-pyrazole-4-carboxylic acid; | 7.6 | 71 |
| 87 | 1-[6-(2,5-dichloro-phenoxy)-7-fluoro-4-oxo-3,4-dihydro-quinazolin-2-yl]-1H-pyrazole-4-carboxylic acid; | 7.7 | 84 |
| 88 | 1-[6-(3,4-dimethyl-phenoxy)-7-fluoro-4-oxo-3,4-dihydro-quinazolin-2-yl]-1H-pyrazole-4-carboxylic acid; | 7.8 | 95 |
| 89 | 1-[6-(3,5-dimethyl-phenoxy)-7-methyl-4-oxo-3,4-dihydro-quinazolin-2-yl]-1H-pyrazole-4-carboxylic acid; | 7.6 | 137 |
| 90 | 1-[6-(2,5-dichloro-phenoxy)-7-methyl-4-oxo-3,4-dihydro-quinazolin-2-yl]-1H-pyrazole-4-carboxylic acid; | 7.6 | 113 |
| 91 | 1-[6-(biphenyl-3-yloxy)-7-methyl-4-oxo-3,4-dihydro-quinazolin-2-yl]-1H-pyrazole-4-carboxylic acid; | 7.6 | 75 |

TABLE 1-continued

| Ex. | Chemical Name | Enzyme pIC50 | Cellular % EPO Stimulation |
|---|---|---|---|
| 92 | 1-[6-(3,4-dimethyl-phenoxy)-7-methyl-4-oxo-3,4-dihydro-quinazolin-2-yl]-1H-pyrazole-4-carboxylic acid; | 7.7 | 137 |
| 93 | 1-[7-methyl-4-oxo-6-(3-trifluoromethyl-phenoxy)-3,4-dihydro-quinazolin-2-yl]-1H-pyrazole-4-carboxylic acid; | 7.7 | 153 |
| 94 | 1-[6-(3,5-dimethyl-phenoxy)-7-fluoro-4-oxo-3,4-dihydro-quinazolin-2-yl]-1H-pyrazole-4-carboxylic acid; | 7.7 | 90 |
| 95 | 1-[7-fluoro-4-oxo-6-(3-trifluoromethyl-phenoxy)-3,4-dihydro-quinazolin-2-yl]-1H-pyrazole-4-carboxylic acid; | 7.7 | 61 |
| 96 | 1-[6-(2-fluoro-3-trifluoromethyl-phenoxy)-4-oxo-3,4-dihydro-quinazolin-2-yl]-1H-pyrazole-4-carboxylic acid; | 7.6 | 51 |
| 97 | 1-[6-(3-fluoro-5-trifluoromethyl-phenoxy)-4-oxo-3,4-dihydro-quinazolin-2-yl]-1H-pyrazole-4-carboxylic acid; | 7.7 | 37 |
| 98 | 1-[6-(3,5-dimethyl-phenoxy)-4-oxo-3,4-dihydro-quinazolin-2-yl]-1H-pyrazole-4-carboxylic acid; | 7.7 | 85 |
| 99 | 1-[6-(biphenyl-3-yloxy)-4-oxo-3,4-dihydro-quinazolin-2-yl]-1H-pyrazole-4-carboxylic acid; | 7.6 | 81 |
| 100 | 1-[4-oxo-6-(3-trifluoromethyl-phenoxy)-3,4-dihydro-quinazolin-2-yl]-1H-pyrazole-4-carboxylic acid; | 7.6 | 55 |
| 101 | 1-[6-(2,6-dichloro-phenoxy)-5,7-difluoro-4-oxo-3,4-dihydro-quinazolin-2-yl]-1H-pyrazole-4-carboxylic acid; | 7.6 | 24 |
| 102 | 1-(6-cyclohexyloxy-4-oxo-3,4-dihydro-quinazolin-2-yl)-1H-pyrazole-4-carboxylic acid; | 7.7 | 59 |
| 103 | 1-[6-(4-methyl-piperazin-1-yl)-4-oxo-3,4-dihydro-quinazolin-2-yl]-1H-pyrazole-4-carboxylic acid; | 7.2 | 30 |
| 104 | 1-(6-isopropoxy-4-oxo-3,4-dihydro-quinazolin-2-yl)-1H-pyrazole-4-carboxylic acid; | 7.5 | 75 |
| 105 | 1-(6-benzyl-4-oxo-3,4-dihydro-quinazolin-2-yl)-1H-pyrazole-4-carboxylic acid; | 7.5 | 129 |
| 106 | 1-(4-oxo-6-phenyl-3,4-dihydro-quinazolin-2-yl)-1H-pyrazole-4-carboxylic acid; | 7.5 | 129 |
| 107 | 1-(6-morpholin-4-yl-4-oxo-3,4-dihydro-quinazolin-2-yl)-1H-pyrazole-4-carboxylic acid; | 7.4 | 45 |
| 108 | 1-[6-(1H-Indol-6-yl)-4-oxo-3,4-dihydro-quinazolin-2-yl]-1H-pyrazole-4-carboxylic acid; | 7.6 | 85 |
| 109 | 1-(6-Cyclopropyl-4-oxo-3,4-dihydro-quinazolin-2-yl)-1H-pyrazole-4-carboxylic acid; | 7.6 | 100 |
| 110 | 1-(6-Cyclohexyl-7-fluoro-4-oxo-3,4-dihydro-quinazolin-2-yl)-1H-pyrazole-4-carboxylic acid; | 6.8 | 47 |
| 111 | 1-(4-Oxo-8-phenyl-3,4-dihydro-quinazolin-2-yl)-1H-pyrazole-4-carboxylic acid; | 6.9 | 24 |
| 112 | 1-(4-Oxo-8-phenoxy-3,4-dihydro-quinazolin-2-yl)-1H-pyrazole-4-carboxylic acid; | 6.8 | 18 |
| 113 | 1-(4-Oxo-8-phenylsulfanyl-3,4-dihydro-quinazolin-2-yl)-1H-pyrazole-4-carboxylic acid; | 6.7 | 17 |
| 114 | 1-(8-Isopropyl-4-oxo-3,4-dihydro-quinazolin-2-yl)-1H-pyrazole-4-carboxylic acid; | 6.6 | 16 |
| 115 | 1-(8-tert-Butyl-4-oxo-3,4-dihydro-quinazolin-2-yl)-1H-pyrazole-4-carboxylic acid; | 6.8 | 27 |
| 116 | 1-(5,8-Difluoro-4-oxo-3,4-dihydro-quinazolin-2-yl)-1H-pyrazole-4-carboxylic acid; | 6.7 | 17 |
| 117 | 1-(4-Oxo-8-trifluoromethoxy-3,4-dihydro-quinazolin-2-yl)-1H-pyrazole-4-carboxylic acid; | 6.1 | 12 |
| 118 | 1-(8-Fluoro-4-oxo-3,4-dihydro-quinazolin-2-yl)-1H-pyrazole-4-carboxylic acid; | 7.1 | 16 |
| 119 | 1-(6-Isopropyl-4-oxo-3,4-dihydro-quinazolin-2-yl)-1H-pyrazole-4-carboxylic acid; | 7.8 | 115 |
| 120 | 1-(6-sec-Butyl-4-oxo-3,4-dihydro-quinazolin-2-yl)-1H-pyrazole-4-carboxylic acid; | 7.7 | 68 |
| 121 | 1-(6-Ethoxy-4-oxo-3,4-dihydro-quinazolin-2-yl)-1H-pyrazole-4-carboxylic acid; | 8 | 30 |
| 122 | 1-(6-Methoxy-4-oxo-3,4-dihydro-quinazolin-2-yl)-1H-pyrazole-4-carboxylic acid; | 7.6 | 16 |
| 123 | 1-(4-Oxo-6-pyrrolidin-1-yl-3,4-dihydro-quinazolin-2-yl)-1H-pyrazole-4-carboxylic acid; | 7.4 | 17 |
| 124 | 1-(4-Oxo-6-piperidin-1-yl-3,4-dihydro-quinazolin-2-yl)-1H-pyrazole-4-carboxylic acid; | 7.4 | 71 |
| 125 | 1-(6-Dimethylamino-4-oxo-3,4-dihydro-quinazolin-2-yl)-1H-pyrazole-4-carboxylic acid; | 7.3 | 19 |

TABLE 1-continued

| Ex. | Chemical Name | Enzyme pIC50 | Cellular % EPO Stimulation |
|---|---|---|---|
| 126 | 1-(4-Oxo-3,4-dihydro-quinazolin-2-yl)-1H-pyrazole-4-carboxylic acid; | 7.2 | 9 |
| 127 | 1-(6-Bromo-7-fluoro-4-oxo-3,4-dihydro-quinazolin-2-yl)-1H-pyrazole-4-carboxylic acid; | 7.5 | 9 |
| 128 | 1-(6-Ethyl-4-oxo-3,4-dihydro-quinazolin-2-yl)-1H-pyrazole-4-carboxylic acid; | 7.4 | 53 |
| 129 | 1-(4-Oxo-6-propyl-3,4-dihydro-quinazolin-2-yl)-1H-pyrazole-4-carboxylic acid; | 7.5 | 94 |
| 130 | 1-(6-Bromo-8-fluoro-4-oxo-3,4-dihydro-quinazolin-2-yl)-1H-pyrazole-4-carboxylic acid; | 7.1 | 12 |
| 131 | 1-(5,7-Difluoro-4-oxo-3,4-dihydro-quinazolin-2-yl)-1H-pyrazole-4-carboxylic acid; | 7.2 | 21 |
| 132 | 1-(5,7-Dichloro-4-oxo-3,4-dihydro-quinazolin-2-yl)-1H-pyrazole-4-carboxylic acid; | 6.9 | 16 |
| 133 | 1-(7-Fluoro-4-oxo-3,4-dihydro-quinazolin-2-yl)-1H-pyrazole-4-carboxylic acid; | 7.4 | 10 |
| 134 | 1-(7-Bromo-4-oxo-3,4-dihydro-quinazolin-2-yl)-1H-pyrazole-4-carboxylic acid; | 7.3 | 18 |
| 135 | 1-(7-Methoxy-4-oxo-3,4-dihydro-quinazolin-2-yl)-1H-pyrazole-4-carboxylic acid; | 7.1 | 17 |
| 136 | 1-(7-Benzyl-4-oxo-3,4-dihydro-quinazolin-2-yl)-1H-pyrazole-4-carboxylic acid; | 7.5 | 23 |
| 137 | 1-(4-Oxo-3,4,8,9-tetrahydro-7H-6,10-dioxa-1,3-diaza-cyclohepta[b]naphthalen-2-yl)-1H-pyrazole-4-carboxylic acid; | 7.3 | 15 |
| 138 | 1-(8-Oxo-2,3,7,8-tetrahydro-1,4-dioxa-5,7-diaza-phenanthren-6-yl)-1H-pyrazole-4-carboxylic acid; | 6.6 | 40 |
| 139 | 1-(4-Oxo-3,4,7,8-tetrahydro-[1,4]dioxino[2,3-g]quinazolin-2-yl)-1H-pyrazole-4-carboxylic acid; | 7.45 | 15 |
| 140 | 1-(4-Oxo-4,6,7,8-tetrahydro-3H-cyclopenta[g]quinazolin-2-yl)-1H-pyrazole-4-carboxylic acid; | 7.45 | 62 |
| 141 | 1-(6-Oxo-2,3,6,7-tetrahydro-1H-7,9-diaza-cyclopenta[a]naphthalen-8-yl)-1H-pyrazole-4-carboxylic acid; | 6.3 | 25 |
| 142 | 1-(4-Oxo-3,4,7,8,9,10-hexahydro-benzo[h]quinazolin-2-yl)-1H-pyrazole-4-carboxylic acid; | 6.6 | 23 |
| 143 | 1-(4-Oxo-3,4,6,7,8,9-hexahydro-benzo[g]quinazolin-2-yl)-1H-pyrazole-4-carboxylic acid; | 7.5 | 75 |
| 144 | 1-(1-Oxo-1,2,7,8,9,10-hexahydro-benzo[f]quinazolin-3-yl)-1H-pyrazole-4-carboxylic acid; | 7.4 | 42 |
| 145 | 1-(5,7-Dimethyl-4-oxo-3,4-dihydro-quinazolin-2-yl)-1H-pyrazole-4-carboxylic acid; | 6.4 | 16 |
| 146 | 1-(7-Isopropyl-4-oxo-3,4-dihydro-quinazolin-2-yl)-1H-pyrazole-4-carboxylic acid; | 6.9 | 16 |
| 147 | 1-(7-tert-Butyl-4-oxo-3,4-dihydro-quinazolin-2-yl)-1H-pyrazole-4-carboxylic acid; | 6.4 | 11 |
| 148 | 1-(4-Oxo-7-trifluoromethoxy-3,4-dihydro-quinazolin-2-yl)-1H-pyrazole-4-carboxylic acid; | 6.9 | 10 |
| 149 | 1-(7-Isopropoxy-4-oxo-3,4-dihydro-quinazolin-2-yl)-1H-pyrazole-4-carboxylic acid; | 6.4 | 9 |
| 150 | 1-(7-Dimethylamino-4-oxo-3,4-dihydro-quinazolin-2-yl)-1H-pyrazole-4-carboxylic acid; | 6.8 | 24 |
| 151 | 1-(5-Dimethylamino-4-oxo-3,4-dihydro-quinazolin-2-yl)-1H-pyrazole-4-carboxylic acid; | 6.2 | 11 |
| 152 | 1-(7-Ethoxy-4-oxo-3,4-dihydro-quinazolin-2-yl)-1H-pyrazole-4-carboxylic acid; | 6.8 | 38 |
| 153 | 1-(6-Chloro-4-oxo-3,4-dihydro-quinazolin-2-yl)-1H-pyrazole-4-carboxylic acid; | 7.4 | 22 |
| 154 | 1-(7-Hydroxy-4-oxo-3,4-dihydro-quinazolin-2-yl)-1H-pyrazole-4-carboxylic acid; | 7.3 | 12 |
| 155 | 1-(6-Methylsulfanyl-4-oxo-3,4-dihydro-quinazolin-2-yl)-1H-pyrazole-4-carboxylic acid; | 7.5 | 40 |
| 156 | 1-(4-Oxo-6-trifluoromethylsulfanyl-3,4-dihydro-quinazolin-2-yl)-1H-pyrazole-4-carboxylic acid; | 7.5 | 19 |
| 157 | 1-(6-Methanesulfonyl-4-oxo-3,4-dihydro-quinazolin-2-yl)-1H-pyrazole-4-carboxylic acid; | 7.5 | 17 |
| 158 | 1-(7-Chloro-6-methylsulfanyl-4-oxo-3,4-dihydro-quinazolin-2-yl)-1H-pyrazole-4-carboxylic acid; | 7.4 | 15 |
| 159 | 1-(7-Chloro-4-oxo-6-trifluoromethylsulfanyl-3,4-dihydro-quinazolin-2-yl)-1H-pyrazole-4-carboxylic acid; | 7.6 | 16 |

TABLE 1-continued

| Ex. | Chemical Name | Enzyme pIC50 | Cellular % EPO Stimulation |
|---|---|---|---|
| 160 | 1-(7-Chloro-4-oxo-6-trifluoromethanesulfinyl-3,4-dihydro-quinazolin-2-yl)-1H-pyrazole-4-carboxylic acid; | 7.4 | 13 |
| 161 | 1-[4-Oxo-6-(pyrrolidine-1-sulfonyl)-3,4-dihydro-quinazolin-2-yl]-1H-pyrazole-4-carboxylic acid; | 7.4 | 17 |
| 162 | 1-[4-Oxo-6-(pyrrolidine-1-carbonyl)-3,4-dihydro-quinazolin-2-yl]-1H-pyrazole-4-carboxylic acid; | 7.5 | 15 |
| 163 | 1-[6-(2,6-Dimethyl-phenylcarbamoyl)-4-oxo-3,4-dihydro-quinazolin-2-yl]-1H-pyrazole-4-carboxylic acid; | 7.4 | 14 |
| 164 | 1-(6-Nitro-4-oxo-3,4-dihydro-quinazolin-2-yl)-1H-pyrazole-4-carboxylic acid | 7.6 | 17 |
| 165 | 1-(6-Benzoylamino-4-oxo-3,4-dihydro-quinazolin-2-yl)-1H-pyrazole-4-carboxylic acid; | 7.6 | 19 |
| 166 | 1-[6-(2,6-Dimethyl-benzoylamino)-4-oxo-3,4-dihydro-quinazolin-2-yl]-1H-pyrazole-4-carboxylic acid; | 7.5 | 11 |
| 167 | 1-(6-Acetylamino-4-oxo-3,4-dihydro-quinazolin-2-yl)-1H-pyrazole-4-carboxylic acid; | 7.5 | 26 |
| 168 | 1-[4-Oxo-6-(3-phenyl-ureido)-3,4-dihydro-quinazolin-2-yl]-1H-pyrazole-4-carboxylic acid; | 7.5 | 4 |
| 169 | 1-(6-Benzenesulfonylamino-4-oxo-3,4-dihydro-quinazolin-2-yl)-1H-pyrazole-4-carboxylic acid; | 7.6 | 34 |
| 170 | 1-(6-Methanesulfonylamino-4-oxo-3,4-dihydro-quinazolin-2-yl)-1H-pyrazole-4-carboxylic acid; | 7.5 | 15 |
| 171 | 1-(6-Benzylamino-4-oxo-3,4-dihydro-quinazolin-2-yl)-1H-pyrazole-4-carboxylic acid; | 7.6 | 34 |
| 172 | 1-(6-Ethylamino-4-oxo-3,4-dihydro-quinazolin-2-yl)-1H-pyrazole-4-carboxylic acid; | 7.6 | 20 |
| 173 | 1-[6-(2-Methyl-benzylamino)-4-oxo-3,4-dihydro-quinazolin-2-yl]-1H-pyrazole-4-carboxylic acid; | 7.7 | 101 |
| 174 | 1-[6-(2-Chloro-benzylamino)-4-oxo-3,4-dihydro-quinazolin-2-yl]-1H-pyrazole-4-carboxylic acid; | 7.7 | 24 |
| 175 | 1-[6-(2,6-Dimethyl-benzylamino)-4-oxo-3,4-dihydro-quinazolin-2-yl]-1H-pyrazole-4-carboxylic acid; | 7.5 | 97 |
| 176 | 1-[6-(2,6-Difluoro-benzylamino)-4-oxo-3,4-dihydro-quinazolin-2-yl]-1H-pyrazole-4-carboxylic acid; | 7.4 | 26 |
| 177 | 1-[6-(2-Cyano-benzylamino)-4-oxo-3,4-dihydro-quinazolin-2-yl]-1H-pyrazole-4-carboxylic acid; | 7.3 | 13 |
| 178 | 1-[6-(3-Cyano-benzylamino)-4-oxo-3,4-dihydro-quinazolin-2-yl]-1H-pyrazole-4-carboxylic acid; | 7.7 | 12 |
| 179 | 1-[6-(3-Carbamoyl-benzylamino)-4-oxo-3,4-dihydro-quinazolin-2-yl]-1H-pyrazole-4-carboxylic acid; | 7.6 | 12 |
| 180 | 1-[6-amino-4-oxo-3,4-dihydro-quinazolin-2-yl]-1H-pyrazole-4-carboxylic acid; | 7.2 | 8 |
| 181 | 1-[6-(2,6-Dichloro-benzylamino)-4-oxo-3,4-dihydro-quinazolin-2-yl]-1H-pyrazole-4-carboxylic acid; | 7.6 | 118 |
| 182 | 1-[6-(3-Chloro-benzylamino)-4-oxo-3,4-dihydro-quinazolin-2-yl]-1H-pyrazole-4-carboxylic acid; | 7.6 | 26 |
| 183 | 1-[6-(4-methyl-benzylamino)-4-oxo-3,4-dihydro-quinazolin-2-yl]-1H-pyrazole-4-carboxylic acid; | 7.8 | 89 |
| 184 | 1-(4-Oxo-7-phenyl-3,4-dihydro-quinazolin-2-yl)-1H-pyrazole-4-carboxylic acid; | 7.1 | 12 |
| 185 | 1-[7-(2-Chloro-phenyl)-4-oxo-3,4-dihydro-quinazolin-2-yl]-1H-pyrazole-4-carboxylic acid; | 7 | 15 |
| 186 | 1-[7-(3-Chloro-phenyl)-4-oxo-3,4-dihydro-quinazolin-2-yl]-1H-pyrazole-4-carboxylic acid; | 7.3 | 26 |
| 187 | 1-[7-(4-Chloro-phenyl)-4-oxo-3,4-dihydro-quinazolin-2-yl]-1H-pyrazole-4-carboxylic acid; | 7.2 | 24 |
| 188 | 1-(4-Oxo-7-o-tolyl-3,4-dihydro-quinazolin-2-yl)-1H-pyrazole-4-carboxylic acid; | 7.1 | 11 |
| 189 | 1-(4-Oxo-7-m-tolyl-3,4-dihydro-quinazolin-2-yl)-1H-pyrazole-4-carboxylic acid; | 7.3 | 25 |
| 190 | 1-(4-Oxo-6-m-tolyl-3,4-dihydro-quinazolin-2-yl)-1H-pyrazole-4-carboxylic acid; | 7.6 | 91 |
| 191 | 1-(4-Oxo-6-p-tolyl-3,4-dihydro-quinazolin-2-yl)-1H-pyrazole-4-carboxylic acid; | 7.7 | 31 |
| 192 | 1-[6-(2-Chloro-phenyl)-4-oxo-3,4-dihydro-quinazolin-2-yl]-1H-pyrazole-4-carboxylic acid; | 7.5 | 87 |
| 193 | 1-[6-(3-Chloro-phenyl)-4-oxo-3,4-dihydro-quinazolin-2-yl]-1H-pyrazole-4-carboxylic acid; | 7.5 | 141 |
| 194 | 1-[6-(4-Chloro-phenyl)-4-oxo-3,4-dihydro-quinazolin-2-yl]-1H-pyrazole-4-carboxylic acid; | 7.7 | 62 |

TABLE 1-continued

| Ex. | Chemical Name | Enzyme pIC50 | Cellular % EPO Stimulation |
|---|---|---|---|
| 195 | 1-[6-(2-Fluoro-phenyl)-4-oxo-3,4-dihydro-quinazolin-2-yl]-1H-pyrazole-4-carboxylic acid; | 7.6 | 100 |
| 196 | 1-[6-(3-Fluoro-phenyl)-4-oxo-3,4-dihydro-quinazolin-2-yl]-1H-pyrazole-4-carboxylic acid; | 7.4 | 92 |
| 197 | 1-[6-(4-Fluoro-phenyl)-4-oxo-3,4-dihydro-quinazolin-2-yl]-1H-pyrazole-4-carboxylic acid; | 7.7 | 108 |
| 198 | 1-[6-(2-Methoxy-phenyl)-4-oxo-3,4-dihydro-quinazolin-2-yl]-1H-pyrazole-4-carboxylic acid; | 7.7 | 178 |
| 199 | 1-[6-(3-Methoxy-phenyl)-4-oxo-3,4-dihydro-quinazolin-2-yl]-1H-pyrazole-4-carboxylic acid; | 7.6 | 119 |
| 200 | 1-[6-(4-Methoxy-phenyl)-4-oxo-3,4-dihydro-quinazolin-2-yl]-1H-pyrazole-4-carboxylic acid; | 7.8 | 118 |
| 201 | 1-[4-Oxo-6-(2-trifluoromethyl-phenyl)-3,4-dihydro-quinazolin-2-yl]-1H-pyrazole-4-carboxylic acid; | 7.6 | 78 |
| 202 | 1-[4-Oxo-6-(2-trifluoromethoxy-phenyl)-3,4-dihydro-quinazolin-2-yl]-1H-pyrazole-4-carboxylic acid; | 7.8 | 29 |
| 203 | 1-[6-(2-Ethyl-phenyl)-4-oxo-3,4-dihydro-quinazolin-2-yl]-1H-pyrazole-4-carboxylic acid; | 7.5 | 77 |
| 204 | 1-[6-(2,3-Dihydro-benzo[1,4]dioxin-5-yl)-4-oxo-3,4-dihydro-quinazolin-2-yl]-1H-pyrazole-4-carboxylic acid; | 7.8 | 111 |
| 205 | 1-[4-Oxo-6-(3-trifluoromethoxy-phenyl)-3,4-dihydro-quinazolin-2-yl]-1H-pyrazole-4-carboxylic acid; | 7.6 | 58 |
| 206 | 1-[6-(3-Methanesulfonyl-phenyl)-4-oxo-3,4-dihydro-quinazolin-2-yl]-1H-pyrazole-4-carboxylic acid; | 7.6 | 13 |
| 207 | 1-(6-Benzo[1,3]dioxol-5-yl-4-oxo-3,4-dihydro-quinazolin-2-yl)-1H-pyrazole-4-carboxylic acid; and | 7.6 | 84 |
| 208 | 1-(7-Iodo-4-oxo-3,4-dihydro-quinazolin-2-yl)-1H-pyrazole-4-carboxylic acid. | 6.9 | 20 |

Histology

Various animal models are assessed for histological analysis. In one example, a canine study was used to assess the effect of 1-[6-(2,6-dimethyl-phenoxy)-7-fluoro-4-oxo-3,4-dihydro-quinazolin-2-yl]-1H-pyrazole-4-carboxylic acid when administered orally by stomach tube in a Single Dose Escalation (SDE) phase, and then subsequently for up to 5 days during the Repeat Dose (RD) phase. The results of this histological analysis are provided in Table 1 below.

TABLE 1

| Organ | 10 mg/kg/day-1001 (Male) | 10 mg/kg/day-1501 (female) |
|---|---|---|
| Lung | NSL | NSL |
| Heart | NSL | NSL |
| Kidney | Slight, bilateral, acute multi-focal inflammation; pelvic interstitium Slight, pelvic mineral deposition (right kidney) | NSL |
| Liver | Slight, acute central-lobular inflammation with individual hepatocyte necrosis Slight, acute portal inflammation | Slight, acute central-lobular inflammation Slight, acute portal inflammation |
| Spleen | Mild EMH, with mild, increased megakaryocytes Slight, intra-macrophage brown pigment | Mild EMH, with mild, increased megakaryocytes Slight, intra-macrophage brown pigment |
| Stomach | NSL | NSL |
| Testis/Epididymis | NSL | |
| Bone Marrow | NSL | NSL |
| | 45 mg/kg/day-2001 (Male) | 45 mg/kg/day-2501 (female) |
| Lung | NSL | NSL |
| Heart | NSL | |
| Kidney | Slight, bilateral, acute multi-focal inflammation; pelvic interstitium Multiple cysts with slight interstitial inflammation and basophilic tubules Slight, renal papillary mineralization | Slight, bilateral, acute-multi-focal inflammation; pelvic interstitium Slight tubular vacuolization |

TABLE 1-continued

| | | |
|---|---|---|
| Liver | Mild, acute central-lobular inflammation and necrosis | Mild, acute central-lobular inflammation and necrosis |
| | Mild, acute portal inflammation and necrosis | Mild, acute portal inflammation and necrosis |
| | Mild, apoptotic and pyknotic cells in sinusoids | Mild bile duct hyperplasia |
| | Mild, multifocal, portal tract lymphatic dilatation | Multifocal portal tract thrombosis |
| | | Mild, apoptotic and pyknotic cells in sinusoids |
| | | Slight, portal tract lymphatic dilatation |
| | | Slight, Kupffer cell brown pigment deposition |
| Spleen | Mild EMH | Mild EMH |
| | Mild, increased megkaryocytes | Mild, increased megkaryocytes |
| | Slight intra-macrophage brown pigment | Slight intra-macrophage brown pigment |
| Stomach | NSL | NSL |
| Test/Epididymis | NSL | |
| Bone Marrow | BSL | NSL |

NSL = No Significant Lesion,
EMH = extramedulary hemapoiesis

While the invention has been illustrated by reference to exemplary and preferred embodiments, it will be understood that the invention is intended not to be limited to the foregoing detailed description.

What is claimed is:

1. A compound of the formula (I):

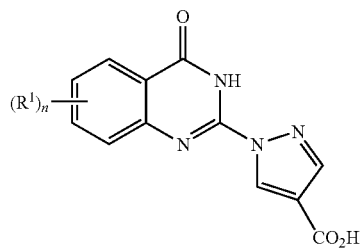

wherein:

n is 1-3

$R^1$ is a member independently selected from the group consisting of halo, —$C_{1-4}$alkyl, —$C_{2-4}$alkynyl, —$C_{2-4}$ alkenyl optionally substituted with halo, —$CF_3$, —$OCF_3$, —$SCF_3$, $S(O)CF_3$, —C(O)—$R^c$, —OH, —$NO_2$, —CN, —$OC_{1-4}$alkyl, —$SC_{1-4}$alkyl, —S(O)—$C_{1-4}$alkyl, —$SO_2$—$C_{1-4}$alkyl, —S—$R^c$, —S(O)—$R^c$, —$SO_2$—$R^c$, —O—$R^c$, —$NR^aR^b$, 2,3-dihydro-benzo[1,4]dioxine, benzo[1,3]dioxole, 1H-indole, benzyl, biphenyl optionally substituted with one or more $R^d$ members, benzyloxy optionally substituted with one or more $R^d$ members, phenyl or monocyclic heteroaryl optionally substituted with one or more $R^d$ members, and —$C_{3-8}$cycloalkyl optionally substituted with one or more $R^d$ members;

$R^a$ and $R^b$ are independently selected from the group consisting of H, $C_{1-4}$alkyl, —C(O)$C_{1-4}$alkyl, —C(O)—$R^c$, —C(O)NH—$R^c$, —$SO_2$—$R^c$, —$SO_2$—$C_{1-4}$alkyl, phenyl optionally substituted with $R^d$, benzyl optionally substituted with $R^d$ or monocyclic heteroaryl ring optionally substituted with $R^d$; or $R^a$ and $R^b$ can be taken together with the nitrogen to which they are attached to form a monocyclic heterocycloalkyl ring containing one or more O, S or N optionally substituted with methyl or methoxyphenyl;

$R^c$ is a member independently selected from the group consisting of —$C_{3-8}$cycloalkyl, —$C_{3-8}$heterocycloalkyl, biphenyl, phenyl optionally substituted with one or more $R^d$ members, benzyl optionally substituted with $R^d$, naphthyl, indanyl, 5,6,7,8-tetrahydro-naphthyl, and pyridyl optionally substituted with one or more $R^d$ members;

$R^d$ is a member independently selected from the group consisting of —H, halo, —OH, —$C_{1-4}$alkyl, —$SO_2$—$C_{1-4}$alkyl, —CN, —$CF_3$, —$OCF_3$, —$OC_{1-4}$ alkyl, —$C(O)NH_2$, phenyl, —O-phenyl, and —O-benzyl;

or an enantiomer, diastereomer, racemate, or pharmaceutically acceptable salt thereof.

2. A compound as defined in claim 1, where $R^1$ is a member independently selected from the group consisting of halo, —$C_{1-4}$alkyl, —$OCF_3$, —$CF_3$, —OH, —$NO_2$, —CN, —$OC_{1-4}$ alkyl, —$SC_{1-4}$alkyl, —S(O)—$C_{1-4}$alkyl, —$SC_2$-$C_{1-4}$ alkyl, —S—$R^c$, —S(O)—$R^c$, —$SO_2$—$R^c$, —O—$R^c$, —$NR^aR^b$, benzyloxy optionally substituted with $R^d$, and phenyl or monocyclic heteroaryl optionally substituted with one or more $R^d$ members.

3. A compound of claim 1 where n is 1.

4. A compound of claim 1 where n is 2.

5. A compound of claim 1 where n is 3.

6. A compound as defined in claim 1, where —$R^aR^b$ is a member independently selected from the group consisting of —H, —$CH_3$, —$CH_2CH_3$, benzoyl, 2,6-dimethylbenzoyl, acetyl, —C(O)NH-phenyl, benzenesulfonyl, methanesulfonyl, benzyl, 2-methylbenzyl, 2-chlorobenzyl, 2,6-dimethylbenzyl, 2,6-difluorobenzyl, 2-cyanobenzyl, 3-cyanobenzyl, 3-carbamoyl-benzyl, 2,6-dichlorobenzyl, 3-chlorobenzyl, and 4-methylbenzyl.

7. A compound as defined in claim 1, where $R^1$ is optionally substituted N-methylpiperazin-1-yl, piperidinyl, morpholin-4-yl, or pyrrolidinyl.

8. A compound of claim 1 where $R^c$ is a member independently selected from the group consisting of phenyl, cyclohexyl, 4-tert-butyl-phenyl, 3,4-dimethoxy-phenyl, 2,6-dimethyl-phenyl, 3,4,5-trimethoxy-phenyl, naphthalen-1-yl, 3-chloro-phenyl, 4-chloro-phenyl, 3-methoxy-phenyl, 4-fluoro-phenyl, 2-fluoro-phenyl, 3-fluoro-phenyl, 3,5-di-tert-butyl-phenyl, m-tolyl, o-tolyl, 2,6-dichloro-phenyl, 2,4-dichloro-phenyl, 2,5-dichloro-phenyl, 4-methoxy-phenyl, naphthalen-2-yl, 5,6,7,8-tetrahydro-naphthalen-1-yl, p-tolyl, indan-5-yl, 2,3-dichloro-phenyl, and pyridin-3-yl.

9. A compound of claim 1 where $R^d$ is a member independently selected from the group consisting of —H, chloro, fluoro, bromo, iodo, —$C_{1-4}$alkyl, —$CF_3$, —$OCF_3$, —$OC_{1-4}$alkyl, phenyl, —O-phenyl, or —O-benzyl.

10. A compound as defined in claim 1, where $R^1$ is independently selected from the group consisting of chloro, fluoro, bromo, iodo, —$NO_2$, —OH, —$CF_3$, —$CH_3$, —$CH_2CH_3$, —$CH_2CH_2CH_3$, —$OCF_3$, —$OCH_3$, —$OCH_2CH_3$, —$SCH_3$, —$SCF_3$, —$S(O)CF_3$, —$SO_2CH_3$, —$NH_2$, —$N(CH_3)_2$, —$NH(CH_2CH_3)$, cyano, isopropoxy, isopropyl, sec-butyl, tert-butyl, ethynyl, 1-chloro-vinyl, 4-methyl-piperazinyl, morpholin-4-yl, pyrrolidinyl, pyrrolidine-1-carbonyl, piperidinyl, phenyl, benzyl, biphenyl, tolyl, phenoxy, cyclopropyl, cyclohexyl, phenylsulfanyl, 3,4-dimethoxy-phenylsulfanyl, 4-tert-butyl-phenylsulfanyl, 2,6-dimethyl-phenoxy, 3,4,5-trimethoxy-phenoxy, naphthalen-1-yloxy, naphthalen-2-yloxy, 5,6,7,8-tetrahydro-naphthalen-1-yloxy, indan-5-yloxy, 3-chlorophenoxy, 4-chlorophenoxy, 2,3-dichloro-phenoxy, 3-methoxy-phenoxy, 4-fluorophenoxy, 2-fluorophenoxy, 3-fluorophenoxy, 3,5-di-tert-butyl-phenoxy, 3-methylphenoxy, 2,6-dichloro-phenoxy, 2,5-dichlorophenoxy, 4-methoxyphenoxy, pyridin-3-yloxy, tetrahydro-pyran-4-yl, 3-methoxyphenyl-piperidinyl, and benzenesulfonyl.

11. A compound selected from the group consisting of:
1-(7-Chloro-4-oxo-3,4-dihydro-quinazolin-2-yl)-1H-pyrazole-4-carboxylic acid;
1-(7-Trifluoromethyl-4-oxo-3,4-dihydro-quinazolin-2-yl)-1H-pyrazole-4-carboxylic acid;
1-(6,7-Dichloro-4-oxo-3,4-dihydro-quinazolin-2-yl)-1H-pyrazole-4-carboxylic acid;
1-(6-Fluoro-4-oxo-3,4-dihydro-quinazolin-2-yl)-1H-pyrazole-4-carboxylic acid;
1-(6,7-Difluoro-4-oxo-3,4-dihydro-quinazolin-2-yl)-1H-pyrazole-4-carboxylic acid;
1-(5-Chloro-4-oxo-3,4-dihydro-quinazolin-2-yl)-1H-pyrazole-4-carboxylic acid;
1-(8-Methoxy-4-oxo-3,4-dihydro-quinazolin-2-yl)-1H-pyrazole-4-carboxylic acid;
1-(6-Methyl-4-oxo-3,4-dihydro-quinazolin-2-yl)-1H-pyrazole-4-carboxylic acid;
1-(8-Methyl-4-oxo-3,4-dihydro-quinazolin-2-yl)-1H-pyrazole-4-carboxylic acid;
1-(7-Methyl-4-oxo-3,4-dihydro-quinazolin-2-yl)-1H-pyrazole-4-carboxylic acid;
1-(8-Bromo-4-oxo-3,4-dihydro-quinazolin-2-yl)-1H-pyrazole-4-carboxylic acid;
1-(6-Iodo-4-oxo-3,4-dihydro-quinazolin-2-yl)-1H-pyrazole-4-carboxylic acid;
1-(6-Bromo-4-oxo-3,4-dihydro-quinazolin-2-yl)-1H-pyrazole-4-carboxylic acid;
1-(8-Chloro-4-oxo-3,4-dihydro-quinazolin-2-yl)-1H-pyrazole-4-carboxylic acid;
1-(4-Oxo-6-trifluoromethoxy-3,4-dihydro-quinazolin-2-yl)-1H-pyrazole-4-carboxylic acid;
1-(4-Oxo-8-trifluoromethyl-3,4-dihydro-quinazolin-2-yl)-1H-pyrazole-4-carboxylic acid;
1-(6,7-Dimethoxy-4-oxo-3,4-dihydro-quinazolin-2-yl)-1H-pyrazole-4-carboxylic acid;
1-(5,6,7-Trimethoxy-4-oxo-3,4-dihydro-quinazolin-2-yl)-1H-pyrazole-4-carboxylic acid
1-(6-tert-Butyl-4-oxo-3,4-dihydro-quinazolin-2-yl)-1H-pyrazole-4-carboxyl is acid;
1-(4-Oxo-6-phenoxy-3,4-dihydro-quinazolin-2-yl)-1H-pyrazole-4-carboxylic acid;
1-(6-Cyclohexyl-4-oxo-3,4-dihydro-quinazolin-2-yl)-1H-pyrazole-4-carboxylic acid;
1-(7-Chloro-4-oxo-6-trifluoromethoxy-3,4-dihydro-quinazolin-2-yl)-1H-pyrazole-4-carboxylic acid;
1-(1-Oxo-2,7-dihydro-1H-pyrrolo[3,2-f]quinazolin-3-yl)-1H-pyrazole-4-carboxylic acid;
1-[6-(4-tert-Butyl-phenylsulfanyl)-7-chloro-4-oxo-1,4-dihydro-quinazolin-2-yl]-1H-pyrazole-4-carboxylic acid;
1-(7-Chloro-4-oxo-6-phenylsulfanyl-1,4-dihydro-quinazolin-2-yl)-1H-pyrazole-4-carboxylic acid;
1-[7-Chloro-6-(3,4-dimethoxy-phenylsulfanyl)-4-oxo-1,4-dihydro-quinazolin-2-yl]-1H-pyrazole-4-carboxylic acid;
1-[6-(2,6-Dimethyl-phenoxy)-7-methyl-4-oxo-3,4-dihydro-quinazolin-2-yl]-1H-pyrazole-4-carboxylic acid;
1-[4-Oxo-6-(3,4,5-trimethoxy-phenoxy)-3,4-dihydro-quinazolin-2-yl]-1H-pyrazole-4-carboxylic acid;
1-[6-(naphthalen-1-yloxy)-4-oxo-3,4-dihydro-quinazolin-2-yl]-1H-pyrazole-4-carboxylic acid;
1-[6-(3-Chloro-phenoxy)-4-oxo-3,4-dihydro-quinazolin-2-yl]-1H-pyrazole-4-carboxylic acid;
1-[6-(3-Methoxy-phenoxy)-4-oxo-3,4-dihydro-quinazolin-2-yl]-1H-pyrazole-4-carboxylic acid;
1-[6-(4-Fluoro-phenoxy)-4-oxo-3,4-dihydro-quinazolin-2-yl]-1H-pyrazole-4-carboxylic acid;
1-[6-(2-Fluoro-phenoxy)-4-oxo-3,4-dihydro-quinazolin-2-yl]-1H-pyrazole-4-carboxylic acid;
1-[6-(3-Fluoro-phenoxy)-4-oxo-3,4-dihydro-quinazolin-2-yl]-1H-pyrazole-4-carboxylic acid;
1-[6-(3,5-Di-tert-butyl-phenoxy)-4-oxo-3,4-dihydro-quinazolin-2-yl]-1H-pyrazole-4-carboxylic acid;
1-(4-Oxo-6-m-tolyloxy-3,4-dihydro-quinazolin-2-yl)-1H-pyrazole-4-carboxylic acid;
1-(4-Oxo-6-o-tolyloxy-3,4-dihydro-quinazolin-2-yl)-1H-pyrazole-4-carboxylic acid;
1-[6-(2,6-Dichloro-phenoxy)-4-oxo-3,4-dihydro-quinazolin-2-yl]-1H-pyrazole-4-carboxylic acid;
1-[6-(2,4-Dichloro-phenoxy)-4-oxo-3,4-dihydro-quinazolin-2-yl]-1H-pyrazole-4-carboxylic acid;
1-[6-(2,5-Dichloro-phenoxy)-4-oxo-3,4-dihydro-quinazolin-2-yl]-1H-pyrazole-4-carboxylic acid;
1-[6-(4-Methoxy-phenoxy)-4-oxo-3,4-dihydro-quinazolin-2-yl]-1H-pyrazole-4-carboxylic acid;
1-[6-(2,6-Dimethyl-phenoxy)-4-oxo-3,4-dihydro-quinazolin-2-yl]-1H-pyrazole-4-carboxylic acid;
1-[6-(Naphthalen-2-yloxy)-4-oxo-3,4-dihydro-quinazolin-2-yl]-1H-pyrazole-4-carboxylic acid;
1-[4-Oxo-6-(5,6,7,8-tetrahydro-naphthalen-1-yloxy)-3,4-dihydro-quinazolin-2-yl]-1H-pyrazole-4-carboxylic acid;
1-(4-Oxo-6-phenoxy-3,4-dihydro-quinazolin-2-yl)-1H-pyrazole-4-carboxylic acid;
1-[6-(4-Chloro-phenoxy)-4-oxo-3,4-dihydro-quinazolin-2-yl]-1H-pyrazole-4-carboxylic acid;
1-(4-Oxo-6-p-tolyloxy-3,4-dihydro-quinazolin-2-yl)-1H-pyrazole-4-carboxylic acid;
1-[7-Chloro-6-(4-chloro-phenoxy)-4-oxo-3,4-dihydro-quinazolin-2-yl]-1H-pyrazole-4-carboxylic acid;
1-[7-Chloro-6-(2,6-dimethyl-phenoxy)-4-oxo-3,4-dihydro-quinazolin-2-yl]-1H-pyrazole-4-carboxylic acid;
1-[6-(2,6-Dichloro-phenoxy)-7-fluoro-4-oxo-3,4-dihydro-quinazolin-2-yl]-1H-pyrazole-4-carboxylic acid;
1-[6-(2,6-Dimethyl-phenoxy)-7-fluoro-4-oxo-3,4-dihydro-quinazolin-2-yl]-1H-pyrazole-4-carboxylic acid;
1-[7-Fluoro-6-(naphthalen-2-yloxy)-4-oxo-3,4-dihydro-quinazolin-2-yl]-1H-pyrazole-4-carboxylic acid;
1-[7-Chloro-6-(naphthalen-1-yloxy)-4-oxo-3,4-dihydro-quinazolin-2-yl]-1H-pyrazole-4-carboxylic acid;

1-[7-Chloro-6-(naphthalen-2-yloxy)-4-oxo-3,4-dihydro-quinazolin-2-yl]-1H-pyrazole-4-carboxylic acid;
1-[7-Chloro-4-oxo-6-(5,6,7,8-tetrahydro-naphthalen-1-yloxy)-3,4-dihydro-quinazolin-2-yl]-1H-pyrazole-4-carboxylic acid;
1-[7-Fluoro-6-(3-fluoro-phenoxy)-4-oxo-3,4-dihydro-quinazolin-2-yl]-1H-pyrazole-4-carboxylic acid;
1-[7-Fluoro-6-(naphthalen-1-yloxy)-4-oxo-3,4-dihydro-quinazolin-2-yl]-1H-pyrazole-4-carboxylic acid;
1-[7-Fluoro-6-(indan-5-yloxy)-4-oxo-3,4-dihydro-quinazolin-2-yl]-1H-pyrazole-4-carboxylic acid;
1-(7-Methyl-4-oxo-6-phenoxy-3,4-dihydro-quinazolin-2-yl)-1H-pyrazole-4-carboxylic acid;
1-[6-(2,3-dichloro-phenoxy)-4-oxo-3,4-dihydro-quinazolin-2-yl]-1H-pyrazole-4-carboxylic acid;
1-[6-(2,6-Dimethyl-phenoxy)-7-methoxy-4-oxo-3,4-dihydro-quinazolin-2-yl]-1H-pyrazole-4-carboxylic acid;
1-(7-Methoxy-4-oxo-6-phenoxy-3,4-dihydro-quinazolin-2-yl)-1H-pyrazole-4-carboxylic acid;
1-[6-(2,6-Dimethyl-phenoxy)-5,7-difluoro-4-oxo-3,4-dihydro-quinazolin-2-yl]-1H-pyrazole-4-carboxylic acid;
1-(5,7-Difluoro-4-oxo-6-phenoxy-3,4-dihydro-quinazolin-2-yl)-1H-pyrazole-4-carboxylic acid;
1-[4-Oxo-6-(pyridin-3-yloxy)-3,4-dihydro-quinazolin-2-yl]-1H-pyrazole-4-carboxylic acid;
1-(4-Oxo-7-phenoxy-3,4-dihydro-quinazolin-2-yl)-1H-pyrazole-4-carboxylic acid;
1-[4-Oxo-7-(tetrahydro-pyran-4-yl)-3,4-dihydro-quinazolin-2-yl]-1H-pyrazole-4-carboxylic acid tris(hydroxymethyl)aminomethane salt;
1-(7-Chloro-4-oxo-6-phenyl-3,4-dihydro-quinazolin-2-yl)-1H-pyrazole-4-carboxylic acid;
1-(4-Oxo-6-o-tolyl-3,4-dihydro-quinazolin-2-yl)-1H-pyrazole-4-carboxylic acid;
1-(6-Biphenyl-3-yl-4-oxo-3,4-dihydro-quinazolin-2-yl)-1H-pyrazole-4-carboxylic acid;
1-[7-Chloro-6-(3,4-dimethoxy-benzenesulfonyl)-4-oxo-3,4-dihydro-quinazolin-2-yl]-1H-pyrazole-4-carboxylic acid;
1-[6-(4-tert-Butyl-benzenesulfonyl)-7-chloro-4-oxo-3,4-dihydro-quinazolin-2-yl]-1H-pyrazole-4-carboxylic acid;
1-(7,7-Dimethyl-4-oxo-3,7-dihydro-4H-8-oxa-1,3-diaza-anthracen-2-yl)-1H-pyrazole-4-carboxylic acid;
1-(4-Oxo-6-phenoxymethyl-3,4-dihydro-quinazolin-2-yl)-1H-pyrazole-4-carboxylic acid;
1-[6-(2,6-Dimethyl-phenoxymethyl)-4-oxo-3,4-dihydro-quinazolin-2-yl]-1H-pyrazole-4-carboxylic acid;
1-(6-Ethynyl-4-oxo-3,4-dihydro-quinazolin-2-yl)-1H-pyrazole-4-carboxylic acid;
1-[6-(1-Chloro-vinyl)-4-oxo-3,4-dihydro-quinazolin-2-yl]-1H-pyrazole-4-carboxylic acid;
1-(4-Oxo-7-phenylsulfanyl-3,4-dihydro-quinazolin-2-yl)-1H-pyrazole-4-carboxylic acid;
1-[7-(4-Chloro-phenylsulfanyl)-4-oxo-3,4-dihydro-quinazolin-2-yl]-1H-pyrazole-4-carboxylic acid;
1-[7-(2-Chloro-phenylsulfanyl)-4-oxo-3,4-dihydro-quinazolin-2-yl]-1H-pyrazole-4-carboxylic acid;
1-(7-Benzenesulfonyl-4-oxo-3,4-dihydro-quinazolin-2-yl)-1H-pyrazole-4-carboxylic acid;
1-[7-(4-Chloro-benzenesulfonyl)-4-oxo-3,4-dihydro-quinazolin-2-yl]-1H-pyrazole-4-carboxylic acid;
1-[7-(2-Chloro-benzenesulfonyl)-4-oxo-3,4-dihydro-quinazolin-2-yl]-1H-pyrazole-4-carboxylic acid;
1-[7-Chloro-6-(3,4-dihydro-1H-isoquinolin-2-yl)-4-oxo-3,4-dihydro-quinazolin-2-yl]-1H-pyrazole-4-carboxylic acid;
1-[6-(7-Bromo-3,4-dihydro-1H-isoquinolin-2-yl)-7-chloro-4-oxo-3,4-dihydro-quinazolin-2-yl]-1H-pyrazole-4-carboxylic acid;
(rac)-1-{7-Chloro-6-[3-(3-methoxy-phenyl)-piperidin-1-yl]-4-oxo-3,4-dihydro-quinazolin-2-yl}-1H-pyrazole-4-carboxylic acid;
1-[6-(2,5-dichloro-phenoxy)-7-fluoro-4-oxo-3,4-dihydro-quinazolin-2-yl]-1H-pyrazole-4-carboxylic acid;
1-[6-(3,4-dimethyl-phenoxy)-7-fluoro-4-oxo-3,4-dihydro-quinazolin-2-yl]-1H-pyrazole-4-carboxylic acid;
1-[6-(3,5-dimethyl-phenoxy)-7-methyl-4-oxo-3,4-dihydro-quinazolin-2-yl]-1H-pyrazole-4-carboxylic acid;
1-[6-(2,5-dichloro-phenoxy)-7-methyl-4-oxo-3,4-dihydro-quinazolin-2-yl]-1H-pyrazole-4-carboxylic acid;
1-[6-(biphenyl-3-yloxy)-7-methyl-4-oxo-3,4-dihydro-quinazolin-2-yl]-1H-pyrazole-4-carboxylic acid;
1-[6-(3,4-dimethyl-phenoxy)-7-methyl-4-oxo-3,4-dihydro-quinazolin-2-yl]-1H-pyrazole-4-carboxylic acid;
1-[7-methyl-4-oxo-6-(3-trifluoromethyl-phenoxy)-3,4-dihydro-quinazolin-2-yl]-1H-pyrazole-4-carboxylic acid;
1-[6-(3,5-dimethyl-phenoxy)-7-fluoro-4-oxo-3,4-dihydro-quinazolin-2-yl]-1H-pyrazole-4-carboxylic acid;
1-[7-fluoro-4-oxo-6-(3-trifluoromethyl-phenoxy)-3,4-dihydro-quinazolin-2-yl]-1H-pyrazole-4-carboxylic acid;
1-[6-(2-fluoro-3-trifluoromethyl-phenoxy)-4-oxo-3,4-dihydro-quinazolin-2-yl]-1H-pyrazole-4-carboxylic acid;
1-[6-(3-fluoro-5-trifluoromethyl-phenoxy)-4-oxo-3,4-dihydro-quinazolin-2-yl]-1H-pyrazole-4-carboxylic acid;
1-[6-(3,5-dimethyl-phenoxy)-4-oxo-3,4-dihydro-quinazolin-2-yl]-1H-pyrazole-4-carboxylic acid;
1-[6-(biphenyl-3-yloxy)-4-oxo-3,4-dihydro-quinazolin-2-yl]-1H-pyrazole-4-carboxylic acid;
1-[4-oxo-6-(3-trifluoromethyl-phenoxy)-3,4-dihydro-quinazolin-2-yl]-1H-pyrazole-4-carboxylic acid;
1-[6-(2,6-dichloro-phenoxy)-5,7-difluoro-4-oxo-3,4-dihydro-quinazolin-2-yl]-1H-pyrazole-4-carboxylic acid;
1-(6-cyclohexyloxy-4-oxo-3,4-dihydro-quinazolin-2-yl)-1H-pyrazole-4-carboxylic acid;
1-[6-(4-methyl-piperazin-1-yl)-4-oxo-3,4-dihydro-quinazolin-2-yl]-1H-pyrazole-4-carboxylic acid;
1-(6-isopropoxy-4-oxo-3,4-dihydro-quinazolin-2-yl)-1H-pyrazole-4-carboxylic acid;
1-(6-benzyl-4-oxo-3,4-dihydro-quinazolin-2-yl)-1H-pyrazole-4-carboxylic acid;
1-(4-oxo-6-phenyl-3,4-dihydro-quinazolin-2-yl)-1H-pyrazole-4-carboxylic acid;
1-(6-morpholin-4-yl-4-oxo-3,4-dihydro-quinazolin-2-yl)-1H-pyrazole-4-carboxylic acid;
1-[6-(1H-Indol-6-yl)-4-oxo-3,4-dihydro-quinazolin-2-yl]-1H-pyrazole-4-carboxylic acid;
1-(6-Cyclopropyl-4-oxo-3,4-dihydro-quinazolin-2-yl)-1H-pyrazole-4-carboxylic acid;
1-(6-Cyclohexyl-7-fluoro-4-oxo-3,4-dihydro-quinazolin-2-yl)-1H-pyrazole-4-carboxylic acid;
1-(4-Oxo-8-phenyl-3,4-dihydro-quinazolin-2-yl)-1H-pyrazole-4-carboxylic acid;
1-(4-Oxo-8-phenoxy-3,4-dihydro-quinazolin-2-yl)-1H-pyrazole-4-carboxylic acid;
1-(4-Oxo-8-phenylsulfanyl-3,4-dihydro-quinazolin-2-yl)-1H-pyrazole-4-carboxylic acid;
1-(8-Isopropyl-4-oxo-3,4-dihydro-quinazolin-2-yl)-1H-pyrazole-4-carboxylic acid;
1-(8-tert-Butyl-4-oxo-3,4-dihydro-quinazolin-2-yl)-1H-pyrazole-4-carboxyl is acid;
1-(5,8-Difluoro-4-oxo-3,4-dihydro-quinazolin-2-yl)-1H-pyrazole-4-carboxylic acid;

1-(4-Oxo-8-trifluoromethoxy-3,4-dihydro-quinazolin-2-yl)-1H-pyrazole-4-carboxylic acid;
1-(8-Fluoro-4-oxo-3,4-dihydro-quinazolin-2-yl)-1H-pyrazole-4-carboxylic acid;
1-(6-Isopropyl-4-oxo-3,4-dihydro-quinazolin-2-yl)-1H-pyrazole-4-carboxylic acid;
1-(6-sec-Butyl-4-oxo-3,4-dihydro-quinazolin-2-yl)-1H-pyrazole-4-carboxylic acid;
1-(6-Ethoxy-4-oxo-3,4-dihydro-quinazolin-2-yl)-1H-pyrazole-4-carboxylic acid;
1-(6-Methoxy-4-oxo-3,4-dihydro-quinazolin-2-yl)-1H-pyrazole-4-carboxylic acid;
1-(4-Oxo-6-pyrrolidin-1-yl-3,4-dihydro-quinazolin-2-yl)-1H-pyrazole-4-carboxylic acid;
1-(4-Oxo-6-piperidin-1-yl-3,4-dihydro-quinazolin-2-yl)-1H-pyrazole-4-carboxylic acid;
1-(6-Dimethylamino-4-oxo-3,4-dihydro-quinazolin-2-yl)-1H-pyrazole-4-carboxylic acid;
1-(4-Oxo-3,4-dihydro-quinazolin-2-yl)-1H-pyrazole-4-carboxylic acid;
1-(6-Bromo-7-fluoro-4-oxo-3,4-dihydro-quinazolin-2-yl)-1H-pyrazole-4-carboxylic acid;
1-(6-Ethyl-4-oxo-3,4-dihydro-quinazolin-2-yl)-1H-pyrazole-4-carboxylic acid;
1-(4-Oxo-6-propyl-3,4-dihydro-quinazolin-2-yl)-1H-pyrazole-4-carboxylic acid;
1-(6-Bromo-8-fluoro-4-oxo-3,4-dihydro-quinazolin-2-yl)-1H-pyrazole-4-carboxylic acid;
1-(5,7-Difluoro-4-oxo-3,4-dihydro-quinazolin-2-yl)-1H-pyrazole-4-carboxylic acid;
1-(5,7-Dichloro-4-oxo-3,4-dihydro-quinazolin-2-yl)-1H-pyrazole-4-carboxylic acid;
1-(7-Fluoro-4-oxo-3,4-dihydro-quinazolin-2-yl)-1H-pyrazole-4-carboxylic acid;
1-(7-Bromo-4-oxo-3,4-dihydro-quinazolin-2-yl)-1H-pyrazole-4-carboxylic acid;
1-(7-Methoxy-4-oxo-3,4-dihydro-quinazolin-2-yl)-1H-pyrazole-4-carboxylic acid;
1-(7-Benzyl-4-oxo-3,4-dihydro-quinazolin-2-yl)-1H-pyrazole-4-carboxylic acid;
1-(4-Oxo-3,4,8,9-tetrahydro-7H-6,10-dioxa-1,3-diaza-cyclohepta[b]naphthalen-2-yl)-1H-pyrazole-4-carboxylic acid;
1-(8-Oxo-2,3,7,8-tetrahydro-1,4-dioxa-5,7-diaza-phenanthren-6-yl)-1H-pyrazole-4-carboxylic acid;
1-(4-Oxo-3,4,7,8-tetrahydro-[1,4]dioxino[2,3-g]quinazolin-2-yl)-1H-pyrazole-4-carboxylic acid;
1-(4-Oxo-4,6,7,8-tetrahydro-3H-cyclopenta[g]quinazolin-2-yl)-1H-pyrazole-4-carboxylic acid;
1-(6-Oxo-2,3,6,7-tetrahydro-1H-7,9-diaza-cyclopenta[a]naphthalen-8-yl)-1H-pyrazole-4-carboxylic acid;
1-(4-Oxo-3,4,7,8,9,10-hexahydro-benzo[h]quinazolin-2-yl)-1H-pyrazole-4-carboxylic acid;
1-(4-Oxo-3,4,6,7,8,9-hexahydro-benzo[g]quinazolin-2-yl)-1H-pyrazole-4-carboxylic acid;
1-(1-Oxo-1,2,7,8,9,10-hexahydro-benzo[f]quinazolin-3-yl)-1H-pyrazole-4-carboxylic acid;
1-(5,7-Dimethyl-4-oxo-3,4-dihydro-quinazolin-2-yl)-1H-pyrazole-4-carboxylic acid;
1-(7-Isopropyl-4-oxo-3,4-dihydro-quinazolin-2-yl)-1H-pyrazole-4-carboxylic acid;
1-(7-tert-Butyl-4-oxo-3,4-dihydro-quinazolin-2-yl)-1H-pyrazole-4-carboxyl is acid;
1-(4-Oxo-7-trifluoromethoxy-3,4-dihydro-quinazolin-2-yl)-1H-pyrazole-4-carboxylic acid;
1-(7-Isopropoxy-4-oxo-3,4-dihydro-quinazolin-2-yl)-1H-pyrazole-4-carboxylic acid;
1-(7-Dimethylamino-4-oxo-3,4-dihydro-quinazolin-2-yl)-1H-pyrazole-4-carboxylic acid;
1-(5-Dimethylamino-4-oxo-3,4-dihydro-quinazolin-2-yl)-1H-pyrazole-4-carboxylic acid;
1-(7-Ethoxy-4-oxo-3,4-dihydro-quinazolin-2-yl)-1H-pyrazole-4-carboxylic acid;
1-(6-Chloro-4-oxo-3,4-dihydro-quinazolin-2-yl)-1H-pyrazole-4-carboxylic acid;
1-(7-Hydroxy-4-oxo-3,4-dihydro-quinazolin-2-yl)-1H-pyrazole-4-carboxylic acid;
1-(6-Methylsulfanyl-4-oxo-3,4-dihydro-quinazolin-2-yl)-1H-pyrazole-4-carboxylic acid;
1-(4-Oxo-6-trifluoromethylsulfanyl-3,4-dihydro-quinazolin-2-yl)-1H-pyrazole-4-carboxylic acid;
1-(6-Methanesulfonyl-4-oxo-3,4-dihydro-quinazolin-2-yl)-1H-pyrazole-4-carboxylic acid;
1-(7-Chloro-6-methylsulfanyl-4-oxo-3,4-dihydro-quinazolin-2-yl)-1H-pyrazole-4-carboxylic acid;
1-(7-Chloro-4-oxo-6-trifluoromethylsulfanyl-3,4-dihydro-quinazolin-2-yl)-1H-pyrazole-4-carboxylic acid;
1-(7-Chloro-4-oxo-6-trifluoromethanesulfinyl-3,4-dihydro-quinazolin-2-yl)-1H-pyrazole-4-carboxylic acid;
1-[4-Oxo-6-(pyrrolidine-1-sulfonyl)-3,4-dihydro-quinazolin-2-yl]-1H-pyrazole-4-carboxylic acid;
1-[4-Oxo-6-(pyrrolidine-1-carbonyl)-3,4-dihydro-quinazolin-2-yl]-1H-pyrazole-4-carboxylic acid;
1-[6-(2,6-Dimethyl-phenylcarbamoyl)-4-oxo-3,4-dihydro-quinazolin-2-yl]-1H-pyrazole-4-carboxylic acid;
1-(6-Nitro-4-oxo-3,4-dihydro-quinazolin-2-yl)-1H-pyrazole-4-carboxylic acid
1-(6-Benzoylamino-4-oxo-3,4-dihydro-quinazolin-2-yl)-1H-pyrazole-4-carboxylic acid;
1-[6-(2,6-Dimethyl-benzoylamino)-4-oxo-3,4-dihydro-quinazolin-2-yl]-1H-pyrazole-4-carboxylic acid;
1-(6-Acetylamino-4-oxo-3,4-dihydro-quinazolin-2-yl)-1H-pyrazole-4-carboxylic acid;
1-[4-Oxo-6-(3-phenyl-ureido)-3,4-dihydro-quinazolin-2-yl]-1H-pyrazole-4-carboxylic acid;
1-(6-Benzenesulfonylamino-4-oxo-3,4-dihydro-quinazolin-2-yl)-1H-pyrazole-4-carboxylic acid;
1-(6-Methanesulfonylamino-4-oxo-3,4-dihydro-quinazolin-2-yl)-1H-pyrazole-4-carboxylic acid;
1-(6-Benzylamino-4-oxo-3,4-dihydro-quinazolin-2-yl)-1H-pyrazole-4-carboxylic acid;
1-(6-Ethylamino-4-oxo-3,4-dihydro-quinazolin-2-yl)-1H-pyrazole-4-carboxylic acid;
1-[6-(2-Methyl-benzylamino)-4-oxo-3,4-dihydro-quinazolin-2-yl]-1H-pyrazole-4-carboxylic acid;
1-[6-(2-Chloro-benzylamino)-4-oxo-3,4-dihydro-quinazolin-2-yl]-1H-pyrazole-4-carboxylic acid;
1-[6-(2,6-Dimethyl-benzylamino)-4-oxo-3,4-dihydro-quinazolin-2-yl]-1H-pyrazole-4-carboxylic acid;
1-[6-(2,6-Difluoro-benzylamino)-4-oxo-3,4-dihydro-quinazolin-2-yl]-1H-pyrazole-4-carboxylic acid;
1-[6-(2-Cyano-benzylamino)-4-oxo-3,4-dihydro-quinazolin-2-yl]-1H-pyrazole-4-carboxylic acid;
1-[6-(3-Cyano-benzylamino)-4-oxo-3,4-dihydro-quinazolin-2-yl]-1H-pyrazole-4-carboxylic acid;
1-[6-(3-Carbamoyl-benzylamino)-4-oxo-3,4-dihydro-quinazolin-2-yl]-1H-pyrazole-4-carboxylic acid;
1-[6-amino-4-oxo-3,4-dihydro-quinazolin-2-yl]-1H-pyrazole-4-carboxylic acid;
1-[6-(2,6-Dichloro-benzylamino)-4-oxo-3,4-dihydro-quinazolin-2-yl]-1H-pyrazole-4-carboxylic acid;
1-[6-(3-Chloro-benzylamino)-4-oxo-3,4-dihydro-quinazolin-2-yl]-1H-pyrazole-4-carboxylic acid;

1-[6-(4-methyl-benzylamino)-4-oxo-3,4-dihydro-quinazolin-2-yl]-1H-pyrazole-4-carboxylic acid;
1-(4-Oxo-7-phenyl-3,4-dihydro-quinazolin-2-yl)-1H-pyrazole-4-carboxylic acid;
1-[7-(2-Chloro-phenyl)-4-oxo-3,4-dihydro-quinazolin-2-yl]-1H-pyrazole-4-carboxylic acid;
1-[7-(3-Chloro-phenyl)-4-oxo-3,4-dihydro-quinazolin-2-yl]-1H-pyrazole-4-carboxylic acid;
1-[7-(4-Chloro-phenyl)-4-oxo-3,4-dihydro-quinazolin-2-yl]-1H-pyrazole-4-carboxylic acid;
1-(4-Oxo-7-o-tolyl-3,4-dihydro-quinazolin-2-yl)-1H-pyrazole-4-carboxylic acid;
1-(4-Oxo-7-m-tolyl-3,4-dihydro-quinazolin-2-yl)-1H-pyrazole-4-carboxylic acid;
1-(4-Oxo-6-m-tolyl-3,4-dihydro-quinazolin-2-yl)-1H-pyrazole-4-carboxylic acid;
1-(4-Oxo-6-p-tolyl-3,4-dihydro-quinazolin-2-yl)-1H-pyrazole-4-carboxylic acid;
1-[6-(2-Chloro-phenyl)-4-oxo-3,4-dihydro-quinazolin-2-yl]-1H-pyrazole-4-carboxylic acid;
1-[6-(3-Chloro-phenyl)-4-oxo-3,4-dihydro-quinazolin-2-yl]-1H-pyrazole-4-carboxylic acid;
1-[6-(4-Chloro-phenyl)-4-oxo-3,4-dihydro-quinazolin-2-yl]-1H-pyrazole-4-carboxylic acid;
1-[6-(2-Fluoro-phenyl)-4-oxo-3,4-dihydro-quinazolin-2-yl]-1H-pyrazole-4-carboxylic acid;
1-[6-(3-Fluoro-phenyl)-4-oxo-3,4-dihydro-quinazolin-2-yl]-1H-pyrazole-4-carboxylic acid;
1-[6-(4-Fluoro-phenyl)-4-oxo-3,4-dihydro-quinazolin-2-yl]-1H-pyrazole-4-carboxylic acid;
1-[6-(2-Methoxy-phenyl)-4-oxo-3,4-dihydro-quinazolin-2-yl]-1H-pyrazole-4-carboxylic acid;
1-[6-(3-Methoxy-phenyl)-4-oxo-3,4-dihydro-quinazolin-2-yl]-1H-pyrazole-4-carboxylic acid;
1-[6-(4-Methoxy-phenyl)-4-oxo-3,4-dihydro-quinazolin-2-yl]-1H-pyrazole-4-carboxylic acid;
1-[4-Oxo-6-(2-trifluoromethyl-phenyl)-3,4-dihydro-quinazolin-2-yl]-1H-pyrazole-4-carboxylic acid;
1-[4-Oxo-6-(2-trifluoromethoxy-phenyl)-3,4-dihydro-quinazolin-2-yl]-1H-pyrazole-4-carboxylic acid;
1-[6-(2-Ethyl-phenyl)-4-oxo-3,4-dihydro-quinazolin-2-yl]-1H-pyrazole-4-carboxylic acid;
1-[6-(2,3-Dihydro-benzo[1,4]dioxin-5-yl)-4-oxo-3,4-dihydro-quinazolin-2-yl]-1H-pyrazole-4-carboxylic acid;
1-[4-Oxo-6-(3-trifluoromethoxy-phenyl)-3,4-dihydro-quinazolin-2-yl]-1H-pyrazole-4-carboxylic acid;
1-[6-(3-Methanesulfonyl-phenyl)-4-oxo-3,4-dihydro-quinazolin-2-yl]-1H-pyrazole-4-carboxylic acid;
1-(6-Benzo[1,3]dioxol-5-yl-4-oxo-3,4-dihydro-quinazolin-2-yl)-1H-pyrazole-4-carboxylic acid;
1-(7-Iodo-4-oxo-3,4-dihydro-quinazolin-2-yl)-1H-pyrazole-4-carboxylic acid;
1-(6-Benzenesulfinyl-7-chloro-4-oxo-3,4-dihydro-quinazolin-2-yl)-1H-pyrazole-4-carboxylic acid;
1-(6-Benzenesulfonyl-7-chloro-4-oxo-3,4-dihydro-quinazolin-2-yl)-1H-pyrazole-4-carboxylic acid; and
1-(4-Oxo-7-piperidin-1-yl-3,4-dihydro-quinazolin-2-yl)-1H-pyrazole-4-carboxylic acid; or a pharmaceutically acceptable salt thereof.

12. A pharmaceutical composition comprising a pharmaceutically acceptable excipient and an effective amount of a compound having PHD inhibitor activity of formula (I):

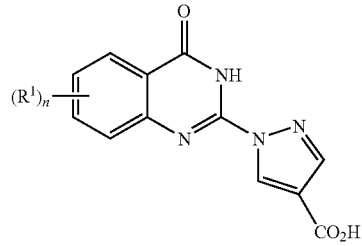

wherein:
n is 1-3
$R^1$ is a member independently selected from the group consisting of halo, —$C_{1-4}$alkyl, —$C_{2-4}$alkynyl, —$C_{2-4}$ alkenyl optionally substituted with halo, —$CF_3$, —$OCF_3$, —$SCF_3$, $S(O)CF_3$, —C(O)—$R^c$, —OH, —$NO_2$, —CN, —$OC_{1-4}$alkyl, —$SC_{1-4}$alkyl, —S(O)—$C_{1-4}$alkyl, —$SO_2$—$C_{1-4}$alkyl, —S—$R^c$, —S(O)—$R^c$, —$SO_2$—$R^c$, —O—$R^c$, —$NR^aR^b$, 2,3-dihydro-benzo[1,4]dioxine, benzo[1,3]dioxole, 1H-indole, benzyl, biphenyl optionally substituted with one or more $R^d$ members, benzyloxy optionally substituted with one or more $R^d$ members, phenyl or monocyclic heteroaryl optionally substituted with one or more $R^d$ members, and —$C_{3-8}$cycloalkyl optionally substituted with one or more $R^d$ members;
$R^a$ and $R^b$ are independently selected from the group consisting of H, $C_{1-4}$alkyl, —C(O)$C_{1-4}$alkyl, —C(O)—$R^c$, —C(O)NH—$R^c$, —$SO_2$—$R^c$, —$SO_2$—$C_{1-4}$alkyl, phenyl optionally substituted with $R^d$, benzyl optionally substituted with $R^d$ or monocyclic heteroaryl ring optionally substituted with $R^d$; or $R^a$ and $R^b$ can be taken together with the nitrogen to which they are attached to form a monocyclic heterocycloalkyl ring containing one or more O, S or N optionally substituted with methyl or methoxyphenyl;
$R^c$ is a member independently selected from the group consisting of —$C_{3-8}$cycloalkyl, —$C_{3-8}$heterocycloalkyl, biphenyl, phenyl optionally substituted with one or more $R^d$ members, benzyl optionally substituted with $R^d$, naphthyl, indanyl, 5,6,7,8-tetrahydronaphthyl, and pyridyl optionally substituted with one or more $R^d$ members;
$R^d$ is a member independently selected from the group consisting of —H, halo, —OH, —$C_{1-4}$alkyl, —$SO_2$—$C_{1-4}$alkyl, —CN, —$CF_3$, —$OCF_3$, —$OC_{1-4}$alkyl, —C(O)$NH_2$, —O-phenyl, and —O-benzyl;
or an enantiomer, diastereomer, racemate, or pharmaceutically acceptable salt thereof.

13. A pharmaceutical composition comprising a pharmaceutically acceptable excipient and a compound selected from the group consisting of:
1-(7-Chloro-4-oxo-3,4-dihydro-quinazolin-2-yl)-1H-pyrazole-4-carboxylic acid;
1-(7-Trifluoromethyl-4-oxo-3,4-dihydro-quinazolin-2-yl)-1H-pyrazole-4-carboxylic acid;
1-(6,7-Dichloro-4-oxo-3,4-dihydro-quinazolin-2-yl)-1H-pyrazole-4-carboxylic acid;
1-(6-Fluoro-4-oxo-3,4-dihydro-quinazolin-2-yl)-1H-pyrazole-4-carboxylic acid;
1-(6,7-Difluoro-4-oxo-3,4-dihydro-quinazolin-2-yl)-1H-pyrazole-4-carboxylic acid;

1-(5-Chloro-4-oxo-3,4-dihydro-quinazolin-2-yl)-1H-pyrazole-4-carboxylic acid;
1-(8-Methoxy-4-oxo-3,4-dihydro-quinazolin-2-yl)-1H-pyrazole-4-carboxylic acid;
1-(6-Methyl-4-oxo-3,4-dihydro-quinazolin-2-yl)-1H-pyrazole-4-carboxylic acid;
1-(8-Methyl-4-oxo-3,4-dihydro-quinazolin-2-yl)-1H-pyrazole-4-carboxylic acid;
1-(7-Methyl-4-oxo-3,4-dihydro-quinazolin-2-yl)-1H-pyrazole-4-carboxylic acid;
1-(8-Bromo-4-oxo-3,4-dihydro-quinazolin-2-yl)-1H-pyrazole-4-carboxylic acid;
1-(6-Iodo-4-oxo-3,4-dihydro-quinazolin-2-yl)-1H-pyrazole-4-carboxylic acid;
1-(6-Bromo-4-oxo-3,4-dihydro-quinazolin-2-yl)-1H-pyrazole-4-carboxylic acid;
1-(8-Chloro-4-oxo-3,4-dihydro-quinazolin-2-yl)-1H-pyrazole-4-carboxylic acid;
1-(4-Oxo-6-trifluoromethoxy-3,4-dihydro-quinazolin-2-yl)-1H-pyrazole-4-carboxylic acid;
1-(4-Oxo-8-trifluoromethyl-3,4-dihydro-quinazolin-2-yl)-1H-pyrazole-4-carboxylic acid;
1-(6,7-Dimethoxy-4-oxo-3,4-dihydro-quinazolin-2-yl)-1H-pyrazole-4-carboxylic acid;
1-(5,6,7-Trimethoxy-4-oxo-3,4-dihydro-quinazolin-2-yl)-1H-pyrazole-4-carboxylic acid
1-(6-tert-Butyl-4-oxo-3,4-dihydro-quinazolin-2-yl)-1H-pyrazole-4-carboxyl is acid;
1-(4-Oxo-6-phenoxy-3,4-dihydro-quinazolin-2-yl)-1H-pyrazole-4-carboxylic acid;
1-(6-Cyclohexyl-4-oxo-3,4-dihydro-quinazolin-2-yl)-1H-pyrazole-4-carboxylic acid;
1-(7-Chloro-4-oxo-6-trifluoromethoxy-3,4-dihydro-quinazolin-2-yl)-1H-pyrazole-4-carboxylic acid;
1-(1-Oxo-2,7-dihydro-1H-pyrrolo[3,2-f]quinazolin-3-yl)-1H-pyrazole-4-carboxylic acid;
1-[6-(4-tert-Butyl-phenylsulfanyl)-7-chloro-4-oxo-1,4-dihydro-quinazolin-2-yl]-1H-pyrazole-4-carboxylic acid;
1-(7-Chloro-4-oxo-6-phenylsulfanyl-1,4-dihydro-quinazolin-2-yl)-1H-pyrazole-4-carboxylic acid;
1-[7-Chloro-6-(3,4-dimethoxy-phenylsulfanyl)-4-oxo-1,4-dihydro-quinazolin-2-yl]-1H-pyrazole-4-carboxylic acid;
1-[6-(2,6-Dimethyl-phenoxy)-7-methyl-4-oxo-3,4-dihydro-quinazolin-2-yl]-1H-pyrazole-4-carboxylic acid;
1-[4-Oxo-6-(3,4,5-trimethoxy-phenoxy)-3,4-dihydro-quinazolin-2-yl]-1H-pyrazole-4-carboxylic acid;
1-[6-(naphthalen-1-yloxy)-4-oxo-3,4-dihydro-quinazolin-2-yl]-1H-pyrazole-4-carboxylic acid;
1-[6-(3-Chloro-phenoxy)-4-oxo-3,4-dihydro-quinazolin-2-yl]-1H-pyrazole-4-carboxylic acid;
1-[6-(3-Methoxy-phenoxy)-4-oxo-3,4-dihydro-quinazolin-2-yl]-1H-pyrazole-4-carboxylic acid;
1-[6-(4-Fluoro-phenoxy)-4-oxo-3,4-dihydro-quinazolin-2-yl]-1H-pyrazole-4-carboxylic acid;
1-[6-(2-Fluoro-phenoxy)-4-oxo-3,4-dihydro-quinazolin-2-yl]-1H-pyrazole-4-carboxylic acid;
1-[6-(3-Fluoro-phenoxy)-4-oxo-3,4-dihydro-quinazolin-2-yl]-1H-pyrazole-4-carboxylic acid;
1-[6-(3,5-Di-tert-butyl-phenoxy)-4-oxo-3,4-dihydro-quinazolin-2-yl]-1H-pyrazole-4-carboxylic acid;
1-(4-Oxo-6-m-tolyloxy-3,4-dihydro-quinazolin-2-yl)-1H-pyrazole-4-carboxylic acid;
1-(4-Oxo-6-o-tolyloxy-3,4-dihydro-quinazolin-2-yl)-1H-pyrazole-4-carboxylic acid;
1-[6-(2,6-Dichloro-phenoxy)-4-oxo-3,4-dihydro-quinazolin-2-yl]-1H-pyrazole-4-carboxylic acid;
1-[6-(2,4-Dichloro-phenoxy)-4-oxo-3,4-dihydro-quinazolin-2-yl]-1H-pyrazole-4-carboxylic acid;
1-[6-(2,5-Dichloro-phenoxy)-4-oxo-3,4-dihydro-quinazolin-2-yl]-1H-pyrazole-4-carboxylic acid;
1-[6-(4-Methoxy-phenoxy)-4-oxo-3,4-dihydro-quinazolin-2-yl]-1H-pyrazole-4-carboxylic acid;
1-[6-(2,6-Dimethyl-phenoxy)-4-oxo-3,4-dihydro-quinazolin-2-yl]-1H-pyrazole-4-carboxylic acid;
1-[6-(Naphthalen-2-yloxy)-4-oxo-3,4-dihydro-quinazolin-2-yl]-1H-pyrazole-4-carboxylic acid;
1-[4-Oxo-6-(5,6,7,8-tetrahydro-naphthalen-1-yloxy)-3,4-dihydro-quinazolin-2-yl]-1H-pyrazole-4-carboxylic acid;
1-(4-Oxo-6-phenoxy-3,4-dihydro-quinazolin-2-yl)-1H-pyrazole-4-carboxylic acid;
1-[6-(4-Chloro-phenoxy)-4-oxo-3,4-dihydro-quinazolin-2-yl]-1H-pyrazole-4-carboxylic acid;
1-(4-Oxo-6-p-tolyloxy-3,4-dihydro-quinazolin-2-yl)-1H-pyrazole-4-carboxylic acid;
1-[7-Chloro-6-(4-chloro-phenoxy)-4-oxo-3,4-dihydro-quinazolin-2-yl]-1H-pyrazole-4-carboxylic acid;
1-[7-Chloro-6-(2,6-dimethyl-phenoxy)-4-oxo-3,4-dihydro-quinazolin-2-yl]-1H-pyrazole-4-carboxylic acid;
1-[6-(2,6-Dichloro-phenoxy)-7-fluoro-4-oxo-3,4-dihydro-quinazolin-2-yl]-1H-pyrazole-4-carboxylic acid;
1-[6-(2,6-Dimethyl-phenoxy)-7-fluoro-4-oxo-3,4-dihydro-quinazolin-2-yl]-1H-pyrazole-4-carboxylic acid;
1-[7-Fluoro-6-(naphthalen-2-yloxy)-4-oxo-3,4-dihydro-quinazolin-2-yl]-1H-pyrazole-4-carboxylic acid;
1-[7-Chloro-6-(naphthalen-1-yloxy)-4-oxo-3,4-dihydro-quinazolin-2-yl]-1H-pyrazole-4-carboxylic acid;
1-[7-Chloro-6-(naphthalen-2-yloxy)-4-oxo-3,4-dihydro-quinazolin-2-yl]-1H-pyrazole-4-carboxylic acid;
1-[7-Chloro-4-oxo-6-(5,6,7,8-tetrahydro-naphthalen-1-yloxy)-3,4-dihydro-quinazolin-2-yl]-1H-pyrazole-4-carboxylic acid;
1-[7-Fluoro-6-(3-fluoro-phenoxy)-4-oxo-3,4-dihydro-quinazolin-2-yl]-1H-pyrazole-4-carboxylic acid;
1-[7-Fluoro-6-(naphthalen-1-yloxy)-4-oxo-3,4-dihydro-quinazolin-2-yl]-1H-pyrazole-4-carboxylic acid;
1-[7-Fluoro-6-(indan-5-yloxy)-4-oxo-3,4-dihydro-quinazolin-2-yl]-1H-pyrazole-4-carboxylic acid;
1-(7-Methyl-4-oxo-6-phenoxy-3,4-dihydro-quinazolin-2-yl)-1H-pyrazole-4-carboxylic acid;
1-[6-(2,3-dichloro-phenoxy)-4-oxo-3,4-dihydro-quinazolin-2-yl]-1H-pyrazole-4-carboxylic acid;
1-[6-(2,6-Dimethyl-phenoxy)-7-methoxy-4-oxo-3,4-dihydro-quinazolin-2-yl]-1H-pyrazole-4-carboxylic acid;
1-(7-Methoxy-4-oxo-6-phenoxy-3,4-dihydro-quinazolin-2-yl)-1H-pyrazole-4-carboxylic acid;
1-[6-(2,6-Dimethyl-phenoxy)-5,7-difluoro-4-oxo-3,4-dihydro-quinazolin-2-yl]-1H-pyrazole-4-carboxylic acid;
1-(5,7-Difluoro-4-oxo-6-phenoxy-3,4-dihydro-quinazolin-2-yl)-1H-pyrazole-4-carboxylic acid;
1-[4-Oxo-6-(pyridin-3-yloxy)-3,4-dihydro-quinazolin-2-yl]-1H-pyrazole-4-carboxylic acid;
1-(4-Oxo-7-phenoxy-3,4-dihydro-quinazolin-2-yl)-1H-pyrazole-4-carboxylic acid;
1-[4-Oxo-7-(tetrahydro-pyran-4-yl)-3,4-dihydro-quinazolin-2-yl]-1H-pyrazole-4-carboxylic acid tris(hydroxymethyl)aminomethane salt;
1-(7-Chloro-4-oxo-6-phenyl-3,4-dihydro-quinazolin-2-yl)-1H-pyrazole-4-carboxylic acid;
1-(4-Oxo-6-o-tolyl-3,4-dihydro-quinazolin-2-yl)-1H-pyrazole-4-carboxylic acid;

1-(6-Biphenyl-3-yl-4-oxo-3,4-dihydro-quinazolin-2-yl)-1H-pyrazole-4-carboxylic acid;
1-[7-Chloro-6-(3,4-dimethoxy-benzenesulfonyl)-4-oxo-3,4-dihydro-quinazolin-2-yl]-1H-pyrazole-4-carboxylic acid;
1-[6-(4-tert-Butyl-benzenesulfonyl)-7-chloro-4-oxo-3,4-dihydro-quinazolin-2-yl]-1H-pyrazole-4-carboxylic acid;
1-(7,7-Dimethyl-4-oxo-3,7-dihydro-4H-8-oxa-1,3-diaza-anthracen-2-yl)-1H-pyrazole-4-carboxylic acid;
1-(4-Oxo-6-phenoxymethyl-3,4-dihydro-quinazolin-2-yl)-1H-pyrazole-4-carboxylic acid;
1-[6-(2,6-Dimethyl-phenoxymethyl)-4-oxo-3,4-dihydro-quinazolin-2-yl]-1H-pyrazole-4-carboxylic acid;
1-(6-Ethynyl-4-oxo-3,4-dihydro-quinazolin-2-yl)-1H-pyrazole-4-carboxylic acid;
1-[6-(1-Chloro-vinyl)-4-oxo-3,4-dihydro-quinazolin-2-yl]-1H-pyrazole-4-carboxylic acid;
1-(4-Oxo-7-phenylsulfanyl-3,4-dihydro-quinazolin-2-yl)-1H-pyrazole-4-carboxylic acid;
1-[7-(4-Chloro-phenylsulfanyl)-4-oxo-3,4-dihydro-quinazolin-2-yl]-1H-pyrazole-4-carboxylic acid;
1-[7-(2-Chloro-phenylsulfanyl)-4-oxo-3,4-dihydro-quinazolin-2-yl]-1H-pyrazole-4-carboxylic acid;
1-(7-Benzenesulfonyl-4-oxo-3,4-dihydro-quinazolin-2-yl)-1H-pyrazole-4-carboxylic acid;
1-[7-(4-Chloro-benzenesulfonyl)-4-oxo-3,4-dihydro-quinazolin-2-yl]-1H-pyrazole-4-carboxylic acid;
1-[7-(2-Chloro-benzenesulfonyl)-4-oxo-3,4-dihydro-quinazolin-2-yl]-1H-pyrazole-4-carboxylic acid;
1-[7-Chloro-6-(3,4-dihydro-1H-isoquinolin-2-yl)-4-oxo-3,4-dihydro-quinazolin-2-yl]-1H-pyrazole-4-carboxylic acid;
1-[6-(7-Bromo-3,4-dihydro-1H-isoquinolin-2-yl)-7-chloro-4-oxo-3,4-dihydro-quinazolin-2-yl]-1H-pyrazole-4-carboxylic acid;
(rac)-1-{7-Chloro-6-[3-(3-methoxy-phenyl)-piperidin-1-yl]-4-oxo-3,4-dihydro-quinazolin-2-yl}-1H-pyrazole-4-carboxylic acid;
1-[6-(2,5-dichloro-phenoxy)-7-fluoro-4-oxo-3,4-dihydro-quinazolin-2-yl]-1H-pyrazole-4-carboxylic acid;
1-[6-(3,4-dimethyl-phenoxy)-7-fluoro-4-oxo-3,4-dihydro-quinazolin-2-yl]-1H-pyrazole-4-carboxylic acid;
1-[6-(3,5-dimethyl-phenoxy)-7-methyl-4-oxo-3,4-dihydro-quinazolin-2-yl]-1H-pyrazole-4-carboxylic acid;
1-[6-(2,5-dichloro-phenoxy)-7-methyl-4-oxo-3,4-dihydro-quinazolin-2-yl]-1H-pyrazole-4-carboxylic acid;
1-[6-(biphenyl-3-yloxy)-7-methyl-4-oxo-3,4-dihydro-quinazolin-2-yl]-1H-pyrazole-4-carboxylic acid;
1-[6-(3,4-dimethyl-phenoxy)-7-methyl-4-oxo-3,4-dihydro-quinazolin-2-yl]-1H-pyrazole-4-carboxylic acid;
1-[7-methyl-4-oxo-6-(3-trifluoromethyl-phenoxy)-3,4-dihydro-quinazolin-2-yl]-1H-pyrazole-4-carboxylic acid;
1-[6-(3,5-dimethyl-phenoxy)-7-fluoro-4-oxo-3,4-dihydro-quinazolin-2-yl]-1H-pyrazole-4-carboxylic acid;
1-[7-fluoro-4-oxo-6-(3-trifluoromethyl-phenoxy)-3,4-dihydro-quinazolin-2-yl]-1H-pyrazole-4-carboxylic acid;
1-[6-(2-fluoro-3-trifluoromethyl-phenoxy)-4-oxo-3,4-dihydro-quinazolin-2-yl]-1H-pyrazole-4-carboxylic acid;
1-[6-(3-fluoro-5-trifluoromethyl-phenoxy)-4-oxo-3,4-dihydro-quinazolin-2-yl]-1H-pyrazole-4-carboxylic acid;
1-[6-(3,5-dimethyl-phenoxy)-4-oxo-3,4-dihydro-quinazolin-2-yl]-1H-pyrazole-4-carboxylic acid;
1-[6-(biphenyl-3-yloxy)-4-oxo-3,4-dihydro-quinazolin-2-yl]-1H-pyrazole-4-carboxylic acid;
1-[4-oxo-6-(3-trifluoromethyl-phenoxy)-3,4-dihydro-quinazolin-2-yl]-1H-pyrazole-4-carboxylic acid;
1-[6-(2,6-dichloro-phenoxy)-5,7-difluoro-4-oxo-3,4-dihydro-quinazolin-2-yl]-1H-pyrazole-4-carboxylic acid;
1-(6-cyclohexyloxy-4-oxo-3,4-dihydro-quinazolin-2-yl)-1H-pyrazole-4-carboxylic acid;
1-[6-(4-methyl-piperazin-1-yl)-4-oxo-3,4-dihydro-quinazolin-2-yl]-1H-pyrazole-4-carboxylic acid;
1-(6-isopropoxy-4-oxo-3,4-dihydro-quinazolin-2-yl)-1H-pyrazole-4-carboxylic acid;
1-(6-benzyl-4-oxo-3,4-dihydro-quinazolin-2-yl)-1H-pyrazole-4-carboxylic acid;
1-(4-oxo-6-phenyl-3,4-dihydro-quinazolin-2-yl)-1H-pyrazole-4-carboxylic acid;
1-(6-morpholin-4-yl-4-oxo-3,4-dihydro-quinazolin-2-yl)-1H-pyrazole-4-carboxylic acid;
1-[6-(1H-Indol-6-yl)-4-oxo-3,4-dihydro-quinazolin-2-yl]-1H-pyrazole-4-carboxylic acid;
1-(6-Cyclopropyl-4-oxo-3,4-dihydro-quinazolin-2-yl)-1H-pyrazole-4-carboxylic acid;
1-(6-Cyclohexyl-7-fluoro-4-oxo-3,4-dihydro-quinazolin-2-yl)-1H-pyrazole-4-carboxylic acid;
1-(4-Oxo-8-phenyl-3,4-dihydro-quinazolin-2-yl)-1H-pyrazole-4-carboxylic acid;
1-(4-Oxo-8-phenoxy-3,4-dihydro-quinazolin-2-yl)-1H-pyrazole-4-carboxylic acid;
1-(4-Oxo-8-phenylsulfanyl-3,4-dihydro-quinazolin-2-yl)-1H-pyrazole-4-carboxylic acid;
1-(8-Isopropyl-4-oxo-3,4-dihydro-quinazolin-2-yl)-1H-pyrazole-4-carboxylic acid;
1-(8-tert-Butyl-4-oxo-3,4-dihydro-quinazolin-2-yl)-1H-pyrazole-4-carboxyl is acid;
1-(5,8-Difluoro-4-oxo-3,4-dihydro-quinazolin-2-yl)-1H-pyrazole-4-carboxylic acid;
1-(4-Oxo-8-trifluoromethoxy-3,4-dihydro-quinazolin-2-yl)-1H-pyrazole-4-carboxylic acid;
1-(8-Fluoro-4-oxo-3,4-dihydro-quinazolin-2-yl)-1H-pyrazole-4-carboxylic acid;
1-(6-Isopropyl-4-oxo-3,4-dihydro-quinazolin-2-yl)-1H-pyrazole-4-carboxylic acid;
1-(6-sec-Butyl-4-oxo-3,4-dihydro-quinazolin-2-yl)-1H-pyrazole-4-carboxylic acid;
1-(6-Ethoxy-4-oxo-3,4-dihydro-quinazolin-2-yl)-1H-pyrazole-4-carboxylic acid;
1-(6-Methoxy-4-oxo-3,4-dihydro-quinazolin-2-yl)-1H-pyrazole-4-carboxylic acid;
1-(4-Oxo-6-pyrrolidin-1-yl-3,4-dihydro-quinazolin-2-yl)-1H-pyrazole-4-carboxylic acid;
1-(4-Oxo-6-piperidin-1-yl-3,4-dihydro-quinazolin-2-yl)-1H-pyrazole-4-carboxylic acid;
1-(6-Dimethylamino-4-oxo-3,4-dihydro-quinazolin-2-yl)-1H-pyrazole-4-carboxylic acid;
1-(4-Oxo-3,4-dihydro-quinazolin-2-yl)-1H-pyrazole-4-carboxylic acid;
1-(6-Bromo-7-fluoro-4-oxo-3,4-dihydro-quinazolin-2-yl)-1H-pyrazole-4-carboxylic acid;
1-(6-Ethyl-4-oxo-3,4-dihydro-quinazolin-2-yl)-1H-pyrazole-4-carboxylic acid;
1-(4-Oxo-6-propyl-3,4-dihydro-quinazolin-2-yl)-1H-pyrazole-4-carboxylic acid;
1-(6-Bromo-8-fluoro-4-oxo-3,4-dihydro-quinazolin-2-yl)-1H-pyrazole-4-carboxylic acid;
1-(5,7-Difluoro-4-oxo-3,4-dihydro-quinazolin-2-yl)-1H-pyrazole-4-carboxylic acid;
1-(5,7-Dichloro-4-oxo-3,4-dihydro-quinazolin-2-yl)-1H-pyrazole-4-carboxylic acid;

1-(7-Fluoro-4-oxo-3,4-dihydro-quinazolin-2-yl)-1H-pyrazole-4-carboxylic acid;
1-(7-Bromo-4-oxo-3,4-dihydro-quinazolin-2-yl)-1H-pyrazole-4-carboxylic acid;
1-(7-Methoxy-4-oxo-3,4-dihydro-quinazolin-2-yl)-1H-pyrazole-4-carboxylic acid;
1-(7-Benzyl-4-oxo-3,4-dihydro-quinazolin-2-yl)-1H-pyrazole-4-carboxylic acid;
1-(4-Oxo-3,4,8,9-tetrahydro-7H-6,10-dioxa-1,3-diaza-cyclohepta[b]naphthalen-2-yl)-1H-pyrazole-4-carboxylic acid;
1-(8-Oxo-2,3,7,8-tetrahydro-1,4-dioxa-5,7-diaza-phenanthren-6-yl)-1H-pyrazole-4-carboxylic acid;
1-(4-Oxo-3,4,7,8-tetrahydro-[1,4]dioxino[2,3-g]quinazolin-2-yl)-1H-pyrazole-4-carboxylic acid;
1-(4-Oxo-4,6,7,8-tetrahydro-3H-cyclopenta[g]quinazolin-2-yl)-1H-pyrazole-4-carboxylic acid;
1-(6-Oxo-2,3,6,7-tetrahydro-1H-7,9-diaza-cyclopenta[a]naphthalen-8-yl)-1H-pyrazole-4-carboxylic acid;
1-(4-Oxo-3,4,7,8,9,10-hexahydro-benzo[h]quinazolin-2-yl)-1H-pyrazole-4-carboxylic acid;
1-(4-Oxo-3,4,6,7,8,9-hexahydro-benzo[g]quinazolin-2-yl)-1H-pyrazole-4-carboxylic acid;
1-(1-Oxo-1,2,7,8,9,10-hexahydro-benzo[f]quinazolin-3-yl)-1H-pyrazole-4-carboxylic acid;
1-(5,7-Dimethyl-4-oxo-3,4-dihydro-quinazolin-2-yl)-1H-pyrazole-4-carboxylic acid;
1-(7-Isopropyl-4-oxo-3,4-dihydro-quinazolin-2-yl)-1H-pyrazole-4-carboxylic acid;
1-(7-tert-Butyl-4-oxo-3,4-dihydro-quinazolin-2-yl)-1H-pyrazole-4-carboxyl is acid;
1-(4-Oxo-7-trifluoromethoxy-3,4-dihydro-quinazolin-2-yl)-1H-pyrazole-4-carboxylic acid;
1-(7-Isopropoxy-4-oxo-3,4-dihydro-quinazolin-2-yl)-1H-pyrazole-4-carboxylic acid;
1-(7-Dimethylamino-4-oxo-3,4-dihydro-quinazolin-2-yl)-1H-pyrazole-4-carboxylic acid;
1-(5-Dimethylamino-4-oxo-3,4-dihydro-quinazolin-2-yl)-1H-pyrazole-4-carboxylic acid;
1-(7-Ethoxy-4-oxo-3,4-dihydro-quinazolin-2-yl)-1H-pyrazole-4-carboxylic acid;
1-(6-Chloro-4-oxo-3,4-dihydro-quinazolin-2-yl)-1H-pyrazole-4-carboxylic acid;
1-(7-Hydroxy-4-oxo-3,4-dihydro-quinazolin-2-yl)-1H-pyrazole-4-carboxylic acid;
1-(6-Methylsulfanyl-4-oxo-3,4-dihydro-quinazolin-2-yl)-1H-pyrazole-4-carboxylic acid;
1-(4-Oxo-6-trifluoromethylsulfanyl-3,4-dihydro-quinazolin-2-yl)-1H-pyrazole-4-carboxylic acid;
1-(6-Methanesulfonyl-4-oxo-3,4-dihydro-quinazolin-2-yl)-1H-pyrazole-4-carboxylic acid;
1-(7-Chloro-6-methylsulfanyl-4-oxo-3,4-dihydro-quinazolin-2-yl)-1H-pyrazole-4-carboxylic acid;
1-(7-Chloro-4-oxo-6-trifluoromethylsulfanyl-3,4-dihydro-quinazolin-2-yl)-1H-pyrazole-4-carboxylic acid;
1-(7-Chloro-4-oxo-6-trifluoromethanesulfinyl-3,4-dihydro-quinazolin-2-yl)-1H-pyrazole-4-carboxylic acid;
1-[4-Oxo-6-(pyrrolidine-1-sulfonyl)-3,4-dihydro-quinazolin-2-yl]-1H-pyrazole-4-carboxylic acid;
1-[4-Oxo-6-(pyrrolidine-1-carbonyl)-3,4-dihydro-quinazolin-2-yl]-1H-pyrazole-4-carboxylic acid;
1-[6-(2,6-Dimethyl-phenylcarbamoyl)-4-oxo-3,4-dihydro-quinazolin-2-yl]-1H-pyrazole-4-carboxylic acid;
1-(6-Nitro-4-oxo-3,4-dihydro-quinazolin-2-yl)-1H-pyrazole-4-carboxylic acid
1-(6-Benzoylamino-4-oxo-3,4-dihydro-quinazolin-2-yl)-1H-pyrazole-4-carboxylic acid;
1-[6-(2,6-Dimethyl-benzoylamino)-4-oxo-3,4-dihydro-quinazolin-2-yl]-1H-pyrazole-4-carboxylic acid;
1-(6-Acetylamino-4-oxo-3,4-dihydro-quinazolin-2-yl)-1H-pyrazole-4-carboxylic acid;
1-[4-Oxo-6-(3-phenyl-ureido)-3,4-dihydro-quinazolin-2-yl]-1H-pyrazole-4-carboxylic acid;
1-(6-Benzenesulfonylamino-4-oxo-3,4-dihydro-quinazolin-2-yl)-1H-pyrazole-4-carboxylic acid;
1-(6-Methanesulfonylamino-4-oxo-3,4-dihydro-quinazolin-2-yl)-1H-pyrazole-4-carboxylic acid;
1-(6-Benzylamino-4-oxo-3,4-dihydro-quinazolin-2-yl)-1H-pyrazole-4-carboxylic acid;
1-(6-Ethylamino-4-oxo-3,4-dihydro-quinazolin-2-yl)-1H-pyrazole-4-carboxylic acid;
1-[6-(2-Methyl-benzylamino)-4-oxo-3,4-dihydro-quinazolin-2-yl]-1H-pyrazole-4-carboxylic acid;
1-[6-(2-Chloro-benzylamino)-4-oxo-3,4-dihydro-quinazolin-2-yl]-1H-pyrazole-4-carboxylic acid;
1-[6-(2,6-Dimethyl-benzylamino)-4-oxo-3,4-dihydro-quinazolin-2-yl]-1H-pyrazole-4-carboxylic acid;
1-[6-(2,6-Difluoro-benzylamino)-4-oxo-3,4-dihydro-quinazolin-2-yl]-1H-pyrazole-4-carboxylic acid;
1-[6-(2-Cyano-benzylamino)-4-oxo-3,4-dihydro-quinazolin-2-yl]-1H-pyrazole-4-carboxylic acid;
1-[6-(3-Cyano-benzylamino)-4-oxo-3,4-dihydro-quinazolin-2-yl]-1H-pyrazole-4-carboxylic acid;
1-[6-(3-Carbamoyl-benzylamino)-4-oxo-3,4-dihydro-quinazolin-2-yl]-1H-pyrazole-4-carboxylic acid;
1-[6-amino-4-oxo-3,4-dihydro-quinazolin-2-yl]-1H-pyrazole-4-carboxylic acid;
1-[6-(2,6-Dichloro-benzylamino)-4-oxo-3,4-dihydro-quinazolin-2-yl]-1H-pyrazole-4-carboxylic acid;
1-[6-(3-Chloro-benzylamino)-4-oxo-3,4-dihydro-quinazolin-2-yl]-1H-pyrazole-4-carboxylic acid;
1-[6-(4-methyl-benzylamino)-4-oxo-3,4-dihydro-quinazolin-2-yl]-1H-pyrazole-4-carboxylic acid;
1-(4-Oxo-7-phenyl-3,4-dihydro-quinazolin-2-yl)-1H-pyrazole-4-carboxylic acid;
1-[7-(2-Chloro-phenyl)-4-oxo-3,4-dihydro-quinazolin-2-yl]-1H-pyrazole-4-carboxylic acid;
1-[7-(3-Chloro-phenyl)-4-oxo-3,4-dihydro-quinazolin-2-yl]-1H-pyrazole-4-carboxylic acid;
1-[7-(4-Chloro-phenyl)-4-oxo-3,4-dihydro-quinazolin-2-yl]-1H-pyrazole-4-carboxylic acid;
1-(4-Oxo-7-o-tolyl-3,4-dihydro-quinazolin-2-yl)-1H-pyrazole-4-carboxylic acid;
1-(4-Oxo-7-m-tolyl-3,4-dihydro-quinazolin-2-yl)-1H-pyrazole-4-carboxylic acid;
1-(4-Oxo-6-m-tolyl-3,4-dihydro-quinazolin-2-yl)-1H-pyrazole-4-carboxylic acid;
1-(4-Oxo-6-p-tolyl-3,4-dihydro-quinazolin-2-yl)-1H-pyrazole-4-carboxylic acid;
1-[6-(2-Chloro-phenyl)-4-oxo-3,4-dihydro-quinazolin-2-yl]-1H-pyrazole-4-carboxylic acid;
1-[6-(3-Chloro-phenyl)-4-oxo-3,4-dihydro-quinazolin-2-yl]-1H-pyrazole-4-carboxylic acid;
1-[6-(4-Chloro-phenyl)-4-oxo-3,4-dihydro-quinazolin-2-yl]-1H-pyrazole-4-carboxylic acid;
1-[6-(2-Fluoro-phenyl)-4-oxo-3,4-dihydro-quinazolin-2-yl]-1H-pyrazole-4-carboxylic acid;
1-[6-(3-Fluoro-phenyl)-4-oxo-3,4-dihydro-quinazolin-2-yl]-1H-pyrazole-4-carboxylic acid;
1-[6-(4-Fluoro-phenyl)-4-oxo-3,4-dihydro-quinazolin-2-yl]-1H-pyrazole-4-carboxylic acid;
1-[6-(2-Methoxy-phenyl)-4-oxo-3,4-dihydro-quinazolin-2-yl]-1H-pyrazole-4-carboxylic acid;

1-[6-(3-Methoxy-phenyl)-4-oxo-3,4-dihydro-quinazolin-2-yl]-1H-pyrazole-4-carboxylic acid;
1-[6-(4-Methoxy-phenyl)-4-oxo-3,4-dihydro-quinazolin-2-yl]-1H-pyrazole-4-carboxylic acid;
1-[4-Oxo-6-(2-trifluoromethyl-phenyl)-3,4-dihydro-quinazolin-2-yl]-1H-pyrazole-4-carboxylic acid;
1-[4-Oxo-6-(2-trifluoromethoxy-phenyl)-3,4-dihydro-quinazolin-2-yl]-1H-pyrazole-4-carboxylic acid;
1-[6-(2-Ethyl-phenyl)-4-oxo-3,4-dihydro-quinazolin-2-yl]-1H-pyrazole-4-carboxylic acid;
1-[6-(2,3-Dihydro-benzo[1,4]dioxin-5-yl)-4-oxo-3,4-dihydro-quinazolin-2-yl]-1H-pyrazole-4-carboxylic acid;
1-[4-Oxo-6-(3-trifluoromethoxy-phenyl)-3,4-dihydro-quinazolin-2-yl]-1H-pyrazole-4-carboxylic acid;
1-[6-(3-Methanesulfonyl-phenyl)-4-oxo-3,4-dihydro-quinazolin-2-yl]-1H-pyrazole-4-carboxylic acid;
1-(6-Benzo[1,3]dioxol-5-yl-4-oxo-3,4-dihydro-quinazolin-2-yl)-1H-pyrazole-4-carboxylic acid;
1-(7-Iodo-4-oxo-3,4-dihydro-quinazolin-2-yl)-1H-pyrazole-4-carboxylic acid;
1-(6-Benzenesulfinyl-7-chloro-4-oxo-3,4-dihydro-quinazolin-2-yl)-1H-pyrazole-4-carboxylic acid;
1-(6-Benzenesulfonyl-7-chloro-4-oxo-3,4-dihydro-quinazolin-2-yl)-1H-pyrazole-4-carboxylic acid; and
1-(4-Oxo-7-piperidin-1-yl-3,4-dihydro-quinazolin-2-yl)-1H-pyrazole-4-carboxylic acid or a pharmaceutically acceptable salt thereof.

* * * * *